(12) United States Patent
Kusuda et al.

(10) Patent No.: US 8,003,642 B2
(45) Date of Patent: Aug. 23, 2011

(54) NITROGENATED HETEROCYCLIC DERIVATIVE, AND PHARMACEUTICAL AGENT COMPRISING THE DERIVATIVE AS ACTIVE INGREDIENT

(75) Inventors: Shinya Kusuda, Osaka (JP); Toshihiko Nishiyama, Osaka (JP); Kazuya Hashimura, Shiga (JP); Junya Ueda, Osaka (JP); Shiro Shibayama, Ibaraki (JP)

(73) Assignee: Ono Pharmaceutical Co., Ltd., Osaka-shi (JP)

( * ) Notice: Subject to any disclaimer, the term of this patent is extended or adjusted under 35 U.S.C. 154(b) by 303 days.

(21) Appl. No.: 12/282,464

(22) PCT Filed: Mar. 9, 2007

(86) PCT No.: PCT/JP2007/054684
§ 371 (c)(1),
(2), (4) Date: Jan. 9, 2009

(87) PCT Pub. No.: WO2007/105637
PCT Pub. Date: Sep. 20, 2007

(65) Prior Publication Data
US 2009/0131403 A1    May 21, 2009

(30) Foreign Application Priority Data
Mar. 10, 2006  (JP) .............................. P. 2006-066451

(51) Int. Cl.
*A61K 31/5377* (2006.01)
*A61K 31/4545* (2006.01)
*C07D 413/14* (2006.01)
*C07D 401/14* (2006.01)

(52) U.S. Cl. .................... 514/235.5; 514/318; 544/124; 544/129; 546/187; 546/194

(58) Field of Classification Search ............... 514/235.5, 514/318; 544/124, 129; 546/187, 194
See application file for complete search history.

(56) References Cited

U.S. PATENT DOCUMENTS

| | | | |
|---|---|---|---|
| 3,375,256 A | 3/1968 | Bach et al. | |
| 5,169,855 A | 12/1992 | Cain | |
| 5,486,534 A | 1/1996 | Lee et al. | |
| 6,096,780 A | 8/2000 | Shiraishi | |
| 6,268,354 B1 | 7/2001 | Nishimura | |
| 6,376,536 B1 | 4/2002 | Shiraishi | |
| 6,515,027 B1 | 2/2003 | Bondinell | |
| 6,720,321 B2 | 4/2004 | Cirillo et al. | |
| 6,765,009 B2 | 7/2004 | Francesco et al. | |
| 6,894,063 B2 | 5/2005 | Greenlee et al. | |
| 6,903,085 B1 | 6/2005 | Thom et al. | |
| 7,053,090 B2 | 5/2006 | Habashita et al. | |
| 7,071,213 B2 | 7/2006 | Friary et al. | |
| 7,247,725 B2 | 7/2007 | Butora et al. | |
| 2002/0165223 A1 | 11/2002 | Greenlee et al. | |
| 2003/0069276 A1 | 4/2003 | Edlin et al. | |
| 2003/0083333 A1 | 5/2003 | Cirillo et al. | |
| 2003/0100608 A1 | 5/2003 | Cirillo et al. | |
| 2003/0114517 A1 | 6/2003 | Greenlee et al. | |
| 2003/0195192 A1 | 10/2003 | Haviv et al. | |
| 2004/0006081 A1 | 1/2004 | Burrows et al. | |
| 2004/0010013 A1 | 1/2004 | Friary et al. | |
| 2004/0082584 A1 | 4/2004 | Habashita et al. | |
| 2004/0158067 A1 | 8/2004 | Hutchison et al. | |
| 2005/0038100 A1 | 2/2005 | Greenlee et al. | |
| 2005/0215557 A1 | 9/2005 | Habashita et al. | |
| 2005/0250792 A1 | 11/2005 | Thom et al. | |
| 2005/0261325 A1 | 11/2005 | Butora et al. | |
| 2005/0267114 A1 | 12/2005 | Takaoka et al. | |
| 2005/0282861 A1 | 12/2005 | Friary et al. | |
| 2006/0178397 A1 | 8/2006 | MacDonald et al. | |
| 2006/0178399 A1 | 8/2006 | Nishizawa et al. | |
| 2007/0066624 A1 | 3/2007 | Zhou et al. | |
| 2007/0167459 A1 | 7/2007 | Habashita et al. | |
| 2007/0254886 A1 | 11/2007 | Habashita et al. | |
| 2008/0057074 A1 | 3/2008 | Takaoka et al. | |

FOREIGN PATENT DOCUMENTS

EP    0 449 187 A2    10/1991

(Continued)

OTHER PUBLICATIONS

Khanapure et al., "Synthesis and Structure—Activity Relationship of Novel, Highly Potent Metharyl and Methcycloalkyl Cyclooxygenase-2 (COX-2) Selective Inhibitors", Journal of Medicinal Chemistry, pp. 5484-5504, vol. 46, No. 25, American Chemical Society (2003).

(Continued)

*Primary Examiner* — Rebecca Anderson
*Assistant Examiner* — Samantha Shterengarts
(74) *Attorney, Agent, or Firm* — Sughrue Mion, PLLC

(57) ABSTRACT

The compound represented by formula (I), a salt thereof, an N-oxide thereof, a solvate thereof, or a prodrug thereof specifically binds CCR5, so it is useful for preventing and/or treating CCR5-related diseases, for example, various inflammatory diseases (asthma, nephritis, nephropathy, hepatitis, arthritis, rheumatoid arthritis, rhinitis, conjunctivitis, ulcerative colitis, etc.), immunological diseases (autoimmune diseases, rejection in organ transplantation, immunosuppression, psoriasis, multiple sclerosis, etc.), infectious diseases (infection with human immunodeficiency virus, acquired immunodeficiency syndrome, etc.), allergic diseases (atopic dermatitis, urticaria, allergic bronchopulmonary aspergillosis, allergic eosinophilic gastroenteritis, etc.), ischemic reperfusion injury, acute respiratory distress syndrome, shock accompanying bacterial infection diabetes cancer metastasis and so on (I)

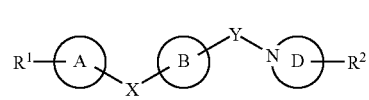

Wherein all symbols in formula are as defined in the specification.

3 Claims, No Drawings

FOREIGN PATENT DOCUMENTS

| | | | |
|---|---|---|---|
| EP | 0 748 805 | A1 | 12/1996 |
| EP | 1 020 445 | A1 | 7/2000 |
| EP | 1 236 726 | A1 | 9/2002 |
| EP | 1378510 | A1 | 1/2004 |
| EP | 1422219 | A1 | 5/2004 |
| EP | 1541574 | A1 | 6/2005 |
| EP | 1 604 981 | A1 | 12/2005 |
| EP | 1790637 | A1 | 5/2007 |
| JP | 04-356462 | A | 12/1992 |
| JP | 2000-128782 | A2 | 5/2000 |
| JP | 2001-518505 | A | 10/2001 |
| JP | 2004-528318 | A | 9/2004 |
| JP | 2004-534787 | A | 11/2004 |
| JP | 2007-063268 | A | 3/2007 |
| RU | 2199535 | C2 | 2/2003 |
| WO | 96/10012 | A1 | 4/1996 |
| WO | 97/36903 | A1 | 10/1997 |
| WO | 99/01127 | A1 | 1/1999 |
| WO | 99/17773 | A1 | 4/1999 |
| WO | 99/31062 | A1 | 6/1999 |
| WO | 99/32100 | A2 | 7/1999 |
| WO | 02/24636 | A2 | 3/2002 |
| WO | 02/053560 | A1 | 7/2002 |
| WO | 02/074758 | A2 | 9/2002 |
| WO | 02/074770 | A1 | 9/2002 |
| WO | 02/079186 | A2 | 10/2002 |
| WO | 02/083628 | A1 | 10/2002 |
| WO | 02/098869 | A2 | 12/2002 |
| WO | 03/020703 | A1 | 3/2003 |
| WO | 03037271 | A2 | 5/2003 |
| WO | 03/066592 | A1 | 8/2003 |
| WO | 03/104230 | A1 | 12/2003 |
| WO | 2004/026873 | A1 | 4/2004 |
| WO | 2004/043925 | A2 | 5/2004 |
| WO | 2004/046101 | A1 | 6/2004 |
| WO | 2004/080966 | A1 | 9/2004 |
| WO | 2004/096131 | A2 | 11/2004 |
| WO | 2006/030925 | A1 | 3/2006 |
| WO | 2007/022371 | A2 | 2/2007 |
| WO | 2007/105637 | A1 | 9/2007 |

OTHER PUBLICATIONS

Ledniger et al., "Mammalian Antifertility Agents. IV. Basic 3,4-Dihydronaphthalenes and 1,2,3,4-Tetrahydro-1-Naphthols", pp. 79-84, vol. 10, Jounal Medicinal Chemistry (1967).
International Search Report dated Jun. 1, 2004 in PCT/JP2004/003333.
Chinese Office Action dated May 11, 2007 in Application No. 2004800130029.
Russian Office Action dated Aug. 30, 2007 in Application No. 2005131833.
Statement of Third Party Observations dated May 13, 2008 in European Application No. 05785808.6.
Millet, "Potent and Selective Farnesy/Transferase Inhibitors", J.Med. Chem., vol. 47, pp. 6812-6820 (2004).
Supplementary European Search Report dated Nov. 26, 2008.
Mashkovskiy, M.D., "Medicinal Drugs", p. 11, vol. 1, 14th Ed., S.B. Divov, Moscow (2001).
Russian Office Action dated Jul. 9, 2009 in Application No. 2007113814.
U.S. Office Action dated Jun. 20, 2008 in U.S. Appl. No. 10/549,120.
U.S. Office Action dated Nov. 26, 2008 in U.S. Appl. No. 10/549,120.
U.S. Office Action dated Feb. 13, 2009 in U.S. Appl. No. 10/549,120.
U.S. Office Action dated Oct. 9, 2009 in U.S. Appl. No. 10/549,120.
European Office Action dated Dec. 15, 2009 issued in Application No. 04720257.7.
Singaporean Office Action dated Jan. 19, 2010 in Singapore Application No. 200806533-6.
Extended European Search Report dated Feb. 18, 2010 in European Application No. 05785808.6-1521.
Chinese Office Action dated Mar. 10, 2010 in Chinese application No. 200810133648.0.
Office Action issued on Apr. 14, 2010 in the counterpart Russian Application No. 2007113814 of co-pending U.S. Appl. No. 10/549,120.
New Zealand Office Action issued Apr. 8, 2010 in corresponding New Zealand application No. 571019.
Vietnamese Office Action issued Jun. 10, 2010 in Vietnamese application No. 1-2005-01233.
Office Action issued May 11, 2010 in the counterpart Chinese Application No. 200810133649.5 of co-pending U.S. Appl. No. 10/549,120.
Japanese Office Action issued May 18, 2010 in Japanese Application No. 2005-503613.
Shomir Ghosh et. al.: "Design, Synthesis, and Progress toward Optimization of Potent Small Molecule Antagonists of CC Chemokine Receptor 8 (CCR8)", Journal of Medicinal Chemistry, vol. 49. No. 9, May 4, 2006; pp. 2669-2672.
Office Action issued on Sep. 10, 2010 in counterpart European application No. 04 720 257.7 of co-pending U.S. Appl. No. 10/549,120.
Office Action issued on Sep. 23, 2010 in counterpart Norwegian application No. 2005 4244 of co-pending U.S. Appl. No. 10/549,120.
Office Action issued on Sep. 28, 2010 in counterpart European application No. 05 785 808.6 of co-pending U.S. Appl. No. 11/662,639.
European Search Report issued on Oct. 19, 2010 in corresponding European application No. 07 738 169.7.
The Second Office Action dated Oct. 12, 2010 from The Patent Office of the People's Republic of China issued Chinese application No. 200580038925.4 which is a counterpart application to co-pending U.S. Appl. No. 11/662,639.
Office Action dated Oct. 19, 2010 from the Canadian Intellectual Property Office issued Canadian Application No. 2,517,888, which is a counterpart to co-pending U.S. Appl. No. 10/549,120.
Australian Office Action issued in Application No. 2005-283326; dated Nov. 9, 2010.

NITROGENATED HETEROCYCLIC DERIVATIVE, AND PHARMACEUTICAL AGENT COMPRISING THE DERIVATIVE AS ACTIVE INGREDIENT

TECHNICAL FIELD

The present invention relates to a nitrogen-containing heterocyclic derivative which is useful as medicament and a drug containing the same as the active ingredient.

Explaining in more detail about the present invention, it relates to
(1) a compound represented by formula (I):

wherein all symbols have the same meanings as described hereinafter, a salts thereof, an N-oxide thereof or a solvate thereof, or prodrugs thereof,
(2) an agent for prevention and/or treatment of CCR5-related diseases, comprising a compound represented by formula (I), a salt thereof, an N-oxide thereof or a solvate thereof, or prodrugs thereof, as an active ingredient, and
(3) a process for the preparation thereof.

BACKGROUND OF THE INVENTION

Chemokine is known as an endogeneous basic protein having leukocyte chemotactic and activating abilities and strong heparin-binding abilities. At present, it is considered that chemokine is related to not only the control of infiltration of specific leukocyte at the time of inflammations and immune responses but also the development and homing of lymphocyte under physiological conditions and migration of hemocyte precursor cells and somatic cells.

Differentiation, proliferation and cell death of hemocytes are controlled by various types of cytokine. In the living body, inflammations are found topically and differentiation, maturation and the like of lymphocytes are carried out at certain specified sites. That is, various necessary cells migrate into certain specified sites and accumulate therein to cause a series of inflammations and immune responses. Accordingly, migration of cells is also an indispensable phenomenon in addition to differentiation, proliferation and death of cells.

Migration of hemocytes in the living body starts firstly in the development stage by the shift of hematopoiesis started in the aorta-gonad-mesonephros (AGM) region into permanent hematopoiesis in bone marrow via fetal liver. Furthermore, precursor cells of T cells and thymus dendritic cells migrate from the fetal liver into the bone marrow and then into the thymus gland and cytodifferentiate under thymus environment. The T cell which received clone selection migrates into secondary lymphoid tissues and takes part in an immune response in the periphery. The Langerhans' cell of the skin activated and differentiated by capturing an antigen migrates into the T cell region of a topical lymph node and activates naive T cell therein as a dendritic cell. The memory T cell performs its homing again into the lymph node via lymphatic and blood vessels. Also, B cell, T cell in the intestinal epithelium, γδ T cell, NKT cell and dendritic cell migrate from bone marrow without passing through the thymus gland and differentiate to take part in an immune response.

Chemokine deeply takes part in the migration of such various cells. Chemokine receptors are greatly related to the control of inflammation and immune responses through a mechanism in which they are expressed at certain specified periods in variously specific cells and the effector cells are accumulated in a region where chemokine is produced.

For example, it is reported an investigation in animal models such as CCR5-knockout mouse suggesting that CCR5 as a chemokine receptor plays a significant role in rejection in organ transplantation or autoimmune disease, etc. (Transplantation, Vol. 72(7), 1199-1205 (2001); Diabetes, Vol. 51(8), 2489-2495 (2002); Journal of Virology, Vol. 77(1), 191-198 (2003); Journal of Immunology, Vol. 164(12), 6303-6312 (2000)). It is also reported which make a comparison a risk of developing several diseases and a length of the survival of the transplanted graft, etc. between a human having inactive CCR5 and a human having wild-type one (The Lancet, Vol. 357, 1758-1761 (2001); Arthritis & Rheumatism, Vol. 42(5), 989-992 (1999); The Lancet, Vol. 354, 1264-1265 (1999); European Journal of Immunogenetics, Vol. 29(6) 525-528 (2002)). It is suggested that CCR5 is related to several diseases, but they make no reference to the effect of drugs which antagonizes CCR5 in their reports. At present, immunosuppressive treatment for diseases in transplantation area is provided.

That is, a calcineurin inhibitor such as cyclosporin or tacrolimus (FK506) is used mainly with various type of an immunosuppressant agent, for example, a TOR (target of rapamycin) inhibitor such as sirolimus (rapamycin), a non-specific antiphlogistic such as corticosteroids, an antiproliferative drug such as azathioprine, mycophenolate mofetil, etc. However, it frequently causes a chronic rejection or a severe side effect, so it is desired an useful novel immunosuppressant agent which prolongs a length of the survival of the transplanted graft and reduces the side effects in comparison with existing drugs.

An antiinflammatory drug or a drug which modulates immune function such as nonsteroidal antiinflammatory drug (NSAIDs) which have an inhibitory activity against cyclooxygenase (COX), disease modifying anti-rheumatic drug (DMARDs), steroids, etc. is used for treatment for autoimmune disease or allergic diseases. The more effective a drug is, the severer a side effect caused by it is, and it is suggested that the treatment with these drugs is not an underlying remedy for the disease, but a mere symptomatic treatment.

At the same time, acquired immunodeficiency syndrome (hereinafter referred to as "AIDS") which is induced by human immunodeficiency virus (hereinafter referred to as "HIV") is one of the diseases of which their therapeutic methods are most earnestly desired in recent years. Once infection with HIV is completed in a CD4-positive cell which is a principal target cell, HIV repeats its proliferation in the body of the patient and, sooner or later, completely destroys T cell which takes charge of the immunological function. During this process, the immunological function is gradually reduced to cause fever, diarrhea, lymph node enlargement and the like various immunodeficiency conditions which are apt to cause complications with *pneumocystis carinii* pneumonia and the like various opportunistic infections. Such conditions are the onset of AIDS, and it is well known that they induce and worsen Kaposi sarcoma and the like malignant tumors.

As the recent preventive and/or therapeutic methods for AIDS, attempts have been made to, e.g., (1) inhibit growth of HIV by the administration of a reverse transcriptase inhibitor or a protease inhibitor and (2) prevent or alleviate opportunistic infections by the administration of a drug having immunopotentiation activity.

Helper T cells which take charge of the central of immune system are mainly infected with HIV. It is known since 1985 that HIV uses the membrane protein CD4 expressing on the membrane of T cells in the infection (Cell, 52, 631 (1985)). The CD4 molecule is composed of 433 amino acid residues, and its expression can be found in macrophages, some B cells, vascular endothelial cells, Langerhans' cells in skin tissues, dendritic cells in lymphoid tissues, glia cells of the central nervous system and the like, in addition to the mature helper T cells. However, since it has been revealed that the infection with HIV is not completed by the CD4 molecule alone, a possibility has been suggested on the presence of factors other than the CD4 molecule, which are related to the infection of cells with HIV.

CCR5, which is a receptor of RANTES, MIP-1α and MIP-1β, is also used at the time of the infection with a macrophage tropic (R5) HIV (Science, 272, 1955 (1996)).

Accordingly, substances which can compete with CCR5 for HIV, or which can bind to HIV virus thus causing the virus unable to bind to CCR5, could become HIV infection inhibitors.

It is also reported a possibility that the CCR5 is used in the infection with Respiratory Syncytial Virus (hereinafter referred to as "RSV").

It is reported that CCR5 are expressed in arteriosclerotic plaque, so it is considered that chemokine receptor modulators are also useful in treating cardiovascular diseases.

Based on the above, it is considered that chemokine (for example, RANTES, MIP-1α, MIP-1β, etc.) receptors, especially CCR5 are deeply related to the inflammation, immunological diseases, infectious diseases (infection with HIV, infection with RSV, etc.; and cardiovascular diseases. For example, it is considered that they are related to various inflammatory diseases (asthma, nephritis, nephropathy, hepatitis, arthritis, rheumatoid arthritis, rhinitis, conjunctivitis, inflammatory bowel disease such as ulcerative colitis, etc.; immunological diseases (autoimmune diseases, rejection in organ transplantation (rejection of graft of solid organ, rejection of graft of pancreatic islet cells in therapy for diabetes, GVHD (graft-versus-host disease), etc.; immunosuppression, psoriasis, multiple sclerosis, etc.; infectious diseases (infection with human immunodeficiency virus, acquired immunodeficiency syndrome, infection with RSV, etc.; allergic diseases (atopic dermatitis, urticaria, allergic bronchopulmonary aspergillosis, allergic eosinophilic gastroenteritis, etc.; cardiovascular diseases (arteriosclerosis, ischemic reperfusion injury, etc.; acute respiratory distress syndrome, shock accompanying bacterial infection, diabetes mellitus, cancer metastasis and the like.

It is reported that a compound represented by formula (AA):

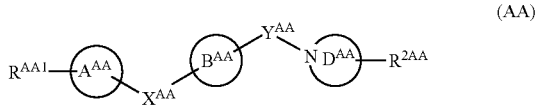

(AA)

wherein $R^{AA1}$ is a hydrogen atom, or an acidic group which may be protected; $X^{AA}$ and $Y^{AA}$ each independently represents a bond or a spacer containing 1 or 3 atoms as a main chain; ring $A^{AA}$ and ring $B^{AA}$ may be the same or different and represent a 3- to 15-membered homocyclic, or a heterocyclic group which may have further substituent(s); ring $D^{AA}$ represents a 3- to 15-membered nitrogen-containing heterocyclic group which may have further substituent(s); $R^{2AA}$ represents (1) a hydrogen atom, (2) a hydrocarbon group which may have a substituent(s), (3) a cyano group, (4) a hydroxyl group which may be protected, (5) an amino group which may have a substituent(s), (6) an oxo group, (7) a 3- to 15-membered heterocyclic group which may have a substituent(s), or (8) =N—OR$^{6AA}$, wherein R$^{6AA}$ a hydrogen atom or a C1-4 alkyl group, a salt thereof or a solvate thereof, or prodrugs thereof is useful as an agent for treatment and/or prevention of CCR5-related diseases (ref. Patent Reference 1).

It is reported that the aminopiperidine derivatives represented by formula (Z):

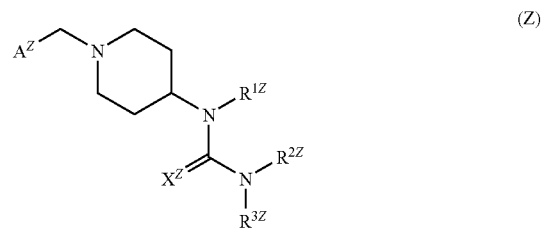

(Z)

wherein $R^{1Z}$ is a hydrogen atom or a C1-12 alkyl group; $R^{2Z}$ and $R^{3Z}$ each independently represents a hydrogen atom or a C1-12 alkyl group; $X^Z$ is a nitrogen atom or an oxygen atom; and $A^Z$ is

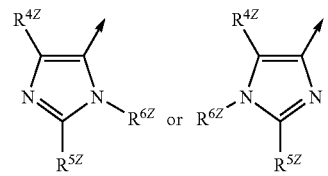

wherein $R^{4Z}$ is a hydrogen atom, a C1-12 alkyl group, a C3-8 cycloalkyl group, an aryl group, a substituted aryl group, aryl-C(=O)—, or aryl-CH(OH)—; $R^{5Z}$ is a hydrogen atom, a C1-12 alkyl group, a C1-4 alkoxy group, a halogen atom, or COR$^Z$; and $R^{6Z}$ is a hydrogen atom, a C1-12 alkyl group, or a substituted C1-4 alkyl group as long as the definition of each symbol is an excerpt partially, are useful as inhibitors of the chemokine receptors (ref. Patent Reference 2).

It is disclosed that the sulfonic acid compounds represented by formula (W):

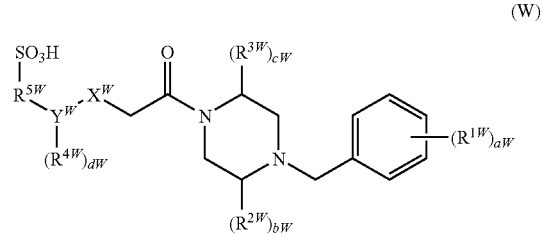

(W)

wherein $X^W$ is —O—, —S—, —CH$_2$— or —NR$^{6W}$; $Y^W$ is C6-10 aryl or C2-9 heteroaryl; $R^{1W}$ is selected from the group consisting of a hydrogen atom, —OH, a halogen atom, and a C1-8 alkyl group which may be substituted with 1 to 3 fluorine atom(s), etc.; $R^{2W}$ and $R^{3W}$ are selected from the group consisting of a hydrogen atom, oxo group, and a C1-8 alkyl group which may be substituted with 1 to 3 fluorine atom(s), etc.; $R^{4W}$ is selected from the group consisting of a hydrogen atom, —OH, a halogen atom, and —CN, etc.; $R^{5W}$ is a C1-8 alkyl group; aW is 0 to 5; bW is 0 to 2; cW is 0 to 2; and dW is 0 to 4. With the proviso that the definition of each symbol is an excerpt partially,
pharmacological acceptable salts thereof and prodrugs thereof are selective antagonists of CCR1 (ref Patent Reference 3).

Moreover, 1-(4-pyridyl)-piperazine derivatives are described as CCR5 antagonists (ref Patent Reference 4).

On the other hand, it is reported that triazaspiro[5.5]undecane derivatives, quaternary ammonium salts thereof or N-oxides thereof, or pharmacologically acceptable salts thereof regulate the effect of chemokine/chemokine receptor (CCR), so they are useful for prevention and/or treatment of various inflammatory diseases, asthma, atopic dermatitis, urticaria, allergic diseases (allergic bronchopulmonary aspergillosis or allergic eosinophilic gastroenteritis, etc.), nephritis, nephropathy, hepatitis, arthritis, rheumatoid arthritis, psoriasis, rhinitis, conjunctivitis, ischemic reperfusion disorder, multiple sclerosis, ulcerative colitis, acute respiratory distress syndrome, cytotoxic shock, diabetes, autoimmune disease, in transplanted organ rejection reactions, immunosuppression, cancer metastasis and acquired immune deficiency syndrome (ref Patent Reference 5).

It is also described that the compounds represented by formula (M):

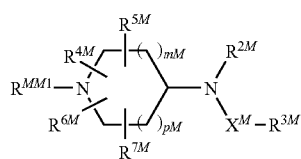

(M)

are modulators of chemokine receptor activity (ref Patent Reference 6).
Patent Reference 1: WO2004/080966
Patent Reference 2: WO02/079186
Patent Reference 3: WO02/102787
Patent Reference 4: U.S. Pat. No. 6,391,865
Patent Reference 5: WO01/040227
Patent Reference 6: WO01/087839

DISCLOSURE OF THE INVENTION

Problems to be Solved by the Invention

The compound having an antagonistic activity against CCR5 is useful as an agent for prevention and/or treatment of CCR5-related diseases, and it is known that various side effects (for example, liver damage, etc.) are caused by drug metabolizing enzyme inhibitory activity such as cytochrome P450 (hereinafter referred to as CYP) according to a partial structure of the compound. Therefore, it is desired to develop CCR5 antagonists which exert fewer side effects and can be used safely.

Means for Solving the Problems

In order to find a compound which has an antagonistic activity against a chemokine receptor, especially CCR5, the present inventors have conducted intensive studies and found that the compound represented by formula (I) of the present invention specifically binds CCR5, and also found surprisingly that the compound of the present invention exerts less influence on a drug metabolizing enzyme such as CYP, which was a problem of conventionally known CCR5 antagonists, and therefore exerts less side effects such as liver damage when used as CCR5 antagonists and have very high safety. Thus, the present invention has been completed.

The present invention relates to
1. A compound represented by formula (I):

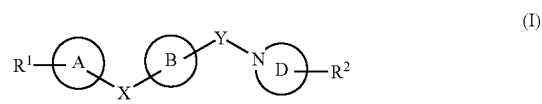

(I)

wherein $R^1$ represents (1) —N($R^{1A}$)SO$_2$—$R^{1B}$, (2) —SO$_2$NR$^{1C}$R$^{1D}$, (3) —COOR$^{1E}$, (4) —OR$^{1F}$, (5) —S(O)$_m$R$^{1G}$, (6) —CONR$^{1H}$R$^{1J}$, (7) —NR$^{1K}$COR$^{1L}$, (8) a cyano group, (9) a nitro group, (10) —NR$^{1M}$R$^{1N}$, (11) —N($R^{1P}$)SO$_2$NR$^{1Q}$R$^{1R}$, (12) —N($R^{1S}$)SO$_2$N($R^{1T}$)COOR$^{1U}$, (13) —N($R^{1AA}$)C(=O)NR$^{1BB}$R$^{1CC}$, (14) —N($R^{1DD}$)C(=S)NR$^{1EE}$R$^{1FF}$, (15) —COR$^{1GG}$, (16) —C($R^{1HH}$R$^{1JJ}$)OR$^{1KK}$, (17) —C($R^{1LL}$R$^{1MM}$)N($R^{1NN}$)SO$_2$—$R^{1PP}$, (18) —C($R^{1QQ}$R$^{1RR}$)SO$_2$NR$^{1SS}$R$^{1TT}$, (19) —C($R^{1AAA}$R$^{1BBB}$)S(O)$_m$R$^{1CCC}$, or (20) 3- to 15-membered heterocyclic group which may have a substituent(s);

wherein m is 0, 1 or 2;

$R^{1A}$, $R^{1B}$, $R^{1C}$, $R^{1D}$, $R^{1E}$, $R^{1F}$, $R^{1G}$, $R^{1H}$, $R^{1J}$, $R^{1K}$, $R^{1L}$, $R^{1M}$, $R^{1N}$, $R^{1P}$, $R^{1Q}$, $R^{1R}$, $R^{1S}$, $R^{1T}$, $R^{1U}$, $R^{1AA}$, $R^{1BB}$, $R^{1CC}$, $R^{1DD}$, $R^{1EE}$, $R^{1FF}$, $R^{1GG}$, $R^{1HH}$, $R^{1JJ}$, $R^{1KK}$, $R^{1LL}$, $R^{1MM}$, $R^{1NN}$, $R^{1PP}$, $R^{1QQ}$, $R^{1RR}$, $R^{1SS}$, $R^{1TT}$, $R^{1AAA}$, $R^{1BBB}$, and $R^{1CCC}$ each independently represents a hydrogen atom, a hydrocarbon group which may have a substituent(s), or a 3- to 15-membered heterocyclic group which may have a substituent(s), as long as $R^{1C}$ and $R^{1D}$, $R^{1H}$ and $R^{1J}$, $R^{1M}$ and $R^{1N}$, $R^{1Q}$ and $R^{1R}$, $R^{1BB}$ and $R^{1CC}$, $R^{1EE}$ and $R^{1FF}$, or $R^{1SS}$ and $R^{1TT}$ may form a nitrogen-containing heterocyclic group which may have a substituent(s) together with a nitrogen atom to which they bind, and $R^{1HH}$ and $R^{1JJ}$, $R^{1LL}$ and $R^{1MM}$, $R^{1QQ}$ and $R^{1RR}$, or $R^{1AAA}$ and $R^{1BBB}$ may form a carbocyclic group which may have a substituent(s) together with a carbon atom to which they bind;

X and Y each independently represents a bond or a spacer containing 1 or 3 atoms as a main chain;

ring A and ring B may be the same or different and represent a 3- to 15-membered carbocyclic or a heterocyclic group which may have further substituent(s);

ring D represents a 3- to 15-membered nitrogen-containing heterocyclic group which may have further substituent(s); and $R^2$ represents (1) a hydrogen atom, (2) a hydrocarbon group which may have a substituent(s), (3) a cyano group, (4) a hydroxyl group which may be protected, (5) an amino group which may have a substituent(s), (6) an oxo group, (7) a 3- to 15-membered heterocyclic group which may have a substituent(s), or (8) =N—OR$^6$;

wherein $R^6$ represents a hydrogen atom or a C1-4 alkyl group, as long as $R^1$ and a substituent of ring A may form a ring which may have a substituent(s);

a salt thereof, an N-oxide thereof, a solvate thereof, or prodrugs thereof;

2. the compound according to the above-described 1, which is represented by formula (Ia):

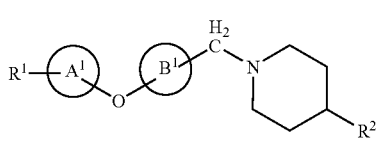

wherein ring $A^1$ and ring $B^1$ may be the same or different and represent a benzene or pyridine ring which may have further substituent(s); and other symbols have the same meaning as described in the above-described 1, as long as $R^2$ does not represent an oxo group, or =N—$OR^6$, wherein $R^6$ represents a hydrogen atom or C1-4 alkyl group, a salt thereof, an N-oxide thereof, a solvate thereof, or prodrugs thereof;

3. the compound according to the above-described 2, wherein $R^2$ is:

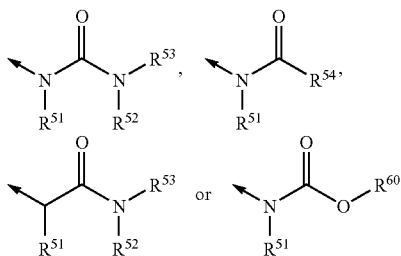

wherein the arrow represents a binding position to piperidine ring; $R^{51}$, $R^{52}$, $R^{53}$ and $R^{54}$ each independently represents (1) a hydrogen atom, (2) a hydrocarbon group which may have a substituent(s), (3) a 3- to 15-membered heterocyclic group which may have a substituent(s), (4) a C1-4 alkoxy group which may have a substituent(s), (5) a phenoxy group which may have a substituent(s), or (6) a benzyloxy group which may have a substituent(s); and $R^{60}$ represents (1) a hydrogen atom, (2) a hydrocarbon group which may have a substituent(s), or (3) a 3- to 15-membered heterocyclic group which may have a substituent(s), a salt thereof, an N-oxide thereof, a solvate thereof, or prodrugs thereof;

4. the compound according to the above-described 3, wherein $R^{51}$, $R^{53}$, $R^{54}$ and $R^{60}$ each independently represents (1) a benzene ring which may have a substituent(s), (2) a pyridine ring which may have a substituent(s), or (3) a benzyl group which may have a substituent(s); and $R^{52}$ is a hydrogen atom, a salt thereof, an N-oxide thereof, a solvate thereof, or prodrugs thereof;

5. the compound according to the above-described 4, wherein the substituent is a halogen atom or a C1-4 alkyl group which may have a substituent(s), a salt thereof, an N-oxide thereof, a solvate thereof, or prodrugs thereof;

6. the compound according to the above-described 4, wherein the substituent is a fluorine atom, a chlorine atom, a methyl group, or a trifluoromethyl group, a salt thereof, an N-oxide thereof, a solvate thereof, or prodrugs thereof;

7. the compound according to the above-described 3, which is represented by formula (Ia-1):

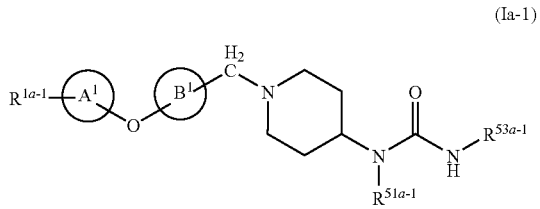

wherein $R^{1a-1}$ represents —$CONR^{1H}R^{1J}$ or —$COR^{1GG}$, wherein all symbols have the same meanings as described in the above-described 1; $R^{51a-1}$ represents a hydrocarbon group which may have a substituent(s); $R^{53a-1}$ represents (1) a benzene ring which may have a substituent(s) or (2) a pyridine ring which may have a substituent(s); and other symbols have the same meanings as described in the above-described 2, a salt thereof, an N-oxide thereof, a solvate thereof, or prodrugs thereof;

8. the compound according to the above-described 7, wherein $R^{1GG}$ is a 3- to 15-membered heterocyclic group which may have a substituent(s), a salt thereof, an N-oxide thereof, a solvate thereof, or prodrugs thereof;

9. the compound according to the above-described 8, wherein $R^{1GG}$ is a 3- to 8-membered nitrogen-containing saturated heterocyclic group which may have a substituent(s), a salt thereof, an N-oxide thereof, a solvate thereof, or prodrugs thereof;

10. the compound according to the above-described 9, wherein the 3- to 8-membered nitrogen-containing saturated heterocyclic group is a piperidine, piperazine or morpholine ring, a salt thereof, an N-oxide thereof, a solvate thereof, or prodrugs thereof;

11. the compound according to the above-described 7, which is

N-(3-fluorophenyl)-N-{1-[(6-{4-[(4-methyl-1-piperazinyl)sulfonyl]phenoxy}-3-pyridinyl)methyl]-4-piperidinyl}-N'-(6-methyl-3-pyridinyl)urea, 4-[(5-{[4-((3-fluorophenyl) {[(6-methyl-3-pyridinyl)amino]carbonyl}amino)-1-piperidinyl]methyl}-2-pyridinyl)oxy]-N-(2-methoxyethyl)benzenesulfonamide, N-(3-fluorophenyl)-N'-(6-methyl-3-pyridinyl)-N-[1-({6-[4-(4-morpholinylsulfonyl)phenoxy]-3-pyridinyl}methyl)-4-piperidinyl]urea, N-(3-fluorophenyl)-N'-(6-methyl-3-pyridinyl)-N-{1-[(6-{4-[(4-oxo-1-piperidinyl)sulfonyl]phenoxy}-3-pyridinyl)methyl]-4-piperidinyl}urea, N-(3-fluorophenyl)-N-{1-[(6-{4-[(4-hydroxy-1-piperidinyl)sulfonyl]phenoxy}-3-pyridinyl)methyl]-4-piperidinyl}-N'-(6-methyl-3-pyridinyl)urea, N-{1-[(6-{4-[(aminosulfonyl)amino]phenoxy}-3-pyridinyl)methyl]-4-piperidinyl}-N-(3-fluorophenyl)-N'-(6-methyl-3-pyridinyl)urea, 4-[(5-{[4-((3-fluorophenyl) {[(6-methyl-3-pyridinyl)amino]carbonyl}amino)-1-piperidinyl]methyl}-2-pyridinyl)oxy]-N-(2-hydroxyethyl)benzenesulfonamide, N-(3-fluorophenyl)-N-[1-({6-[4-(6-methyl-1,1-dioxide-1,2,6-thiadiazinan-2-yl)phenoxy]-3-pyridinyl}methyl)-4-piperidinyl]-N'-(6-methyl-3-pyridinyl)urea, 4-[(5-{[4-((3-fluorophenyl) {[(6-methyl-3-pyridinyl)amino]carbonyl}amino)-1-piperidinyl]methyl}-2-pyridinyl)oxy]-N-(2-hydroxy-2-methylpropyl)benzenesulfonamide, 4-[(5-{[4-((3-fluorophenyl) {[(6-methyl-3-pyridinyl)amino]carbonyl}amino)-1-piperidinyl]methyl}-2-pyridinyl)oxy]-N-(3-methoxypropyl)benzenesulfonamide, N-{4-[(5-{[4-((3-fluorophenyl) {[(6-methyl-3-pyridinyl)amino]carbonyl}amino)-1-piperidinyl]methyl}-2-pyridinyl)oxy]phenyl}cyclopropanesulfonamide, or 4-[(5-{[4-((3-fluorophenyl) {[(6-methyl-3-pyridinyl)amino]carbonyl}amino)-1-piperidinyl]methyl}-2-pyridinyl)oxy]-N-(3-hydroxy-3-methylbutyl)benzenesulfonamide, a salt thereof, an N-oxide thereof, a solvate thereof, or prodrugs thereof;

12. the compound according to the above-described 7, which is

5-{[(1-{[6-(4-acetylphenoxy)-2-methyl-3-pyridinyl]methyl}-4-piperidinyl)(butyl)carbamoyl]amino}-2,4-difluorobenzamide, 5-({butyl[1-({2-methyl-6-[4-(methylcarbamoyl)phenoxy]-3-pyridinyl}methyl)-4-piperidinyl]carbamoyl}amino)-2,4-difluorobenzamide, 5-{[{1-[(6-{4-[(4-acetyl-1-piperazinyl)carbonyl]phenoxy}-2-methyl-3-pyridinyl)methyl]-4-piperidinyl}(butyl)carbamoyl]amino}-2,4-difluorobenzamide, 5-({butyl[1-({6-[4-(dimethylcarbamoyl)phenoxy]-2-methyl-3-pyridinyl}methyl)-4-piperidinyl]carbamoyl}amino)-2,4-difluorobenzamide, 5-({butyl[1-({6-[4-(ethylcarbamoyl)phenoxy]-2-methyl-3-pyridinyl}methyl)-4-piperidinyl]carbamoyl}amino)-2,4-difluorobenzamide, 5-[(butyl {1-[(2-methyl-6-{4-[(4-methyl-1-piperazinyl)carbonyl]phenoxy}-3-pyridinyl)methyl]-4-piperidinyl}carbamoyl)amino]-2,4-difluorobenzamide, 5-[(butyl {1-[(6-{4-[(4-hydroxy-1-piperidinyl)carbonyl]phenoxy}-2-methyl-3-pyridinyl)methyl]-4-piperidinyl}carbamoyl)amino]-2,4-difluorobenzamide, 5-({butyl[1-({2-methyl-6-[4-(4-morpholinylcarbonyl)phenoxy]-3-pyridinyl}methyl)-4-piperidinyl]carbamoyl}amino)-2,4-difluorobenzamide, 5-{[butyl(1-{[2-methyl-6-(4-{[4-(trifluoromethyl)-1-piperidinyl]carbonyl}phenoxy)-3-pyridinyl]methyl}-4-piperidinyl)carbamoyl]amino}-2,4-difluorobenzamide, 5-{[{1-[(6-{4-[(4-acetyl-1-piperazinyl)carbonyl]phenoxy}-2-methyl-3-pyridinyl)methyl]-4-piperidinyl}(propyl)carbamoyl]amino}-2,4-difluorobenzamide, or 5-{[{1-[(6-{4-[(4-acetyl-1-piperazinyl)carbonyl]phenoxy}-2-methyl-3-pyridinyl)methyl]-4-piperidinyl}(2-butyn-1-yl)carbamoyl]amino}-2,4-difluorobenzamide, a salt thereof, an N-oxide thereof, a solvate thereof, or prodrugs thereof;

13. a pharmaceutical composition comprising the compound represented by formula (I) according to the above-described 1, a salt thereof, an N-oxide thereof, a solvate thereof, or prodrugs thereof;

14. the pharmaceutical composition according to the above-described 13, which is a chemokine receptor antagonist;

15. the pharmaceutical composition according to the above-described 14, which is a CCR5 antagonist;

16. the pharmaceutical composition according to the above-described 15, which is an agent for prevention and/or treatment of CCR5-related diseases;

17. the pharmaceutical composition according to the above-described 16, wherein the CCR5-related diseases are infectious diseases, immunological diseases, inflammatory diseases and/or cardiovascular diseases;

18. the pharmaceutical composition according to the above-described 16, wherein the CCR5-related diseases are infection with human immunodeficiency virus, acquired immunodeficiency syndrome, infection with Respiratory Syncytial Virus, rejection in organ transplantation, multiple sclerosis, inflammatory bowel disease, and/or asthma;

19. a medicament comprising a combination of the compound represented by formula (I) according to the above-described 1, a salt thereof, an N-oxide thereof, a solvate thereof, or a prodrug thereof, and one or more agent(s) selected from a reverse transcriptase inhibitor, a protease inhibitor, an integrase inhibitor, a CCR2 antagonist, a CCR3 antagonist, a CCR4 antagonist, a CCR5 antagonist, a CXCR3 antagonist, a CXCR4 antagonist, a fusion inhibitor, an antibody against a surface antigen of HIV, and a vaccine of HIV, an immunosuppressant agent, a nonsteroidal antiinflammatory drug, a disease modifying anti-rheumatic drug, steroids, an antiinflammatory enzyme preparations, a chondroprotective agents, a T-cell inhibitor, a TNFα inhibitor, a prostaglandin synthase inhibitor, an IL-1 inhibitor, an IL-6 inhibitor, an interferon gamma agonist, prostaglandins, a phosphodiesterase inhibitor, and a metalloproteinase inhibitor;

20. a method for preventing or treating a CCR5-related disease in a mammal, which comprises administering to a mammal an effective amount of the compound represented by formula (I) according to the above-described 1, a salt thereof, an N-oxide thereof, a solvate thereof, or a prodrug thereof;

21. use of the compound represented by formula (I) according to the above-described 1, a salt thereof, an N-oxide thereof, a solvate thereof, or a prodrug thereof for the manufacture of an agent for prevention and/or treatment of a CCR5-related disease; and 22. a process for preparation of the compound represented by formula (I) according to the above-described 1, a salt thereof, an N-oxide thereof or a solvate thereof, or a prodrug thereof Effect of the Invention The compound of the present invention specifically binds chemokine receptor, especially CCR5, and have an antagonistic activity against it, so they may be used as CCR5 antagonists, so it is useful as an agent for prevention and/or treatment of CCR5-related diseases. It does not exhibit CYP inhibitory activity and scarcely cause various side effects caused by drug metabolizing enzyme inhibition, and thus they can be used very safely.

BEST MODE FOR CARRYING OUT THE INVENTION

The "hydrocarbon group" in the "hydrocarbon group which may have a substituent(s)" represented by $R^{1A}$, $R^{1B}$, $R^{1C}$, $R^{1D}$, $R^{1E}$, $R^{1F}$, $R^{1G}$, $R^{1H}$, $R^{1J}$, $R^{1K}$, $R^{1L}$, $R^{1M}$, $R^{1N}$, $R^{1P}$, $R^{1Q}$, $R^{1R}$, $R^{1S}$, $R^{1T}$, $R^{1U}$, $R^{1AA}$, $R^{1BB}$, $R^{1CC}$, $R^{1DD}$, $R^{1EE}$, $R^{1FF}$, $R^{1GG}$, $R^{1HH}$, $R^{1JJ}$, $R^{1KK}$, $R^{1LL}$, $R^{1MM}$, $R^{1NN}$, $R^{1PP}$, $R^{1QQ}$, $R^{1RR}$, $R^{1SS}$, $R^{1TT}$, $R^{1AAA}$, $R^{1BBB}$, and $R^{1CCC}$ includes, for example, (a) a C1-15 alkyl group such as methyl, ethyl, propyl, isopropyl, butyl, isobutyl, sec-butyl, tert-butyl, pentyl, hexyl, heptyl, octyl, nonyl, decyl, undecyl, dodecyl, tridecyl, tetradecyl, pentadecyl group, etc.; (b) a C3-8 cycloalkyl group such as cyclopropyl, cyclobutyl, cyclopentyl, cyclohexyl group, etc.; (c) a C2-10 alkenyl group such as vinyl, allyl, 2-methylallyl, 2-butenyl, 3-butenyl, 3-octenyl group, etc.; (d) a C2-10 alkynyl group such as ethynyl, 2-propynyl, 3-hexynyl group, etc.; (e) a C3-10 cycloalkenyl group such as cyclopropenyl, cyclopentenyl, cyclohexenyl group, etc.; (f) a C6-14 aryl group such as phenyl, naphthyl group, etc.; (g) a C7-16 aralkyl group such as benzyl, phenylethyl group, etc.;

(h) a (C3-8 cycloalkyl)-(C1-4 alkyl) group such as cyclohexylmethyl, cyclohexylethyl, cyclohexylpropyl, 1-methyl-1-cyclohexylmethyl, cyclopropylethyl group, etc.

The "3- to 15-membered heterocyclic group" in the "3- to 15-membered heterocyclic group which may have a substituent(s)" represented by $R^{1A}$, $R^{1B}$, $R^{1C}$, $R^{1D}$, $R^{1E}$, $R^{1F}$, $R^{1G}$, $R^{1H}$, $R^{1J}$, $R^{1K}$, $R^{1L}$, $R^{1M}$, $R^{1N}$, $R^{1P}$, $R^{1Q}$, $R^{1R}$, $R^{1S}$, $R^{1T}$, $R^{1U}$, $R^{1AA}$, $R^{1BB}$, $R^{1CC}$, $R^{1DD}$, $R^{1EE}$, $R^{1FF}$, $R^{1GG}$, $R^{1HH}$, $R^{1JJ}$, $R^{1KK}$, $R^{1LL}$, $R^{1MM}$, $R^{1NN}$, $R^{1PP}$, $R^{1QQ}$, $R^{1RR}$, $R^{1SS}$, $R^{1TT}$, $R^{1AAA}$, $R^{1BBB}$, and $R^{1CCC}$ includes a "3- to 15-membered unsaturated heterocycle" or a "3- to 15-membered saturated heterocycle". The "3- to 15-membered unsaturated heterocycle" includes, for example, pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolidine, purine, phthalazine, naphthylidine, quinoxaline, quinazoline, cinnoline, benzoxazole, benzothiazole, benzimidazole, chromene, benzoxepine, benzoxazepine, benzoxadiazepine, benzothiepine, benzothiazepine, benzothiadiazepine, benzazepine, benzodiazepine, benzofurazan, benzothiadiazole, benzotriazole, carbazole, β-carboline, acridine, phenazine, dibenzofuran, xanthene, dibenzothiophene, phenothiazine, phenoxadine, phenoxathiin, thianthrene, phenanthridine, phenanthroline, perimidine, pyrroline, imidazoline, triazoline, tetrazoline, pyrazoline, dihydropyridine, tetrahydropyridine, dihydropyrazine, tetrahydropyrazine, dihydropyrimidine, tetrahydropyrimidine, dihydropyridazine, tetrahydropyridazine, dihydroazepine, tetrahydroazepine, dihydrodiazepine, tetrahydrodiazepine, dihydrofuran, dihydropyran, dihydrooxepine, tetrahydrooxepine, dihydrothiophene, dihydrothiopyran, dihydrothiepine, tetrahydrothiepine, dihydrooxazole, dihydroisoxazole, dihydrothiazole, dihydroisothiazole, dihydrofurazan, dihydrooxadiazole, dihydrooxazine, dihydrooxadiazine, dihydrooxazepine, tetrahydrooxazepine, dihydrooxadiazepine, tetrahydrooxadiazepine, dihydrothiadiazole, dihydrothiazine, dihydrothiadiazine, dihydrothiazepine, tetrahydrothiazepine, dihydrothiadiazepine, tetrahydrothiadiazepine, indoline, isoindoline, dihydrobenzofuran, dihydroisobenzofuran, dihydrobenzothiophene, dihydroisobenzothiophene, dihydroindazole, dihydroquinoline, tetrahydroquinoline, dihydro isoquinoline, tetrahydroisoquinoline, dihydrophthalazine, tetrahydrophthalazine, dihydronaphthylidine, tetrahydronaphthylidine, dihydroquinoxaline, tetrahydroquinoxaline, dihydro quinazoline, tetrahydroquinazoline, dihydrocinnoline, tetrahydrocinnoline, benzoxathiane, dihydrobenzoxazine, dihydrobenzothiazine, pyrazinomorpholine, dihydrobenzoxazole, dihydrobenzothiazole, dihydrobenzimidazole, dihydrobenzazepine, tetrahydrobenzazepine, dihydrobenzodiazepine, tetrahydrobenzodiazepine, benzodioxepane, dihydrobenzoxazepine, tetrahydrobenzoxazepine, dihydro carbazole, tetrahydro carbazole, dihydro acridine, tetrahydroacridine, dihydrodibenzofuran, dihydrodibenzothiophene, tetrahydrodibenzofuran, tetrahydrodibenzothiophene, dioxaindane, benzodioxane, chroman, benzodithiolane, benzodithiane ring, etc. The "3- to 15-membered saturated heterocycle" includes, for example, aziridine, azetidine, azocane, pyrrolidine, imidazolidine, triazolidine, tetrazolidine, pyrazolidine, piperidine, piperazine, perhydropyrimidine, perhydropyridazine, azepane (perhydroazepine), perhydrodiazepine, oxilane, oxetane, tetrahydrofuran, tetrahydropyran, perhydrooxepine, thiirane, thietane, tetrahydrothiophene, tetrahydrothiopyran, perhydrothiepine, tetrahydrooxazole (oxazolidine), tetrahydroisoxazole (isooxazolidine), tetrahydrothiazole (thiazolidine), tetrahydroisothiazole (isothiazolidine), tetrahydrofurazan, tetrahydrooxadiazole (oxadiazolidine), tetrahydrooxazine, tetrahydrooxadiazine, perhydrooxazepine, perhydrooxadiazepine, tetrahydrothiadiazole (thiadiazolidine), tetrahydrothiazine, tetrahydrothiadiazine, perhydrothiazepine, perhydrothiadiazepine, morpholine, thiomorpholine, oxathiane, perhydrobenzofuran, perhydroisobenzofuran, perhydrobenzothiophene, perhydroisobenzothiophene, perhydroindazole, perhydroquinoline, perhydroisoquinoline, perhydrophthalazine, perhydronaphthylidine, perhydroquinoxaline, perhydroquinazoline, perhydro cinnoline, perhydrobenzoxazole, perhydrobenzothiazole, perhydrobenzimidazole, perhydro carbazole, perhydro acridine, perhydro dibenzofuran, perhydrodibenzothiophene, dioxolane, dioxane, dithiolane, dithiane,

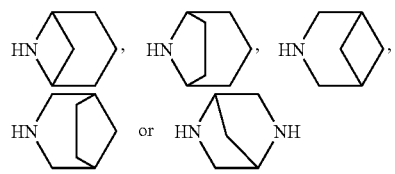

etc.

The "3- to 8-membered nitrogen-containing saturated heterocyclic group" in the "3- to 8-membered nitrogen-containing saturated heterocyclic group which may have a substituent(s)" represented by $R^{1GG}$ includes, for example, a 3- to 8-membered saturated heterocycle containing at least one nitrogen atom in the ring among the above-described "3- to 15-membered saturated heterocyclic group". The "3- to 8-membered nitrogen-containing saturated heterocyclic group" includes, for example, aziridine, azetidine, azocane, pyrrolidine, imidazolidine, triazolidine, tetrazolidine, pyrazolidine, piperidine, piperazine, perhydropyrimidine, perhydropyridazine, azepane (perhydroazepine), perhydrodiazepine, tetrahydrooxazole (oxazolidine), tetrahydroisoxazole (isooxazolidine), tetrahydrothiazole (thiazo lidine), tetrahydro isothiazole (isothiazolidine), tetrahydrofurazan, tetrahydrooxadiazole (oxadiazolidine), tetrahydrooxazine, tetrahydrooxadiazine, perhydrooxazepine, perhydrooxadiazepine, tetrahydrothiadiazole (thiadiazolidine), tetrahydrothiazine, tetrahydrothiadiazine, perhydrothiazepine, perhydrothiadiazepine, morpholine, etc.

The 3- to 15-membered heterocyclic group which may have a substituent(s) represented by $R^{1GG}$ is more preferably a 3- to 8-membered nitrogen-containing saturated heterocyclic group which may have a substituent(s), particularly preferably aziridine, azetidine, azocane, pyrrolidine, piperidine, piperazine, perhydropyrimidine, azepane (perhydroazepine), perhydrodiazepine, or morpholine which may have a substituent(s), and still more preferably piperazine, piperidine, or morpholine which may have a substituent(s).

The "substituent" in the "hydrocarbon group which may have a substituent(s)" or "3- to 15-membered heterocyclic group which may have a substituent(s)" represented by $R^{1A}$, $R^{1B}$, $R^{1C}$, $R^{1D}$, $R^{1E}$, $R^{1F}$, $R^{1G}$, $R^{1H}$, $R^{1J}$, $R^{1K}$, $R^{1L}$, $R^{1M}$, $R^{1N}$, $R^{1P}$, $R^{1Q}$, $R^{1R}$, $R^{1S}$, $R^{1T}$, $R^{1U}$, $R^{1AA}$, $R^{1BB}$, $R^{1CC}$, $R^{1DD}$, $R^{1EE}$, $R^{1FF}$, $R^{1GG}$, $R^{1HH}$, $R^{1JJ}$, $R^{1KK}$, $R^{1LL}$, $R^{1MM}$, $R^{1NN}$, $R^{1PP}$, $R^{1QQ}$, $R^{1RR}$, $R^{1SS}$, $R^{1TT}$, $R^{1AAA}$, $R^{1BBB}$, and $R^{1CCC}$ includes, for example, (1) a nitro group, (2) a hydroxyl group, (3) an oxo group, (4) a thioxo group, (5) a cyano group, (6) a carbamoyl group, (7) an aminocarbonyl group substituted by one or two C1-8 hydrocarbon group(s) substituted by one or two substituent(s) selected from (a) a hydroxyl group, (b) an amino group, (c) a C1-4 alkoxy group, (d) a mono- or disubstituted amino substituted by a C1-8 hydrocarbon group, etc. (herein, the "C1-8 hydrocarbon group" is the hydrocarbon group having 1 to 8 carbon atoms.), (e) a carboxyl group, and (f) a C1-6 alkoxy-carbonyl, etc. (herein, the "C1-8 hydrocarbon group" is the "hydrocarbon group" having 1 to 8 carbon atoms among beforementioned "hydrocarbon group".) (e.g., N-methylaminocarbonyl, N-ethylaminocarbonyl, N-propylaminocarbonyl, N-butylaminocarbonyl, N-cyclohexylmethylaminocarbonyl, N,N-dimethylaminocarbonyl, N-butyl-N-cyclohexylmethylaminocarbonyl, N-cyclohexylaminocarbonyl, phenylaminocarbonyl, N-(2-methoxyethyl)aminocarbonyl, N-(2-hydroxyethyl)aminocarbonyl, N-(2-aminoethyl)aminocarbonyl, N-[2-(N',N'-dimethylamino)ethyl]aminocarbonyl, N-(2-carboxyethyl)aminocarbonyl, N-(2-methoxycarbonylethyl)aminocarbonyl, etc.), (8) a carboxyl group, (9) a C1-6 alkoxycarbonyl group (e.g., methoxycarbonyl, ethoxycarbonyl, propoxycarbonyl, isopropoxycarbonyl, butoxycarbonyl, isobutoxycarbonyl, tert-butoxycarbonyl group, etc.), (10) a sulfo group ($-SO_3H$), (11) a halogen atom (e.g., fluorine, chlorine, bromine, iodine), (12) a C1-6 alkoxy group which may have a substituent(s) by a halogen atom (e.g., methoxy, ethoxy, propoxy, isopropoxy, butoxy, isobutoxy, sec-butoxy, tert-butoxy, difluoromethoxy, trifluoromethoxy group, etc.), (13) a phenoxy group, (14) a halogenophenoxy group (e.g., o-, m- or p-chlorophenoxy, o-, m- or p-bromophenoxy group, etc.), (15) a C1-6 alkylthio group (e.g., methylthio, ethylthio, propylthio, isopropylthio, butylthio, tert-butylthio group, etc.), (16) a phenylthio group, (17) a C1-6 alkylsulfinyl group (e.g., methylsulfinyl, ethylsulfinyl, propylsulfinyl, butylsulfinyl group, etc.), (18) a C1-6 alkylsulfonyl group (e.g., methylsulfonyl, ethylsulfonyl, propylsulfonyl, butylsulfonyl group, etc.), (19) an amino group, (20) a C1-6 lower acylamino group (e.g., acetylamino, propionylamino, etc.), (21) an amino group which is mono- or disubstituted by a hydrocarbon group (the "hydrocarbon group" has the same meaning as described in the "hydrocarbon group" and may be substituted by oxo, amino which may have a substituent(s) by an optional substituent (e.g., hydrocarbon group, etc.), carbamoyl, a halogen atom, hydroxyl group, etc., for example, methylamino, ethylamino, propylamino, isopropylamino, butylamino, dimethylamino, diethylamino, cyclohexylamino, 1-carbamoyl-2-cyclohexylethylamino, N-butyl-N-cyclohexylmethylamino, phenylamino group, etc.), (22) a C1-8 acyl group (e.g., formyl, acetyl, propionyl, butyryl, isobutyryl, cyclohexylcarbonyl group, etc.), (23) a C6-10 aryl-C1-4 lower acyl group (e.g., benzoyl, benzylcarbonyl group, etc.), (24) a 3- to 15-membered heterocyclic group which may have 1 to 4 substituents(s) selected from the group consisting of (a) a halogen atom such as bromine, chlorine, fluorine, etc., (b) a hydrocarbon group which may have a substituent(s) by oxo or hydroxy (this "hydrocarbon group" has the same meaning as described in the "hydrocarbon group", for example, methyl, ethyl, propyl, isopropyl, benzyl, cyclohexyl, cyclohexylmethyl, cyclohexylethyl group, etc.), (c) a halogenophenoxy group (e.g., o-, m- or p-chlorophenoxy, o-, m- or p-bromophenoxy group, etc.), and (d) oxo, and contains 1 to 4 hetero atom(s) selected from the group consisting of oxygen, sulfur and nitrogen other than a carbon atom (e.g., thienyl, furyl, pyrazolyl, tetrahydropyranyl, thiazolyl, isothiazolyl, oxazolyl, isooxazolyl, imidazolyl, triazolyl, tetrazolyl, pyridyl, pyrimidyl, pyridazinyl, quinolyl, isoquinolyl, indolyl, aziridinyl, azetidinyl, pyrrolidinyl, pyrrolinyl, pyrrolyl, imidazolidinyl, piperidino, morpholino, dihydropyridyl, N-methylpiperazinyl, N-ethylpiperazinyl group, etc.), (25) a C1-10 haloalkyl group (e.g., difluoromethyl, trifluoromethyl, trifluoroethyl, chloromethyl, dichloromethyl, trichloroethyl group, etc.), (26) a hydroxyimino group, (27) a C1-4 alkyloxyimino group (e.g., methyloxyimino, ethyloxyimino group, etc., (28) a C1-4 alkylsulfonyl amino group (for example, methylsulfonyl amino, ethylsulfonyl amino, benzylsulfonyl amino group, etc., (29) arylsulfonyl amino group (e.g., phenylsulfonyl amino, p-toluenesulfonyl amino group, etc.), (30) a cyclic aminocarbonyl group (e.g., 1-aziridinylcarbonyl, 1-azetidinylcarbonyl, 1-pyrrolidinylcarbonyl, 1-piperidinylcarbonyl, N-methylpiperazinylcarbonyl, morpholinocarbonyl group, etc.), (31) a C1-8 hydrocarbon group substituted by 1 to 2 group(s) selected from the group consisting of (a) a hydroxyl group, (b) an amino group, (c) a C1-4 alkoxy group, (d) an amino group which is mono- or disubstituted by a C1-8 hydrocarbon group, (e) an aminocarbonyl group which is mono- or disubstituted by a C1-8 hydrocarbon group which may have a substituent(s) (the substituent includes, for example, (a) a hydroxyl group, (b) an amino group, (c) a C1-4 alkoxy group, (d) an amino group which is mono- or disubstituted by a C1-8 hydrocarbon group, (e) a carboxyl group, and (f) a C1-6 alkoxy-carbonyl group, and may be substituted by 1 to 2 substituents.) (herein, the "C1-8 hydrocarbon group" is the "hydrocarbon group" having 1 to 8 carbon atoms.) (e.g., hydroxymethyl, hydroxyethyl, aminomethyl, methoxymethyl, N,N-dimethylaminomethyl, carbamoylmethyl, N-methylaminocarbonylmethyl, N,N-dimethylaminocarbonylmethyl group, etc.), (32) a (C1-4 alkoxy)-(C1-4 alkyl) group (e.g., methoxyethyl group, etc.), (33) a C1-8 acyloxy group (e.g., formyloxy, acetyloxy, propionyloxy, butyryloxy, isobutyryloxy, cyclohexylcarbonyloxy group, etc.), or a benzoyloxy group, (34) an amidino group, (35) an imino group, (36) an acylamino group having 1 to 8 carbon atoms which may be substituted by halogen (e.g., formamide, acetamide, trifluoroacetamide, propionylamino, butyrylamino, isobutyrylamino, cyclohexylcarbonylamino group, etc.), (37) a benzamide group, (38) a carbamoylamino group, (39) an N—C1-4 alkylcarbamoylamino group (e.g., N-methylcarbamoylamino, N-ethylcarbamoylamino, N-propylcarbamoylamino, N-isopropylcarbamoylamino, N-butylcarbamoylamino group, etc.), (40) an N,N-di-C1-4 alkylcarbamoylamino group (e.g., N,N-dimethylcarbamoylamino, N,N-diethylcarbamoylamino, N,N-dipropylcarbamoylamino, N,N-dibutylcarbamoylamino group, etc.), (41) a C1-3 alkylenedioxy group (e.g., methylenedioxy, ethylenedioxy group, etc.), (42) $-B(OH)_2$, (43) an epoxy group, (44) a mercapto group, (45) a sulfino group, (46) a phosphono group, (47) a sulfamoyl group, (48) a C1-6 monoalkylsulfamoyl group (e.g., N-methylsulfamoyl, N-ethylsulfamoyl, N-propylsulfamoyl, N-isopropylsulfamoyl, N-butylsulfamoyl group, etc.), (49) a di-C1-4 alkylsulfamoyl group (e.g., N,N-dimethylsulfamoyl, N,N-diethylsulfamoyl, N,N-dipropylsulfamoyl, N,N-dibutylsulfamoyl group, etc.), (50) a phenylsulfinyl group, (51) a phenylsulfonyl group, (52) an azide group, or (53) a hydrocarbon group which may have a substituent(s) by 1 to 2 groups selected from the group consisting of (a) a hydroxyl group, (b) an amino group, (c) a carboxyl group, and (d) a C1-6 alkoxy group (this "hydrocarbon group" has the same meaning as described in the "hydrocarbon group" and includes, for example, methyl, ethyl, propyl, isopropyl, vinyl, ethynyl, cyclohexenyl, phenyl, naphthyl, benzyl, cyclohexyl, cyclohexylmethyl, cyclohexylethyl, 2-hydroxyethyl, 2-aminoethyl, 2-carboxyethyl, 2-methoxyethyl, 3-methoxypropyl group, etc.). The "hydrocarbon group which may have a substituent(s)" or "3- to 15-membered heterocyclic group which may have a substituent(s)" may have 1 to 10 substituent(s) selected from the above-described (1) to (53). When the number of substituents is two or more, each substituent may be same or different.

The "substituents" in the "3- to 8-membered nitrogen-containing saturated heterocyclic group which may have a substituent(s)" represented by $R^{1GG}$ has the same meaning as the "substituents" in the "hydrocarbon group which may have a substituent(s)" or the "3- to 15-membered heterocyclic group which may have a substituent(s)" represented by $R^{1A}$, $R^{1B}$, $R^{1C}$, $R^{1D}$, $R^{1E}$, $R^{1F}$, $R^{1G}$, $R^{1H}$, $R^{1J}$, $R^{1K}$, $R^{1L}$, $R^{1M}$, $R^{1N}$, $R^{1P}$, $R^{1Q}$, $R^{1R}$, $R^{1S}$, $R^{1T}$, $R^{1U}$, $R^{1AA}$, $R^{1BB}$, $R^{1CC}$, $R^{1DD}$, $R^{1EE}$, $R^{1FF}$, $R^{1GG}$, $R^{1HH}$, $R^{1JJ}$, $R^{1KK}$, $R^{1LL}$, $R^{1MM}$, $R^{1NN}$, $R^{1PP}$, $R^{1QQ}$, $R^{1RR}$, $R^{1SS}$, $R^{1TT}$, $R^{1AAA}$, $R^{1BBB}$, and $R^{1CCC}$.

The "nitrogen-containing heterocyclic group" in the "nitrogen-containing heterocyclic group which may have a substituent(s)" formed by $R^{1C}$ and $R^{1D}$, $R^{1H}$ and $R^{1J}$, $R^{1M}$ and $R^{1N}$, $R^{1Q}$ and $R^{1R}$, $R^{1BB}$ and $R^{1CC}$, $R^{1EE}$ and $R^{1FF}$, or $R^{1SS}$ and $R^{1TT}$ together with a nitrogen atom to which they bind include, for example, aziridine, azetidine, pyrroline, pyrrolidine, imidazoline, imidazolidine, dihydropyridine, tetrahydropyridine, piperidine, dihydropyrazine, tetrahydropyrazine, piperazine, perhydropyrimidine, perhydropyridazine, tetrahydroazepine, azepane (perhydroazepine), tetrahydrodiazepine, perhydrodiazepine, tetrahydrooxazole (oxazolidine), tetrahydrothiazole (thiazolidine), tetrahydrooxazine, perhydrooxazepine, tetrahydrothiazine, perhydrothiazepine, morpholine, thiomorpholine ring, etc.

The "substituents" in the "nitrogen-containing heterocyclic group which may have a substituent(s)" formed by $R^{1C}$ and $R^{1D}$, $R^{1H}$ and $R^{1J}$, $R^{1M}$ and $R^{1N}$, $R^{1Q}$ and $R^{1R}$, $R^{1BB}$ and $R^{1CC}$, $R^{1EE}$ and $R^{1FF}$, or $R^{1SS}$ and $R^{1TT}$ together with a nitrogen atom to which they bind have the same meanings as the "substituents" in the "hydrocarbon group which may have a substituent(s)" or "3- to 15-membered heterocyclic group which may have a substituent(s)" defined in $R^{1A}$, $R^{1B}$, $R^{1C}$, $R^{1D}$, $R^{1E}$, $R^{1F}$, $R^{1G}$, $R^{1H}$, $R^{1J}$, $R^{1K}$, $R^{1L}$, $R^{1M}$, $R^{1N}$, $R^{1P}$, $R^{1Q}$, $R^{1R}$, $R^{1S}$, $R^{1T}$, $R^{1U}$, $R^{1AA}$, $R^{1BB}$, $R^{1CC}$, $R^{1DD}$, $R^{1EE}$, $R^{1FF}$, $R^{1GG}$, $R^{1HH}$, $R^{1JJ}$, $R^{1KK}$, $R^{1LL}$, $R^{1MM}$, $R^{1NN}$, $R^{1PP}$, $R^{1QQ}$, $R^{1RR}$, $R^{1SS}$, $R^{1TT}$, $R^{1AAA}$, $R^{1BBB}$, and $R^{1CCC}$. The 1 to 5 substituents may exist wherever possible. When the number of substituents is two or more, each substituent may be same or different.

The "carbocyclic group" in the "carbocyclic group which may have a substituent(s)" formed by $R^{1HH}$ and $R^{1JJ}$, $R^{1LL}$ and $R^{1MM}$, $R^{1QQ}$ and $R^{1RR}$, or $R^{1AAA}$ and $R^{1BBB}$ together with a carbon atom to which they bind includes, for example, a C3-8 cycloalkyl group (e.g., cyclopropyl, cyclobutyl, cyclopentyl, cyclohexyl, cycloheptyl, etc.; and a C3-10 cycloalkenyl group (e.g., cyclopropenyl, cyclopentenyl, cyclohexenyl group, etc.).

The "substituents" in the "carbocyclic group which may have a substituent(s)" formed by $R^{1HH}$ and $R^{1JJ}$, $R^{1LL}$ and $R^{1MM}$, $R^{1QQ}$ and $R^{1RR}$, or $R^{1AAA}$ and $R^{1BBB}$ together with a carbon atom to which they bind have the same meaning as the "substituents" in the "hydrocarbon group which may have a substituent(s)" or "3- to 15-membered heterocyclic group which may have a substituent(s)" defined in $R^{1A}$, $R^{1B}$, $R^{1C}$, $R^{1D}$, $R^{1E}$, $R^{1F}$, $R^{1G}$, $R^{1H}$, $R^{1J}$, $R^{1K}$, $R^{1L}$, $R^{1M}$, $R^{1N}$, $R^{1P}$, $R^{1Q}$, $R^{1R}$, $R^{1S}$, $R^{1T}$, $R^{1U}$, $R^{1AA}$, $R^{1BB}$, $R^{1CC}$, $R^{1DD}$, $R^{1EE}$, $R^{1FF}$, $R^{1GG}$, $R^{1HH}$, $R^{1JJ}$, $R^{1KK}$, $R^{1LL}$, $R^{1MM}$, $R^{1NN}$, $R^{1PP}$, $R^{1QQ}$, $R^{1RR}$, $R^{1SS}$, $R^{1TT}$, $R^{1AAA}$, $R^{1BBB}$, and $R^{1CCC}$. The 1 to 5 substituents may exist wherever possible. When the number of substituents is two or more, each substituent may be same or different.

The "3- to 15-membered heterocyclic group" in the "3- to 15-membered heterocyclic group which may have a substituent(s)" represented by $R^1$ includes, for example, the "3- to 15-membered heterocyclic group" in the "3- to 15-membered heterocyclic group which may have a substituent(s)" defined in $R^{1A}$, $R^{1B}$, $R^{1C}$, $R^{1D}$, $R^{1E}$, $R^{1F}$, $R^{1G}$, $R^{1H}$, $R^{1J}$, $R^{1K}$, $R^{1L}$, $R^{1M}$, $R^{1N}$, $R^{1P}$, $R^{1Q}$, $R^{1R}$, $R^{1S}$, $R^{1T}$, $R^{1U}$, $R^{1AA}$, $R^{1BB}$, $R^{1CC}$, $R^{1DD}$, $R^{1EE}$, $R^{1FF}$, $R^{1GG}$, $R^{1HH}$, $R^{1JJ}$, $R^{1KK}$, $R^{1LL}$, $R^{1MM}$, $R^{1NN}$, $R^{1PP}$, $R^{1QQ}$, $R^{1RR}$, $R^{1SS}$, $R^{1TT}$, $R^{1AAA}$, $R^{1BBB}$, and $R^{1CCC}$ and the ring formed by together with $R^{1A}$ and $R^{1B}$, $R^{1K}$ and $R^{1L}$, $R^{1P}$ and $R^{1Q}$, $R^{1S}$ and $R^{1U}$, $R^{1AA}$ and $R^{1BB}$ or $R^{1DD}$ and $R^{1EE}$. The ring formed by $R^{1A}$ and $R^{1B}$, $R^{1K}$ and $R^{1L}$, $R^{1P}$ and $R^{1Q}$, $R^{1S}$ and $R^{1U}$, $R^{1AA}$ and $R^{1BB}$, or $R^{1DD}$ and $R^{1EE}$ includes, for example, 1,2-thiazinane 1,1-dioxide, 2-piperidinone, tetrahydro-2(1H)-pyrimidinone, 1,2,6-thiadiazinane 1,1-dioxide, tetrahydro-2(1H)-pyrimidinethione, isothiazolidine 1,1-dioxide, 2-pyrrolidinone, 2-imidazolidinone, 1,2,5-thiadiazolidine 1,1-dioxide, 2-imidazolidinethione, 1,2-thiazepane 1,1-dioxide, 2-azepanone, 1,3-diazepan-2-one, 1,2,7-thiadiazepane 1,1-dioxide, 1,3-diazepane-2-thione, 2,5-piperazinedione, 1,4,3,5-oxathiadiazepan-2-one 4,4-dioxide, 1,4,3,5-oxathiadiazepane 4,4-dioxide ring, etc.

The "substituents" in the "3- to 15-membered heterocyclic group which may have a substituent(s)" in $R^1$ have the same meanings as the "substituents" in the "hydrocarbon group which may have a substituent(s)" or "3- to 15-membered heterocyclic group which may have a substituent(s)" defined in $R^{1A}$, $R^{1B}$, $R^{1C}$, $R^{1D}$, $R^{1E}$, $R^{1F}$, $R^{1G}$, $R^{1H}$, $R^{1J}$, $R^{1K}$, $R^{1L}$, $R^{1M}$, $R^{1N}$, $R^{1P}$, $R^{1Q}$, $R^{1R}$, $R^{1S}$, $R^{1T}$, $R^{1U}$, $R^{1AA}$, $R^{1BB}$, $R^{1CC}$, $R^{1DD}$, $R^{1EE}$, $R^{1FF}$, $R^{1GG}$, $R^{1HH}$, $R^{1JJ}$, $R^{1KK}$, $R^{1LL}$, $R^{1MM}$, $R^{1NN}$, $R^{1PP}$, $R^{1QQ}$, $R^{1RR}$, $R^{1SS}$, $R^{1TT}$, $R^{1AAA}$, $R^{1BBB}$, and $R^{1CCC}$. The 1 to 10 substituents may exist wherever possible. When the number of substituents is two or more, each substituent may be same or different.

The "spacer containing 1 to 3 atoms as a main chain" represented by X and Y means a space formed by 1 to 3 continued atoms of a main chain. In this case, the "number of atoms as a main chain" should be counted such that atoms as a main chain become minimum. The "spacer containing 1 or 3 atoms as a main chain" includes, for example, a bivalent group comprising 1 to 3 selected from —$CR^7R^8$—, —$NR^9$—, —CO—, —O—, —S—, —SO—, —$SO_2$— and —$C(=N—OR^{10})$— (wherein $R^7$ and $R^8$ are each independently a hydrogen atom, C1-4 alkyl, —$OR^{11}$, benzyl or phenyl, $R^9$ is hydrogen atom, C1-4 alkyl, benzyl or phenyl, $R^{10}$ and $R^{11}$ are each independently hydrogen atom or C1-4 alkyl.). In the case, the "C1-4 alkyl group" represented by $R^7$ to $R^{10}$ includes, for example, methyl, ethyl, propyl, isopropyl, butyl, isobutyl, sec-butyl, tert-butyl group, etc. Concretely, the "spacer having from 1 to 3 atoms as a main chain" include, for example, —$CR^7R^8$—, —$NR^9$—, —CO—, —O—, —S—, —$C(=N—OR^{10})$—, —$NR^9CO$—, —$CONR^9$—, —$NR^9COCR^7R^8$— or —$CONR^9CR^7R^8$—(wherein $R^7$ to $R^{10}$ have the same meanings as described above.).

The "3- to 15-membered carbocyclic group" in the "3- to 15-membered carbocyclic group or heterocyclic group which may have a substituent(s)" represented by ring A and ring B includes, for example, a "C3-15 cyclic hydrocarbon", etc. The "cyclic hydrocarbon" in the "C3-15 cyclic hydrocarbon" includes, for example, an "unsaturated cyclic hydrocarbon" or a "saturated cyclic hydrocarbon". The "saturated cyclic hydrocarbon" includes, for example, cycloalkane such as cyclopropane, cyclobutane, cyclopentane, cyclohexane, cycloheptane, cyclooctane, cyclononane, cyclodecane, cycloundecane, cyclododecane, cyclotridecane, cyclotetradecane or cyclopentadecane etc; perhydropentalene; perhydroazulene; perhydroindene; perhydronaphthalene; perhydroheptalene; spiro[4.4]nonane; spiro[4.5]decane; spiro[5.5]undecane; bicyclo[2.2.1]heptane; bicyclo[3.1.1]heptane; bicyclo[2.2.2]octane; adamantane; noradamantane, etc. The "unsaturated cyclic hydrocarbon" includes, for example, cycloalkene such as cyclopentene, cyclohexene, cycloheptene, cyclooctene, cyclopentadiene, cyclohexadiene, cycloheptadiene or cyclooctadiene etc; benzene; pentalene; azulene; indene; indan; naphthalene; dihydronaphthalene; tetrahydronaphthalene; heptalene; biphenylene; as-indacene; s-indacene; acenaphthene; acenaphthylene; fluorene; phenalene; phenanthrene; anthracene; bicyclo[2.2.1]hept-2-ene; bicyclo[3.1.1]hept-2-ene; bicyclo[2.2.2]oct-2-ene, etc.

The "3- to 15-membered heterocyclic group" in the "3- to 15-membered carbocyclic or heterocyclic group which may have a substituent(s)" represented by ring A and ring B has the same meaning as the "3- to 15-membered heterocyclic group" in the "3- to 15-membered heterocyclic group which may have a substituent(s)" defined in $R^{1A}$, $R^{1B}$, $R^{1C}$, $R^{1D}$, $R^{1E}$, $R^{1F}$, $R^{1G}$, $R^{1H}$, $R^{1J}$, $R^{1K}$, $R^{1L}$, $R^{1M}$, $R^{1N}$, $R^{1P}$, $R^{1Q}$, $R^{1R}$, $R^{1S}$, $R^{1T}$, $R^{1U}$, $R^{1AA}$, $R^{1BB}$, $R^{1CC}$, $R^{1DD}$, $R^{1EE}$, $R^{1FF}$, $R^{1GG}$, $R^{1HH}$, $R^{1JJ}$, $R^{1KK}$, $R^{1LL}$, $R^{1MM}$, $R^{1NN}$, $R^{1PP}$, $R^{1QQ}$, $R^{1RR}$, $R^{1SS}$, $R^{1TT}$, $R^{1AAA}$, $R^{1BBB}$, and $R^{1CCC}$.

The "substituents" in the "3- to 15-membered carbocyclic or heterocyclic group which may have a substituent(s)" represented by ring A and ring B have the same meanings as the "substituents" in the "hydrocarbon group which may have a substituent(s)" or "3- to 15-membered heterocyclic group which may have a substituent(s)" defined in $R^{1A}$, $R^{1B}$, $R^{1C}$, $R^{1D}$, $R^{1E}$, $R^{1F}$, $R^{1G}$, $R^{1H}$, $R^{1J}$, $R^{1K}$, $R^{1L}$, $R^{1M}$, $R^{1N}$, $R^{1P}$, $R^{1Q}$, $R^{1R}$, $R^{1S}$, $R^{1T}$, $R^{1U}$, $R^{1AA}$, $R^{1BB}$, $R^{1CC}$, $R^{1DD}$, $R^{1EE}$, $R^{1FF}$, $R^{1GG}$, $R^{1HH}$, $R^{1JJ}$, $R^{1KK}$, $R^{1LL}$, $R^{1MM}$, $R^{1NN}$, $R^{1PP}$, $R^{1QQ}$, $R^{1RR}$, $R^{1SS}$, $R^{1TT}$, $R^{1AAA}$, $R^{1BBB}$, and $R^{1CCC}$. The 1 to 10 substituents may exist wherever possible. When the number of substituents is two or more, each substituent may be same or different.

The "5- to 6-membered aromatic ring group" in the "5- to 6-membered aromatic ring group which may have a substituent(s)" represented by ring A and ring B includes, for example, benzene, pyrrole, imidazole, triazole, tetrazole, pyrazole, pyridine, pyrazine, pyrimidine, pyridazine, triazine, furan, thiophene, oxazole, isoxazole, thiazole, isothiazole, furazan, oxadiazole, thiadiazolering, etc.

The "substituents" in the "5- to 6-membered aromatic ring group which may have a substituent(s)" represented by ring A and ring B have the same meanings as the "substituents" in the "hydrocarbon group which may have a substituent(s)" or "3- to 15-membered heterocyclic group which may have a substituent(s)" defined in $R^{1A}$, $R^{1B}$, $R^{1C}$, $R^{1D}$, $R^{1E}$, $R^{1F}$, $R^{1G}$, $R^{1H}$, $R^{1J}$, $R^{1K}$, $R^{1L}$, $R^{1M}$, $R^{1N}$, $R^{1P}$, $R^{1Q}$, $R^{1R}$, $R^{1S}$, $R^{1T}$, $R^{1U}$, $R^{1AA}$, $R^{1BB}$, $R^{1CC}$, $R^{1DD}$, $R^{1EE}$, $R^{1FF}$, $R^{1GG}$, $R^{1HH}$, $R^{1JJ}$, $R^{1KK}$, $R^{1LL}$, $R^{1MM}$, $R^{1NN}$, $R^{1PP}$, $R^{1QQ}$, $R^{1RR}$, $R^{1SS}$, $R^{1TT}$, $R^{1AAA}$, $R^{1BBB}$, and $R^{1CCC}$. The 1 to 10 substituents may exist wherever possible. When the number of substituents is two or more, each substituent may be same or different.

The "nitrogen-containing heterocyclic group" in the "3- to 15-membered nitrogen-containing heterocyclic group which may have further substituent(s)" represented by ring D includes, for example, heterocyclic group which contains at least one nitrogen atom, in addition to a carbon atom, and also contains 1 to 3 hetero atoms selected from a nitrogen atom, an oxygen atom and a sulfur atom. The "3- to 15-membered nitrogen-containing heterocyclic group" includes, for example, a "3- to 15-membered nitrogen-containing unsaturated heterocyclic group" and a "3- to 15-membered nitrogen-containing saturated heterocyclic group".

The "3- to 15-membered nitrogen-containing unsaturated heterocyclic group" includes, for example, pyrrole, imidazole, triazole, tetrazole, pyrazole, indole, isoindole, indazole, purine, benzimidazole, benzazepine, benzodiazepine, benzotriazole, carbazole, β-carboline, phenothiazine, phenoxazine, perimidine, pyrroline, imidazoline, triazoline, tetrazoline, pyrazoline, dihydropyridine, tetrahydropyridine, dihydropyrazine, tetrahydropyrazine, dihydropyrimidine, tetrahydropyrimidine, dihydropyridazine, tetrahydropyridazine, dihydroazepine, tetrahydroazepine, dihydrodiazepine, tetrahydrodiazepine, dihydrooxazole, dihydroisoxazole, dihydrothiazole, dihydroisothiazole, dihydrofurazan, dihydrooxadiazole, dihydrooxazine, dihydrooxadiazine, dihydrooxazepine, tetrahydrooxazepine, dihydrooxadiazepine, tetrahydrooxadiazepine, dihydrothiadiazole, dihydrothiazine, dihydrothiadiazine, dihydrothiazepine, dihydrothiadiazepine, tetrahydrothiadiazepine, indoline, isoindoline, dihydro indazole, dihydroquinoline, tetrahydroquinoline, dihydroisoquinoline, tetrahydroisoquinoline, dihydrophthalazine, tetrahydrophthalazine, dihydronaphthylidine, tetrahydronaphthylidine, dihydroquinoxaline, tetrahydroquinoxaline, dihydroquinazoline, tetrahydro quinazoline, dihydrocinnoline, tetrahydrocinnoline, dihydrobenzoxazine, dihydrobenzothiazine, pyrazinomorpholine, dihydrobenzoxazole, dihydrobenzothiazole, dihydrobenzimidazole, dihydrobenzazepine, tetrahydrobenzazepine, dihydrobenzodiazepine, tetrahydrobenzodiazepine, dihydrobenzoxazepine, tetrahydrobenzoxazepine, dihydrocarbazole, tetrahydrocarbazole, dihydroacridine, tetrahydroacridine, etc. The 3- to 15-membered nitrogen-containing saturated heterocyclic group" includes, for example, aziridine, azetidine, azocane, pyrrolidine, imidazolidine, triazolidine, tetrazolidine, pyrazolidine, piperidine, piperazine, perhydropyrimidine, perhydropyridazine, azepane (perhydroazepine), perhydrodiazepine, tetrahydrooxazole (oxazolidine), tetrahydroisoxazole (isooxazolidine), tetrahydrothiazole (thiazolidine), tetrahydroisothiazole (isothiazolidine), tetrahydrofurazan, tetrahydrooxadiazole (oxadiazolidine), tetrahydrooxazine, tetrahydrooxadiazine, perhydrooxazepine, perhydrooxadiazepine, tetrahydrothiadiazole (thiadiazolidine), tetrahydrothiazine, tetrahydrothiadiazine, tetrahydrothiazepine, perhydrothiazepine, perhydrothiadiazepine, morpholine, thiomorpholine, perhydro indazole, perhydroquinoline, perhydroisoquinoline, perhydrophthalazine, perhydronaphthylidine, perhydroquinoxaline, perhydroquinazoline, perhydro cinnoline, perhydrobenzoxazole, perhydrobenzothiazole, perhydrobenzimidazole, perhydro carbazole, perhydro acridine,

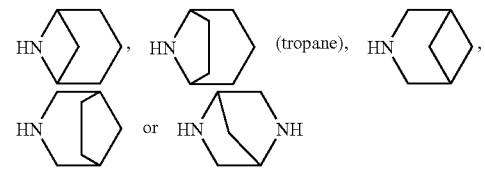

etc.

The "substituents" in the "3- to 15-membered nitrogen-containing heterocyclic group which may have further substituent(s)" represented by ring D have the same meanings as the "substituents" in the "hydrocarbon group which may have a substituent(s)" or "3- to 15-membered heterocyclic group which may have a substituent(s)" defined in $R^{1A}$, $R^{1B}$, $R^{1C}$, $R^{1D}$, $R^{1E}$, $R^{1F}$, $R^{1G}$, $R^{1H}$, $R^{1J}$, $R^{1K}$, $R^{1L}$, $R^{1M}$, $R^{1N}$, $R^{1P}$, $R^{1Q}$, $R^{1R}$, $R^{1S}$, $R^{1T}$, $R^{1U}$, $R^{1AA}$, $R^{1BB}$, $R^{1CC}$, $R^{1DD}$, $R^{1EE}$, $R^{1FF}$, $R^{1GG}$, $R^{1HH}$, $R^{1JJ}$, $R^{1KK}$, $R^{1LL}$, $R^{1MM}$, $R^{1NN}$, $R^{1PP}$, $R^{1QQ}$, $R^{1RR}$, $R^{1SS}$, $R^{1TT}$, $R^{1AAA}$, $R^{1BBB}$, and $R^{1CCC}$. The 1 to 10 substituents may exist wherever possible. When the number of substituents is two or more, each substituent may be same or different.

The "5- to 10-membered nitrogen-containing heterocyclic group" in the "5- to 10-membered nitrogen-containing heterocyclic group which may have further substituent(s)" represented by ring D includes, for example, "5- to 10-membered nitrogen-containing heterocyclic group" among the "3- to 15-membered nitrogen-containing heterocyclic group" represented by ring D, and specific examples thereof include pyrrolidine, piperidine, piperazine, azepane, tropane ring, etc.

The "hydroxyl group which may be protected" represented by $R^2$ means a "hydroxyl group" which may be protected with a "protective group" and the "protective group" of the hydroxyl group includes, for example, (1) a C1-6 alkyl group which may have 1 to 4 substituent(s) selected from the group consisting of (a) a halogen atom (e.g., chlorine, bromine, fluorine, etc.), (b) a C6-10 aryl group (e.g., phenyl, naphthyl, etc.), (c) a C7-12 aralkyl group (e.g., benzyl, phenylethyl, etc.) and (d) a nitro group (e.g., methyl, ethyl, propyl, isopropyl, butyl, tert-butyl group, etc.; (2) a C6-10 aryl group which may have 1 to 4 substituent(s) selected from the group consisting of (a) a halogen atom (e.g., chlorine, bromine, fluorine, etc.), (b) a C1-6 alkyl group (e.g., methyl, ethyl, propyl group, etc.), (c) a C6-10 aryl group (e.g., phenyl, naphthyl group, etc.), (d) a C7-12 aralkyl group (e.g., benzyl, phenylethyl group, etc.) and (e) a nitro group (e.g., phenyl, naphthyl group, etc.), (3) a C7-12 aralkyl group which may have 1 to 4 substituent(s) selected from the group consisting of (a) a halogen atom (e.g., chlorine, bromine, fluorine, etc.), (b) a C1-6 alkyl group (e.g., methyl, ethyl, propyl group, etc.), (c) a C6-10 aryl (e.g., phenyl, naphthyl group, etc.), (d) a C7-12 aralkyl group (e.g., benzyl, phenylethyl group, etc.) and (e) a nitro group (e.g., benzyl, phenylethyl, naphthylmethyl group, etc.), (4) a formyl group, (5) a C1-6 alkyl-carbonyl group which may have 1 to 3 substituent(s) selected from the group consisting of (a) a halogen atom (e.g., chlorine, bromine, fluorine, etc.), (b) a C1-6 alkyl group (for example, methyl, ethyl, propyl group, etc.), (c) a C6-10 aryl (for example, phenyl, naphthyl group, etc.), (d) a C7-12 aralkyl group (for example, benzyl, phenylethyl group, etc.) and (e) a nitro group (e.g., acetyl, propionyl group, etc.), (6) a C6-10 aryloxycarbonyl group which may have 1 to 4 substituent(s) selected from the group consisting of (a) a halogen atom (e.g., chlorine, bromine, fluorine, etc.), (b) a C1-6 alkyl group (e.g., methyl, ethyl, propyl group, etc.), (c) a C6-10 aryl (e.g., phenyl, naphthyl group, etc.), (d) a C7-12 aralkyl group (e.g., benzyl, phenylethyl group, etc.) and (e) a nitro group (for example, phenyloxycarbonyl, naphthyloxycarbonyl group, etc.), (7) a C6-10 arylcarbonyl group which may have 1 to 4 substituent(s) selected from the group consisting of (a) a halogen atom (e.g., chlorine, bromine, fluorine, etc.), (b) a C1-6 alkyl group (e.g., methyl, ethyl, propyl group, etc.), (c) a C6-10 aryl (e.g., phenyl, naphthyl group, etc.), (d) a C7-12 aralkyl group (e.g., benzyl, phenylethyl group, etc.) and (e) a nitro group (e.g., benzoyl, naphthylcarbonyl group, etc.), (8) a C7-12 aralkyl-carbonyl group which may have 1 to 4 substituent(s) selected from the group consisting of (a) a halogen atom (e.g., chlorine, bromine, fluorine, etc.), (b) a C1-6 alkyl group (e.g., methyl, ethyl, propyl group, etc.), (c) a C6-10 aryl (e.g., phenyl, naphthyl group, etc.), (d) a C7-12 aralkyl group (for example, benzyl, phenylethyl group, etc.) and (e) a nitro group (e.g., benzylcarbonyl, phenethylcarbonyl group, etc.), (9) a pyranyl or furanyl group which may have 1 to 4 substituent(s) selected from the group consisting of (a) a halogen atom (e.g, chlorine, bromine, fluorine, etc.), (b) a C1-6 alkyl group (e.g., methyl, ethyl, propyl group, etc.), (c) a C6-10 aryl (e.g., phenyl, naphthyl group, etc.), (d) a C7-12 aralkyl group (e.g., benzyl, phenylethyl group, etc.) and (e) a nitro group, and (10) a silyl group which is tri-substituted by a C1-4 alkyl or phenyl group (for example, trimethylsilyl, triethylsilyl, tert-butyldimethylsilyl, tert-butyldiphenylsilyl group, etc.).

The "substituents" in the "amino group which may have a substituent(s)" represented by $R^2$ represent a hydrocarbon group which may have a substituent(s), $-SO_2R^{201}$, or $=NR^{202}$ wherein $R^{201}$ and $R^{202}$ represent a hydrocarbon group which may have a substituent(s). Herein, the "hydrocarbon group which may have a substituent(s)" has the same meaning as the "hydrocarbon group which may have a substituent(s)" defined in $R^{1A}$, $R^{1B}$, $R^{1C}$, $R^{1D}$, $R^{1E}$, $R^{1F}$, $R^{1G}$, $R^{1H}$, $R^{1J}$, $R^{1K}$, $R^{1L}$, $R^{1M}$, $R^{1N}$, $R^{1P}$, $R^{1Q}$, $R^{1R}$, $R^{1S}$, $R^{1T}$, $R^{1U}$, $R^{1AA}$, $R^{1BB}$, $R^{1CC}$, $R^{1DD}$, $R^{1EE}$, $R^{1FF}$, $R^{1GG}$, $R^{1HH}$, $R^{1JJ}$, $R^{1KK}$, $R^{1LL}$, $R^{1MM}$, $R^{1NN}$, $R^{1PP}$, $R^{1QQ}$, $R^{1RR}$, $R^{1SS}$, $R^{1TT}$, $R^{1AAA}$, $R^{1BBB}$, and $R^{1CCC}$. The 1 to 2 substituents of the amino group may exist wherever possible. When the number of substituents is two, each substituent may be same or different. Moreover, the "amino group which may have a substituent(s)" represented by $R^2$ represents

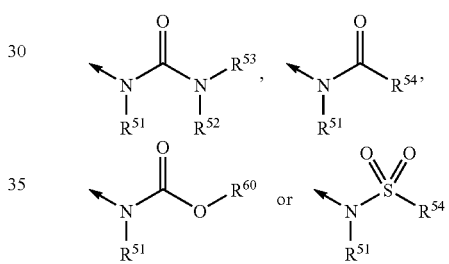

wherein the arrow represents a binding position to ring D; $R^{51}$, $R^{52}$, $R^{53}$ and $R^{54}$ each independently represents (1) a hydrogen atom, (2) a hydrocarbon group which may have a substituent(s), (3) a 3- to 15-membered heterocyclic group which may have a substituent(s), (4) a C1-4 alkoxy group which may have a substituent(s), (5) a phenoxy group which may have a substituent(s), or (6) a benzyloxy group which may have a substituent(s); and $R^{60}$ represents (1) a hydrogen atom, (2) a hydrocarbon group which may have a substituent(s), or a 3- to 15-membered heterocyclic group which may have a substituent(s). Herein, the "hydrocarbon group which may have a substituent(s)" and the "3- to 15-membered heterocyclic group which may have a substituent(s)" each has the same meaning as the "hydrocarbon group which may have a substituent(s)" and the "3- to 15-membered heterocyclic group which may have a substituent(s)" defined in $R^{1A}$, $R^{1B}$, $R^{1C}$, $R^{1D}$, $R^{1E}$, $R^{1F}$, $R^{1G}$, $R^{1H}$, $R^{1J}$, $R^{1K}$, $R^{1L}$, $R^{1M}$, $R^{1N}$, $R^{1P}$, $R^{1Q}$, $R^{1R}$, $R^{1S}$, $R^{1T}$, $R^{1U}$, $R^{1AA}$, $R^{1BB}$, $R^{1CC}$, $R^{1DD}$, $R^{1EE}$, $R^{1FF}$, $R^{1GG}$, $R^{1HH}$, $R^{1JJ}$, $R^{1KK}$, $R^{1LL}$, $R^{1MM}$, $R^{1NN}$, $R^{1PP}$, $R^{1QQ}$, $R^{1RR}$, $R^{1SS}$, $R^{1TT}$, $R^{1AAA}$, $R^{1BBB}$, and $R^{1CCC}$. The "C1-4 alkoxy group" in the "C1-4 alkoxy group which may have a substituent(s)" includes, for example, a methoxy, ethoxy, propoxy, isopropoxy, butoxy, isobutoxy, sec-butoxy or tert-butoxy group. Herein, the "substituents" in the "C1-4 alkoxy 15 group which may have a substituent(s)", "phenoxy group which may have a substituent(s)" and "benzyloxy group which may have a substituent(s)" include, for example, "substituents" in the "hydrocarbon group which may have a substituent(s)" or "3- to 15-membered heterocyclic group which may have a substituent(s)" defined in $R^{1A}$, $R^{1B}$, $R^{1C}$, $R^{1D}$, $R^{1E}$, $R^{1F}$, $R^{1G}$, $R^{1H}$, $R^{1J}$, $R^{1K}$, $R^{1L}$, $R^{1M}$, $R^{1N}$, $R^{1P}$, $R^{1Q}$, $R^{1R}$, $R^{1S}$, $R^{1T}$, $R^{1U}$, $R^{1AA}$, $R^{1BB}$, $R^{1CC}$, $R^{1DD}$, $R^{1EE}$, $R^{1FF}$, $R^{1GG}$, $R^{1HH}$, $R^{1JJ}$, $R^{1KK}$, $R^{1LL}$, $R^{1MM}$, $R^{1NN}$, $R^{1PP}$, $R^{1QQ}$, $R^{1RR}$, $R^{1SS}$, $R^{1TT}$, $R^{1AAA}$, $R^{1BBB}$, and $R^{1CCC}$.

The "hydrocarbon group which may have a substituent(s)" represented by $R^2$ have the same meaning as the "hydrocarbon group which may have a substituent(s)" defined in $R^{1A}$, $R^{1B}$, $R^{1C}$, $R^{1D}$, $R^{1E}$, $R^{1F}$, $R^{1G}$, $R^{1H}$, $R^{1J}$, $R^{1K}$, $R^{1L}$, $R^{1M}$, $R^{1N}$, $R^{1P}$, $R^{1Q}$, $R^{1R}$, $R^{1S}$, $R^{1T}$, $R^{1U}$, $R^{1AA}$, $R^{1BB}$, $R^{1CC}$, $R^{1DD}$, $R^{1EE}$, $R^{1FF}$, $R^{1GG}$, $R^{1HH}$, $R^{1JJ}$, $R^{1KK}$, $R^{1LL}$, $R^{1MM}$, $R^{1NN}$, $R^{1PP}$, $R^{1QQ}$, $R^{1RR}$, $R^{1SS}$, $R^{1TT}$, $R^{1AAA}$, $R^{1BBB}$, and $R^{1CCC}$. The 1 to 10 substituents may exist wherever possible. When the number of substituents is two or more, each substituent may be same or different. Moreover, the "hydrocarbon group which may have a substituent(s)" represented by $R^2$ represents

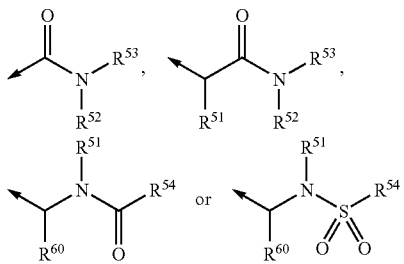

wherein the arrow represents a binding position to ring D; and $R^{51}$, $R^{52}$, $R^{53}$, $R^{54}$ and $R^{60}$ have the same meaning as those described above.

The "3- to 15-membered heterocyclic group which may have a substituent(s)" represented by $R^2$ has the same meaning as the "3- to 15-membered heterocyclic group which may have a substituent(s)" defined in $R^{1A}$, $R^{1B}$, $R^{1C}$, $R^{1D}$, $R^{1E}$, $R^{1F}$, $R^{1G}$, $R^{1H}$, $R^{1J}$, $R^{1K}$, $R^{1L}$, $R^{1M}$, $R^{1N}$, $R^{1P}$, $R^{1Q}$, $R^{1R}$, $R^{1S}$, $R^{1T}$, $R^{1U}$, $R^{1AA}$, $R^{1BB}$, $R^{1CC}$, $R^{1DD}$, $R^{1EE}$, $R^{1FF}$, $R^{1GG}$, $R^{1HH}$, $R^{1JJ}$, $R^{1KK}$, $R^{1LL}$, $R^{1MM}$, $R^{1NN}$, $R^{1PP}$, $R^{1QQ}$, $R^{1RR}$, $R^{1SS}$, $R^{1TT}$, $R^{1AAA}$, $R^{1BBB}$, and $R^{1CCC}$. The 1 to 10 substituents may exist wherever possible. When the number of substituents is two or more, each substituent may be same or different.

The "C1-4 alkyl group" represented by $R^6$ includes, for example, a methyl, ethyl, propyl, isopropyl, butyl, isobutyl, sec-butyl or tert-butyl group.

The "aromatic ring group" in the "aromatic ring group which may have a substituent(s) represented by $R^{51}$, $R^{53}$, $R^{54}$ and $R^{60}$ includes, for example, a mono-, bi- or tricyclic carbocyclic or heterocyclic group having aromaticity among the "hydrocarbon group" of the "hydrocarbon group which may have a substituent(s)" and the "3- to 15-membered heterocyclic group" of the "3- to 15-membered heterocyclic group which may have a substituent(s)" represented by $R^{51}$. The mono-, bi- or tricyclic carbocyclic group having aromaticity includes, for example, a benzene, azulene, naphthalene, phenanthrene or anthracene ring. The mono-, bi- or tricyclic heterocyclic group having aromaticity includes, for example, pyrrole, imidazole, triazole, tetrazole, pyrazole, pyridine, pyrazine, pyrimidine, pyridazine, furan, thiophene, oxazole, isoxazole, thiazole, isothiazole, furazan, oxadiazole, thiadiazole, indole, isoindole, benzofuran, isobenzofuran, benzothiophene, isobenzothiophene, indazole, quinoline, isoquinoline, purine, phthalazine, pteridine, naphthylidine, quinoxaline, quinazoline, cinnoline, benzoxazole, benzothiazole, benzimidazole, benzofurazan, benzothiadiazole, benzotriazole, carbazole, β-carboline, acridine, phenazine, dibenzofuran, dibenzothiophene, phenanthridine, phenanthroline, perimidine ring, etc.

The "substituents" in the "aromatic ring group which may have a substituent(s)" represented by $R^{51}$, $R^{53}$, $R^{54}$ and $R^{60}$ have the same meanings as the "substituents" in the "hydrocarbon group which may have a substituent(s)" or "3- to 15-membered heterocyclic group which may have a substituent(s)" defined in $R^{1A}$, $R^{1B}$, $R^{1C}$, $R^{1D}$, $R^{1E}$, $R^{1F}$, $R^{1G}$, $R^{1H}$, $R^{1J}$, $R^{1K}$, $R^{1L}$, $R^{1M}$, $R^{1N}$, $R^{1P}$, $R^{1Q}$, $R^{1R}$, $R^{1S}$, $R^{1T}$, $R^{1U}$, $R^{1AA}$, $R^{1BB}$, $R^{1CC}$, $R^{1DD}$, $R^{1EE}$, $R^{1FF}$, $R^{1GG}$, $R^{1HH}$, $R^{1JJ}$, $R^{1KK}$, $R^{1LL}$, $R^{1MM}$, $R^{1NN}$, $R^{1PP}$, $R^{1QQ}$, $R^{1RR}$, $R^{1SS}$, $R^{1TT}$, $R^{1AAA}$, $R^{1BBB}$, and $R^{1CCC}$. The 1 to 10 substituents may exist wherever possible. When the number of substituents is two or more, each substituent may be same or different.

The "ring" in the "ring which may have a substituent(s)" formed by $R^1$ together with the substituent of ring A includes, for example, 3,4-dihydro-1H-2,1,3-benzothiadiazine 2,2-dioxide, 1H-2,1,3-benzothiadiazine 2,2-dioxide, 1H-2,1,3-benzothiadiazin-4(3H)-one 2,2-dioxide, 2,4(1H,3H)-quinazolinedione, 3,4-dihydro-2(1H)-quinazolinone, 2(1H)-quinazolinone, 1-isoindolinone, 1H-isoindol-1-one, 2,3-dihydro-1,2-benzisothiazole 1,1-dioxide, 1,2-benzisothiazole 1,1-dioxide, 3,4-dihydro-2H-1,2-benzothiazine 1,1-dioxide, 3,4-dihydro-1(2H)-isoquinolinone ring, etc.

The "substituents" in the "ring which may have a substituent(s)" formed by $R^1$ together with the substituent of ring A have the same meanings as the "substituents" in the "hydrocarbon group which may have a substituent(s)" or "3- to 15-membered heterocyclic group which may have a substituent(s)" defined in $R^{1A}$, $R^{1B}$, $R^{1C}$, $R^{1D}$, $R^{1E}$, $R^{1F}$, $R^{1G}$, $R^{1H}$, $R^{1J}$, $R^{1K}$, $R^{1L}$, $R^{1M}$, $R^{1N}$, $R^{1P}$, $R^{1Q}$, $R^{1R}$, $R^{1S}$, $R^{1T}$, $R^{1U}$, $R^{1AA}$, $R^{1BB}$, $R^{1CC}$, $R^{1DD}$, $R^{1EE}$, $R^{1FF}$, $R^{1GG}$, $R^{1HH}$, $R^{1JJ}$, $R^{1KK}$, $R^{1LL}$, $R^{1MM}$, $R^{1NN}$, $R^{1PP}$, $R^{1QQ}$, $R^{1RR}$, $R^{1SS}$, $R^{1TT}$, $R^{1AAA}$, $R^{1BBB}$, and $R^{1CCC}$.

Unless otherwise specifically mentioned, all isomers are included in the present invention. For example, alkyl, alkenyl, alkynyl, alkoxy, alkylthio, alkylene, alkenylene and alkynylene groups include straight chain and branched ones. Moreover, all of isomers due to double bond, ring and fused ring (E-, Z-, cis- and trans-forms), isomers due to presence of asymmetric carbon(s), etc. (R-, S-forms, α- and β-configuration, enantiomer and diastereomer), optically active substances having optical rotation (D-, L-, d- and l-forms), polar compound by chromatographic separation (more polar compound and less polar compound), equilibrium compounds, rotational isomers, a mixture thereof in any proportion and a racemic mixture are included in the present invention.

In the present invention, symbol ⬊ represents β-configuration and symbol ⬈ represents α-configuration, and symbol ⬊ represents α-configuration, β-configuration or the mixture of them. There is no particular limitation for the ratio of α-configuration and β-configuration in the mixture.

Salts:

Salts of the compound represented by formula (I) include all of nontoxic salts and pharmacologically acceptable salts. Pharmacologically acceptable salts are preferably low-toxic and water-soluble. Examples of appropriate salts of the compound of formula (I) are salt with alkaline metal (such as potassium, sodium and lithium), salt with alkaline earth metal (such as calcium and magnesium), ammonium salt (such as tetramethylammonium salt and tetrabutylammonium salt), salt with organic amine (such as triethylamine, methylamine, dimethylamine, cyclopentylamine, benzylamine, phenethylamine, piperidine, monoethanolamine, diethanolamine, tris (hydroxymethyl)methylamine, lysine, arginine and N-methyl-D-glucamine) and acid addition salt [such as inorganic acid salt (e.g., hydrochloride, hydrobromide, hydroiodide, sulfate, phosphate and nitrate) and organic acid salt (e.g., acetate, trifluoroacetate, lactate, tartrate, oxalate, fumarate, maleate, benzoate, citrate, methanesulfonate, ethanesulfonate, benzenesulfonate, toluenesulfonate, isethionate, glucuronate and gluconate), etc.]. The salt of the compound of the present invention also includes solvates and also solvates with the above-mentioned alkaline (earth) metal salt, ammonium salt, organic amine salt and acid addition salt. The solvate is preferably low-toxic and water-soluble. Examples of an appropriate solvate are solvates with water and with alcoholic solvent (such as ethanol). The compounds of the present invention are converted to low-toxic salts or pharmaceutically acceptable salts by known methods.

Moreover, the salt includes a quaternary ammonium salt. The quaternary ammonium salt of the compound represented by formula (I) is the compound where nitrogen of the compounds represented by formula (I) is quarternalized by an $R^0$ group ($R^0$ group is a C1-8 alkyl group (e.g., methyl, ethyl, propyl, isopropyl, butyl, isobutyl, sec-butyl, tert-butyl, pentyl, hexyl, heptyl, octyl, etc.; a C1-8 alkyl group substituted by a phenyl group (e.g., benzyl, phenylethyl group, etc.).

The salt also includes an N-oxide. The compound of the present invention can be converted into an N-oxide by known methods. The N-oxide is the compound where nitrogen of the compound represented by formula (I) is oxidized.

Prodrugs:

A prodrug of the compound of formula (I) means a compound which is converted to the compound of formula (I) by reaction with an enzyme, gastric acid or the like in the living body. For example, with regard to a prodrug of the compound of formula (I), when the compound of formula (I) has an amino group, compounds in which the amino group is, for example, acylated, alkylated or phosphorylated (e.g., compounds in which the amino group of the compound of formula (I) is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, acetoxymethylated, tert-butylated, etc.); when the compound of formula (I) has a hydroxyl group, compounds where the hydroxyl group is, for example, acylated, alkylated, phosphorylated or borated (e.g., compounds in which the hydroxyl group of the compound of formula (I) is acetylated, palmitoylated, propanoylated, pivaloylated, succinylated, fumarylated, alanylated or dimethylaminomethylcarbonylated); and that the carboxyl group of the compound of formula (I) is, for example, esterified or amidated (e.g., compounds in which the carboxyl group of the compound of formula (I) is made into ethyl ester, phenyl ester, carboxymethyl ester, dimethylaminomethyl ester, pivaloyloxymethyl ester, 1-{(ethoxycarbonyl)oxy}ethyl ester, phthalidyl ester, (5-methyl-2-oxo-1,3-dioxolen-4-yl)methyl ester, 1-{[(cyclohexyloxy)carbonyl]oxy}ethyl ester or methylamide). Those compounds may be produced by a known method per se. The prodrug of the compound of formula (I) may be either a hydrate or a non-hydrate. A prodrug of the compound of formula (I) may also be a compound which is converted to the compound of formula (I) under physiologic condition as described in "Iyakuhin no kaihatsu, Vol. 7 (Bunshi-sekkei), pp. 163-198 (Hirokawa-Shoten), 1990". And the compound of formula (I) may also be labeled by a radio isotope (such as $^3$H, $^{14}$C, $^{35}$S, $^{125}$I, etc,).

All definition represented by $R^1$, X, Y, ring A, ring B, ring D, and $R^2$ in the formula (I) in the present invention is preferred. All symbols in each preferred group listed below have the same meanings as described above.

Preferred as $R^1$ is, for example, $-N(R^{1A})SO_2-R^{1B}$, $-SO_2NR^{1C}R^{1D}$, $-S(O)_mR^{1G}$, $-CONR^{1H}R^{1J}$, $-NR^{1K}COR^{1L}$, $-N(R^{1P})SO_2NR^{1Q}R^{1R}$, $-N(R^{1AA})C(=O)NR^{1BB}R^{1CC}$, $-COR^{1GG}$, $-C(R^{1LL}R^{1MM})N(R^{1NN})SO_2-R^{1PP}$, $-C(R^{1QQ}R^{1RR})SO_2NR^{1SS}R^{1TT}$, $-C(R^{1AAA}R^{1BBB})S(O)_mR^{1CCC}$, etc, more preferred is, for example $-SO_2NR^{1C}R^{1D}$, $-CONR^{1H}R^{1J}$, $-N(R^{1P})SO_2NR^{1Q}R^{1R}$, $-COR^{1GG}$, etc. Preferred as $R^{1A}$, $R^{1B}$, $R^{1C}$, $R^{1D}$, $R^{1E}$, $R^{1F}$, $R^{1G}$, $R^{1H}$, $R^{1J}$, $R^{1K}$, $R^{1L}$, $R^{1M}$, $R^{1N}$, $R^{1P}$, $R^{1Q}$, $R^{1R}$, $R^{1S}$, $R^{1T}$, $R^{1U}$, $R^{1AA}$, $R^{1BB}$, $R^{1CC}$, $R^{1DD}$, $R^{1EE}$, $R^{1FF}$, $R^{1GG}$, $R^{1HH}$, $R^{1JJ}$, $R^{1KK}$, $R^{1LL}$, $R^{1MM}$, $R^{1NN}$, $R^{1PP}$, $R^{1QQ}$, $R^{1RR}$, $R^{1SS}$, $R^{1TT}$, $R^{1AAA}$, $R^{1BBB}$, and $R^{1CCC}$ is for example, a hydrogen atom, a hydrocarbon group which may have a substituent(s) or 3- to 15-membered heterocyclic group which may have a substituent(s), and a nitrogen-containing heterocyclic group which may have a substituent(s) formed by $R^{1C}$ and $R^{1D}$ together with a nitrogen atom to which they bind are also preferred. $R^{1H}$ and $R^{1J}$ are preferably C1-6 alkyl groups, and more preferably methyl and ethyl groups. Particularly preferred as $R^1$ is, for example, $-SO_2NHCH_2CH_2OCH_3$,

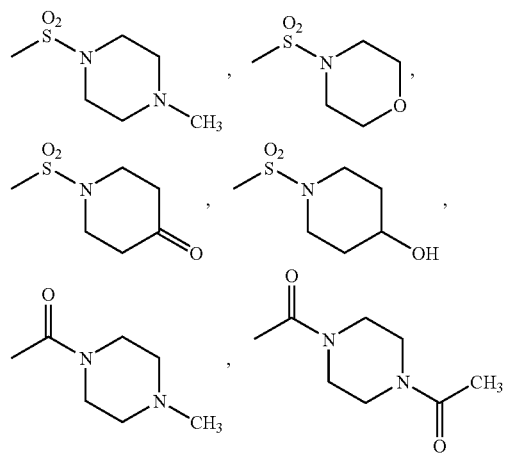

$-CONHCH_3$, $-CON(CH_3)_2$, $-NHSO_2NH_2$, etc.

Preferred as X is, for example, a bond, $-CR^7R^8-$, $-NR^9-$, $-CO-$, $-O-$, $-S-$, $-SO-$, $-SO_2-$, or $-C(=N-OR^{10})-$, etc. More preferably, X is a bond, $-O-$, or $-CH_2-$, etc., and particularly preferably, X is $-O-$ etc.

Preferred as Y is, for example, methylene, ethylene or propylene, etc. More preferably, Y is methylene, ethylene. Most preferably, Y is methylene.

Preferably, ring A or ring B is, for example, a "5- to 10-membered carbocyclic group or heterocyclic group" (it refers to 5- to 10-membered carbocyclic group or heterocyclic group of the above-described 3- to 15-membered carbocyclic or heterocyclic group), etc. More preferably is, for example, a "5- to 10-membered unsaturated carbocyclic group or heterocyclic group" (it refers to 5- to 10-membered unsaturated carbocyclic group or heterocyclic group of the above-described 3- to 15-membered carbocyclic or heterocyclic group), etc. More preferred is, for example, 5- or 6-aromatic ring such as benzene, pyrrole, imidazole, triazole, tetrazole, pyrazole, pyridine, pyrazine, pyrimidine, pyridazine, triazine, furan, thiophene, oxazole, isoxazole, thiazole, isothiazole, furazan, oxadiazole or thiadiazole ring, etc. Most preferred is, for example, benzene or pyridine ring, etc. Preferably, the ring A or ring B has no substituent or substituted with a hydrocarbon group, an alkoxy group, a halogen atom, a carboxy group, an alkanoylamide group, etc., and more preferably, the ring A or ring B has no substituent or substituted with a hydrocarbon group, alkoxy group, halogen atom, etc., and most preferably the ring A or ring B has no substituent or substituted with a chloro atom, a methyl group, or a methoxy group, etc.

Preferably, ring D is, for example, a "5- to 10-membered nitrogen-containing heterocyclic group" (it refers to 5- to 10-membered nitrogen-containing heterocyclic group of the above-described 3- to 15-membered nitrogen-containing heterocyclic group), etc., and more preferred is, for example, tropane, pyrrolidine, piperidine, azepane, or piperazine ring, etc., and most preferred is, for example, a piperidine ring. Preferably, ring D has no substituent or is substituted by hydrocarbon group, mono-C1-4 alkylamino group or di-C1-4 alkylamino group, etc. More preferably, ring D has no substituent.

Preferred as $R^2$ is, for example, hydrocarbon group which may have a substituent(s) or amino group which may have a substituent(s), etc. Preferred as the "substituents" is the "hydrocarbon group which may have a substituent(s)". Concretely, more preferred as $R^2$, for example,

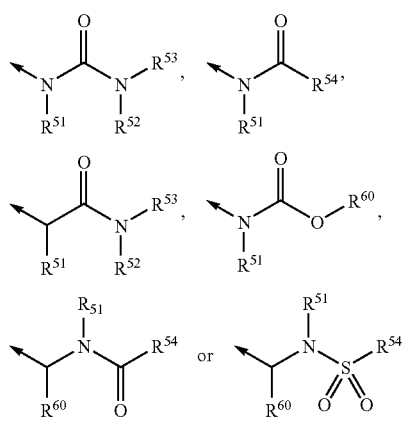

wherein the arrow represents a binding position to ring D, each $R^{51}$, $R^{52}$, $R^{53}$, $R^{54}$ and $R^{60}$ has the same meanings as described above, etc., independently. Preferably, $R^{51}$, $R^{53}$, $R^{54}$ or $R^{60}$ is, for example, a hydrocarbon group which may have a substituent(s) or 3- to 15-membered heterocyclic group which may have a substituent(s), etc. More preferred is, for example, a C1-15 alkyl group which may have a substituent(s), an aromatic group which may have a substituent(s), a benzyl group which may have a substituent(s), etc. Particularly preferred is, for example, a butyl group, a propyl group, a benzene ring which may have a substituent(s), a pyridine ring which may have a substituent(s), a benzyl group which may have a substituent(s), etc. $R^{52}$ is preferably a hydrogen atom. Particularly preferred as $R^2$ is, for example,

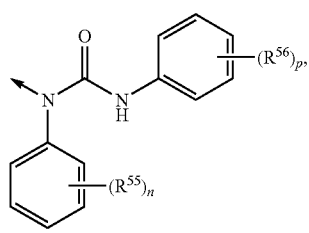

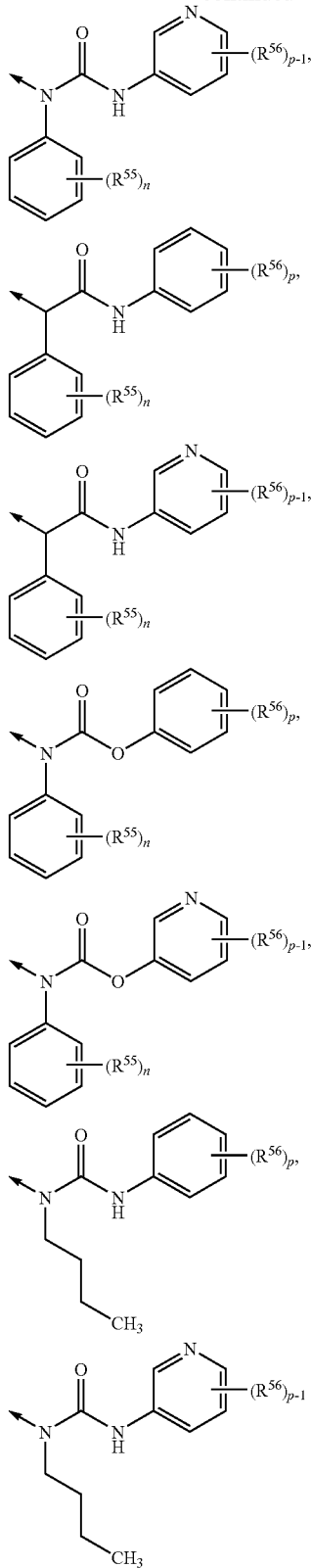

wherein $R^{55}$ or $R^{56}$ represents the "substituents" in the "hydrocarbon group which may have a substituent(s)" or "3- to 15-membered heterocyclic group which may have a substituent(s)" defined in $R^{1A}$, $R^{1B}$, $R^{1C}$, $R^{1D}$, $R^{1E}$, $R^{1F}$, $R^{1G}$, $R^{1H}$, $R^{1J}$, $R^{1K}$, $R^{1L}$, $R^{1M}$, $R^{1N}$, $R^{1P}$, $R^{1Q}$, $R^{1R}$, $R^{1S}$, $R^{1T}$, $R^{1U}$, $R^{1AA}$, $R^{1BB}$, $R^{1CC}$, $R^{1DD}$, $R^{1EE}$, $R^{1FF}$, $R^{1GG}$, $R^{1HH}$, $R^{1JJ}$, $R^{1KK}$, $R^{1LL}$, $R^{1MM}$, $R^{1NN}$, $R^{1PP}$, $R^{1QQ}$, $R^{1RR}$, $R^{1SS}$, $R^{1TT}$, $R^{1AAA}$, $R^{1BBB}$, and $R^{1CCC}$; n or p is 0 to 5; p−1 is 0 to 4; and other symbols have the same meaning as those described above. Herein, $R^{55}$ is preferably a methyl group, a methoxy group, a trifluoromethyl group, a chlorine atom or a fluorine atom, and particularly preferably a methyl group, a chlorine atom or a fluorine atom. $R^{56}$ is preferably a halogen atom, carbamoyl, or an aminocarbonyl group substituted by a C1-8 hydrocarbon group, more preferably a fluorine atom, a chlorine atom, a methyl group, carbamoyl, or an N-methylaminocarbonyl group, and particularly preferably a fluorine atom or a carbamoyl group; n or p−1 is preferably 0 to 2. p is preferably 0 to 3, and more preferably 2 to 3.

In the present invention, the compound represented by formula (I) including the combination of the above-described preferable group and ring is preferred.

For example, a compound wherein ring A and ring B represent a benzene or pyridine ring which may have further substituent(s), X is —O—, ring D is a piperidine ring and Y is a methylene group, i.e., a compound represented by formula (Ia):

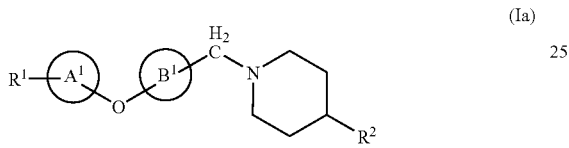

(Ia)

wherein all symbols have the same meaning as those described above;
a compound wherein $R^1$ is —CONR$^{1H}$R$^{1J}$ or —COR$^{1GG}$ [wherein all symbols have the same meaning as those described above.], ring A and ring B represent a benzene or pyridine ring which may have a substituent(s), X is —O—, ring D is a piperidine ring, Y is a methylene group, $R^2$ is

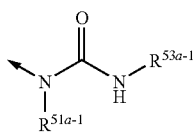

wherein the arrow represents a binding position to piperidine ring, $R^{51a-1}$ is a hydrocarbon group which may have a substituent(s) (the "hydrocarbon group which may have a substituent(s)" has the same meaning as the "hydrocarbon group which may have a substituent(s)" represented by $R^{51}$, $R^{52}$, $R^{53}$ and $R^{54}$"), $R^{53a-1}$ is (1) a benzene ring which may have a substituent(s) (the "benzene ring which may have a substituent(s)" has the same meaning as the "benzene ring which may have a substituent(s)" represented by $R^{51}$, $R^{52}$, $R^{53}$ and $R^{54}$), or (2) a pyridine ring which may have a substituent(s) (the "pyridine ring which may have a substituent(s)" has the same meaning as the "pyridine ring which may have a substituent(s)" represented by $R^{51}$, $R^{52}$, $R^{53}$ and $R^{54}$], i.e., a compound represented by formula (Ia-1):

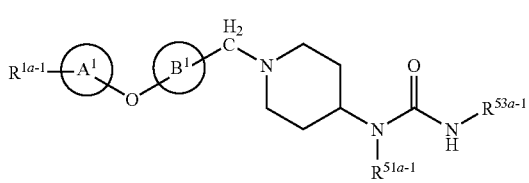

(Ia-1)

wherein all symbols have the same meaning as those described above;

a compound wherein ring A and ring B represent a benzene or pyridine ring which may have a substituent(s), X is —O—, ring D is a tropane ring, and Y is a methylene group, i.e., a compound represented by formula (Ib):

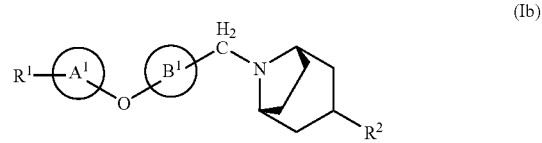

(Ib)

wherein all symbols have the same meaning as those described above;
a compound wherein ring A and ring B represent a benzene or pyridine ring which may have a substituent(s), X is —O—, ring D is a pyrrolidine ring, and Y is a methylene group, i.e., a compound represented by formula (Ic):

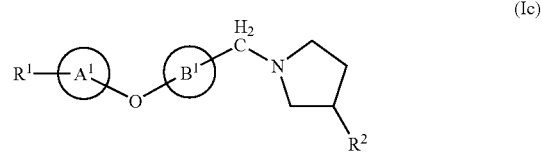

(Ic)

wherein all symbols have the same meaning as those described above;
a compound wherein ring A and ring B represent a benzene or pyridine ring which may have a substituent(s), X is —O—, ring D is an azepane ring, and Y is a methylene group, i.e., a compound represented by formula (Id):

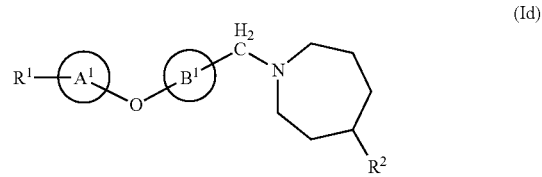

(Id)

wherein all symbols have the same meaning as those described above, salts thereof, N-oxides thereof, solvates thereof, and prodrugs thereof are preferred.

Preferred are compounds described in Examples, salts thereof, N-oxides thereof, solvates thereof, and prodrugs thereof. More preferred are N-(3-fluorophenyl)-N-{1-[(6-{4-[(4-methyl-1-piperazinyl)sulfonyl]phenoxy}-3-pyridinyl) methyl]-4-piperidinyl}-N'-(6-methyl-3-pyridinyl)urea, 4-[(5-{[4-((3-fluorophenyl) {[(6-methyl-3-pyridinyl)amino] carbonyl}amino)-1-piperidinyl]methyl}-2-pyridinyl)oxy]-N-(2-methoxyethyl)benzenesulfonamide, N-(3-fluorophenyl)-N'-(6-methyl-3-pyridinyl)-N-[1-({6-[4-(4-morpholinylsulfonyl)phenoxy]-3-pyridinyl}methyl)-4-piperidinyl]urea, N-(3-fluorophenyl)-N'-(6-methyl-3-pyridinyl)-N-{1-[(6-{4-[(4-oxo-1-piperidinyl)sulfonyl] phenoxy}-3-pyridinyl)methyl]-4-piperidinyl}urea, N-(3-fluorophenyl)-N-{1-[(6-{4-[(4-hydroxy-1-piperidinyl) sulfonyl]phenoxy}-3-pyridinyl)methyl]-4-piperidinyl}-N'-(6-methyl-3-pyridinyl)urea, N-{1-[(6-{4-[(aminosulfonyl) amino]phenoxy}-3-pyridinyl)methyl]-4-piperidinyl}-N-(3-fluorophenyl)-N'-(6-methyl-3-pyridinyl)urea, 4-[(5-{[4-((3-fluorophenyl) {[(6-methyl-3-pyridinyl)amino]

carbonyl}amino)-1-piperidinyl]methyl}-2-pyridinyl)oxy]-N-(2-hydroxyethyl)benzenesulfonamide, N-(3-fluorophenyl)-N-[1-({6-[4-(6-methyl-1,1-dioxido-1,2,6-thiadiazinan-2-yl)phenoxy]-3-pyridinyl}methyl)-4-piperidinyl]-N'-(6-methyl-3-pyridinyl)urea, 4-[(5-{[4-((3-fluorophenyl) {[(6-methyl-3-pyridinyl)amino]carbonyl}amino)-1-piperidinyl]methyl}-2-pyridinyl)oxy]-N-(2-hydroxy-2-methylpropyl)benzenesulfonamide, 4-[(5-{[4-((3-fluorophenyl) {[(6-methyl-3-pyridinyl)amino]carbonyl}amino)-1-piperidinyl]methyl}-2-pyridinyl)oxy]-N-(3-methoxypropyl)benzenesulfonamide, N-{4-[(5-{[4-((3-fluorophenyl) {[(6-methyl-3-pyridinyl)amino]carbonyl}amino)-1-piperidinyl]methyl}-2-pyridinyl)oxy]phenyl}cyclopropanesulfonamide, 4-[(5-{[4-((3-fluorophenyl) {[(6-methyl-3-pyridinyl)amino]carbonyl}amino)-1-piperidinyl]methyl}-2-pyridinyl)oxy]-N-(3-hydroxy-3-methylbutyl)benzenesulfonamide, 5-{[(1-{[6-(4-acetylphenoxy)-2-methyl-3-pyridinyl]methyl}-4-piperidinyl)(butyl)carbamoyl]amino}-2,4-difluorobenzamide, 5-({butyl[1-({2-methyl-6-[4-(methylcarbamoyl)phenoxy]-3-pyridinyl}methyl)-4-piperidinyl]carbamoyl}amino)-2,4-difluorobenzamide, 5-{[{1-[(6-{4-[(4-acetyl-1-piperazinyl)carbonyl]phenoxy}-2-methyl-3-pyridinyl)methyl]-4-piperidinyl}(butyl)carbamoyl]amino}-2,4-difluorobenzamide, 5-({butyl[1-({6-[4-(dimethylcarbamoyl)phenoxy]-2-methyl-3-pyridinyl}methyl)-4-piperidinyl]carbamoyl}amino)-2,4-difluorobenzamide, 5-({butyl[1-({6-[4-(ethylcarbamoyl)phenoxy]-2-methyl-3-pyridinyl}methyl)-4-piperidinyl]carbamoyl}amino)-2,4-difluorobenzamide, or 5-[(butyl {1-[(2-methyl-6-{4-[(4-methyl-1-piperazinyl)carbonyl]phenoxy}-3-pyridinyl)methyl]-4-piperidinyl}carbamoyl)amino]-2,4-difluorobenzamide, 5-[(butyl{1-[(6-{4-[(4-hydroxy-1-piperidinyl)carbonyl]phenoxy}-2-methyl-3-pyridinyl)methyl]-4-piperidinyl}carbamoyl)amino]-2,4-difluorobenzamide, 5-({butyl[1-({2-methyl-6-[4-(4-morpholinylcarbonyl)phenoxy]-3-pyridinyl}methyl)-4-piperidinyl]carbamoyl}amino)-2,4-difluorobenzamide, 5-{[butyl(1-{[2-methyl-6-(4-{[4-(trifluoromethyl)-1-piperidinyl]carbonyl}phenoxy)-3-pyridinyl]methyl}-4-piperidinyl)carbamoyl]amino}-2,4-difluorobenzamide, 5-{[{1-[(6-{4-[(4-acetyl-1-piperazinyl)carbonyl]phenoxy}-2-methyl-3-pyridinyl)methyl]-4-piperidinyl}(propyl)carbamoyl]amino}-2,4-difluorobenzamide, and 5-{[[{1-[(6-{4-[(4-acetyl-1-piperazinyl)carbonyl]phenoxy}-2-methyl-3-pyridinyl)methyl]-4-piperidinyl}(2-butyn-1-yl)carbamoyl]amino}-2,4-difluorobenzamide, salt thereof, N-oxides thereof, solvate thereofs, and prodrugs thereof, etc.

Processes for the preparation of the compound of the present invention:

The compound of the present invention represented by formula (I) can be prepared by methods which properly improved and combined known methods, such as methods described below, methods described in Examples or methods described in Comprehensive Organic Transformations: A Guide to Functional Group Preparations, 2nd Edition (Richard C. Larock, John Wiley & Sons Inc, 1999). In each method described below, a starting material can be used as a salt thereof. An example of the salt includes a salt of compound of formula (I) described above.

Among the compounds represented by formula (I), a compound wherein a spacer which is adjacent with ring D is —$CH_2$—, —CO— or —$SO_2$— can be prepared by alkylation, amidation or sulfonamidation of a compound represented by formula (1):

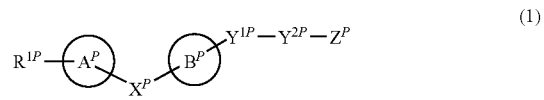

(1)

wherein Z is a hydroxy group or a leaving group (e.g., halogen atom, p-toluenesulfonyloxy group, methanesulfonyloxy group, trifluoromethanesulfonyloxy group, etc.), $Y^{1P}$ is a bond or a spacer containing 1 or 2 atoms as a main chain, $Y^{2P}$ is —$CH_2$—, —CO— or —$SO_2$—, and $R^{PP1}$, $X^P$, ring $A^P$ and ring $B^P$ have the same meanings as $R^1$, X, ring A and ring B respectively. With the proviso that, a carboxy group, a hydroxy group, an amino group or a mercapto group in $R^{PP1}$, $X^P$, $Y^{1P}$, $Y^{2P}$, ring $A^P$ or ring $B^P$ may be protected, if necessary. with a compound represented by formula (2):

(2)

wherein $R^{2P}$ and ring $D^P$ have the same meanings as $R^2$ and D respectively. With the proviso that, a carboxy group, a hydroxy group, an amino group or a mercapto group in $R^{2P}$ or ring $D^P$ may be protected, if necessary, if necessary, followed by removal of the protecting group.

The alkylation is well known. For example, it may be carried out in an organic solvent (e.g., dimethylformamide, dimethylsulfoxide), in the presence of alkaline (e.g., potassium carbonate, sodium carbonate, triethylamine, etc.); and in the presence or absence of sodium iodide or potassium iodide at about 0 to 150° C.

The amidation is known. For example, it includes the method (1) via an acyl halide,
(2) via a mixed acid anhydride,
(3) using a condensing agent.

These methods are explained as follows.

(1) The method via an acyl halide may be carried out, for example, by reacting carboxylic acid with an acyl halide (e.g., oxalyl chloride or thionyl chloride) in an organic solvent (e.g., chloroform, dichloromethane, diethyl ether or tetrahydrofuran) or without a solvent at about −20° C. to reflux temperature. And then the obtained acyl halide derivative may be reacted with amine in an organic solvent (e.g., chloroform, dichloromethane, diethyl ether or tetrahydrofuran) in the presence of a base (e.g., pyridine, triethylamine, dimethylaniline, dimethylaminopyridine or diisopropylethylamine, etc.) at about 0 to 40° C. As an alternative, the obtained acyl halide derivative may be reacted with amine in an organic solvent (e.g., dioxane, tetrahydrofuran) using an alkaline aqueous solution (e.g., sodium hydrogen carbonate, sodium hydroxide) at about −78 to 40° C.

(2) The method via a mixed acid anhydride may be carried out, for example, by reacting carboxylic acid with an acyl halide (e.g., pivaloyl chloride, p-toluenesulfonyl chloride or methanesulfonyl chloride) or an acid derivative (e.g., ethyl chloroformate or isobutyl chloroformate) in an organic solvent (e.g., chloroform, dichloromethane, diethyl ether, tetrahydrofuran) or without a solvent, in the presence of a base (e.g., pyridine, triethylamine, dimethylaniline, dimethylaminopyridine or diisopropylethylamine) at about 0 to 40° C. And then the obtained mixed acid anhydride derivative may be reacted with amine in an organic solvent (e.g., chloroform, dichloromethane, diethyl ether or tetrahydrofuran), at about 0 to 40° C.

(3) The method using a condensing agent may be carried out, for example, by reacting carboxylic acid with amine in an organic solvent (e.g., chloroform, dichloromethane, dimethylformamide, diethyl ether or tetrahydrofuran) or without a solvent, in the presence or absence of a base (e.g., pyridine, triethylamine, dimethylaniline or dimethylaminopyridine), using a condensing agent (e.g., 1,3-dicyclohexyl carbodiimide (DCC), 1-ethyl-3-[3-(dimethylamino) propyl]carbodiimide (EDC), 1,1'-carbonyldiimidazole (CDI), 2-chloro-1-methylpyridinium iodide, or 1-propanephosphonic acid cyclic anhydride (PPA)), in the presence or absence of 1-hydroxybenzotriazole (HOBt), at about 0 to 40° C.

The reaction described in (1), (2) and (3) may be carried out under an inert gas (e.g., argon, nitrogen) and under unhydrous condition in order to obtain a preferable result.

The sulfoneamidation is well known. For example, it may be carried out by reacting sulfonic acid with halide (e.g., oxalyl chloride or thionyl chloride, phosphorus pentachloride or phosphorus trichloride) in an organic solvent (e.g., chloroform, dichloromethane, dichloroethane, diethyl ether, tetrahydrofuran or tert-butyl methyl ether) or without a solvent at about −20° C. to reflux temperature. And then the obtained sulfonyl halide derivative may be reacted with amine in an organic solvent (e.g., chloroform, dichloromethane, diethyl ether or tetrahydrofuran) in the presence of a base (e.g., diisopropylethylamine, pyridine, triethylamine, dimethylaniline or dimethylaminopyridine, etc.) at about 0 to 40° C.

The protective group of carboxyl group includes, for example, a methyl group, an ethyl group, an allyl group, a tert-butyl group, a trichloroethyl group, a benzyl (Bn) group, a phenacyl group, etc.

The protecting group of a hydroxy group includes, for example, a methyl group, a trityl group, a methoxymethyl (MOM) group, a 1-ethoxyethyl (EE) group, a methoxyethoxymethyl (MEM) group, a 2-tetrahydropyranyl (THP) group, a trimethylsilyl (TMS) group, a triethylsilyl (TES) group, a tert-butyldimethylsilyl (TBDMS) group, a tert-butyldiphenylsilyl (TBDPS) group, an acetyl (Ac) group, a pivaloyl group, a benzoyl group, a benzyl (Bn) group, a p-methoxybenzyl group, an allyloxycarbonyl (Alloc) group, a 2,2,2-trichloroethoxycarbonyl (Troc) group, etc.

The protecting group of an amino group includes such as a benzyloxycarbonyl group, a tert-butoxycarbonyl group, an allyloxycarbonyl (Alloc) group, a 1-methyl-1-(4-biphenyl) ethoxycarbonyl (Bpoc) group, a trifluoroacetyl group, a 9-fluorenylmethoxycarbonyl (Fmoc) group, a benzyl (Bn) group, a p-methoxybenzyl group, a benzyloxymethyl (BOM) group, a 2-(trimethylsilyl)ethoxymethyl (SEM) group, etc.

The protective group of a mercapto group includes, for example, a benzyl group, a methoxybenzyl group, a methoxymethyl (MOM) group, a 2-tetrahydropyranyl (THP) group, a diphenylmethyl group, an acetyl (Ac) group, etc.

With regard to the protective group for a carboxyl group, a hydroxyl group, an amino group and a mercapto group, there is no particular limitation to the above ones so far as it is a group which is able to be easily and selectively removed. For example, a deprotection reaction may be carried out by a method mentioned in "T. W. Greene, Protective Groups in Organic Synthesis, John Wiley & Sons Inc, 1999".

The reaction for removing the protective group for a carboxyl group, a hydroxyl group, an amino group or a mercapto group is known and its examples are as follows.

(1) a deprotection reaction by hydrolyzing reaction with an alkali;
(2) a deprotection reaction under an acidic condition;
(3) a deprotection reaction by hydrogenolysis;
(4) a deprotection reaction of a silyl group;
(5) a deprotection reaction using a metal; and
(6) a deprotection reaction using a metal complex.

Those methods will be specifically illustrated as follows.

(1) A deprotection reaction using an alkali is carried out, for example, at about 0 to 40° C. using a hydroxide of alkaline metal (such as sodium hydroxide, potassium hydroxide and lithium hydroxide), a hydroxide of alkaline earth metal (such as barium hydroxide and calcium hydroxide), a carbonate (such as sodium carbonate and potassium carbonate), an aqueous solution thereof or a mixture thereof in an organic solvent (such as methanol, tetrahydrofuran and dioxane, etc.).

(2) A deprotection reaction under an acidic condition is carried out, for example, at about 0 to 100° C. in an organic acid (e.g., acetic acid, trifluoroacetic acid, methanesulfonic acid or p-toluenesulfonic acid), an inorganic acid (e.g., hydrochloric acid and sulfuric acid) or a mixture thereof (such as hydrogen bromide/acetic acid) in an organic solvent (such as dichloromethane, chloroform, dioxane, ethyl acetate and anisole, etc.).

(3) A deprotection reaction by hydrogenolysis is carried out, for example, at about 0 to 200° C. in a hydrogen atmosphere of ordinary pressure or high pressure or in the presence of ammonium formate in the presence of a catalyst (such as palladium-carbon, palladium black, palladium hydroxide, platinum oxide and Raney nickel) in a solvent (an ether such as tetrahydrofuran, dioxane, dimethoxyethane and diethyl ether; an alcohol such as methanol and ethanol; a benzene such as benzene and toluene; a ketone such as acetone and methyl ethyl ketone; a nitrile such as acetonitrile; an amide such as dimethylformamide; water, ethyl acetate, acetic acid or a mixed solvent comprising two or more thereof)

(4) A deprotection reaction of a silyl group is carried out, for example, at about 0 to 40° C. using tetrabutylammonium fluoride in an organic solvent miscible with water (such as tetrahydrofuran and acetonitrile, etc.).

(5) A deprotection reaction using metal is carried out, for example, at about 0 to 40° C. with or without ultrasonic wave in the presence of powdery zinc in an acidic solvent (such as acetic acid, a buffer of pH 4.2 to 7.2 and a mixed solution of a solution thereof with an organic solvent such as tetrahydrofuran).

(6) A deprotection reaction using a metal complex is carried out, for example, at about 0 to 40° C. using a metal complex [such as tetrakistriphenylphosphine palladium (0), bis(triphenylphosphine) palladium (II) dichloride, palladium (II) acetate and tris(triphenylphosphine) rhodium (I) chloride] in the presence or absence of a phosphine agent (such as triphenyl phosphine) in the presence of a trap reagent (such as tributyltin hydride, triethylsilane, dimedone, morpholine, diethylamine and pyrrolidine), an organic acid (such as acetic acid, formic acid and 2-ethylhexanoic acid) and/or an organic acid salt (such as sodium 2-ethylhex anoate and potassium 2-ethylhexanoate) in an organic solvent (such as dichloromethane, dimethylformamide, tetrahydrofuran, ethyl acetate, acetonitrile, dioxane and ethanol), water or a mixed solvent thereof.

Apart from the above, the deprotection may also be effected, for example, according to the methods described in T. W. Greene, Protective Groups in Organic Synthesis, John Wiley & Sons Inc., 1999.

As persons skilled in the art can easily understand that the aimed compound of the present invention is able to be easily produced by using appropriate ones among those deprotection reactions.

Among the compounds of the present invention represented by formula (I), a compound wherein $R^2$ is an amino group which may have a substituent(s), i.e., a compound represented by formula (I-a):

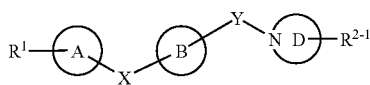

(I-a)

wherein $R^{2-1}$ is amino group which may have a substituent(s) and other symbols have the same meanings as described above, can be prepared by reductive amination of a compound represented by formula (3):

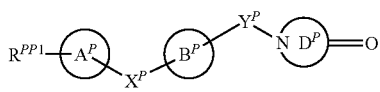

(3)

wherein all symbols have the same meanings as described above, and a compound represented by formula (4):

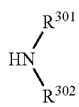

(4)

wherein $R^{301}$ and $R^{302}$ are the same or different and represent a hydrogen atom or have the same meanings as the "substituents" of the above-described "amino group which may have a substituent(s)", and other symbols have the same meanings as described above. With the proviso that, a carboxy group, a hydroxy group, an amino group or a mercapto group in $R^{301}$ or $R^{302}$ may be protected, if necessary, if necessary, followed by removal of the protecting group.

The reductive amination is well known. For example, it may be carried out with reducing agent (e.g., sodium triacetoxyborohydride or sodium cyanoborohydride) at about 0 to 40° C. in an organic solvent (e.g., dichloroethane, dichloromethane or dimethylformamide) in the presence or absence of tertiary amine (e.g., triethylamine or diisopropylethylamine), in the presence or absence of acetic acid.

The removal of the protecting group may be carried out by the above described method.

Among the compound of the present invention represented by formula (I), a compound wherein $R^2$ is

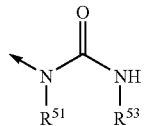

wherein all symbols have the same meanings as described above, i.e., a compound represented by formula (I-d):

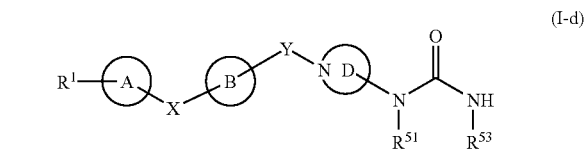

(I-d)

wherein all symbols have the same meanings as described above, can be prepared by a below reaction using a compound represented by formula (5):

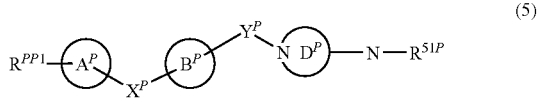

(5)

wherein $R^{51P}$ has the same meaning as $R^{51}$ and other symbols have the same meanings as described above. With the proviso that, a carboxy group, a hydroxy group, an amino group or a mercapto group in $R^{51P}$ may be protected, if necessary, and a compound represented by (6):

$$R^{53P}-COOH \quad (6)$$

wherein $R^{53P}$ has the same meaning as $R^{53}$ and other symbols have the same meanings as described above. With the proviso that, a carboxy group, a hydroxy group, an amino group or a mercapto group in $R^{53P}$ may be protected, if necessary, if necessary, followed by removal of the protecting group.

The reaction is well known. For example, it may be carried out in an organic solvent (e.g., N,N-dimethylformamide, toluene or tetrahydrofuran) with base (e.g., pyridine, triethylamine, dimethylaniline, dimethylaminopyridine or diisopropylethylamine) at about 20 to 120° C. in the presence of diphenylphosphoryl azide.

The removal of the protecting group may be carried out by the above described method.

Moreover, the compound represented by formula (I-d) can be prepared by a urea-forming reaction using the compound represented by formula (5) and a compound represented by formula (7):

$$R^{53P}-NH_2 \quad (7)$$

wherein the symbol has the same meaning as described above, if necessary, followed by removal of the protecting group.

The reaction is well known. For example, it may be carried out in an organic solvent (e.g., tetrahydrofuran or N,N-dimethylformamiden) in the presence of triphosgene with base (e.g., triethylamine) at about 0 to 40° C. Moreover, it may be carried out in an organic solvent (e.g., dichloromethane or N,N-dimethylformamiden) in the presence of 1,1'-carbonyl-bis-1H-imidazole (CDI) with a base (e.g., triethylamine or N-methylmorpholine) or without a base at about 0 to 80° C.

The removal of the protecting group may be carried out by the above described method.

Among a compound of the present invention represented by formula (I), a compound wherein Y is a methylene group, i.e., a compound represented by formula (I-e):

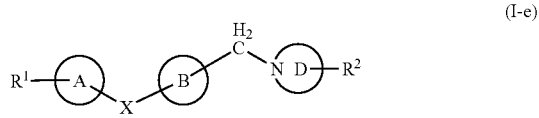

(I-e)

wherein all symbols have the same meanings as described above,
can be prepared by reductive amination of a compound represented by formula (8):

(8)

wherein all symbols have the same meanings as described above,
and the compound represented by formula (2), if necessary, followed by removal of the protecting group.

The reductive amination and the removal of the protecting group may be carried out by the above described method.

Among the compounds represented by formula (I), a compound wherein at least one nitrogen atom is a quaternary ammonium salt, i.e., a compounds of formula (I-2):

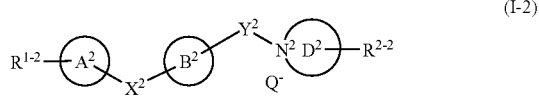

(I-2)

wherein $R^{1-2}$, $R^{2-2}$, $X^2$, $Y^2$, ring $A^2$, ring $B^2$ and ring $D^2$ have the same meanings as $R^1$, $R^2$, X, Y, ring A, ring B and ring D respectively, and $N^2$ is a nitrogen atom. With the proviso that, at least one nitrogen atom is a quaternary ammonium salt, and $Q^-$ is a halogen ion, can be prepared by reacting the compound of formula (I) with the compounds of formula (9):

R⁰-Q           (9)

wherein $R^0$ is a C1-8 alkyl group or a C1-8 alkyl group substituted by a phenyl group, and Q is a halogen atom.

This reaction is well known, and it may be carried out, for example, in an organic solvent (acetone, dimethylformamide or methyl ethyl ketone, etc.) at about 0 to 40° C.

Among the compounds of formula (I), a compound where at least one nitrogen atom is N-oxide. i.e. a compound of formula (I-3):

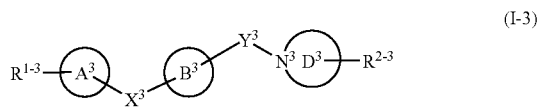

(I-3)

wherein $R^{1-3}$, $R^{2-3}$, $X^3$, $Y^3$, ring $A^3$, ring $B^3$ and ring $D^3$ have the same meanings as $R^1$, $R^2$, X, Y, ring A, ring B and ring D respectively and $N^3$ is a nitrogen atom. With the proviso that, at least one nitrogen atom represents N-oxide, can be prepared by an oxidation of a compound of formula (I).

The oxidation is well known and it may be carried out, for example, in a suitable organic solvent (e.g., dichloromethane, chloroform, benzene, hexane or tert-butyl alcohol) in the presence of an excessive oxidizing reagent (hydrogen peroxide, sodium periodate, acyl nitrite, sodium perborate, peroxidized acid (for example, 3-chloroperbenzoic acid or peracetic acid, etc.), OXONE (brand name, OXONE is an abbreviation for potassium peroxymonosulfate.), potassium permanganate or chromic acid, etc.) at about 20 to 60° C.

The compound of the present invention can be prepared by these reactions or reactions modified a part of them.

Other starting materials or compounds used as reagent are known compounds and can be prepared easily by combination of known methods, for example the methods described in Comprehensive Organic Transformations: A Guide to Functional Group Preparations, 2nd Edition (Richard C. Larock, John Willey & Sons Inc, 1999) or Elmer J. Rauckman et al., J. Org. Chem., Vol. 41, No. 3, 1976, p 564-565, etc.

In each reaction of the specification, the reactions with heating, as will be apparent to those skilled in the art, it may be carried with water bath, oil bath, sand bath and microwave.

In each reaction of the specification, it may be used a solid phase reagent which is supported by polymer (for example, polystyrene, polyacrylamide, polypropylene or polyethylene glycol, etc.).

In each reaction of the specification, the obtained products may be purified by conventional techniques. For example, the purification may be carried out by distillation at atmospheric or reduced pressure, by high performance liquid chromatography with silica gel or magnesium silicate, by thin layer chromatography, by an ion-exchange resin, by a scavenger resin, by column chromatography, by washing or by recrystallization. The purification may be done each reaction or after several reactions.

In a reaction using a polystyrene resin of the specification, the obtained products may be purified by conventional techniques. For example, the purification may be carried out by rinsing them with a solvent (dimethylformamide, dichloromethane, methanol, tetrahydrofuran, toluene, acetic acid/toluene, etc.) more than once.

Toxicity

The toxicity of the compound represented by formula (I), the salt thereof, the N-oxide thereof or the solvate thereof, or the prodrug thereof (hereinafter referred to as "the compound of the present invention") is very low and therefore it may be considered safe for pharmaceutical use.

Application to Pharmaceuticals

The compounds of the present invention have an antagonistic activity against chemokine receptor, especially CCR5, in animals including human, especially human, so they are useful for preventing and/or treating CCR5-related diseases, for example, inflammatory diseases (asthma, nephritis, nephropathy, hepatitis, arthritis, rheumatoid arthritis, rhinitis, conjunctivitis, inflammatory bowel disease such as ulcerative colitis, etc.); immunological diseases (autoimmune diseases, rejection in organ transplantation (rejection of graft of solid organ, rejection of graft of pancreatic islet cells in therapy for diabetes, GVHD (graft-versus-host disease)), etc.); immunosuppression, psoriasis, multiple sclerosis, etc.; infectious diseases (infection with human immunodeficiency virus, acquired immunodeficiency syndrome, infection with RSV, etc.); allergic diseases (atopic dermatitis, urticaria, allergic bronchopulmonary aspergillosis, allergic eosinophilic gastroenteritis, etc.); cardiovascular diseases (arteriosclerosis, ischemic reperfusion injury, etc.); acute respiratory distress syndrome, shock accompanying bacterial infection, diabetes mellitus, cancer metastasis and the like.

The fact that the compound of the present invention has CCR5 antagonism is demonstrated, for example, by the following experiment. The total operation is based on the basic genetic engineering to prepare gene-highly expressing cells, and the ordinary methods are utilized. Also, in the assaying method of the present invention, in order to evaluate the compound of the present invention, assaying accuracy and/or assaying sensitivity is improved as described below. The detailed experimental methods are shown below.

(1) Evaluation of the Antagonistic Activity of the Compound of the Present Invention Against CCR5

The fact that the compound of the present invention has CCR5 antagonism is demonstrated by performing the method described in Japanese Patent Application No. 2004-256531 or the inhibition test on the binding of RANTES, MIP-1α or MIP-1β to CCR5 (activity of chemokine to induce transient increase of Ca ion).

The thus established human CCR5 stably over-expressing CHO cell (CCR5/CHO cell) is suspended in Ham's F-12 medium containing FBS (10%) and seeded at a density of $3.5 \times 10^4$ cells/well into a 96 well plate. One day after culturing at 37° C., the culture supernatant is discarded, and Ham's F-12 medium (containing Fura-2AM (5 µM), Probenecid (2.5 mM) and HEPES (20 mM; pH 7.4)) is dispensed in 80 µL/well portions to carry out 1 hour of incubation at 37° C. under shaded condition. After washing twice with 1× Hanks/HEPES (20 mM; pH 7.4) solution, the same solution is dispensed in 100 µL/well portions. Each of the test compounds is added to the thus Fura-2AM-incorporated CCR5/CHO cell, and 3 minutes thereafter, a recombinant human CCR5 ligand (RANTES, MIP-1α or MIP-1β) (PeproTech) diluted with 1× Hanks/HEPES (20 mM; pH 7.4) solution is added thereto to a final concentration (Rantes: 10 nM; MIP-1α: 30 nM; MIP-1β: 30 nM). Transient increase in the intracellular $Ca^{2+}$ concentration induced by the human CCR5 ligand is measured using a $Ca^{2+}$ detector for 96 well use (Hamamatsu Photonics), and inhibition ratio (%) of the test compound is calculated by the following calculation formula.

Inhibition ratio=$[(Ec-Ea)/Ec]\times 100$

Ec: measured value of $Ca^{2+}$ transient increase by CCR5 ligand

Ea: measured value of $Ca^{2+}$ transient increase by CCR5 ligand when a test compound is added.

The compounds of the present invention have the cell migration inhibitory activity in animals including human, especially human, so they are useful for preventing and/or treating inflammatory diseases (asthma, nephritis, nephropathy, hepatitis, arthritis, rheumatoid arthritis, rhinitis, conjunctivitis, inflammatory bowel disease such as ulcerative colitis, etc.); immunological diseases (autoimmune diseases, rejection in organ transplantation (rejection of graft of solid organ, rejection of graft of pancreatic islet cells in therapy for diabetes, graft-versus-host disease), etc.); immunosuppression, psoriasis, multiple sclerosis, etc.; infectious diseases (infection with human immunodeficiency virus, acquired immunodeficiency syndrome, infection with RSV, etc.); allergic diseases (atopic dermatitis, urticaria, allergic bronchopulmonary aspergillosis, allergic eosinophilic gastroenteritis, etc.); cardiovascular diseases (arteriosclerosis, ischemic reperfusion injury, etc.); acute respiratory distress syndrome, shock accompanying bacterial infection, diabetes mellitus, cancer metastasis and the like.

The fact that the compound of the present invention has the cell migration inhibitory activity is demonstrated, for example, by the following experiment. The total operation is based on the basic genetic engineering to prepare gene-highly expressing cells, and the ordinary methods are utilized. Also, in the assaying method of the present invention, in order to evaluate the compound of the present invention, assaying accuracy and/or assaying sensitivity is improved as described below. The detailed experimental methods are shown below.

(2) Human CCR5 Expression Cell (hCCR5-Ba/F3 Cell) Migration Test of the Compounds of the Present Invention Influence of a test compound on the migration ability of the human CCR5 expressing Ba/F3 cell against RANTES, MIP-1α or MIP-1β is examined. First, 0.3 mL of 0 or 3 nM chemokine (RANTES, MIP-1α or MIP-1)-containing medium is respectively added to the lower well of Chemo Tx96 well plate (Neuro Probe). Next, a filter (pore size: 5 µm) is set and a mixture solution ($1\times10^5$ cells/well) of the test compound and the CCR5-Ba/F3 cell prepared in advance is added at 65 µL. The test compound to be added is prepared by diluting it with 0.1% DMSO-containing medium to give a final concentration on the filter of 0, 0.01, 0.03, 0.1 or 0.3 M. These cells are cultured in a $CO_2$ incubator (37° C., 5% $CO_2$, relative humidity: 95%) for 3 hours, and then the medium and unmigrated cells on the filter are eliminated. Furthermore, the filter is removed, the microplate is centrifuged (1,500 rpm, 10 min, RT) and the supernatant is removed by decantation. The cells on the microplate are suspended in 100 µL of a phosphate buffer (PBS), and 1/10 portion thereof is further diluted with 90 µL of PBS, moves on a white plate for fluorescence assay, and uses as an assay sample for migrated cell numbers (final: 100 µL/well).

Next, Cell Titer-Glo Reagent (trade name, Promega) which is previously prepared at room temperature is added to the above assay sample for migrated cell numbers (100 µL/well), followed by gently mixing (300 rpm, 2 min with IKA-SCHUTTLER MTS4) for lysating the cells, the mixture is incubated at room temperature for 10 minutes, and the fluorescence is measured with wallac ARVO SX 1420 MULTI-LABEL COUNTER (trade name, Perkin Elmer) (detection by count/second).

The migrated cell numbers (naturally falling cell numbers) at a chemokine concentration of 0 nmol/L is used as the background, and the inhibition ratio of the test compound against the 0.1% DMSO control group is calculated.

The inhibition migration ratio (%) of the test compound is calculated by the following equation:

$$\text{Inhibition ratio} = \frac{(Ec - Ea)}{Ec} \times 100$$

Ec: (fluorescence measured value at the addition of 0.1% DMSO)−(fluorescence measured value of the naturally falling cells)

Ea: (fluorescence measured value at the addition of the test compound)−(fluorescence measured value of the naturally falling cells)

(3) Human PBMC Cell Migration Test of the Compounds of the Present Invention

Preparation of PBMC (Peripheral Blood Mononuclear Cell)

Human venous blood (50 mL) collected by using syringe with heparin sodium (final concentration: 10 U/mL, heparin sodium injection 1,000 U/mL, Shimizu Pharmaceutical Co., Ltd.) was stored into 50 mL of conical tube made by polypropylene. To a Lymphoprep tube (NYCOMED PHARMA, Cat.

No 1019818), 16.5 mL of DPBS (−) (GIBCO, Cat. No. 14190-136) and a blood sample were added, jiggled several times, then centrifuged at 3,000 rpm for 10 minutes at room temperature. About 7 mL of PBMC phase (center phase) was collected into 50 mL of conical tube made by polypropylene using a Pasteur pipette, and DPBS (−) was added to a final concentration (50 mL), than centrifuged at 1,200 rpm for 10 minutes at room temperature. After removing a supernatant, residue was redissolved with 50 mL of DPBS (−). The suspension of the cell was centrifuged at 1,500 rpm for 3 minutes at room temperature. The supernatant was removed, then 3 mL of hemolysis buffer (0.8% $NH_4Cl$, 0.1% $KHCO_3$, 1 mmol/L EDTA) was added thereto to suspend enough, then left 2 minutes at room temperature. The suspension was added by 30 mL of DPBS (−), centrifuged at 1,500 rpm for 3 minutes at room temperature. The supernatant was removed to give PBMC.

Culture of Human PBMC

After anti human CD3 antibody OKT3 (Janssen Pharmaceutical K.K., 1 μg/mL) coated 24 well plate overnight at 4° C., it was blocked by culture medium (RPMI 1640 (GIBCO, Cat. No. 11875-085), 10% FBS (GIBCO, Cat. No. 112318-028), 1% PSF (GIBCO, Cat. No. 15240-096)) in 30 minutes at 37° C. Prepared human PBMC was seeded into the plate coated by OKT3 ($2 \times 10^6$ cells/well), cultured in a few days at 37° C. PBMC was collected, and seeded into the plate uncoated by OKT3 ($2 \times 10^6$ cells/well) in the presence of human IL2 (5 ng/mL), then cultured. PBMC was subculture every one or two days.

Analysis of Human CCR5 Expression Using FACS

After 10 μL of FITC labeled anti human CCR5 antibody (2D7) (BD Pharmingen, Cat. No. 555992) and PE labeled anti human CD45RO antibody (BD Pharmingen, Cat. No. 347967) was added to the human PBMC cultured in $1 \times 10^6$ cells, the mixture was shaded 15 minutes or left 30 minutes on the ice, then DPBS (GIBCO) was added thereto and washed. The cell was suspended with 500 μL of DPBS, then fluorescence intensity was measured by using FACS.

In Vitro Experiment of Cell Migration

50 μL of $5 \times 10^5$ cells of the human PBMC suspension (culture medium) and 50 μL of the solution of the test compound (0-2 μmol/L: double concentration of a final concentration) were added to an upper well of transwell (coster), and 300 μL of 60 nmol/L of the human MIP-1β (Pepro tech, Cat. No. 300-09) and 300 μL of a double concentration of the solution of the test compound were added to a lower well. It was prepared that a concentration of DMSO in upper well was 0.01%. The solution was incubated 1.5 hours in the atmosphere of carbon dioxide gas (37° C., 5% $CO_2$, degree of humidity: 95%). After the solvent of upper well was aspirated, 100 μL of 20 μmol/L of EDTA/DPBS (−) was added thereto, and incubated 30 minutes at 4° C., then centrifuged at 1,500 rpm for 5 minutes. 100 μL of the solution was transferred to white 96 well plate for fluorescence from lower well by pipetting, an amount of cells was measured by using Celltiter Glo (Promega) (a measurement of ATP), cell migration inhibition ratio was calculated by the following calculating formula. The value of $IC_{50}$ was calculated from cell migration inhibition ratio of each concentration. The value was an average value (n=3).

Cell migration inhibition ratio=$[(Ea-Ec)/(Eb-Ec)] \times 100$

Ea: measured value when a test compound is added

Eb: measured value when no test compound (0.01% in DMSO) but only DMSO is added

Ec: measured value when no test compound (0.01% in DMSO) but only DMSO is added with no added ligand to lower well The fact that the compound of the present invention has the immunosuppressive effect is demonstrated, for example, by the following experiment. The total operation is based on the basic technique, and the ordinary methods are utilized. Also, in the assaying method of the present invention, in order to evaluate the compound of the present invention, assaying accuracy and/or assaying sensitivity is improved as described below. The detailed experimental methods are shown below.

(4) Immunosuppressive Effect in Model of Renal Allotransplantation in Cynomolgus Monkeys of the Compound of the Present Invention Cynomolgus monkeys (body weight: 3-4.5 kg) that were ABO-compatible, major histocompatibility complex (MHC)-different, more specifically, MLR miss-matched donor (male)-recipient (either sex) combinations underwent bilateral nephrectomy with subsequent implantation of an allogenic kidney from a selected donor animal. Test substances (a compound of the present invention and/or an immunosuppressant agent) was administered daily starting on Day-1 (the day before transplantation) until the day before rejection was defined. The efficacy was assessed by comparing the length of the survival of the transplanted kidney.

The compound of the present invention was administered in combination with subtherapeutic immunosuppressant agent on the market (Cyclosporine, sirolimus, and/or tacrolimus). The efficacy was demonstrated by comparing with administration of immunosuppressant agent alone.

The compound of the present invention was administered, for example, per os (PO), twice a day at a dose level of 3, 10 or 30 mg/kg.

For example, the presence of rejection was suspected if the serum creatinine levels rise. In particular, rejection of transplanted kidney was defined as an increase in the serum creatinine levels to 8 mg/dL.

The compound of the present invention has good solubility and absorbability. And the compound of the present invention has a week inhibitory activity against drug-metabolizing enzyme. These nature are the physical, chemical, and pharmaceutical property required to drugs, and the compound of the present invention have the proper conditions to an excellent drug [Ref (The Merck Manual of Diagnosis and Therapy ($17^{th}$ Ed), Merck & Co.)].

It can be assessed that the compound of the present invention is useful as a drug by various experimental methods described below, methods described in Biological Examples, and their methods which properly improved. It can be also easily assessed that the compound of the present invention has a good pharmacokinetic property such as a length of serum half-life, a stability in the gastrointestinal tract, an absorption of oral preparations, bioavailability, etc. by known methods, for example, a method described in "Yakubutsu bioavailability (Hyouka to kaizen no kagaku), Jul. 6, 1998, Gendaiiryou-sha", etc.

(5) Evaluation Experiment of a Toxicity of the Compound of the Present Invention (i) Single Acute Toxicity Test in Rat The test compound is administered to six-week Crj:CD (SD) rat by single intravenous dose or single oral administration. Toxicity can be evaluated by contrast with value at no addition of the test compound. Basic evaluation of toxicity can be done by, for example, observation of performance status or locomotor activity, etc.

(ii) Evaluation of the Activity of the Compound of the Present Invention Against hERG $I_{Kr}$ Current According to the report by Zou et al. (Biophys. J., Vol. 74, 230-241 (1998)), using HEK293 cell overexpressed of human ether-a-go-go-related gene (hERG), max tale current of hERG $I_{Kr}$ current induced by depolarization pulse followed by repolarization pulse is measured by patch-clamp recording. Rate of change (inhibition rate) is calculated by comparison max tale current between before addition of the test compound and 10 minutes after. The influence of the test compound against hERG $I_{Kr}$ current can be evaluated by the inhibition rate.

(iii) Evaluation of the Activity of the Compound of the Present Invention Against Phospholipidosis According to the report of Kasahara et al. Toxicol. Sci., 90, 1330-141 (2006)) and the report of Narita et al. (attached document "In Vitro Phospholipidosis Detection System using Fluorescent Labelling Phospholipid Analogue", Research Result Presentation Meeting of the Project for Promotion of Multidisciplinary Human Science Research Such As Drug Discovery), the activity of the compound of the present invention against phospholipidosis can be easily evaluated.

(6) Stability Test in Liver Microsome of Monkey

It can be demonstrated that the compounds of the present invention have metabolic stability by the following experiments, for example.

To a solution of 100 mmol/L phosphate buffer (pH 7.4, it was prepared from 100 mmol/L of aqueous solution of dipotassium hydrogen phosphate and 100 mmol/L of aqueous solution of potassium dihydrogen phosphate.), liver microsome of monkey (final concentration: 1 mg/mL) and a test compound (final concentration: 5 μmol/L) was added and the mixture solution was pre-incubated for 5 minutes. The mixture solution was added by NADPH generating system (13 mmol/L β-NADP$^+$ (final concentration: 1.3 mmol/L), 33 mmol/L G-6-P (final concentration: 3.3 mmol/L), 10 U/mL G-6-P DH (from Yeast) (final concentration: 0.4 U/mL), and 33 mmol/L magnesium chloride solution (final concentration: 3.3 mmol/L)). While the mixture was incubated at 37° C., 100 μL of the reaction solution was taken out 0 and 30 minutes after the start, and was added to acetonitrile (2 mL) to terminate the reaction (n=2). After internal standard solution was added thereto, the mixture solution was agitated, then centrifuged at 3,000 rpm for 5 minutes. 100 μL of the resulting supernatant was mixed with 100 μL of mobile phase A, then was analyzed by LC/MS/MS.

The conditions of LC/MS/MS for analysis are outlined below.

LC Conditions:

| | |
|---|---|
| Column: | XTerra RP8 3.5 μm (2.1 mmID × 50 mm) (Waters Corporation) |
| Temperature of column: | 40° C. |
| Mobile phase A: | 5 mmol/L aqueous ammonium acetate solution/acetonitrile (80/20, V/V) |
| Mobile phase B: | 5 mmol/L aqueous ammonium acetate solution/acetonitrile (20/80, V/V) |
| Temperature of sample: | 4° C. |
| Injection volume of sample: | 5 μL |
| Time for analysis: | 10 min |

Composition of mobile phases, and Flow rate:

TABLE 1

| Time (min) | Flow rate (μL/min) | A (%) | B (%) |
|---|---|---|---|
| 0.00 | 300 | 95.0 | 5.0 |
| 1.00 | 300 | 95.0 | 5.0 |
| 1.10 | 300 | 5.0 | 95.0 |
| 5.00 | 300 | 5.0 | 95.0 |
| 5.10 | 300 | 95.0 | 5.0 |
| 10.00 | 300 | 95.0 | 5.0 |

MS/MS Conditions:

| | |
|---|---|
| Measuring equipment: | API3000 (AB/MDS SCIEX) |
| Ionization method: | Electrospray ionization (ESI, Positive) |

The appropriate monitoring ion was selected for an each sample.

The residual ratio of the unmetabolite (%) of the test compound in liver microsome of monkey was calculated by the following calculation formula.

The residual ratio of the unmetabolite(%)=(a concentration of the test compound at 30 minutes)/(a concentration of the test compound at 0 minute)× 100

(7) Pharmacokinetics Test in Blood in Monkey

It can be demonstrated that the compounds of the present invention have a good property of pharmacokinetics in blood by the following experiments, for example.

Each of five test compounds were weighed, and dissolved in Soltol (Trademark; BASF Takeda Vitamins Ltd.)/propylene glycol=7/3 heated to 50° C. to be 5 mg/mL solution thereof. Equal amount of each five samples were weighed, mixed, then diluted with distilled water for injection by five times to make a solution for oral administration. The solution for oral administration (1 mg/kg) was forced intragastric administering to cynomolgus monkey (male, Hamri Co., Ltd) with sonde (n=3). The administering was done in the fasting state but they have freedom to drink water. Each 1 mL of blood samples were collected from superficial cephalic vein, using a heparinized syringe, 5, 15, 30 minutes, 1, 2, 4, 6, 8 and 24 hours after administration. Collected samples were stored into ice, centrifuged at 3,000 rpm for 15 minutes to get plasma. The plasma was stored at −20° C. The plasma sample stored at −20° C. was dissolved, then 100 μL of the resulting solution was added by internal standard solution and acetonitrile (2 mL), agitated, centrifuged at 3,000 rpm for 10 minutes. The resulting supernatant was dried with a centrifuge concentrator. The residue was redissolved in 100 μL of mobile phase A, then 40 μL of the resulting solution was analyzed by LC/MS/MS The conditions of LC/MS/MS for analysis are outlined below.

LC Conditions:

| | |
|---|---|
| Measuring equipment: | Waters 2790 (Waters) |
| Column: | YMC-Pack MB-ODS 5 μm (2.1 mmID × 50 mm) (YMC) |
| Temperature of column: | room temperature |
| Flow rate: | 200 μL/minute |
| Mobile Phase: | 20 mmol/L aqueous ammonium acetate solution/acetonitrile (1/1) |

MS/MS Conditions:

| | |
|---|---|
| Measuring equipment: | QUATTRO Ultima (Micromass) |
| Ionization method: | ES+ |
| Capillary voltage: | 3.20 kV |
| Temperature of source: | 150° C. |
| Temperature of desolvation: | 250° C. |
| Multiplier: | 650 V |

The appropriate monitoring ion was selected for an each sample.

Transition of plasma concentration of the test compound in monkey was analyzed with non-compartment analytic method using WinNonlin 4.0.1 (Pharsight), and AUC was calculated.

(8) Measurement of Bioavailability (BA) of the Compounds of the Present Invention It can be demonstrated that the compounds of the present invention have good bioavailability by the following experiments, for example.

The test compound was weighed, and dissolved in 30% HP-β-CD (Trademark; Mitsubishi Corporation) to make 1 mg/mL solution for intravenous administration. The test compound was weighed, and dissolved in Soltol (Trademark; BASF Takeda Vitamins Ltd.)/propylene glycol=7/3 heated to 50° C. to be 3 mg/mL solution thereof, then diluted with distilled water for injection by five times to make a solution for oral administration. The solution for intravenous administration (1 mg/kg) was administered to cynomolgus monkey (male, Hamri Co., Ltd) via superficial cephalic vein by single intravenous dose (n=3). The solution for oral administration (3 mg/kg) was forced intragastric administering to cynomolgus monkey (male, Hamri Co., Ltd) with sonde (n=3). The administering was done in the fasting state but they have freedom to drink water. Each 1 mL of blood samples were collected from superficial cephalic vein, using a heparinized syringe, 5, 15, 30 minutes, 1, 2, 4, 6, 8 and 24 hours after administration. Collected samples were stored into ice, centrifuged at 3,000 rpm for 15 minutes to get plasma. The plasma was stored at −20° C. The plasma sample stored at −20° C. was dissolved, then 100 μL of the resulting solution was added by internal standard solution and acetonitrile (2 mL), agitated, centrifuged at 3,000 rpm for 10 minutes. The residue was redissolved in 100 μL of mobile phase A, then 40 μL of the resulting solution was analyzed by LC/MS/MS The conditions of LC/MS/MS for analysis are outlined below.

LC Conditions:

| | |
|---|---|
| Measuring equipment: | Waters 2790 (Waters) |
| Column: | YMC-Pack MB-ODS 5 μm (2.1 mmID × 50 mm) |
| (YMC) | |
| Temperature of column: | room temperature |
| Flow rate: | 200 μL/minute |
| Mobile phase: | 20 mmol/L aqueous ammonium acetate solution/acetonitrile (1/1) |

MS/MS Conditions:

| | |
|---|---|
| Measuring equipment: | QUATTRO Ultima (Micromass) |
| Ionization method: | ES+ |
| Capillary voltage: | 3.20 kV |
| Temperature of source: | 150° C. |
| Temperature of desolvation: | 250° C. |
| Multiplier: | 650 V |

The appropriate monitoring ion was selected for an each sample.

Transition of plasma concentration of the test compound in monkey was analyzed with non-compartment analytic method using WinNonlin 4.0.1 (Pharsight), and AUC was calculated.

BA was calculated by the following calculation formula.

$$BA(\%) = (AUC_{p.o.}/Dose_{p.o.})/(AUC_{i.v.}/Dose_{i.v.}) \times 100$$

$AUC_{p.o.}$: AUC when a test compound is orally administered
$Dose_{p.o.}$: Amount of the compound administered orally
$AUC_{i.v.}$: AUC when a test compound is intravenously administered
$Dose_{i.v.}$: Amount of the compound administered intravenously The above measuring methods (1) to (8) are not limited to the above method, and ordinary methods are utilized based on a basic technique.

For the purpose above described, the compounds of the present invention may be normally administered systemically or locally, usually by oral or parenteral administration.

The doses to be administered are determined depending upon, for example, age, body weight, symptom, the desired therapeutic effect, the route of administration, and the duration of the treatment. In the human adult, the doses per person are generally from 1 mg to 1,000 mg, by oral administration, up to several times per day, and from 1 mg to 100 mg, by parenteral administration (preferably intravenous administration), up to several times per day, or continuous administration from 1 to 24 hours per day from vein.

As mentioned above, the doses to be used depend upon various conditions. Therefore, there are cases in which doses lower than or greater than the ranges specified above may be used.

The compounds of the present invention may be administered for example, in the form of solid for oral administration, liquid forms for oral administration, injections, liniments or suppositories for parenteral administration.

Solid forms for oral administration include compressed tablets, pills, capsules, dispersible powders, and granules. Capsules include hard capsules and soft capsules.

In such solid forms, one or more of the active compound(s) may be admixed with vehicles (such as lactose, mannitol, glucose, microcrystalline cellulose or starch), binders (such as hydroxypropyl cellulose, polyvinyl pyrrolidone or magnesium metasilicate aluminate), disintegrants (such as cellulose calcium glycolate), lubricants (such as magnesium stearate), stabilizing agents, and solution adjuvants (such as glutamic acid or aspartic acid) and prepared according to methods well known in normal pharmaceutical practice. The solid forms may, if desired, be coated with coating agents (such as sugar, gelatin, hydroxypropyl cellulose or hydroxypropylmethyl cellulose phthalate), or be coated with two or more films. And further, coating may include containment within capsules of absorbable materials such as gelatin.

Liquid forms for oral administration include pharmaceutically acceptable solutions, suspensions, emulsions, syrups and elixirs. In such forms, one or more of the active compound(s) may be dissolved, suspended or emulsified into diluent(s) commonly used in the art (such as purified water, ethanol or a mixture thereof). Besides such liquid forms may also comprise some additives, such as wetting agents, suspending agents, emulsifying agents, sweetening agents, flavoring agents, aroma, preservative or buffering agent.

Injections for parenteral administration include sterile aqueous, suspensions, emulsions and solid forms which are dissolved or suspended into solvent(s) for injection immediately before use. In injections, one or more of the active compound(s) may be dissolved, suspended or emulsified into solvent(s). The solvents may include distilled water for injection, saline, vegetable oil, propylene glycol, polyethylene glycol, alcohol such as ethanol, or a mixture thereof. Injections may comprise some additives, such as stabilizing agents, solution adjuvants (such as glutamic acid, aspartic acid or POLYSORBATE80 (registered trade mark)), suspending agents, emulsifying agents, soothing agent, buffering agents, preservative. They may be sterilized at a final step, or may be prepared according to sterile methods. They may also be manufactured in the form of sterile solid forms such as freeze-dried products, which may be dissolved in sterile water or some other sterile diluent(s) for injection immediately before use.

Other forms for parenteral administration include liquids for external use, ointments and endermic liniments, inhalations, sprays, suppositories and vaginal suppositories which comprise one or more of the active compound(s) and may be prepared by methods known per se.

The compounds of the present invention may be used together with other drugs, for example, preventive and/or treating agent(s) for HIV infection (particularly agents for prevention and/or treatment of AIDS), or agent(s) for rejection in organ transplantation and/or autoimmune diseases. In that case, the drug as such may be mixed with pharmacologically acceptable excipient, binder, disintegrating agent, lubricant, stabilizer, solubilizer, diluent, etc. either separately or simultaneously to make into a pharmaceutical preparation and that can be administered either orally or parenterally as a pharmaceutical composition for prevention and/or treatment of HIV infection, rejection in organ transplantation and/or autoimmune diseases.

The compounds of the present invention have an infection inhibiting activity to HIV which acquired resistance to other agents for preventive and/or treating HIV infection (particularly agents for prevention and/or treatment of AIDS). Therefore, it is also able to be used for HIV-infected patients to whom other agents for preventive and/or treating HIV infection are no longer effective. In that case, although the compound of the present invention may be used solely, it may be also used together with agents for preventive and/or treating HIV infection where infected HIV strain acquired resistance or with other drugs.

The present invention covers the combination of the compounds of the present invention with drugs which do not inhibit the HIV infection whereby preventive and/or treating effect for HIV infection is enhanced as compared with a single preparation.

Examples of other agent for preventive and/or treating HIV infection used for a combination with the compounds of the present invention are reverse transcriptase inhibitor, protease inhibitor, chemokine antagonist (such as CCR2 antagonist, CCR3 antagonist, CCR4 antagonist, CCR5 antagonist, CXCR3 antagonist and CXCR4 antagonist), integrase inhibitor, fusion inhibitor, antibody to surface antigen of HIV and vaccine of HIV.

Reverse transcriptase inhibitors are concretely (1) nucleoside/nucleotide reverse transcriptase inhibitors: zidovudine (brand name: Retrovir), didanosine (brand name: Videx), zalcitabine (brand name: HIVID), stavudine (brand name: Zerit), lamivudine (brand name: Epivir), abacavir (brand name: Ziagen), adefovir, adefovir dipivoxil, emtricitabine (brand name: Coviracil) or PMPA (brand name: Tenofovir), etc. and (2) nonnucleoside reverse transcriptase inhibitors: nevirapine (brand name: Viramune), delavirdine (brand name: Rescriptor), efavirenz (brand name: Sustiva, Stocklin) or capravirine (AG1549), etc.

Protease inhibitors are concretely indinavir (brand name: Crixivan), ritonavir (brand name: Norvir), nelfinavir (brand name: Viracept), saquinavir (brand name: Invirase, Fortovase), amprenavir (brand name: Agenerase), lopinavir (brand name: Kaletra) or tipranavir, etc.

As chemokine antagonists, internal ligand of chemokine receptor, its derivatives, its non-peptide low molecular compound or antibody of chemokine receptor are included.

The examples of internal ligand of chemokine receptor are concretely, MIP-1α, MIP-1β, RANTES, SDF-1α, SDF-1β, MCP-1, MCP-2, MCP-4, Eotaxin and MDC, etc.

The derivatives of internal ligand are concretely, AOP-RANTES, Met-SDF-1α, Met-SDF-1β, etc.

Antibodies of chemokine receptor are concretely, Pro-140, etc.

CCR2 antagonists are concretely written in specification of WO99/07351, WO99/40913, WO00/46195, WO00/46196, WO00/46197, WO00/46198, WO00/46199, WO00/69432 or WO00/69815 or in Bioorg. Med. Chem. Lett., 10, 1803 (2000), etc.

CCR3 antagonists are written in, for example, specification of DE19837386, WO99/55324, WO99/55330, WO00/04003, WO00/27800, WO00/27835, WO00/27843, WO00/29377, WO00/31032, WO00/31033, WO00/34278, WO00/35449, WO00/35451, WO00/35452, WO00/35453, WO00/35454, WO00/35876, WO00/35877, WO00/41685, WO00/51607, WO00/51608, WO00/51609, WO00/51610, WO00/53172, WO00/53600, WO00/58305, WO00/59497, WO00/59498, WO00/59502, WO00/59503, WO00/62814, WO00/73327 or WO01/09088, etc.

CCR5 antagonists are, for example, TAK-779, SCH-351125 (SCH-C), SCH-417690(SCH-D), UK-427857, GW873140 (ONO-4128), TAK-220, etc. Moreover, it includes compounds written in, for example, specification of WO99/17773, WO99/32100, WO00/06085, WO00/06146, WO00/10965, WO00/06153, WO00/21916, WO00/37455, EP1013276, WO00/38680, WO00/39125, WO00/40239, WO00/42045, WO00/53175, WO00/42852, WO00/66551, WO00/66558, WO00/66559, WO00/66141, WO00/68203, JP2000-309598, WO00/51607, WO00/51608, WO00/51609, WO00/51610, WO00/56729, WO00/59497, WO00/59498, WO00/59502, WO00/59503, WO00/76933, WO98/25605, WO99/04794, WO99/38514, Bioorg. Med. Chem. Lett., 11, 2663 (2003), Curr. Med. Chem. Anti-Infective Agents, 4, 133 (2005), Current Opinion in Pharmacology, 4, 447 (2004), or Current Opinion in Investigational Drugs, 5, 851 (2004), etc.

CXCR3 antagonists are written in, for example, specification of WOO/16114, WO02/083143, WO02/085862, U.S. Pat. No. 6,469,002, or WO03/101970, etc.

CXCR4 antagonists are, for example, AMD-3100, AMD-070, T-22, KRH-1120, KRH-1636, KRH-2731 or the compounds written in specification of WO00/66112, etc.

Integrase inhibitors are Equisetin, Temacrazine, MK0518 (Raltegravir), PL-2500, V-165, NSC-618929, L-870810, L-708906 analog, S-1360, or 1838, etc.

Fusion inhibitors are concretely, T-20 (Pentafuside, Enfuvirtide, Fuseon (brand name)), and T-1249, etc.

The examples of combination agents written above are intended to illustrate the present invention, but do not limit them.

The typical examples of the usual the dosage level in clinical trials of reverse transcriptase inhibitors or protease inhibitors written below are intended to illustrate the present invention, but do not limit them.

| | |
|---|---|
| zidovudine: | 100 mg capsule, 200 mg per dose, 3 times per day; 300 mg tablet, 300 mg per dose, twice per day; |
| didanosine: | 25-200 mg tablet, 125-200 mg per dose, twice per day; |
| zalcitabine: | 0.375-0.75 mg tablet, 0.75 mg per dose, 3 times per day; |
| stavudine: | 15-40 mg capsule, 30-40 mg per dose, twice per day; |
| lamivudine: | 150 mg tablet, 150 mg per dose, twice per day; |

-continued

| | |
|---|---|
| abacavir: | 300 mg tablet, 300 mg per dose, twice per day; |
| nevirapine: | 200 mg tablet, 200 mg per dose, once per day for 14 days and then twice per day; |
| delavirdine: | 100 mg tablet, 400 mg per dose, 3 times per day; |
| efavirenz: | 50-200 mg capsule, 600 mg per dose, once per day; |
| indinavir: | 200-400 mg capsule, 800 mg per dose, 3 times per day; |
| ritonavir: | 100 mg capsule, 600 mg per dose, twice per day; |
| nelfinavir: | 250 mg tablet, 750 mg per dose, 3 times per day; |
| saquinavir: | 200 mg capsule, 1,200 mg per dose, 3 times per day; |
| amprenavir: | 50-150 mg tablet, 1,200 mg per dose, twice per day. |

Examples of other agent for preventive and/or treating rejection in organ transplantation used for a combination with the compounds of the present invention are immunosuppressants.

Examples of the immunosuppressant include tacrolimus (FK506), cyclosporin, sirolimus (rapamycin), corticosteroids, azathioprine, mycophenolate mofetil, FTY-720, cyclophosphamide, or cell-surface ligand antibody, etc.

Examples of the cell-surface ligand antibody include Atgam (brand name), Thymoglobulin (brand name), Simulect (brand name), Zanapax (brand name), or Orthoclone (brand name), etc.

Examples of other agent for preventive and/or treating autoimmune diseases used for a combination with the compounds of the present invention are nonsteroidal antiinflammatory drug, disease modifying anti-rheumatic drug (DMARDs, slow-acting anti-rheumatic drug), steroids, immunosuppressant agent, antiinflammatory enzyme preparations, chondroprotective agents, T-cell inhibitors, TNFα inhibitor (include protein preparation such as anti-TNFα antibody), prostaglandin synthase inhibitor, IL-1 inhibitor, IL-6 inhibitor (include protein preparation such as anti-IL-6 receptor antibody), interferon gamma agonists, prostaglandins, phosphodiesterase inhibitor, metalloproteinase inhibitor, etc.

Examples of the nonsteroidal antiinflammatory drug include sasapyrine, sodium salicylate, aspirin, aspirin dialuminate formulation, diflunisal, indomethacin, suprofen, ufenamate, dimethylisopropyl azulen, bufexamac, felbinac, diclofenac, tolmetin sodium, Clinoril, fenbufen, napmetone, proglumetacin, indomethacin farnesil, acemetacin, proglumetacin maleate, amfenac sodium, mofezolac, etodolac, ibuprofen, ibuprofen piconol, naproxen, flurbiprofen, flurbiprofen axethyl, ketoprofen, fenoprofen calcium, tiaprofenen, oxaprozin, pranoprofen, loxoprofen sodium, aluminoprofen, zaltoprofen, mefenamic acid, aluminum mefenamate, tolfenamic acid, floctafenine, ketophenylbutazone, oxyfenbutazone, piroxicam, tenoxicam, anpiroxicam, napageln cream, epirizole, tiaramide hydrochloride, tinoridine hydrochloride, emorfazone, sulpyrine, Migrenin, Saridon, Sedes G, Amipylo N, Sorbon, pyrine system antipyretics, acetaminophen, phenacetin, dimethothiazine mesylate, simetride formulation, or antipyrine system antipyretics, etc.

Examples of the disease modifying anti-rheumatic drug (DMARDs, slow-acting anti-rheumatic drug) include, for example, gold thioglucose, aurothiomalate sodium, auranofin, actarit, D-penicillamine preparations, lobenzarit disodium, bucillamine, hydroxychloroquine, salazosulfapyridine, methotrexate, or leflunomide, etc.

Examples of the steroids for external application include clobetasol propionate, diflorasone acetate, fluocinonide, monometasone furancarboxylate, betamethasone dipropionate, betamethasone butyrate propionate, betamethasone valerate, difluprednate, budesonide, diflucortolone valerate, amcinonide, halcinonide, dexamethasone, dexamethasone propionate, dexamethasone valerate, dexamethasone acetate, hydrocortisone acetate, hydrocortisone butyrate, hydrocortisone acetate propionate, deprodone propionate, prednisolone valerate acetate, fluocinolone acetonide, beclometasone dipropionate, triamcinonide acetonide, flumethasone pivalate, alclometasone dipropionate, clobetasone butyrate, prednisolone, beclometasone propionate, and fludroxycortide, etc. Examples of the steroids for internal use or injection include cortisone acetate, hydrocortisone, hydrocortisone sodium phosphate, hydrocortisone sodium succinate, fludrocortisone acetate, prednisolone, prednisolone acetate, prednisolone sodium succinate, prednisolone butyrate acetate, prednisolone sodium phosphate, halopredon acetate, methyl prednisolone, methyl predniso lone acetate, methyl predniso lone sodium succinate, triamicinolon, triamicinolon acetate, triamicinonolon acetonide, dexamethasone, dexamethasone acetate, dexamethasone sodium phosphate, dexamethasone palmitate, paramethasone acetate, and betamethasone, etc.

Examples of the steroids as an inhalant include beclomethasone propionate, fluticasone propionate, budesonide, flunisolide, triamicinolon, ST-126P, ciclesonide, dexamethasone palmitate, monometasone furancarboxylate, prasterone sulfonate, deflazacort, methylprednisolone suleptanate, and methylprednisolone sodium succinate, etc.

Examples of the antiinflammatory enzyme preparations include, for example, lysozyme chloride, bromelain, pronase, serrapeptase, or streptokinase-streptodornase, etc.

Examples of the chondroprotective agents include, for example, hyaluronate sodium, glucosamine, chondroitin sulfate, and glucosaminoglycan polysulfate, etc.

Examples of TNFα inhibitor (include protein preparation such as anti-TNFα antibody) include, for example, infliximab, adalimumab, or etanercept, etc.

Examples of the prostaglandin synthase inhibitor include, for example, salazosulfapyridine, mesalazine, olsalazine, 4-aminosalicylic acid, JTE-522, auranofin, carprofen, diphenpyramid, flunoxaprofen, flurbiprofen, indomethacin, ketoprofen, lornoxicam, loxoprofen, Meloxicam, oxaprozin, parsalmide, piproxen, piroxicam, piroxicam betadex, piroxicam cinnamate, tropine indomethacinate, zaltoprofen, and pranoprofen, etc.

Examples of IL-1 inhibitor (include protein preparation such as human IL-1 receptor antagonist) include, for example, anakinra, etc.

Examples of IL-6 inhibitor (include protein preparation such as anti-IL-6 receptor antibody) include, for example, MRA, etc.

Examples of the prostaglandins (hereinafter abbreviated as "PG") include PG receptor agonist, and PG receptor antagonist, etc. Examples of the PG receptor include PGE receptor (EP1, EP2, EP3, EP4), PGD receptor (DP, CRTH2), PGF receptor (FP), PGI receptor (IP), or TX receptor (TP), etc.

Examples of the phosphodiesterase inhibitor include, for example, rolipram, cilomilast (trade name: Ariflo), Bay 19-8004, NIK-616, roflumilast (BY-217), cipamfylline (BGL-61063), atizolam (CP-80633), SCH-351591, YM-976, V-11294A, PD-168787, D-4396, IC-485, or ONO-6126 as PDE4 inhibitor, etc.

Examples of other agent for preventive and/or treating other allergic diseases, for example, asthma used for a combination with the compounds of the present invention are steroids, $\beta_2$ adrenoreceptor stimulant, leukotriene receptor antagonist, thromboxane synthetase inhibitor, thromboxane $A_2$ receptor antagonist, mediator releasing inhibitor, antihistamines, xanthine derivatives, anticholinergic agent, cytokine inhibitor, prostaglandins, forskolin, phosphodiesterase inhibitor, elastase inhibitor, metalloproteinase inhibitor, expectorant, and antibiotic.

Examples of the $\beta_2$ adrenoreceptor stimulant include fenoterol hydrobromide, salbutamol sulfate, terbutaline sulfate, formoterol fumarate, salmeterol xinafoate, isoprotenol sulfate, orciprenalin sulfate, chloroprenalin sulfate, epinephrine, trimetoquinol hydrochloride, hexoprenalinmesyl sulfate, procaterol hydrochloride, tulobuterol hydrochloride, tulobuterol, pirbuterol hydrochloride, clenbuterol hydrochloride, mabuterol hydrochloride, ritodrine hydrochloride, bambuterol, dopexamine hydrochloride, meradrin tartrate, AR-C68397, levosalbutamol, R,R-formoterol, KUR-1246, KUL-7211, AR-C89855, and S-1319, etc.

Examples of the leukotriene receptor antagonist include pranlukast hydrate, montelukast, zafirlukast, seratrodast, MCC-847, KCA-757, CS-615, YM-158, L-740515, CP-195494, LM-1484, RS-635, A-93178, S-36496, BIIL-284, and ONO-4057, etc.

Examples of the thromboxane synthetase inhibitor include ozagrel hydrochloride, and imitrodast sodium, etc.

Examples of the thromboxane $A_2$ receptor antagonist include seratrodast, ramatroban, domitroban calcium dihydrate, and KT-2-962, etc.

Examples of the mediator releasing inhibitor include tranilast, sodium cromoglicate, anlexanox, repirinast, ibudilast, tazanolast, and pemilolast potassium, etc.

Examples of the antihistamines include ketotifen fumarate, mequitazine, azelastine hydrochloride, oxatomide, terfenadine, emedastine fumarate, epinastine hydrochloride, astemizole, ebastin, cetirizine hydrochloride, bepotastine, fexofenadine, lolatadine, deslolatadine, olopatadine hydrochloride, TAK-427, ZCR-2060, NIP-530, mometasone furoate, mizolastine, BP-294, andolast, auranofin, and acribastin, etc.

Examples of the xanthine derivatives include aminophylline, thoeophyline, doxophylline, cipamfylline, and diprophilline, etc.

Examples of the anticholinergic agent include ipratropium bromide, oxitropium bromide, flutropium bromide, cimetropium bromide, temiverine, tiotropium bromide, and revatropate (UK-112166), etc.

Examples of the cytokine inhibitor include suplatast tosilate (trade name: IPD), etc.

Examples of the elastase inhibitors include ONO-5046, ONO-6818, MR-889, PBI-1101, EPI-HNE-4, R-665, ZD-0892, ZD-8321, GW-311616, and AE-3763, etc.

Examples of the expectorant include foeniculated ammonia spirit, sodium hydrogen carbonate, bromhexine hydrochloride, carbocisteine, ambroxol hydrochloride, sustained release ambroxol hydrochloride, methylcysteine hydrochloride, acetyl cysteine, L-ethylcysteine hydrochloride, and tyloxapol, etc.

Examples of antibiotics include cefuroxime sodium, meropenem trihydrate, netilmicin sulfate, sisomicin sulfate, ceftibuten, PA-1806, IB-367, tobramycin, PA-1420, doxorubicin, astromicin sulfate, or cefetamet pivoxil hydrochloride, etc. Examples of antibiotics as an inhalant include PA-1806, IB-367, tobramycin, PA-1420, doxorubicin, astromicin sulfate, or cefetamet pivoxil hydrochloride, etc.

The other pharmaceuticals which supplement and/or enhance the prevention and/or treatment effect of the compound of the present invention is not limited to examples as described above. With regard to other pharmaceuticals which supplement and/or enhance the prevention and/or treatment effect of the compound of the present invention, not only that which has been found up to now but also that which will be found in future on the basis of the above-mentioned mechanism are included.

The nomenclature of compounds of the present invention is described below.

All the compounds described in the present specification were named using ACD/Name Batch (registered trademark, Advanced Chemistry Development Inc.), which is a computer program that names a compound according to IUPAC nomenclature system, or named according to IUPAC nomenclature system. For example, a compound represented by

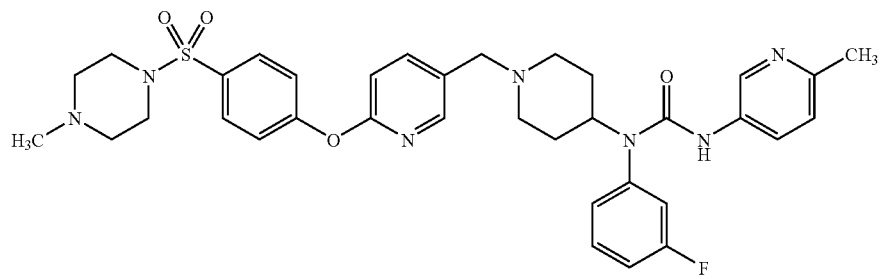

was named N-(3-fluorophenyl)-N-{1-[(6-{4-[(4-methyl-1-piperazinyl)sulfonyl]phenoxy}-3-pyridinyl)methyl]-4-piperidinyl}-N'-(6-methyl-3-pyridinyl)urea.

EXAMPLES

The present invention will be described in detail below by way of Preparation Examples, Biological Examples and Formulation Examples, but the present invention is not limited thereto.

The solvent described in the position of isolation through chromatography and that described in parenthesis in TLC denote an elution solvent or a developing solvent, and the proportion denotes a volume ratio. Commercially available 28% ammonia water was used as ammonia water.

NMR is a measured value of $^1$H-NMR and the solvent in parenthesis described in the position of NMR is a solvent used in the measurement.

Preparation Examples

Example 1 ethyl 6-[4-(chlorosulfonyl)phenoxy]nicotinate

To chlorosulfonic acid (20 mL) was dropped ethyl 6-phenoxynicotinate (5.6 g) on ice bath, and the reaction mixture was stirred for 15 minutes at room temperature, and 3 hours at 60° C. To reaction mixture was added ice, and extracted with tert-butyl methyl ether. The organic layer was washed with water and brine, dried over anhydrous sodium sulfate, and concentrated to give the title compound (7.5 g) having the following physical data.

TLC: Rf 0.44 (hexane:ethyl acetate=4:1);

$^1$H-NMR (d$_6$-DMSO): δ1.29 (t, 3 H), 4.30 (q, 2 H), 7.06-7.17 (m, 3 H), 7.60-7.69 (m, 2 H), 8.29 (dd, 1 H), 8.67 (dd, 1 H).

Example 2 ethyl 6-{4-[(4-methylpiperazin-1-yl)sulfonyl]phenoxy}nicotinate

To a solution of the compound prepared in Example 1 (545 mg) in tetrahydrofuran (10 mL) was added 1-methylpiperazine (222 μL) and triethylamine (420 μL) under atmosphere of argon. The reaction mixture was stirred for 1 hour at room temperature. To reaction mixture was added water, and extracted with ethyl acetate. The organic layer was washed with water and brine, dried over anhydrous sodium sulfate, and concentrated. The obtained residue was purified by column chromatography on silica gel (ethyl acetate:methanol=1:0→9:1) to give the title compound (448 mg) having the following physical data.

TLC: Rf 0.15 (ethyl acetate);

$^1$H-NMR (CDCl$_3$): δ1.40 (t, 3 H), 2.29 (s, 3 H), 2.45-2.57 (m, 4 H), 3.00-3.16 (m, 4 H), 4.40 (q, 2 H), 7.03 (dd, 1 H), 7.27-7.35 (m, 2 H), 7.76-7.85 (m, 2 H), 8.34 (dd, 1 H), 8.82 (dd, 1 H).

Example 3

(6-{4-[(4-methylpiperazin-1-yl)sulfonyl]phenoxy}pyridin-3-yl)methanol

To a solution of the compound prepared in Example 2 (438 mg) in tetrahydrofuran (10 mL) was added 0.99M solution of diisobutylaluminium hydride in toluene (2.2 mL) at −78° C. under atmosphere of argon. The reaction mixture was heated to room temperature and stirred for 2 hours at room temperature. To reaction mixture was added water and a saturated aqueous solution of sodium sulfate. The insoluble was removed by filtration, and the filtrate was concentrated to give the title compound (381 mg) having the following physical data.

TLC: Rf 0.10 (ethyl acetate:methanol=9:1);

$^1$H-NMR (CDCl$_3$): δ1.83-1.93 (m, 1 H), 2.28 (s, 3 H), 2.45-2.55 (m, 4 H), 3.00-3.13 (m, 4H), 4.71 (s, 2 H), 7.00 (dd, 1 H), 7.22-7.29 (m, 2 H), 7.74-7.79 (m, 2 H), 7.81 (dd, 1 H), 8.19 (dd, 1 H).

Example 4

6-{4-[(4-methylpiperazin-1-yl)sulfonyl]phenoxy}nicotinealdehyde

To a solution of the compound prepared in Example 3 (380 mg) in dimethyl sulfoxide (10 mL) and ethyl acetate (10 mL) were added triethylamine (875 μL) and sulfur trioxide-pyridine complex (500 mg) under atmosphere of argon. The reaction mixture was stirred for 1 hour at room temperature. To reaction mixture was added water, and extracted with ethyl acetate. The organic layer was washed with water and brine, dried over anhydrous sodium sulfate, and concentrated. The obtained residue was purified by column chromatography on silica gel (ethyl acetate:methanol=1:0→10:1) to give the title compound (353 mg) having the following physical data.

TLC: Rf 0.26 (ethyl acetate:methanol=9:1);

$^1$H-NMR (CDCl$_3$): δ2.30 (s, 3 H), 2.46-2.58 (m, 4 H), 3.02-3.17 (m, 4 H), 7.13 (dt, 1 H), 7.30-7.37 (m, 2 H), 7.79-7.87 (m, 2 H), 8.25 (dd, 1 H), 8.62 (dd, 1 H), 10.03 (d, 1 H).

Example 5 tert-butyl 4-[(3-fluorophenyl)amino]piperidine-1-carboxylate

To a solution of 1-(t-butoxycarbonyl)-4-piperidone (26.7 g) in dichloroethane (135 ml) were added 4-fluoroaniline (14.2 ml), acetic acid (9.2 ml) and sodium triacetoxyborohydride (39.8 g). The reaction mixture was stirred for 2 hours at room temperature. To reaction mixture was added a saturated aqueous solution of sodium hydrogen carbonate, and extracted with dichloromethane. The organic layer was washed with water and brine, dried over anhydrous sodium sulfate, and concentrated. The obtained crystals were washed with t-butyl methyl ether:hexane=1:4, dried to give the title compound (31.1 g) having the following physical data.

TLC: Rf 0.61 (ethyl acetate:hexane=1:2);

$^1$H-NMR (CDCl$_3$): δ1.25-1.41 (m, 2 H), 1.47 (s, 9 H), 1.98-2.08 (m, 2 H), 2.86-2.99 (m, 2 H), 3.32-3.44 (m, 1 H), 3.97-4.13 (m, 2 H), 6.25-6.41 (m, 3 H), 7.04-7.13 (m, 1 H).

Example 6 tert-butyl 4-{(3-fluorophenyl)[(6-methylpyridin-3-yl)carbamoyl]amino}piperidine-1-carboxylate To a solution of 6-methylnicotinic acid (14.7 g) in toluene (110 ml) was added triethylamine (14.9 ml). The reaction mixture was heated at 105° C., and stirred. Then to this solution was added diphenylphosphorous azide (29.4 g). The reaction mixture was stirred for 15 minutes at same temperature and left at rest until the inner temperature fell in 45° C. To the mixture was added the compound prepared in Example 5 (21.0 g). The reaction mixture was stirred overnight at room temperature. Then, a precipitate was collected from the reaction mixture. The obtained crystals were washed with ethyl acetate, dried to give the title compound (12.6 g) having the following physical data.

TLC: Rf 0.51 (methanol:chloroform=1:9);

$^1$H-NMR (CDCl$_3$): δ1.18-1.35 (m, 2 H), 1.41 (s, 9 H), 1.80-1.91 (m, 2 H), 2.47 (s, 3 H), 2.72-2.90 (m, 2 H), 4.08-4.23 (m, 2 H), 4.60-4.72 (m, 1 H), 5.79 (s, 1 H), 6.95-7.00 (m, 1 H), 7.03-7.08 (m, 2 H), 7.19-7.27 (m, 1 H), 7.47-7.55 (m, 1 H), 7.78 (dd, 1 H), 8.12 (d, 1 H).

Example 7

1-(3-fluorophenyl)-3-(6-methylpyridin-3-yl)-1-piperidin-4-ylurea dihydrochloride To a solution of the compound prepared in Example 6 (12.6 g) in ethyl acetate (10 ml) was added 4N hydrogen chloride in ethyl acetate (50 ml). The reaction mixture was stirred for 1 hour at room temperature. The reaction mixture was concentrated to give the title compound (11.6 g) having the following physical data.

TLC: Rf 0.18 (dichloromethane:methanol:aqueous ammonia=90:10:1);

$^1$H-NMR (CD$_3$OD): δ1.63-1.81 (m, 2 H), 2.11-2.22 (m, 2 H), 2.69 (s, 3 H), 3.07-3.21 (m, 2 H), 3.39-3.50 (m, 2 H), 4.61-4.73 (m, 1 H), 7.18-7.24 (m, 2 H), 7.27-7.34 (m, 1 H), 7.54-7.63 (m, 1 H), 7.75 (d, 1 H), 8.34 (dd, 1 H), 8.98 (d, 1 H).

Example 8

N-(3-fluorophenyl)-N-{1-[(6-{4-[(4-methyl-1-piperazinyl)sulfonyl]phenoxy}-3-pyridinyl)methyl]-4-piperidinyl}-N'-(6-methyl-3-pyridinyl)urea

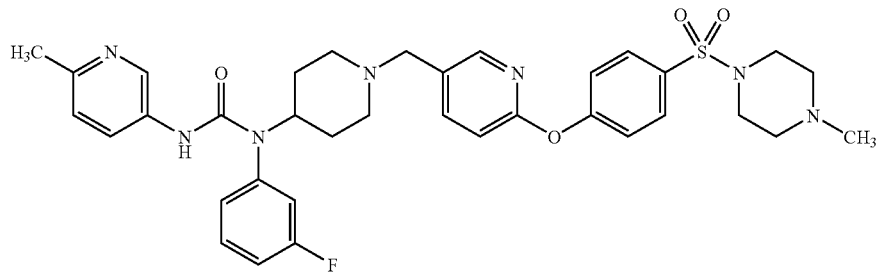

To a solution of the compound prepared in Example 7 (111 mg) and the compound prepared in Example 4 (100 mg) in dimethylformamide (7 mL) were added acetic acid (19 μL), triethylamine (77 μL) and sodium triacetoxyborohydride (117 mg). The reaction mixture was stirred for 1 day at room temperature. To reaction mixture was added a saturated aqueous solution of sodium hydrogen carbonate, and extracted with ethyl acetate. The organic layer was washed with water and brine, dried over anhydrous sodium sulfate, and concentrated. The obtained residue was purified by column chromatography on silica gel (ethyl acetate methanol=10:1→dichloromethane:methanol=10:1) to give the compound of the present invention (151 mg) having the following physical data TLC: Rf 0.34 (dichloromethane:methanol=9:1);

$^1$H-NMR (CDCl$_3$): δ1.33-1.51 (m, 2 H), 1.79-1.92 (m, 2 H), 2.09-2.22 (m, 2 H), 2.28 (s, 3 H), 2.43-2.54 (m, 7 H), 2.83-2.95 (m, 2 H), 2.99-3.13 (m, 4 H), 3.44 (s, 2 H), 4.47-4.62 (m, 1 H), 5.77 (s, 1 H), 6.91 (d, 1 H), 6.99 (dt, 1 H), 7.03-7.10 (m, 2 H), 7.17-7.29 (m, 3 H), 7.50 (td, 1 H), 7.67 (dd, 1 H), 7.72-7.80 (m, 3 H), 8.05 (d, 1 H), 8.11 (d, 1 H).

Examples 8(1)-8(17)

The procedure similar to that of Example 8 was carried out using the compound prepared in Example 7 or a corresponding amine compound, and a corresponding aldehyde compound 10 in place of the compound prepared in Example 4, if necessary, followed by conversion to hydrochloride by usual way, to obtain the following compound of the present invention.

Example 8(1)

4-[(5-{[4-((3-fluorophenyl) {[(6-methyl-3-pyridinyl)amino]carbonyl}amino)-1-piperidinyl]methyl}-2-pyridinyl)oxy]-N-(2-methoxyethyl)benzenesulfonamide dihydrochloride

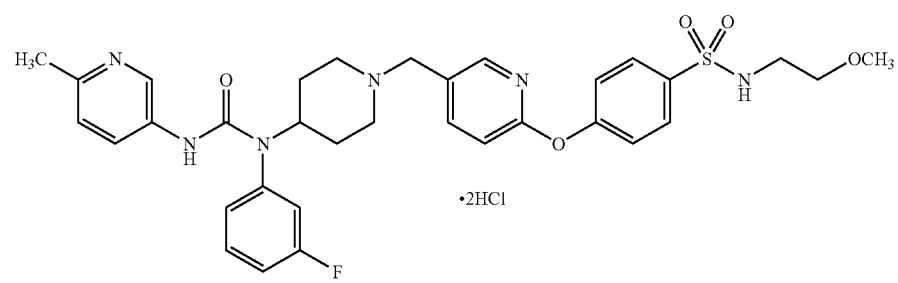

TLC: Rf 0.19 (ethyl acetate:methanol=9:1);
$^1$H-NMR (CD$_3$OD): δ1.68-1.90 (m, 2 H), 2.14-2.27 (m, 2 H), 2.68 (s, 3 H), 3.06 (t, 2 H), 3.15-3.28 (m, 5 H), 3.39 (t, 2 H), 3.49-3.61 (m, 2 H), 4.32 (s, 2 H), 4.63-4.77 (m, 1 H), 7.14-7.23 (m, 3 H), 7.25-7.35 (m, 3 H), 7.52-7.62 (m, 1 H), 7.74 (d, 1 H), 7.87-7.93 (m, 2 H), 8.01 (dd, 1 H), 8.24 (d, 1 H), 8.33 (dd, 1 H), 8.97 (dd, 1 H).

Example 8(2)

N-(3-fluorophenyl)-N'-(6-methyl-3-pyridinyl)-N-[1-({6-[4-(4-morpholinylsulfonyl)phenoxy]-3-pyridinyl}methyl)-4-piperidinyl]urea dihydrochloride

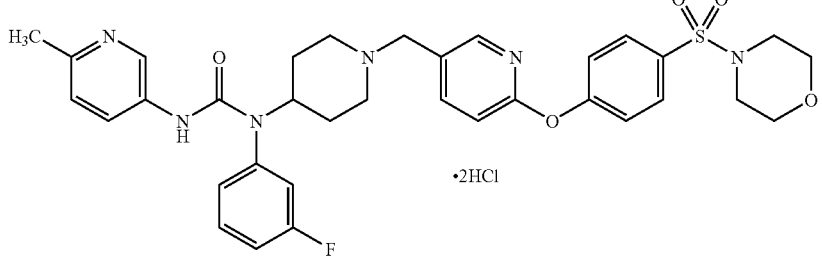

TLC: Rf 0.26 (ethyl acetate:methanol=9:1);
$^1$H-NMR (CD$_3$OD): δ1.71-1.91 (m, 2 H), 2.14-2.27 (m, 2 H), 2.68 (s, 3 H), 2.95-3.03 (m, 4 H), 3.15-3.29 (m, 2 H), 3.50-3.61 (m, 2 H), 3.67-3.76 (m, 4 H), 4.33 (s, 2 H), 4.62-4.78 (m, 1 H), 7.15-7.24 (m, 3 H), 7.25-7.35 (m, 1 H), 7.35-7.42 (m, 2 H), 7.52-7.62 (m, 1 H), 7.74 (d, 1 H), 7.79-7.86 (m, 2 H), 8.04 (dd, 1 H), 8.26 (d, 1 H), 8.30-8.37 (m, 1 H), 8.97 (t, 1 H).

Example 8(3)

N-(1-{[6-(4-cyanophenoxy)-3-pyridinyl]methyl}-4-piperidinyl)-N-(3-fluorophenyl)-N'-(6-methyl-3-pyridinyl)urea TLC: Rf 0.30 (methanol:dichloromethane=1:19);
$^1$H-NMR (CDCl$_3$): δ1.33-1.51 (m, 2 H), 1.79-1.91 (m, 2 H), 2.09-2.22 (m, 2 H), 2.47 (s, 3 H), 2.82-2.94 (m, 2 H), 3.44 (s, 2 H), 4.47-4.61 (m, 1 H), 5.78 (s, 1 H), 6.93 (dd, 1 H), 6.96-7.02 (m, 1 H), 7.03-7.09 (m, 2 H), 7.18-7.28 (m, 3 H), 7.46-7.55 (m, 1 H), 7.63-7.71 (m, 3 H), 7.77 (dd, 1 H), 8.05 (d, 1 H), 8.11 (d, 1 H).

Example 8(4)

N-(3-fluorophenyl)-N'-(6-methyl-3-pyridinyl)-N-[1-({6-[4-(1H-tetrazol-5-yl)phenoxy]-3-pyridinyl}methyl)-4-piperidinyl]urea TLC: Rf 0.38 (methanol:dichloromethane=1:4);
$^1$H-NMR (d$_6$-DMSO): δ1.20-1.39 (m, 2 H), 1.72-1.85 (m, 2 H), 2.11-2.24 (m, 2 H), 2.34 (s, 3H), 2.81-2.95 (m, 2 H), 3.52 (s, 2 H), 4.23-4.39 (m, 1 H), 5.75 (s, 1 H), 6.99-7.10 (m, 3 H), 7.13-7.33 (m, 4 H), 7.45-7.54 (m, 1 H), 7.60-7.66 (m, 2 H), 7.75 (dd, 1 H), 7.98-8.05 (m, 3 H), 8.37 (d, 1 H).

Example 8(5)

4-[(5-{[4-((3-fluorophenyl){[(6-methyl-3-pyridinyl)amino]carbonyl}amino)-1-piperidinyl]methyl}-2-pyridinyl)oxy]-N-1H-tetrazol-5-ylbenzamide TLC: Rf 0.56 (water:methanol:dichloromethane=6:30:70);
$^1$H-NMR (d$_6$-DMSO): δ1.16-1.33 (m, 2 H), 1.70-1.81 (m, 2 H), 1.96-2.10 (m, 2 H), 2.34 (s, 3 H), 2.75-2.85 (m, 2 H), 3.32 (s, 2 H), 4.20-4.35 (m, 1 H), 7.01-7.32 (m, 8 H), 7.45-7.54 (m, 1 H), 7.60 (s, 1 H), 7.64 (dd, 1 H), 7.74 (dd, 1 H), 7.98-8.11 (m, 3 H), 8.37 (d, 1 H), 11.02 (s, 1 H).

Example 8(6)

N-[1-({6-[(2,2-dioxido-1H-2,1,3-benzothiadiazin-6-yl)oxy]-3-pyridinyl}methyl)-4-piperidinyl]-N-(3-fluorophenyl)-N'-(6-methyl-3-pyridinyl)urea TLC: Rf 0.10 (chloroform:methanol:aqueous ammonia=80:17:3);
$^1$H-NMR (CD$_3$OD): δ1.40-1.60 (m, 2H), 1.90-2.05 (m, 2H), 2.30-2.45 (m, 2H), 2.43 (s, 3H), 3.00-3.10 (m, 2H), 3.64 (s, 3H), 4.50 (m, 1H), 6.87 (d, 1H), 6.95 (d, 1H), 7.11-7.24 (m, 5H), 7.51 (m, 1H), 7.61 (m, 1H), 7.68-7.77 (m, 5H), 8.03 (d, 1H), 8.32 (d, 1H), 8.46 (s, 1H).

Example 8(7)

N,N'-bis(4-chlorophenyl)-N-[1-({6-[4-(methylsulfonyl)phenoxy]-3-pyridinyl}methyl)-4-piperidinyl]urea TLC: Rf 0.60 (ethyl acetate:methanol=95:5);
$^1$H-NMR (CDCl$_3$): δ1.29-1.45 (m, 2 H), 1.77-1.88 (m, 2 H), 2.08-2.21 (m, 2 H), 2.82-2.92 (m, 2 H), 3.06 (s, 3 H), 3.43 (s, 2 H), 4.47-4.59 (m, 1 H), 5.78 (s, 1 H), 6.95 (d, 1 H), 7.14-7.21 (m, 6 H), 7.28 (d, 2 H), 7.48 (d, 2 H), 7.68 (dd, 1 H), 7.95 (d, 2 H), 8.05 (d, 1 H).

Example 8(8)

N-{4-[(5-{[4-((4-chlorophenyl){[(4-chlorophenyl)amino]carbonyl}amino)-1-piperidinyl]methyl}-2-pyridinyl)oxy]phenyl}methane sulfonamide TLC: Rf 0.49 (chloroform:methanol=10:1);
$^1$H-NMR (CD$_3$OD): δ1.30-1.50 (m, 2H), 1.80-1.90 (m, 2H), 2.10-2.20 (m, 2H), 2.85-3.00 (m, 2H), 2.95 (s, 3H), 3.45 (s, 2H), 4.40 (m, 1H), 6.90 (d, J=8.4 Hz, 1H), 7.07 (d, 2H), 7.170-7.31 (m, 8H), 7.51 (d, 2H), 7.74 (d, 1H), 7.99 (d, 1H).

Example 8(9)

N-{1-[(6-{4-[(4-acetyl-1-piperazinyl)sulfonyl]phenoxy}-3-pyridinyl)methyl]-4-piperidinyl}-N-(3-fluorophenyl)-N'-(6-methyl-3-pyridinyl)urea TLC: Rf 0.65 (dichloromethane:methanol=9:1);
¹H-NMR (CDCl₃): δ1.33-1.51 (m, 2 H), 1.80-1.91 (m, 2 H), 2.04-2.07 (m, 3 H), 2.09-2.23 (m, 2 H), 2.47 (s, 3 H), 2.82-2.94 (m, 2 H), 2.97-3.09 (m, 4 H), 3.45 (s, 2 H), 3.52-3.60 (m, 2 H), 3.67-3.75 (m, 2 H), 4.48-4.61 (m, 1 H), 5.77 (s, 1 H), 6.95 (d, 1 H), 6.99 (dt, 1 H), 7.02-7.09 (m, 2 H), 7.18-7.29 (m, 3 H), 7.50 (td, 1 H), 7.69 (dd, 1 H), 7.71-7.80 (m, 3 H), 8.07 (d, 1 H), 8.12 (d, 1H).

Example 8(10)

N-(4-{[5-({4-[(anilinocarbonyl)(phenyl)amino]piperidin-1-yl}methyl)pyridin-2-yl]oxy}phenyl)methanesulfonamide TLC: Rf 0.56 (dichloromethane:methanol=9:1);
¹H-NMR (CD₃OD): δ1.62-1.80 (m, 2H), 2.15-2.24 (m, 2H), 2.97 (s, 3H), 3.12-3.23 (m, 2H), 3.49-3.57 (m, 2H), 4.27 (s, 2H), 4.68 (m, 1H), 6.97-7.14 (m, 5H), 7.18-7.22 (m, 4H), 7.28-7.38 (m, 4H), 7.48-7.60 (m, 3H), 7.89 (dd, 1H), 8.17 (d, 1H).

Example 8(11)

N-(3-fluorophenyl)-N'-(6-methyl-3-pyridinyl)-N-(1-{[6-(4-nitrophenoxy)-3-pyridinyl]methyl}-4-piperidinyl)urea TLC: Rf 0.52 (dichloromethane:methanol=9:1);
¹H-NMR (CDCl₃): δ1.34-1.52 (m, 2 H) 1.81-1.91 (m, 2 H) 2.10-2.23 (m, 2 H) 2.47 (s, 3 H) 2.84-2.94 (m, 2 H) 3.45 (s, 2 H) 4.48-4.62 (m, 1 H) 5.78 (s, 1 H) 6.94-7.09 (m, 4 H) 7.18-7.27 (m, 3 H) 7.46-7.55 (m, 1 H) 7.66-7.80 (m, 2 H) 8.07 (d, 1 H) 8.12 (d, 1 H) 8.21-8.31 (m, 2 H).

Example 8(12)

N-(3-fluorophenyl)-N'-(6-methyl-3-pyridinyl)-N-{1-[(6-{4-[(4-oxo-1-piperidinyl)sulfonyl]phenoxy}-3-pyridinyl)methyl]-4-piperidinyl}urea TLC: Rf 0.48 (dichloromethane:methanol=9:1);
¹H-NMR (CDCl₃): δ1.32-1.51 (m, 2 H), 1.78-1.93 (m, 2 H), 2.08-2.22 (m, 2 H), 2.47 (s, 3 H), 2.51-2.61 (m, 4 H), 2.82-2.94 (m, 2 H), 3.35-3.49 (m, 6 H), 4.46-4.62 (m, 1 H), 5.78 (s, 1 H), 6.94 (d, 1 H), 6.99 (dt, 1 H), 7.02-7.09 (m, 2 H), 7.18-7.30 (m, 3 H), 7.50 (td, 1 H), 7.69 (dd, 1 H), 7.73-7.84 (m, 3 H), 8.06 (d, 1 H), 8.12 (d, 1 H).

Example 8(13)

phenyl (3-fluorophenyl) {1-[(6-{4-[(methylsulfonyl)amino]phenoxy}-3-pyridinyl)methyl]-4-piperidinyl}carbamate TLC: Rf 0.58 (chloroform:methanol:aqueous ammonia=90:13:2);
¹H-NMR (CDCl₃): δ1.46-1.62 (m, 2 H), 1.85-1.95 (m, 2 H), 2.05-2.16 (m, 2 H), 2.84-2.93 (m, 2 H), 3.01 (s, 3 H), 3.41 (s, 2 H), 4.27 (tt, 1 H), 6.48 (s, 1 H), 6.86 (dd, 1 H), 6.94 (dt, 1 H), 6.99-7.19 (m, 7 H), 7.21-7.41 (m, 5 H), 7.63 (dd, 1 H), 8.01 (dd, 1 H).

Example 8(14)

phenyl {1-[(6-{4-[(methylsulfonyl)amino]phenoxy}-3-pyridinyl)methyl]-4-piperidinyl}phenylcarbamate

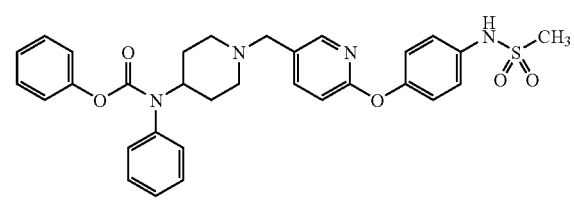

TLC: Rf 0.59 (chloroform:methanol:aqueous ammonia=90:13:2);
¹H-NMR (CDCl₃): δ1.46-1.64 (m, 2 H), 1.85-1.95 (m, 2 H), 2.05-2.16 (m, 2 H), 2.83-2.92 (m, 2 H), 3.00 (s, 3 H), 3.40 (s, 2 H), 4.28 (tt, 1 H), 6.58 (s, 1 H), 6.85 (d, 1 H), 6.98-7.43 (m, 14 H), 7.62 (dd, 1 H), 8.00 (d, 1 H).

Example 8(15)

2-(3-fluorophenyl)-N-(6-methyl-3-pyridinyl)-2-{1-[(6-{4-[(methylsulfonyl)amino]phenoxy}-3-pyridinyl)methyl]-4-piperidinyl}acetamide TLC: Rf 0.35 (dichloromethane:methanol=9:1);

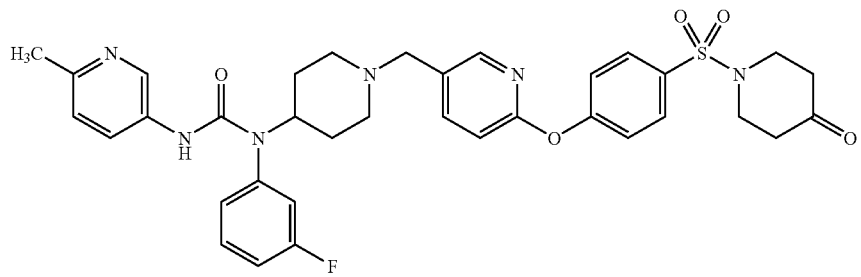

¹H-NMR (CDCl₃): δ1.05-1.44 (m, 3 H), 1.84-2.20 (m, 4 H), 2.49 (s, 3 H), 2.73-2.92 (m, 2 H), 3.02 (s, 3 H), 3.08 (d, 1 H), 3.43 (s, 2 H), 6.88 (d, 1 H), 6.93-7.01 (m, 1 H), 7.07-7.16 (m, 5 H), 7.22-7.33 (m, 4 H), 7.47 (brs, 1 H), 7.66 (dd, 1 H), 7.99-8.06 (m, 2 H), 8.36 (d, 1H).

Example 8(16)

2-(3-fluorophenyl)-N-(6-methyl-3-pyridinyl)-2-[1-({6-[4-(methylsulfonyl)phenoxy]-3-pyridinyl}methyl)-4-piperidinyl]acetamide TLC: Rf 0.38 (dichloromethane:methanol=9:1);
$^1$H-NMR (CDCl$_3$): δ1.05-1.46 (m, 3 H), 1.85-2.23 (m, 4 H), 2.49 (s, 3 H), 2.74-2.92 (m, 2 H), 3.05-3.12 (m, 4 H), 3.45 (s, 2 H), 6.93-7.02 (m, 2 H), 7.07-7.16 (m, 3 H), 7.25-7.45 (m, 4 H), 7.73 (dd, 1 H), 7.92-8.04 (m, 4 H), 8.09 (d, 1 H), 8.37 (d, 1 H).

Example 8(17)

2-(3-fluorophenyl)-2-{1-[(6-{4-[(methylsulfonyl)amino]phenoxy}-3-pyridinyl)methyl]-4-piperidinyl}-N-phenylacetamide TLC: Rf 0.47 (dichloromethane:methanol=9:1);
$^1$H-NMR (CDCl$_3$): δ1.04-1.43 (m, 3 H), 1.83-2.21 (m, 4 H), 2.72-2.91 (m, 2 H), 3.02 (s, 3 H), 3.04 (d, 1H), 3.43 (s, 2 H), 6.88 (dd, 1 H), 6.92-7.00 (m, 1 H), 7.05-7.17 (m, 5 H), 7.21-7.33 (m, 5 H), 7.43-7.50 (m, 2 H), 7.66 (dd, 1 H), 8.04 (d, 1 H).

Example 9

N-(4-{[5-({4-[(anilinocarbonyl)(phenyl)amino]-1-oxido-1-piperidinyl}methyl)-2-pyridinyl]oxy}phenyl)methanesulfonamide

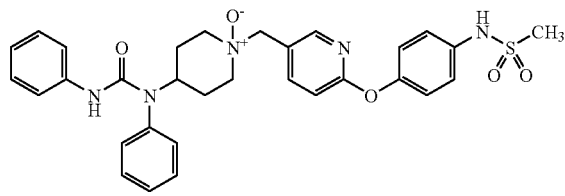

To a solution of the compound prepared in Example 8(10) (361 mg) in chloroform (6.1 ml) was added m-chloroperbenzoic acid (116 mg) on ice bath. The reaction mixture was stirred for 4 hours at room temperature. To reaction mixture was added a saturated aqueous solution of sodium hydrogen carbonate, and extracted with ethyl acetate. The organic layer was washed with brine, dried over anhydrous magnesium sulfate, and concentrated. The obtained residue was washed with chloroform and methanol, dried to give the compound of the present invention (194 mg) having the following physical data.
$^1$H-NMR (d$_6$-DMSO): δ1.60-1.80 (m, 2H), 1.90-2.00 (m, 2H), 2.70-2.80 (m, 2H), 2.96 (s, 3H), 3.30-3.50 (m, 2H), 4.21 (s, 2H), 4.50 (m, 1H), 6.90-6.98 (m, 2H), 7.10-7.30 (m, 10H), 7.41-7.49 (m, 3H), 7.94 (d, 1H), 8.14 (m, 1H).

Example 10

N-(3-fluorophenyl)-N-{1-[(6-{4-[(4-hydroxy-1-piperidinyl)sulfonyl]phenoxy}-3-pyridinyl)methyl]-4-piperidinyl}-N'-(6-methyl-3-pyridinyl)urea

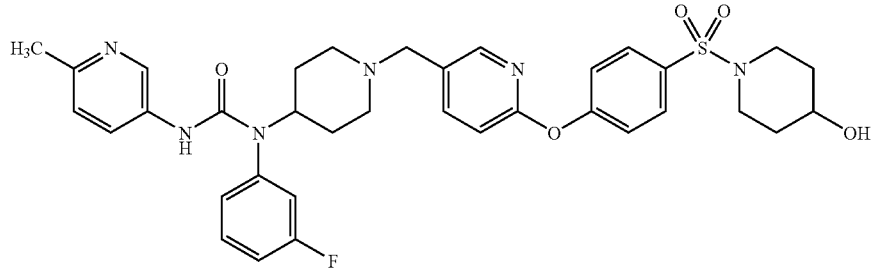

To a solution of the compound prepared in Example 8(12) (127 mg) in tetrahydrofuran (5 mL) and methanol (0.5 mL) was added sodium borohydride (7 mg). The reaction mixture was stirred for 15 minutes at room temperature. To reaction mixture was added a saturated aqueous solution of sodium hydrogen carbonate, and extracted with ethyl acetate. The organic layer was washed with water and brine, dried over anhydrous sodium sulfate, and concentrated. The obtained residue was purified by column chromatography on silica gel (ethyl acetate:methanol=15:1→10:1→dichloromethane:methanol=9:1) to give the compound of the present invention (106 mg) having the following physical data.
TLC: Rf 0.45 (dichloromethane:methanol=9:1);
$^1$H-NMR (CDCl$_3$): δ1.33-1.51 (m, 3 H), 1.53-1.75 (m, 2 H), 1.79-2.02 (m, 4 H), 2.08-2.22 (m, 2 H), 2.47 (s, 3 H), 2.81-2.95 (m, 4 H), 3.30-3.41 (m, 2 H), 3.45 (s, 2 H), 3.73-3.83 (m, 1 H), 4.47-4.61 (m, 1 H), 5.77 (s, 1 H), 6.93 (d, 1 H), 6.99 (dt, 1 H), 7.02-7.10 (m, 2 H), 7.16-7.31 (m, 3 H), 7.50 (td, 1 H), 7.68 (dd, 1 H), 7.72-7.81 (m, 3 H), 8.07 (d, 1 H), 8.11 (d, 1 H).

Example 11

1-(1-{[6-(4-aminophenoxy)pyridin-3-yl]methyl}piperidin-4-yl)-1-(3-fluorophenyl)-3-(6-methylpyridin-3-yl)urea To a solution of the compound prepared in Example 8(11) (611 mg) in ethanol (20 ml) was added 10% palladium on carbon (50% wet) (80 mg). The reaction mixture was stirred for 3.5 hours under atmosphere of hydrogen. The reaction mixture was passed through Celite (trade name), and the filtrate was concentrated. The obtained residue was purified by column chromatography on silica gel (methanol:dichloromethane=1:49) to give the compound of the present invention (526 mg) having the following physical data.
TLC: Rf 0.33 (methanol:dichloromethane=1:19);
$^1$H-NMR (CDCl$_3$): δ1.31-1.49 (m, 2 H), 1.78-1.89 (m, 2 H), 2.04-2.18 (m, 2 H), 2.46 (s, 3 H), 2.81-2.93 (m, 2 H), 3.38

(s, 2 H), 3.61 (brs, 2 H), 4.46-4.58 (m, 1 H), 5.77 (s, 1 H), 6.67-6.77 (m, 3 H), 6.89-7.07 (m, 5 H), 7.17-7.25 (m, 1 H), 7.45-7.56 (m, 2 H), 7.78 (dd, 1 H), 8.00 (d, 1 H), 8.10 (d, 1 H).

Example 12

N-(1-{[6-(4-{[(dimethylamino)sulfonyl]amino}phenoxy)-3-pyridinyl]methyl}-4-piperidinyl)-N-(3-fluorophenyl)-N'-(6-methyl-3-pyridinyl)urea To a solution of the compound prepared in Example 11 (393 mg) in dichloromethane (10 ml) were added triethylamine (0.31 ml) and N,N-dimethylsulfamoyl chloride (160 mg). The reaction mixture was stirred overnight at room temperature. The reaction mixture was washed with a saturated aqueous solution of sodium hydrogen carbonate, water and brine, dried over anhydrous magnesium sulfate, and concentrated. The obtained residue was purified by column chromatography on silica gel (methanol: dichloromethane=1:49) to give the compound of the present invention (98 mg) having the following physical data.

TLC: Rf 0.60 (dichloromethane:methanol=9:1);

$^1$H-NMR (CDCl$_3$): δ1.30-1.50 (m, 2 H), 1.78-1.90 (m, 2 H), 2.06-2.20 (m, 2 H), 2.47 (s, 3 H), 2.81-2.94 (m, 8 H), 3.41 (s, 2 H), 4.47-4.62 (m, 1 H), 5.77 (s, 1 H), 6.37 (s, 1 H), 6.83 (d, 1 H), 6.95-7.11 (m, 5 H), 7.17-7.28 (m, 3 H), 7.45-7.54 (m, 1 H), 7.57-7.65 (m, 1 H), 7.77 (dd, 1 H), 8.01 (d, 1 H), 8.11 (d, 1 H).

Examples 12(1)-12(3)

The procedure similar to that of Example 12 was carried out using a corresponding sulfonyl chloride in place of N,N-dimethylsulfamoyl chloride to obtain the following compound of the present invention.

Example 12(1)

N-(3-fluorophenyl)-N-(1-{[6-(4-{[(methylamino)sulfonyl]amino}phenoxy)-3-pyridinyl]methyl}-4-piperidinyl)-N'-(6-methyl-3-pyridinyl)urea TLC: Rf 0.31 (methanol:dichloromethane=1:19);

$^1$H-NMR (CDCl$_3$): δ1.32-1.49 (m, 2 H), 1.79-1.89 (m, 2 H), 2.07-2.19 (m, 2 H), 2.46 (s, 3 H), 2.75 (s, 3 H), 2.83-2.92 (m, 2 H), 3.41 (s, 2 H), 4.46-4.59 (m, 2 H), 5.78 (s, 1 H), 6.58 (s, 1 H), 6.85 (dd, 1 H), 6.96-7.01 (m, 1 H), 7.03-7.12 (m, 4 H), 7.18-7.26 (m, 3 H), 7.45-7.54 (m, 1 H), 7.61 (dd, 1 H), 7.77 (dd, 1 H), 8.00 (d, 1 H), 8.11 (d, 1 H).

Example 12(2)

N-{1-[(6-{4-[(aminosulfonyl)amino]phenoxy}-3-pyridinyl)methyl]-4-piperidinyl}-N-(3-fluorophenyl)-N'-(6-methyl-3-pyridinyl)urea TLC: Rf 0.41 (dichloromethane:methanol=9:1);

$^1$H-NMR (CDCl$_3$): δ1.32-1.50 (m, 2 H), 1.77-1.89 (m, 2 H), 2.05-2.19 (m, 2 H), 2.46 (s, 3 H), 2.80-2.93 (m, 2 H), 3.40 (s, 2 H), 4.43-4.58 (m, 1 H), 4.96 (brs, 2 H), 5.79 (s, 1 H), 6.86 (d, 1 H), 6.95-7.01 (m, 1 H), 7.02-7.10 (m, 4 H), 7.16-7.27 (m, 3 H), 7.44-7.53 (m, 1 H), 7.61 (dd, 1 H), 7.75 (dd, 1 H), 7.98 (d, 1 H), 8.12 (d, 1H).

Example 12(3)

N-{4-[(5-{[4-((3-fluorophenyl){[(6-methyl-3-pyridinyl)amino]carbonyl}amino)-1-piperidinyl]methyl}-2-pyridinyl)oxy]phenyl}-2-(4-morpholinyl)ethanesulfonamide TLC: Rf 0.49 (dichloromethane:methanol=9:1);

$^1$H-NMR (CDCl$_3$): δ1.33-1.49 (m, 2 H), 1.79-1.90 (m, 2 H), 2.07-2.19 (m, 2 H), 2.47 (s, 3 H), 2.49-2.55 (m, 4 H), 2.83-2.95 (m, 4 H), 3.26 (t, 2 H), 3.41 (s, 2 H), 3.68-3.76 (m, 4 H), 4.46-4.60 (m, 1 H), 5.77 (s, 1 H), 6.85 (dd, 1 H), 6.96-7.01 (m, 1 H), 7.03-7.13 (m, 4 H), 7.18-7.27 (m, 4 H), 7.45-7.55 (m, 1 H), 7.61 (dd, 1 H), 7.77 (dd, 1 H), 8.01 (d, 1 H), 8.11 (d, 1 H).

Example 13

N-(3-fluorophenyl)-N-(1-{[6-(4-{[(methylamino)carbonothioyl]amino}phenoxy)-3-pyridinyl]methyl}-4-piperidinyl)-N'-(6-methyl-3-pyridinyl)urea To a solution of the compound prepared in Example 11 (154 mg) in tetrahydrofuran (5 ml) was added methyl isothiocyanate (24 mg). The reaction mixture was refluxed for 6 hours, then concentrated. The obtained residue was purified by column chromatography on silica gel (methanol: dichloromethane=1:49) to give the compound of the present invention (140 mg) having the following physical data.

TLC: Rf 0.58 (dichloromethane:methanol=9:1);

$^1$H-NMR (CDCl$_3$): δ1.33-1.50 (m, 2 H), 1.80-1.89 (m, 2 H), 2.09-2.20 (m, 2 H), 2.47 (s, 3 H), 2.83-2.93 (m, 2 H), 3.14 (d, 3 H), 3.42 (s, 2 H), 4.47-4.60 (m, 1 H), 5.77 (s, 1 H), 6.03 (d, 1 H), 6.92 (d, 1 H), 6.96-7.02 (m, 1 H), 7.03-7.08 (m, 2 H), 7.15-7.26 (m, 5 H), 7.45-7.56 (m, 2 H), 7.65 (dd, 1 H), 7.77 (dd, 1 H), 8.01 (d, 1 H), 8.11 (d, 1 H).

Example 13(1)

N-(3-fluorophenyl)-N'-(6-methyl-3-pyridinyl)-N-{1-[(6-{4-[({[2-(4-morpholinyl)ethyl]amino}carbonothioyl)amino]phenoxy}-3-pyridinyl)methyl]-4-piperidinyl}urea The procedure similar to that of Example 13 was carried out using 2-(4-morpholino)ethyl isocyanate in place of methyl isothiocyanate to obtain the compound of the present invention having the following physical data.

TLC: Rf 0.50 (dichloromethane:methanol=9:1);

$^1$H-NMR (CDCl$_3$): δ1.33-1.50 (m, 2 H), 1.78-1.90 (m, 2 H), 2.08-2.20 (m, 2 H), 2.36-2.44 (m, 4 H), 2.46 (s, 3 H), 2.54 (t, 2 H), 2.83-2.92 (m, 2 H), 3.42 (s, 2 H), 3.51-3.60 (m, 4 H), 3.63-3.74 (m, 2 H), 4.47-4.59 (m, 1 H), 5.77 (s, 1 H), 6.88-7.08 (m, 5 H), 7.16-7.27 (m, 5 H), 7.46-7.60 (m, 2 H), 7.64 (dd, 1 H), 7.77 (dd, 1 H), 7.99 (d, 1 H), 8.11 (d, 1 H).

Example 14 benzyl [({4-[(5-{[4-((3-fluorophenyl){[(6-methyl-3-pyridinyl)amino]carbonyl}amino)-1-piperidinyl]methyl}-2-pyridinyl)oxy]phenyl}amino)sulfonyl]carbamate

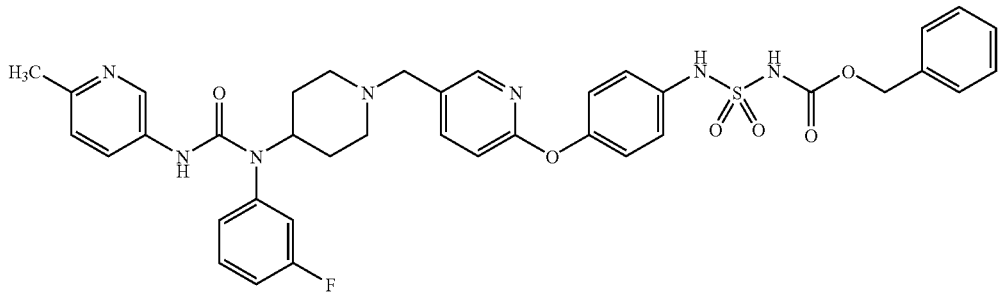

To a solution of chlorosulfonyl isocyanate (75 µL) in dichloromethane (2 mL) was added benzyl alcohol (89 µL) under atmosphere of argon on ice bath. The reaction mixture was stirred for 1.5 hours. To a mixture were added the compound prepared in Example 11 (430 mg) and triethylamine (904 µL), and the mixture was stirred overnight. To reaction mixture was added a saturated aqueous solution of ammonium chloride, and extracted with dichloromethane. The organic layer was washed with brine, dried over anhydrous magnesium sulfate, and concentrated. The obtained residue was purified by column chromatography on silica gel (ethyl acetate→ethyl acetate:methanol=5:1) to give the compound of the present invention (446 mg) having the following physical data.

TLC: Rf 0.44 (dichloromethane:methanol=10:1);

$^1$H-NMR ($d_6$-DMSO): δ1.20-1.40 (m, 2H), 1.75-1.90 (m, 2H), 2.20-2.40 (m, 2H), 2.34 (s, 3H), 2.85-2.95 (m, 2H), 3.56 (brd, 2H), 4.33 (m, 1H), 5.04 (s, 2H), 6.93 (d, 1H), 6.99-7.18 (m, 8H), 7.25-7.33 (m, 7H), 7.49 (m, 1H), 7.61-7.65 (m, 2H), 7.72 (m, 1H), 7.98 (brd, 1H), 8.37 (d, 1H).

Example 14(1)

N-[1-({6-[4-(4,4-dioxido-2-oxo-1,4,3,5-oxathiadiazepan-5-yl)phenoxy]-3-pyridinyl}methyl)-4-piperidinyl]-N-(3-fluorophenyl)-N'-(6-methyl-3-pyridinyl)urea

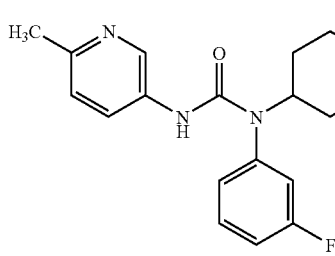

The procedure similar to that of Example 14 was carried out using 2-chloroethanol in place of benzyl alcohol to obtain the title compound having the following physical data.

TLC: Rf 0.40 (dichloromethane:methanol=10:1);

$^1$H-NMR ($d_6$-DMSO): δ1.10-1.30 (m, 2H), 1.70-1.80 (m, 2H), 2.00-2.10 (m, 2H), 2.34 (s, 3H), 2.70-2.90 (m, 2H), 3.40 (s, 2H), 3.87 (t, 2H), 4.25 (m, 1H), 4.31 (t, 2H), 6.93 (d, 1H), 7.05-7.20 (m, 7H), 7.28 (m, 1H), 7.49 (m, 1H), 7.59 (s, 1H), 7.63 (dd, 1H), 7.68 (dd, 1H), 7.96 (d, 1H), 8.37 (d, 1H), 10.89 (brd, 1H).

Examples 15(1)-15(11)

The procedure similar to that of Example 8 was carried out using the compound prepared in Example 7 or a corresponding amine compound, and a corresponding aldehyde compound in place of the compound prepared in Example 4 to obtain the following compound of the present invention.

Example 15(1)

4-[(5-{[4-((3-fluorophenyl){[(6-methyl-3-pyridinyl)amino]carbonyl}amino)-1-piperidinyl]methyl}-2-pyridinyl)oxy]-N-(2-hydroxyethyl)benzenesulfonamide

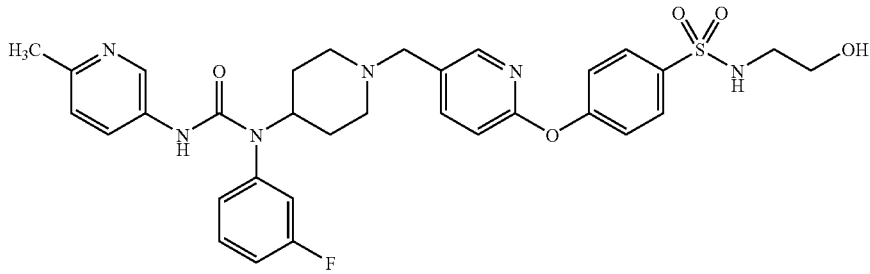

TLC: Rf 0.42 (dichloromethane:methanol=9:1);
¹H-NMR (CDCl₃): δ1.33-1.51 (m, 2 H), 1.79-1.92 (m, 2 H), 2.08-2.23 (m, 2 H), 2.47 (s, 3 H), 2.82-2.95 (m, 2 H), 3.08-3.18 (m, 2 H), 3.44 (s, 2 H), 3.72 (t, 2 H), 4.47-4.61 (m, 1 H), 4.89 (t, 1 H), 5.78 (s, 1 H), 6.94 (d, 1 H), 6.99 (dt, 1 H), 7.03-7.10 (m, 2 H), 7.17-7.29 (m, 3 H), 7.45-7.55 (m, 1 H), 7.68 (dd, 1 H), 7.77 (dd, 1 H), 7.84-7.91 (m, 2 H), 8.05 (d, 1 H), 8.11 (d, 1 H).

Example 15(2)

N-[1-({6-[4-(1,1-dioxido-1,2,6-thiadiazinan-2-yl)phenoxy]-3-pyridinyl}methyl)-4-piperidinyl]-N-(3-fluorophenyl)-N'-(6-methyl-3-pyridinyl)urea TLC: Rf 0.40 (dichloromethane:methanol=10:1);
¹H-NMR (CD₃OD): δ1.40-1.50 (m, 2H), 1.80-2.00 (m, 4H), 2.20-2.35 (m, 2H), 2.43 (s, 3H), 2.90-3.05 (m, 2H), 3.40 (s, 2H), 3.51 (t, 2H), 3.52 (s, 2H), 3.69 (t, 2H), 4.43 (m, 1H), 6.92 (d, 1H), 7.08-7.18 (m, 5H), 7.24 (m, 1H), 7.39-7.54 (m, 3H), 7.68 (dd, 1H), 7.76 (dd, 1H), 8.02 (d, 1H), 8.32 (d, 1H).

Example 15(3)

N-(3-fluorophenyl)-N-[1-({6-[4-(6-methyl-1,1-dioxido-1,2,6-thiadiazinan-2-yl)phenoxy]-3-pyridinyl}methyl)-4-piperidinyl]-N'-(6-methyl-3-pyridinyl)urea TLC: Rf 0.44 (dichloromethane:methanol=10:1);
¹H-NMR (CD₃OD): δ1.35-1.50 (m, 2H), 1.80-2.00 (m, 4H), 2.10-2.25 (m, 2H), 2.43 (s, 3H), 2.85-2.95 (m, 2H), 2.94 (s, 3H), 3.47 (s, 2H), 3.66 (t, 2H), 3.72 (t, 2H), 4.40 (m, 1H), 6.92 (d, 1H), 7.08-7.18 (m, 5H), 7.24 (m, 1H), 7.39-7.56 (m, 3H), 7.68 (dd, 1H), 7.76 (dd, 1H), 8.01 (d, 1H), 8.32 (d, 1H).

Example 15(4)

N-(3-fluorophenyl)-N-{1-[(6-{4-[6-(2-methoxyethyl)-1,1-dioxido-1,2,6-thiadiazinan-2-yl]phenoxy}-3-pyridinyl)methyl]-4-piperidinyl}-N'-(6-methyl-3-pyridinyl)urea TLC: Rf 0.45 (dichloromethane:methanol=10:1);
¹H-NMR (CD₃OD): δ1.35-1.50 (m, 2H), 1.80-2.00 (m, 4H), 2.10-2.25 (m, 2H), 2.43 (s, 3H), 2.85-2.95 (m, 2H), 3.37 (s, 3H), 3.48 (s, 2H), 3.46 (t, 2H), 3.59 (t, 2H), 3.70-3.80 (m, 4H), 4.40 (m, 1H), 6.92 (d, 1H), 7.08-7.18 (m, 5H), 7.24 (m, 1H), 7.40-7.53 (m, 3H), 7.68 (dd, 1H), 7.76 (dd, 1H), 8.01 (d, 1H), 8.32 (d, 1H).

Example 15(5)

2-hydroxy-N-{1-[(6-{4-[(methylsulfonyl)amino]phenoxy}-3-pyridinyl)methyl]-4-piperidinyl}-N,2-diphenylacetamide TLC: Rf 0.59 (dichloromethane:methanol=9:1);
¹H-NMR (CDCl₃): δ1.23-1.42 (m, 2H), 1.68-1.80 (m, 2H), 2.03-2.20 (m, 2H), 2.77-2.88 (m, 2H), 3.01 (s, 3H), 3.38 (s, 2H), 4.50 (d, 1H), 4.57-4.69 (m, 1H), 4.75 (d, 1H), 6.13-6.18 (m, 1H), 6.45 (brs, 1H), 6.76-6.86 (m, 3H), 6.96-7.03 (m, 1H), 7.07-7.28 (m, 8H), 7.29-7.36 (m, 1H), 7.38-7.45 (m, 1H), 7.58 (dd, 1H), 7.98 (d, 1H).

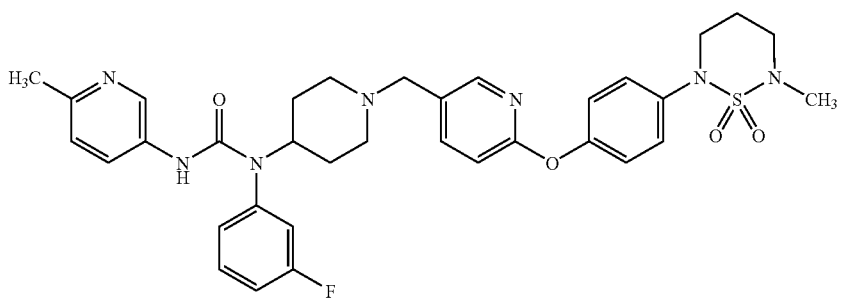

Example 15(6)

4-[(5-{[4-((3-fluorophenyl){[(6-methyl-3-pyridinyl)amino]carbonyl}amino)-1-piperidinyl]methyl}-2-pyridinyl)oxy]-N-(2-hydroxy-2-methylpropyl)benzenesulfonamide

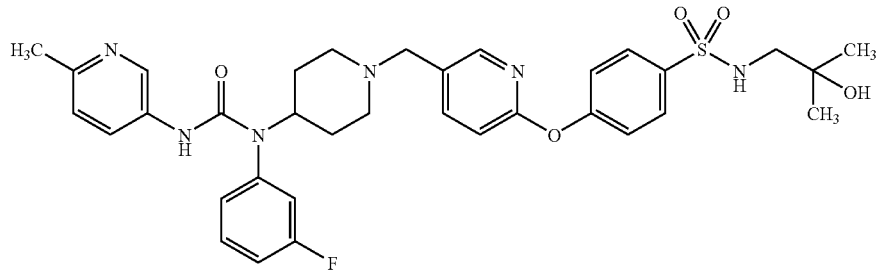

TLC: Rf 0.20 (ethyl acetate:methanol=9:1);
¹H-NMR (CDCl₃): δ1.25 (s, 6 H), 1.30-1.51 (m, 2 H), 1.79-1.91 (m, 2 H), 2.09-2.22 (m, 2 H), 2.47 (s, 3 H), 2.83-2.95 (m, 4 H), 3.44 (s, 2 H), 4.48-4.61 (m, 1 H), 4.82 (t, 1 H), 5.78 (s, 1 H), 6.93 (d, 1 H), 6.99 (dt, 1 H), 7.02-7.10 (m, 2 H), 7.17-7.29 (m, 3 H), 7.45-7.55 (m, 1 H), 7.68 (dd, 1 H), 7.77 (dd, 1 H), 7.82-7.90 (m, 2 H), 8.06 (d, 1 H), 8.11 (d, 1 H).

Example 15(7)

N-(3-fluorophenyl)-2-hydroxy-N-{1-[(6-{4-[(methylsulfonyl)amino]phenoxy}-3-pyridinyl)methyl]-4-piperidinyl}-2-phenylacetamide TLC: Rf 0.30 (dichloromethane:methanol=19:1);
¹H-NMR (CDCl₃): δ1.20-1.41 (m, 2 H), 1.67-1.79 (m, 2 H), 2.05-2.18 (m, 2 H), 2.77-2.90 (m, 2 H), 3.01 (s, 3 H), 3.39 (s, 2 H), 4.41-4.53 (m, 1 H), 4.57-4.69 (m, 1 H), 4.72-4.79 (m, 1 H), 5.77-5.98 (m, 1 H), 6.41 (brs, 1 H), 6.76-7.44 (m, 13 H), 7.59 (dd, 1 H), 7.98 (d, 1 H).

Example 15(8)

4-[(5-{[4-((3-fluorophenyl){[(6-methyl-3-pyridinyl)amino]carbonyl}amino)-1-piperidinyl]methyl}-2-pyridinyl)oxy]-N-(3-methoxypropyl)benzenesulfonamide TLC: Rf 0.28 (ethyl acetate:methanol=9:1);
¹H-NMR (CDCl₃): δ1.32-1.51 (m, 2 H), 1.69-1.80 (m, 2 H), 1.80-1.92 (m, 2 H), 2.07-2.23 (m, 2 H), 2.47 (s, 3 H), 2.82-2.94 (m, 2 H), 3.11 (q, 2 H), 3.30 (s, 3 H), 3.37-3.48 (m, 4 H), 4.47-4.62 (m, 1 H), 5.11 (t, 1 H), 5.78 (s, 1 H), 6.93 (d, 1 H), 6.99 (dt, 1 H), 7.02-7.10 (m, 2 H), 7.16-7.30 (m, 3 H), 7.44-7.56 (m, 1 H), 7.68 (dd, 1 H), 7.77 (dd, 1 H), 7.82-7.91 (m, 2 H), 8.06 (d, 1 H), 8.11 (d, 1 H).

Example 15(9)

N-(3-fluorophenyl)-N-{1-[(6-{4-[(2-hydroxyethyl)sulfonyl]phenoxy}-3-pyridinyl)methyl]-4-piperidinyl}-N'-(6-methyl-3-pyridinyl)urea TLC: Rf 0.53 (chloroform:methanol:aqueous ammonia=90:13:2);
¹H-NMR (CDCl₃): δ1.33-1.50 (m, 2 H) 1.80-1.90 (m, 2 H) 2.10-2.21 (m, 2 H) 2.46 (s, 3 H) 2.81-2.96 (m, 3 H) 3.32-3.38 (m, 2 H) 3.44 (s, 2 H) 3.99-4.06 (m, 2 H) 4.54 (tt, 1 H) 5.78 (s, 1 H) 6.93-7.09 (m, 4 H) 7.18-7.26 (m, 1 H) 7.30 (d, 2 H) 7.50 (dt, 1 H) 7.70 (dd, 1 H) 7.77 (dd, 1 H) 7.93 (d, 2 H) 8.06 (d, 1 H) 8.11 (d, 1 H).

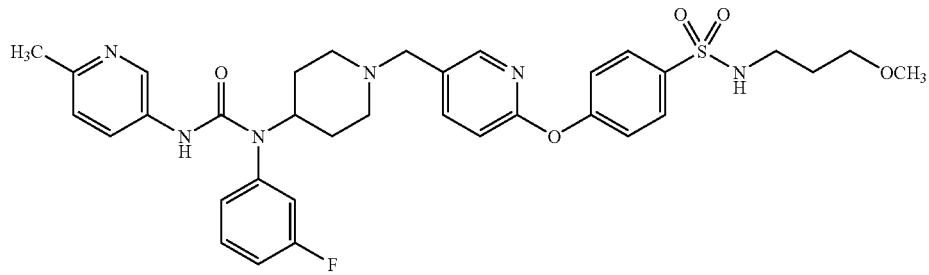

Example 15(10)

N-{4-[(5-{[4-((3-fluorophenyl){[(6-methyl-3-pyridinyl)amino]carbonyl}amino)-1-piperidinyl]methyl}-2-pyridinyl)oxy]phenyl}cyclopropanesulfonamide

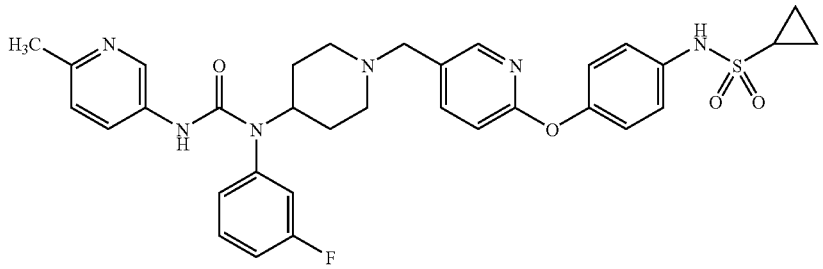

TLC: Rf 0.62 (dichloromethane:methanol=9:1);
$^1$H-NMR (CDCl$_3$): δ0.93-1.02 (m, 2 H), 1.14-1.22 (m, 2 H), 1.33-1.49 (m, 2 H), 1.79-1.89 (m, 2 H), 2.07-2.19 (m, 2 H), 2.42-2.54 (m, 4 H), 2.82-2.93 (m, 2 H), 3.41 (s, 2 H), 4.46-4.60 (m, 1 H), 5.77 (s, 1 H), 6.35 (s, 1 H), 6.85 (d, 1 H), 6.96-7.01 (m, 1 H), 7.02-7.12 (m, 4 H), 7.18-7.31 (m, 3 H), 7.45-7.53 (m, 1 H), 7.61 (dd, 1 H), 7.77 (dd, 1 H), 8.01 (d, 1 H), 8.11 (d, 1 H).

Example 15(11)

4-[(5-{[4-((3-fluorophenyl){[(6-methyl-3-pyridinyl)amino]carbonyl}amino)-1-piperidinyl]methyl}-2-pyridinyl)oxy]-N-(3-hydroxy-3-methylbutyl)benzenesulfonamide

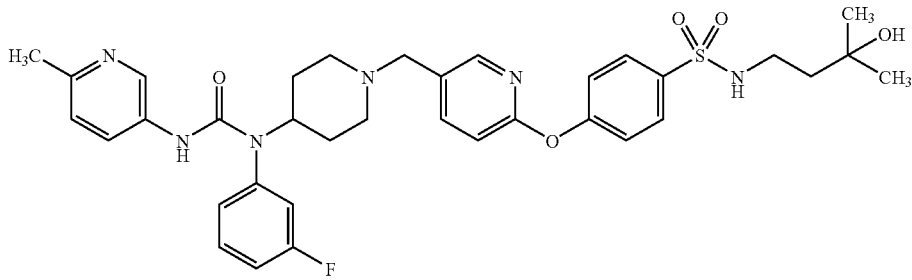

TLC: Rf 0.24 (ethyl acetate:methanol=9:1);
$^1$H-NMR (CDCl$_3$): δ1.19 (s, 6 H), 1.32-1.52 (m, 2 H), 1.65 (t, 2 H), 1.79-1.92 (m, 2 H), 2.09-2.22 (m, 2 H), 2.46 (s, 3 H), 2.82-2.94 (m, 2 H), 3.10-3.19 (m, 2 H), 3.44 (s, 2 H), 4.47-4.61 (m, 1 H), 5.47 (t, 1 H), 5.78 (s, 1 H), 6.92 (d, 1 H), 6.99 (dt, 1 H), 7.02-7.09 (m, 2 H), 7.17-7.28 (m, 3 H), 7.50 (td, 1 H), 7.67 (dd, 1 H), 7.77 (dd, 1 H), 7.83-7.91 (m, 2 H), 8.05 (d, 1 H), 8.11 (d, 1 H).

Examples 16(1)-16(138)

The procedure similar to that of Example 8 was carried out using the compound prepared in Example 7 or a corresponding amine compound, and a corresponding aldehyde compound in place of the compound prepared in Example 4 to obtain the following compound of the present invention.

Example 16(1)

N-(3-fluorophenyl)-N-{1-[(6-{4-[(3-hydroxypropyl)sulfonyl]phenoxy}-3-pyridinyl)methyl]-4-piperidinyl}-N'-(6-methyl-3-pyridinyl)urea TLC: Rf 0.50 (chloroform:methanol:aqueous ammonia=90:13:2);
$^1$H-NMR (CDCl$_3$): δ 1.34-1.50 (m, 2H), 1.80-1.90 (m, 2H), 1.96-2.06 (m, 2H), 2.10-2.21 (m, 2H), 2.46 (s, 3H), 2.84-2.93 (m, 2H), 3.21-3.28 (m, 2H), 3.44 (s, 2H), 3.75 (t, J=6.0 Hz, 2H), 4.54 (tt, J=12.0, 4.0 Hz, 1H), 5.78 (s, 1H), 6.92-7.01 (m, 2H), 7.02-7.09 (m, 2H), 7.18-7.25 (m, 1H), 7.27 (d, J=9.0 Hz, 2H), 7.50 (dt, J=6.5, 8.0 Hz, 1H), 7.69 (dd, J=8.5, 2.5 Hz, 1H), 7.77 (dd, J=8.5, 2.5 Hz, 1H), 7.91 (d, J=9.0 Hz, 2H), 8.06 (d, J=2.5 Hz, 1H), 8.11 (d, J=2.5 Hz, 1H).

Example 16(2)

N-(2-methoxyethyl)-4-[(5-{[4-((6-methyl-3-pyridinyl){[(6-methyl-3-pyridinyl)amino]carbonyl}amino)-1-piperidinyl]methyl}-2-pyridinyl)oxy]benzenesulfonamide TLC: Rf 0.43 (dichloromethane:methanol=9:1);
$^1$H-NMR (CDCl$_3$): δ 1.26-1.44 (m, 2H), 1.79-1.91 (m, 2H), 2.10-2.22 (m, 2H), 2.47 (s, 3H), 2.66 (s, 3H), 2.83-2.92

(m, 2H), 3.11-3.18 (m, 2H), 3.29 (s, 3H), 3.40-3.45 (m, 4H), 4.50-4.62 (m, 1H), 4.81 (t, J=6.0 Hz, 1H), 5.70 (s, 1H), 6.92 (d, J=8.2 Hz, 1H), 7.05 (d, J=8.2 Hz, 1H), 7.19-7.27 (m, 2H), 7.32 (d, J=8.2 Hz, 1H), 7.47 (dd, J=8.2, 2.6 Hz, 1H), 7.66 (dd, J=8.2, 2.4 Hz, 1H), 7.76 (dd, J=8.2, 2.6 Hz, 1H), 7.82-7.89 (m, 2H), 8.04 (d, J=2.4 Hz, 1H), 8.12 (d, J=2.6 Hz, 1H), 8.40 (d, J=2.6 Hz, 1H).

Example 16(3)

N-{1-[(6-{4-[(4-hydroxy-1-piperidinyl)sulfonyl]phenoxy}-3-pyridinyl)methyl]-4-piperidinyl}-N,N'-bis(6-methyl-3-pyridinyl)urea TLC: Rf 0.20 (dichloromethane:methanol=9:1);
$^1$H-NMR (CDCl$_3$): δ 1.27-1.44 (m, 2H), 1.57-1.74 (m, 2H), 1.80-2.01 (m, 4H), 2.10-2.22 (m, 2H), 2.47 (s, 3H), 2.66 (s, 3H), 2.82-2.94 (m, 4H), 3.31-3.40 (m, 2H), 3.44 (s, 2H), 3.72-3.84 (m, 1H), 4.48-4.66 (m, 1H), 5.70 (s, 1H), 6.93 (d, J=8.2 Hz, 1H), 7.05 (d, J=8.4 Hz, 1H), 7.21-7.27 (m, 2H), 7.32 (d, J=8.2 Hz, 1H), 7.47 (dd, J=8.2, 2.6 Hz, 1H), 7.67 (dd, J=8.4, 2.4 Hz, 1H), 7.72-7.79 (m, 3H), 8.06 (d, J=2.4 Hz, 1H), 8.12 (d, J=2.6 Hz, 1H), 8.40 (d, J=2.6 Hz, 1H).

Example 16(4)

4-[(5-{[4-((4-chlorophenyl){[(6-methyl-3-pyridinyl)amino]carbonyl}amino)-1-piperidinyl]methyl}-2-pyridinyl)oxy]-N-(2-methoxyethyl)benzenesulfonamide TLC: Rf 0.35 (chloroform:methanol=10:1);
$^1$H-NMR (CDCl$_3$): δ 1.35-1.40 (m, 2H), 1.75-1.90 (m, 2H), 2.10-2.20 (m, 2H), 2.47 (s, 3H), 2.80-2.90 (m, 2H), 3.14 (q, J=5.4 Hz, 2H), 3.29 (s, 3H), 3.43 (t, J=5.4 Hz, 2H), 3.43 (s, 2H), 4.54 (m, 1H), 4.81 (m, 1H), 5.74 (s, 1H), 6.92 (d, J=8.4 Hz, 1H), 7.05 (d, J=8.4 Hz, 1H), 7.17-7.26 (m, 4H), 7.49 (d, J=8.4 Hz, 2H), 7.66 (dd, J=8.4, 2.4 Hz, 1H), 7.76 (dd, J=8.4, 2.9 Hz, 1H), 7.86 (d, J=8.7 Hz, 2H), 8.01 (d, J=2.4 Hz, 1H), 8.32 (d, J=2.9 Hz, 1H).

Example 16(5)

N-{1-[(6-{4-[(4-methyl-1-piperazinyl)sulfonyl]phenoxy}-3-pyridinyl)methyl]-4-piperidinyl}-N,N'-bis(6-methyl-3-pyridinyl)urea TLC: Rf 0.30 (dichloromethane:methanol=85:15);
$^1$H-NMR (CDCl$_3$): δ 1.28-1.43 (m, 2H), 1.80-1.90 (m, 2H), 2.10-2.21 (m, 2H), 2.28 (s, 3H), 2.44-2.53 (m, 7H), 2.66 (s, 3H), 2.83-2.93 (m, 2H), 3.01-3.12 (m, 4H), 3.43 (s, 2H), 4.51-4.63 (m, 1H), 5.69 (s, 1H), 6.91 (d, J=8.4 Hz, 1H), 7.05 (d, J=8.4 Hz, 1H), 7.20-7.27 (m, 2H), 7.32 (d, J=8.2 Hz, 1H), 7.47 (dd, J=8.2, 2.6 Hz, 1H), 7.65 (dd, J=8.4, 2.2 Hz, 1H), 7.72-7.79 (m, 3H), 8.04 (d, J=2.2 Hz, 1H), 8.12 (d, J=2.6 Hz, 1H), 8.40 (d, J=2.0 Hz, 1H).

Example 16(6)

4-{[5-({4-[{[(5-chloro-2-pyridinyl)amino]carbonyl}(6-methyl-3-pyridinyl)amino]-1-piperidinyl}methyl)-2-pyridinyl]oxy}-N-(2-methoxyethyl)benzenesulfonamide TLC: Rf 0.45 (dichloromethane:methanol=9:1);
$^1$H-NMR (CDCl$_3$): δ 1.28-1.43 (m, 2H), 1.79-1.89 (m, 2H), 2.10-2.21 (m, 2H), 2.64 (s, 3H), 2.84-2.92 (m, 2H), 3.12-3.17 (m, 2H), 3.29 (s, 3H), 3.41-3.45 (m, 4H), 4.49-4.61 (m, 1H), 4.81 (t, J=6.0 Hz, 1H), 6.56 (s, 1H), 6.92 (d, J=8.4 Hz, 1H), 7.20-7.25 (m, 2H), 7.30 (d, J=8.2 Hz, 1H), 7.44 (dd, J=8.2, 2.6 Hz, 1H), 7.60 (dd, J=8.8, 2.4 Hz, 1H), 7.66 (dd, J=8.4, 2.4 Hz, 1H), 7.83-7.89 (m, 2H), 8.02-8.05 (m, 2H), 8.09 (dd, J=8.8, 0.7 Hz, 1H), 8.37 (d, J=2.4 Hz, 1H).

Example 16(7)

5-({[(4-chlorophenyl)(1-{[6-(4-{[(2-methoxyethyl)amino]sulfonyl}phenoxy)-3-pyridinyl]methyl}-4-piperidinyl)amino]carbonyl}amino)-2-fluorobenzamide TLC: Rf 0.49 (chloroform:methanol=10:1);
$^1$H-NMR (CDCl$_3$): δ 1.35-1.40 (m, 2H), 1.75-1.90 (m, 2H), 2.10-2.20 (m, 2H), 2.80-2.90 (m, 2H), 3.14 (q, J=5.4 Hz, 2H), 3.29 (s, 3H), 3.43 (t, J=5.4 Hz, 2H), 3.43 (s, 2H), 4.29 (m, 1H), 4.52 (m, 1H), 4.82 (m, 1H), 5.76 (s, 1H), 5.92 (s, 1H), 6.68 (m, 1H), 6.92 (d, J=8.7 Hz, 1H), 7.04-7.26 (m, 5H), 7.38 (m, 1H), 7.47-7.54 (m, 2H), 7.67 (m, 1H), 7.83 (d, J=8.7 Hz, 2H), 8.00-8.05 (m, 2H).

Example 16(8)

5-{[((4-chlorophenyl){1-[(6-{4-[(4-hydroxy-1-piperidinyl)sulfonyl]phenoxy}-3-pyridinyl)methyl]-4-piperidinyl}amino)carbonyl]amino}-2-fluorobenzamide TLC: Rf 0.45 (chloroform:methanol=10:1);
$^1$H-NMR (CDCl$_3$): δ 1.35-1.40 (m, 2H), 1.60-1.75 (m, 2H), 1.75-1.90 (m, 2H), 1.90-2.00 (m, 2H), 2.10-2.20 (m, 2H), 2.80-2.90 (m, 4H), 3.10-3.20 (m, 2H), 3.77 (m, 1H), 4.52 (m, 1H), 5.73 (s, 1H), 5.92 (s, 1H), 6.68 (m, 1H), 6.93 (d, J=8.4 Hz, 1H), 7.04-7.26 (m, 5H), 7.38 (m, 1H), 7.48 (d, J=8.6 Hz, 2H), 7.67 (dd, J=8.4, 2.3 Hz, 1H), 7.76 (d, J=8.6 Hz, 2H), 8.00-8.05 (m, 2H).

Example 16(9)

N'-(5-chloro-2-pyridinyl)-N-{1-[(6-{4-[(4-hydroxy-1-piperidinyl)sulfonyl]phenoxy}-3-pyridinyl)methyl]-4-piperidinyl}-N-(6-methyl-3-pyridinyl)urea TLC: Rf 0.49 (dichloromethane:methanol=9:1);
$^1$H-NMR (CDCl$_3$): δ 1.28-1.44 (m, 3H), 1.61-1.73 (m, 2H), 1.80-2.00 (m, 4H), 2.10-2.22 (m, 2H), 2.64 (s, 3H), 2.83-2.94 (m, 4H), 3.31-3.41 (m, 2H), 3.44 (s, 2H), 3.72-3.84 (m, 1H), 4.48-4.62 (m, 1H), 6.55 (s, 1H), 6.93 (d, J=8.3 Hz, 1H), 7.21-7.26 (m, 2H), 7.30 (d, J=8.1 Hz, 1H), 7.44 (dd, J=8.1, 2.6 Hz, 1H), 7.60 (dd, J=9.0, 2.6 Hz, 1H), 7.67 (dd, J=8.3, 2.6 Hz, 1H), 7.73-7.78 (m, 2H), 8.03 (dd, J=2.6, 0.7 Hz, 1H), 8.05 (d, J=2.6 Hz, 1H), 8.09 (d, J=9.0 Hz, 1H), 8.37 (d, J=2.6 Hz, 1H).

Example 16(10)

2-fluoro-5-({[(1-{[6-(4-{[(2-methoxyethyl)amino]sulfonyl}phenoxy)-3-pyridinyl]methyl}-4-piperidinyl)(6-methyl-3-pyridinyl)amino]carbonyl}amino)benzamide TLC: Rf 0.40 (dichloromethane:methanol=9:1);
$^1$H-NMR (CDCl$_3$): δ 1.27-1.44 (m, 2H), 1.80-1.89 (m, 2H), 2.10-2.21 (m, 2H), 2.66 (s, 3H), 2.83-2.93 (m, 2H), 3.12-3.18 (m, 2H), 3.29 (s, 3H), 3.41-3.46 (m, 4H), 4.48-4.61

(m, 1H), 4.82 (t, J=6.0 Hz, 1H), 5.76 (br. s, 1H), 5.89 (s, 1H), 6.63-6.73 (m, 1H), 6.92 (d, J=8.4 Hz, 1H), 7.08 (dd, J=11.4, 9.0 Hz, 1H), 7.20-7.25 (m, 2H), 7.31 (d, J=8.4 Hz, 1H), 7.38 (dd, J=6.4, 2.9 Hz, 1H), 7.44 (dd, J=8.4, 2.6 Hz, 1H), 7.66 (dd, J=8.4, 2.4 Hz, 1H), 7.83-7.89 (m, 2H), 8.00-8.07 (m, 2H), 8.38 (d, J=2.4 Hz, 1H).

Example 16(11)

2-fluoro-5-({[{1-[(6-{4-[(4-hydroxy-1-piperidinyl)sulfonyl]phenoxy}-3-pyridinyl)methyl]-4-piperidinyl}(6-methyl-3-pyridinyl)amino]carbonyl}amino)benzamide TLC: Rf 0.37 (dichloromethane:methanol=9:1);
$^1$H-NMR (CDCl$_3$): δ 1.30-1.47 (m, 2H), 1.61-1.72 (m, 2H), 1.79-2.01 (m, 4H), 2.10-2.22 (m, 2H), 2.66 (s, 3H), 2.83-2.94 (m, 4H), 3.31-3.41 (m, 2H), 3.44 (s, 2H), 3.72-3.84 (m, 1H), 4.48-4.62 (m, 1H), 5.75 (s, 1H), 5.88 (s, 1H), 6.64-6.73 (m, 1H), 6.93 (d, J=8.4 Hz, 1H), 7.07 (dd, J=11.4, 9.2 Hz, 1H), 7.21-7.26 (m, 2H), 7.31 (d, J=8.2 Hz, 1H), 7.39 (dd, J=6.4, 2.9 Hz, 1H), 7.44 (dd, J=8.2, 2.7 Hz, 1H), 7.67 (dd, J=8.4, 2.4 Hz, 1H), 7.73-7.78 (m, 2H), 8.00-8.07 (m, 2H), 8.37 (d, J=2.4 Hz, 1H).

Example 16(12)

N-(4-chlorophenyl)-N'-(5-chloro-2-pyridinyl)-N-{1-[(6-{4-[(4-hydroxy-1-piperidinyl)sulfonyl]phenoxy}-3-pyridinyl)methyl]-4-piperidinyl}urea TLC: Rf 0.55 (chloroform:methanol=10:1);
$^1$H-NMR (CDCl$_3$): δ 1.35-1.40 (m, 2H), 1.60-1.75 (m, 2H), 1.75-1.90 (m, 2H), 1.90-2.00 (m, 2H), 2.10-2.20 (m, 2H), 2.80-2.90 (m, 4H), 3.30-3.40 (m, 2H), 3.44 (s, 2H), 3.80 (m, 1H), 4.53 (m, 1H), 6.60 (s, 1H), 6.92 (d, J=8.2 Hz, 1H), 7.16 (d, J=8.6 Hz, 2H), 7.24 (d, J=8.9 Hz, 2H), 7.47 (d, J=8.6 Hz, 1H), 7.59 (dd, J=9.0, 2.6 Hz, 1H), 7.67 (dd, J=8.2, 2.2 Hz, 1H), 7.76 (d, J=8.9 Hz, 2H), 8.03 (d, J=2.6 Hz, 1H), 8.06 (d, J=2.2 Hz, 1H), 8.08 (d, J=9.0 Hz, 1H).

Example 16(13)

4-[(5-{[4-((4-chlorophenyl) {[(5-chloro-2-pyridinyl)amino]carbonyl}amino)-1-piperidinyl]methyl}-2-pyridinyl)oxy]-N-(2-methoxyethyl)benzenesulfonamide TLC: Rf 0.52 (chloroform:methanol=10:1);
$^1$H-NMR (CDCl$_3$): δ 1.35-1.40 (m, 2H), 1.75-1.90 (m, 2H), 2.10-2.20 (m, 2H), 2.80-2.90 (m, 2H), 3.14 (q, J=5.8 Hz, 2H), 3.29 (s, 3H), 3.43 (t, J=5.8 Hz, 2H), 3.43 (s, 2H), 4.53 (m, 1H), 4.80 (t, J=6.0 Hz, 1H), 6.60 (s, 1H), 6.92 (d, J=8.2 Hz, 1H), 7.16 (d, J=8.6 Hz, 2H), 7.23 (d, J=9.0 Hz, 2H), 7.47 (d, J=8.2 Hz, 2H), 7.59 (dd, J=9.0, 2.5 Hz, 1H), 7.66 (dd, J=8.6, 2.5 Hz, 1H), 7.86 (d, J=9.0 Hz, 2H), 8.02 (d, J=2.5 Hz, 1H), 8.03 (d, J=2.5 Hz, 1H), 8.09 (d, J=9.0 Hz, 1H).

Example 16(14)

N-(2-methoxyethyl)-4-[(5-{[4-((5-methyl-2-pyridinyl) {[(6-methyl-3-pyridinyl)amino]carbonyl}amino)-1-piperidinyl]methyl}-2-pyridinyl)oxy]benzenesulfonamide TLC: Rf 0.52 (chloroform:methanol:aqueous ammonia=90:13:2);
$^1$H-NMR (CDCl$_3$): δ 1.65-1.81 (m, 2H), 1.85-1.94 (m, 2H), 2.08-2.19 (m, 2H), 2.41 (s, 3H), 2.46 (s, 3H), 2.85-2.93 (m, 2H), 3.11-3.18 (m, 2H), 3.29 (s, 3H), 3.40-3.45 (m, 2H), 3.45 (s, 2H), 4.40 (tt, J=12.0, 4.0 Hz, 1H), 4.88 (t, J=6.0 Hz, 1H), 6.92 (d, J=8.5 Hz, 1H), 7.04 (d, J=8.5 Hz, 1H), 7.16 (d, J=8.5 Hz, 1H), 7.23 (d, J=9.0 Hz, 2H), 7.33 (s, 1H), 7.64 (ddd, J=8.5, 2.5, 0.5 Hz, 1H), 7.70 (dd, J=8.5, 2.5 Hz, 1H), 7.83 (dd, J=8.5, 2.5 Hz, 1H), 7.86 (d, J=9.0 Hz, 2H), 8.07 (d, J=2.5 Hz, 1H), 8.15 (d, J=2.5 Hz, 1H), 8.41 (d, J=2.5 Hz, 1H).

Example 16(15)

N-{1-[(6-{4-[(4-hydroxy-1-piperidinyl)sulfonyl]phenoxy}-3-pyridinyl)methyl]-4-piperidinyl}-N-(5-methyl-2-pyridinyl)-N'-(6-methyl-3-pyridinyl)urea TLC: Rf 0.53 (chloroform:methanol:aqueous ammonia=90:13:2);
$^1$H-NMR (CDCl$_3$): δ 1.59-1.82 (m, 5H), 1.85-2.00 (m, 4H), 2.08-2.20 (m, 2H), 2.41 (s, 3H), 2.47 (s, 3H), 2.83-2.94 (m, 4H), 3.31-3.41 (m, 2H), 3.46 (s, 2H), 3.73-3.82 (m, 1H), 4.40 (tt, J=12.0, 4.0 Hz, 1H), 6.94 (dd, J=8.5, 0.5 Hz, 1H), 7.05 (d, J=8.5 Hz, 1H), 7.17 (d, J=8.5 Hz, 1H), 7.24 (d, J=9.0 Hz, 2H), 7.34 (s, 1H), 7.64 (ddd, J=8.5, 2.5, 0.5 Hz, 1H), 7.71 (dd, J=8.5, 2.5 Hz, 1H), 7.76 (d, J=9.0 Hz, 2H), 7.83 (dd, J=8.5, 2.5 Hz, 1H), 8.09 (dd, J=2.5, 0.5 Hz, 1H), 8.15 (dd, J=2.5, 0.5 Hz, 1H), 8.41 (d, J=2.5 Hz, 1H).

Example 16(16)

N'-(5-chloro-2-pyridinyl)-N-cyclopropyl-N-{1-[(6-{4-[(4-hydroxy-1-piperidinyl)sulfonyl]phenoxy}-3-pyridinyl)methyl]-4-piperidinyl}urea TLC: Rf 0.18 (ethyl acetate:methanol=9:1);
$^1$H-NMR (CDCl$_3$): δ 0.89-1.11 (m, 4H), 1.33-1.41 (m, 1H), 1.60-1.81 (m, 4H), 1.89-2.02 (m, 2H), 2.02-2.18 (m, 4H), 2.46-2.57 (m, 1H), 2.82-2.99 (m, 4H), 3.31-3.42 (m, 2H), 3.50 (s, 2H), 3.72-3.87 (m, 1H), 3.94-4.09 (m, 1H), 6.97 (dd, J=8.3, 0.7 Hz, 1H), 7.26 (d, J=9.0 Hz, 2H), 7.60 (dd, J=9.2, 2.6 Hz, 1H), 7.72-7.82 (m, 3H), 8.06-8.11 (m, 2H), 8.13 (d, J=2.2 Hz, 1H), 8.15 (dd, J=2.6, 0.7 Hz, 1H).

Example 16(17)

4-{[5-({4-[{[(5-chloro-2-pyridinyl)amino]carbonyl}(cyclopropyl)amino]-1-piperidinyl}methyl)-2-pyridinyl]oxy}-N-(2-methoxyethyl)benzenesulfonamide TLC: Rf 0.37 (ethyl acetate:methanol=9:1);
$^1$H-NMR (CDCl$_3$): δ 0.88-1.12 (m, 4H), 1.69-1.84 (m, 2H), 1.98-2.19 (m, 4H), 2.47-2.57 (m, 1H), 2.85-2.99 (m, 2H), 3.11-3.20 (m, 2H), 3.30 (s, 3H), 3.41-3.46 (m, 2H), 3.49 (s, 2H), 3.95-4.09 (m, 1H), 4.83 (t, J=6.0 Hz, 1H), 6.97 (d, J=8.4 Hz, 1H), 7.25 (d, J=8.8 Hz, 2H), 7.60 (dd, J=9.0, 2.6 Hz, 1H), 7.76 (dd, J=8.4, 2.4 Hz, 1H), 7.87 (d, J=8.8 Hz, 2H), 8.05-8.14 (m, 3H), 8.15 (dd, J=2.6, 0.7 Hz, 1H).

Example 16(18)

1-cyclopropyl-1-{1-[(6-{4-[(4-hydroxy-1-piperidinyl)sulfonyl]phenoxy}-3-pyridinyl)methyl]-4-piperidinyl}-3-(6-methyl-3-pyridinyl)urea TLC: Rf 0.20 (dichloromethane:methanol=9:1);
$^1$H-NMR (CDCl$_3$): δ 0.89-1.07 (m, 4H), 1.37-1.46 (m, 1H), 1.60-1.80 (m, 4H), 1.89-2.01 (m, 2H), 2.01-2.19 (m, 4H), 2.45-2.57 (m, 4H), 2.82-2.98 (m, 4H), 3.31-3.43 (m, 2H), 3.49 (s, 2H), 3.72-3.85 (m, 1H), 3.96-4.12 (m, 1H), 6.97 (d, J=8.4 Hz, 1H), 7.09 (d, J=8.6 Hz, 1H), 7.26 (d, J=9.0 Hz, 2H), 7.33 (s, 1H), 7.72-7.82 (m, 3H), 7.96 (dd, J=8.4, 2.7 Hz, 1H), 8.13 (d, J=2.0 Hz, 1H), 8.32 (d, J=2.7 Hz, 1H).

Example 16(19)

4-({5-[(4-{cyclopropyl[(6-methyl-3-pyridinyl)carbamoyl]amino}-1-piperidinyl)methyl]-2-pyridinyl}oxy)-N-(2-methoxyethyl)benzenesulfonamide TLC: Rf 0.33 (dichloromethane:methanol=9:1);
$^1$H-NMR (CDCl$_3$): δ 0.90-1.08 (m, 4H), 1.70-1.82 (m, 2H), 1.97-2.18 (m, 4H), 2.46-2.58 (m, 4H), 2.87-2.99 (m, 2H), 3.11-3.20 (m, 2H), 3.30 (s, 3H), 3.39-3.46 (m, 2H), 3.49 (s, 2H), 3.98-4.12 (m, 1H), 4.82 (t, J=6.0 Hz, 1H), 6.96 (d, J=8.4 Hz, 1H), 7.09 (d, J=8.4 Hz, 1H), 7.25 (d, J=8.8 Hz, 2H), 7.33 (s, 1H), 7.76 (dd, J=8.4, 2.4 Hz, 1H), 7.87 (d, J=8.8 Hz, 2H), 7.96 (dd, J=8.4, 2.4 Hz, 1H), 8.12 (d, J=2.4 Hz, 1H), 8.32 (d, J=2.4 Hz, 1H).

Example 16(20)

2-fluoro-5-{[(1-{[6-(4-{[(2-methoxyethyl)amino]sulfonyl}phenoxy)-3-pyridinyl]methyl}-4-piperidinyl)(5-methyl-2-pyridinyl)carbamoyl]amino}benzamide TLC: Rf 0.50 (chloroform:methanol:aqueous ammonia=90:13:2);
$^1$H-NMR (CDCl$_3$): δ 1.61-1.77 (m, 2H), 1.85-1.95 (m, 2H), 2.08-2.19 (m, 2H), 2.42 (s, 3H), 2.84-2.93 (m, 2H), 3.11-3.18 (m, 2H), 3.29 (s, 3H), 3.40-3.47 (m, 4H), 4.40 (tt, J=12.0, 4.0 Hz, 1H), 4.83 (t, J=6.0 Hz, 1H), 5.77 (brs, 1H), 6.69 (brd, J=12.0 Hz, 1H), 6.93 (d, J=8.5 Hz, 1H), 7.06 (dd, J=11.5, 9.0 Hz, 1H), 7.14 (d, J=8.0 Hz, 1H), 7.23 (d, J=9.0 Hz, 2H), 7.22 (s, 1H), 7.44 (dd, J=6.5, 3.0 Hz, 1H), 7.64 (ddd, J=8.0, 2.5, 0.5 Hz, 1H), 7.70 (dd, J=8.5, 2.5 Hz, 1H), 7.86 (d, J=9.0 Hz, 2H), 8.03-8.11 (m, 2H), 8.43 (d, J=2.5 Hz, 1H).

Example 16(21)

2-fluoro-5-{[{1-[(6-{4-[(4-hydroxy-1-piperidinyl)sulfonyl]phenoxy}-3-pyridinyl)methyl]-4-piperidinyl}(5-methyl-2-pyridinyl)carbamoyl]amino}benzamide TLC: Rf 0.46 (chloroform:methanol:aqueous ammonia=90:13:2);
$^1$H-NMR (CDCl$_3$): δ 1.57-1.78 (m, 5H), 1.85-2.00 (m, 4H), 2.08-2.20 (m, 2H), 2.42 (s, 3H), 2.82-2.94 (m, 4H), 3.30-3.42 (m, 2H), 3.46 (s, 2H), 3.72-3.83 (m, 1H), 4.39 (tt, J=12.0, 4.0 Hz, 1H), 5.78 (brs, 1H), 6.69 (brd, J=12.0 Hz, 1H), 6.93 (d, J=8.5 Hz, 1H), 7.06 (dd, J=11.5, 9.0 Hz, 1H), 7.14 (d, J=8.0 Hz, 1H), 7.21-7.26 (m, 3H), 7.44 (dd, J=6.5, 3.0 Hz, 1H), 7.64 (ddd, J=8.0, 2.5, 0.5 Hz, 1H), 7.70 (dd, J=8.5, 2.5 Hz, 1H), 7.76 (d, J=9.0 Hz, 2H), 8.02-8.10 (m, 2H), 8.42 (d, J=2.5 Hz, 1H).

Example 16(22)

5-[(cyclopropyl {1-[(6-{4-[(4-hydroxy-1-piperidinyl)sulfonyl]phenoxy}-3-pyridinyl)methyl]-4-piperidinyl}carbamoyl)amino]-2-fluorobenzamide TLC: Rf 0.38 (dichloromethane:methanol=9:1);
$^1$H-NMR (CDCl$_3$): δ 0.87-1.08 (m, 4H), 1.39-1.80 (m, 5H), 1.89-2.01 (m, 2H), 2.01-2.18 (m, 4H), 2.44-2.54 (m, 1H), 2.80-3.00 (m, 4H), 3.30-3.43 (m, 2H), 3.49 (s, 2H), 3.73-3.83 (m, 1H), 3.94-4.09 (m, 1H), 5.73-5.85 (m, 1H), 6.68-6.79 (m, 1H), 6.97 (d, J=8.2 Hz, 1H), 7.10 (dd, J=11.4, 9.0 Hz, 1H), 7.26 (d, J=8.8 Hz, 2H), 7.48 (s, 1H), 7.70 (dd, J=6.6, 2.9 Hz, 1H), 7.74-7.81 (m, 3H), 8.10 (ddd, J=9.0, 4.6, 2.9 Hz, 1H), 8.13 (d, J=2.6 Hz, 1H).

Example 16(23)

5-{[cyclopropyl(1-{[6-(4-{[(2-methoxyethyl)amino]sulfonyl}phenoxy)-3-pyridinyl]methyl}-4-piperidinyl)carbamoyl]amino}-2-fluorobenzamide TLC: Rf 0.40 (dichloromethane:methanol=9:1);
$^1$H-NMR (CDCl$_3$): δ 0.88-1.08 (m, 4H), 1.68-1.82 (m, 2H), 1.97-2.16 (m, 4H), 2.43-2.54 (m, 1H), 2.85-3.00 (m, 2H), 3.10-3.20 (m, 2H), 3.30 (s, 3H), 3.39-3.47 (m, 2H), 3.49 (s, 2H), 3.93-4.10 (m, 1H), 4.83 (t, J=6.0 Hz, 1H), 5.72-5.85 (m, 1H), 6.65-6.81 (m, 1H), 6.96 (d, J=8.3 Hz, 1H), 7.10 (dd, J=11.4, 9.0 Hz, 1H), 7.25 (d, J=8.8 Hz, 2H), 7.49 (s, 1H), 7.70 (dd, J=6.5, 3.0 Hz, 1H), 7.76 (dd, J=8.3, 2.3 Hz, 1H), 7.87 (d, J=8.8 Hz, 2H), 8.06-8.15 (m, 2H).

Example 16(24)

4-({5-[(4-{cyclobutyl[(6-methyl-3-pyridinyl)carbamoyl]amino}-1-piperidinyl)methyl]-2-pyridinyl}oxy)-N-(2-methoxyethyl)benzenesulfonamide TLC: Rf 0.47 (dichloromethane:methanol=9:1);
$^1$H-NMR (CDCl$_3$): δ 1.60-1.89 (m, 4H), 2.00-2.14 (m, 2H), 2.15-2.47 (m, 6H), 2.49 (s, 3H), 2.88-2.99 (m, 2H), 3.10-3.21 (m, 2H), 3.30 (s, 3H), 3.40-3.46 (m, 2H), 3.48 (s, 2H), 3.48-3.61 (m, 1H), 4.05-4.20 (m, 1H), 4.82 (t, J=6.2 Hz, 1H), 6.21 (s, 1H), 6.96 (d, J=8.4 Hz, 1H), 7.08 (d, J=8.6 Hz, 1H), 7.19-7.30 (m, 2H), 7.78 (dd, J=8.4, 2.0 Hz, 1H), 7.83-7.93 (m, 3H), 8.09 (d, J=2.0 Hz, 1H), 8.25 (d, J=2.6 Hz, 1H).

Example 16(25)

1-cyclobutyl-1-{1-[(6-{4-[(4-hydroxy-1-piperidinyl)sulfonyl]phenoxy}-3-pyridinyl)methyl]-4-piperidinyl}-3-(6-methyl-3-pyridinyl)urea TLC: Rf 0.34 (dichloromethane:methanol=9:1);
$^1$H-NMR (CDCl$_3$): δ 1.57-1.87 (m, 7H), 1.88-2.01 (m, 2H), 2.02-2.16 (m, 2H), 2.16-2.44 (m, 6H), 2.49 (s, 3H), 2.83-2.99 (m, 4H), 3.30-3.41 (m, 2H), 3.49 (s, 2H), 3.49-3.60 (m, 1H), 3.74-3.85 (m, 1H), 4.06-4.22 (m, 1H), 6.22 (s, 1H), 6.97 (d, J=8.4 Hz, 1H), 7.08 (d, J=8.6 Hz, 1H), 7.26 (d, J=9.0 Hz, 2H), 7.72-7.82 (m, 3H), 7.90 (dd, J=8.4, 2.2 Hz, 1H), 8.11 (d, J=1.8 Hz, 1H), 8.24 (d, J=2.2 Hz, 1H).

Example 16(26)

4-({5-[(4-{2-butyn-1-yl[(6-methyl-3-pyridinyl)carbamoyl]amino}-1-piperidinyl)methyl]-2-pyridinyl}oxy)-N-(2-methoxyethyl)benzenesulfonamide TLC: Rf 0.52 (dichloromethane:methanol=9:1);
$^1$H-NMR (CDCl$_3$): δ 1.67-1.80 (m, 4H), 1.83-1.90 (m, 3H), 2.06-2.20 (m, 2H), 2.50 (s, 3H), 2.88-2.99 (m, 2H), 3.11-3.20 (m, 2H), 3.30 (s, 3H), 3.40-3.47 (m, 2H), 3.48 (s, 2H), 3.88-3.98 (m, 2H), 4.19-4.38 (m, 1H), 4.82 (t, J=6.0 Hz, 1H), 6.90 (s, 1H), 6.96 (d, J=8.3 Hz, 1H), 7.09 (d, J=8.4 Hz, 1H), 7.21-7.30 (m, 2H), 7.74 (dd, J=8.3, 2.4 Hz, 1H), 7.81-7.92 (m, 3H), 8.11 (d, J=2.4 Hz, 1H), 8.31 (d, J=2.6 Hz, 1H).

Example 16(27)

1-(2-butyn-1-yl)-1-{1-[(6-{4-[(4-hydroxy-1-piperidinyl)sulfonyl]phenoxy}-3-pyridinyl)methyl]-4-piperidinyl}-3-(6-methyl-3-pyridinyl)urea TLC: Rf 0.43 (dichloromethane:methanol=9:1);
$^1$H-NMR (CDCl$_3$): δ 1.46 (s, 1H), 1.56-1.82 (m, 6H), 1.83-1.90 (m, 3H), 1.89-2.01 (m, 2H), 2.06-2.20 (m, 2H), 2.50 (s, 3H), 2.82-2.99 (m, 4H), 3.30-3.42 (m, 2H), 3.49 (s, 2H), 3.72-3.85 (m, 1H), 3.88-3.97 (m, 2H), 4.20-4.37 (m, 1H), 6.90 (s, 1H), 6.97 (d, J=8.4 Hz, 1H), 7.09 (d, J=8.4 Hz, 1H), 7.26 (d, J=9.0 Hz, 2H), 7.71-7.81 (m, 3H), 7.85 (dd, J=8.4, 2.2 Hz, 1H), 8.13 (d, J=2.0 Hz, 1H), 8.31 (d, J=2.2 Hz, 1H).

Example 16(28)

2,4-difluoro-5-{[(1-{[6-(4-{[(2-methoxyethyl)amino]sulfonyl}phenoxy)-3-pyridinyl]methyl}-4-piperidinyl)(3-methylbutyl)carbamoyl]amino}benzamide TLC: Rf 0.36 (chloroform:methanol=10:1);
$^1$H-NMR (CD$_3$OD): δ 0.95 (d, J=6.3 Hz, 6H), 1.50-1.90 (m, 7H), 2.10-2.20 (m, 2H), 2.90-3.00 (m, 2H), 3.04 (t, J=5.4 Hz, 2H), 3.26 (s, 3H), 3.20-3.30 (m, 2H), 3.39 (t, J=5.4 Hz, 2H), 3.55 (s, 2H), 4.01 (m, 1H), 7.05-7.15 (m, 2H), 7.26 (d, J=8.7 Hz, 2H), 7.85-7.91 (m, 4H), 8.11 (d, J=2.1 Hz, 1H).

Example 16(29)

2,4-difluoro-5-{[{1-[(6-{4-[(4-hydroxy-1-piperidinyl)sulfonyl]phenoxy}-3-pyridinyl)methyl]-4-piperidinyl}(3-methylbutyl)carbamoyl]amino}benzamide TLC: Rf 0.27 (chloroform:methanol=10:1);
$^1$H-NMR (CD$_3$OD): δ 0.95 (d, J=6.6 Hz, 6H), 1.50-1.90 (m, 11H), 2.10-2.20 (m, 2H), 2.70-2.85 (m, 2H), 2.90-3.00 (m, 2H), 3.20-3.40 (m, 4H), 3.56 (s, 2H), 3.64 (m, 1H), 4.01 (m, 1H), 7.07-7.15 (m, 2H), 7.30 (d, J=8.9 Hz, 2H), 7.80 (d, J=8.9 Hz, 2H), 7.85-7.91 (m, 2H), 8.12 (d, J=2.1 Hz, 1H).

Example 16(30)

5-{[(cyclobutylmethyl)(1-{[6-(4-{[(2-methoxyethyl)amino]sulfonyl}phenoxy)-3-pyridinyl]methyl}-4-piperidinyl)carbamoyl]amino}-2,4-difluorobenzamide TLC: Rf 0.27 (chloroform:methanol=10:1);
$^1$H-NMR (CD$_3$OD): δ 1.60-1.90 (m, 8H), 2.00-2.20 (m, 4H), 2.65 (m, 1H), 2.90-3.00 (m, 2H), 3.05 (t, J=5.6 Hz, 2H), 3.20-3.40 (m, 2H), 3.26 (s, 3H), 3.39 (t, J=5.6 Hz, 2H), 3.55 (s, 2H), 3.90 (m, 1H), 7.05-7.15 (m, 2H), 7.26 (d, J=9.0 Hz, 2H), 7.83-7.90 (m, 4H), 8.12 (d, J=1.8 Hz, 1H).

Example 16(31)

5-{[(cyclopropylmethyl)(1-{[6-(4-{[(2-methoxyethyl)amino]sulfonyl}phenoxy)-3-pyridinyl]methyl}-4-piperidinyl)carbamoyl]amino}-2,4-difluorobenzamide TLC: Rf 0.35 (chloroform:methanol=10:1);
$^1$H-NMR (CD$_3$OD): δ 0.33-0.38 (m, 2H), 0.55-0.61 (m, 2H), 1.06 (m, 1H), 1.75-1.95 (m, 4H), 2.10-2.20 (m, 2H), 2.90-3.10 (m, 2H), 3.05 (t, J=5.7 Hz, 2H), 3.23 (d, J=6.3 Hz, 2H), 3.26 (s, 3H), 3.39 (t, J=5.7 Hz, 2H), 3.56 (s, 2H), 3.98 (m, 1H), 7.05-7.15 (m, 2H), 7.26 (d, J=9.0 Hz, 2H), 7.87-7.94 (m, 4H), 8.11 (d, J=2.1 Hz, 1H).

Example 16(32)

2,4-difluoro-5-{[(2-hydroxybutyl)(1-{[6-(4-{[(2-methoxyethyl)amino]sulfonyl}phenoxy)-3-pyridinyl]methyl}-4-piperidinyl)carbamoyl]amino}benzamide TLC: Rf 0.31 (chloroform:methanol=10:1);
$^1$H-NMR (CD$_3$OD): δ 1.00 (t, J=7.5 Hz, 3H), 1.40-1.60 (m, 2H), 1.70-1.85 (m, 4H), 2.10-2.25 (m, 2H), 2.90-3.00 (m, 2H), 3.05 (t, J=5.5 Hz, 2H), 3.20-3.40 (m, 2H), 3.26 (s, 3H), 3.39 (t, J=5.5 Hz, 2H), 3.55 (s, 2H), 3.65 (m, 1H), 4.05 (m, 1H), 7.04-7.10 (m, 2H), 7.26 (d, J=9.3 Hz, 2H), 7.86-7.90 (m, 3H), 8.11-8.20 (m, 2H).

Example 16(33)

5-{[3-butyn-1-yl(1-{[6-(4-{[(2-methoxyethyl)amino]sulfonyl}phenoxy)-3-pyridinyl]methyl}-4-piperidinyl)carbamoyl]amino}-2,4-difluorobenzamide TLC: Rf 0.36 (chloroform:methanol=10:1);
$^1$H-NMR (CD$_3$OD): δ 1.70-1.90 (m, 4H), 2.10-2.25 (m, 2H), 2.37 (m, 1H), 2.45-2.55 (m, 2H), 2.90-3.10 (m, 2H), 3.05 (t, J=5.6 Hz, 2H), 3.26 (s, 3H), 3.39 (t, J=5.6 Hz, 2H), 3.48 (t, J=7.2 Hz, 2H), 3.55 (s, 2H), 3.95 (m, 1H), 7.05-7.15 (m, 2H), 7.26 (d, J=8.9 Hz, 2H), 7.80-7.90 (m, 2H), 7.88 (d, J=8.9 Hz, 2H), 8.11 (d, J=1.5 Hz, 1H).

Example 16(34)

1-{1-[(6-{4-[(4-hydroxy-1-piperidinyl)sulfonyl]phenoxy}-3-pyridinyl)methyl]-4-piperidinyl}-1-isobutyl-3-(6-methyl-3-pyridinyl)urea TLC: Rf 0.45 (chloroform:methanol:aqueous ammonia=90:13:2);
$^1$H-NMR (CDCl$_3$): δ 1.00 (d, J=6.5 Hz, 6H), 1.61-1.86 (m, 6H), 1.86-2.03 (m, 4H), 2.06-2.17 (m, 2H), 2.49 (s, 3H), 2.85-2.99 (m, 4H), 3.06 (d, J=7.5 Hz, 2H), 3.30-3.42 (m, 2H), 3.49 (s, 2H), 3.74-3.83 (m, 1H), 3.95-4.07 (m, 1H), 6.31 (s, 1H), 6.97 (dd, J=8.5, 0.5 Hz, 1H), 7.08 (d, J=8.5 Hz, 1H), 7.26 (d, J=9.0 Hz, 2H), 7.75 (dd, J=8.5, 2.5 Hz, 1H), 7.77 (d, J=9.0 Hz, 2H), 7.87 (dd, J=8.5, 2.5 Hz, 1H), 8.12 (dd, J=2.5, 0.5 Hz, 1H), 8.26 (dd, J=2.5, 0.5 Hz, 1H).

Example 16(35)

5-{[2-butyn-1-yl(1-{[6-(4-{[(2-methoxyethyl)amino]sulfonyl}phenoxy)-3-pyridinyl]methyl}-4-piperidinyl)carbamoyl]amino}-2-fluorobenzamide TLC: Rf 0.50 (dichloromethane:methanol=9:1);
$^1$H-NMR (CDCl$_3$): δ 1.68-1.80 (m, 4H), 1.87 (t, J=2.2 Hz, 3H), 2.06-2.22 (m, 2H), 2.89-2.98 (m, 2H), 3.12-3.19 (m, 2H), 3.30 (s, 3H), 3.41-3.46 (m, 2H), 3.48 (s, 2H), 3.87-3.96 (m, 2H), 4.17-4.32 (m, 1H), 4.83 (t, J=6.0 Hz, 1H), 5.78 (s, 1H), 6.64-6.80 (m, 1H), 6.92-7.01 (m, 2H), 7.10 (dd, J=11.4, 9.0 Hz, 1H), 7.20-7.30 (m, 2H), 7.67-7.79 (m, 2H), 7.87 (d, J=8.8 Hz, 2H), 7.92-8.00 (m, 1H), 8.11 (d, J=2.0 Hz, 1H).

Example 16(36)

5-[(2-butyn-1-yl {1-[(6-{4-[(4-hydroxy-1-piperidinyl)sulfonyl]phenoxy}-3-pyridinyl)methyl]-4-piperidinyl}carbamoyl)amino]-2-fluorobenzamide TLC: Rf 0.41 (dichloromethane:methanol=9:1);
$^1$H-NMR (CDCl$_3$): δ 1.39-1.51 (m, 1H), 1.60-1.80 (m, 6H), 1.87 (t, J=2.2 Hz, 3H), 1.89-2.02 (m, 2H), 2.06-2.20 (m, 2H), 2.83-2.99 (m, 4H), 3.31-3.42 (m, 2H), 3.49 (s, 2H), 3.72-3.84 (m, 1H), 3.88-3.96 (m, 2H), 4.17-4.32 (m, 1H), 5.79 (s, 1H), 6.64-6.80 (m, 1H), 6.93-7.01 (m, 2H), 7.10 (dd, J=11.4, 9.0 Hz, 1H), 7.26 (d, J=8.6 Hz, 2H), 7.68-7.81 (m, 4H), 7.91-7.99 (m, 1H), 8.13 (d, J=2.0 Hz, 1H).

Example 16(37)

2-fluoro-5-{[{1-[(6-{4-[(4-hydroxy-1-piperidinyl)sulfonyl]phenoxy}-3-pyridinyl)methyl]-4-piperidinyl}(isobutyl)carbamoyl]amino}benzamide TLC: Rf 0.39 (chloroform:methanol:aqueous ammonia=90:13:2);
$^1$H-NMR (CDCl$_3$): δ 0.99 (d, J=7.0 Hz, 6H), 1.58-1.87 (m, 6H), 1.87-2.04 (m, 4H), 2.06-2.17 (m, 2H), 2.84-2.99 (m, 4H), 3.05 (d, J=7.5 Hz, 2H), 3.31-3.41 (m, 2H), 3.49 (s, 2H), 3.73-3.83 (m, 1H), 3.91-4.03 (m, 1H), 5.82 (s, 1H), 6.47 (s, 1H), 6.67-6.79 (m, 1H), 6.98 (dd, J=8.5, 0.5 Hz, 1H), 7.09 (dd, J=11.5, 9.0 Hz, 1H), 7.26 (d, J=9.0 Hz, 2H), 7.65 (dd, J=6.5, 3.0 Hz, 1H), 7.73-7.80 (m, 3H), 7.99 (ddd, J=9.0, 4.5, 3.0 Hz, 1H), 8.12 (dd, J=2.5, 0.5 Hz, 1H).

Example 16(38)

1-(3-fluorophenyl)-1-{1-[(6-{4-[(4-methoxy-1-piperidinyl)sulfonyl]phenoxy}-3-pyridinyl)methyl]-4-piperidinyl}-3-(6-methyl-3-pyridinyl)urea TLC: Rf 0.51 (ethyl acetate:methanol=9:1);
$^1$H-NMR (CDCl$_3$): δ 1.35-1.50 (m, 2H), 1.68-1.80 (m, 2H), 1.81-1.95 (m, 4H), 2.10-2.22 (m, 2H), 2.47 (s, 3H), 2.84-2.93 (m, 2H), 2.94-3.04 (m, 2H), 3.13-3.23 (m, 2H), 3.24-3.32 (m, 1H), 3.27 (s, 3H), 3.45 (s, 2H), 4.54 (tt, J=12.0, 4.0 Hz, 1H), 5.77 (s, 1H), 6.93 (dd, J=8.5, 0.5 Hz, 1H), 6.96-7.02 (m, 1H), 7.03-7.08 (m, 2H), 7.18-7.27 (m, 3H), 7.45-7.54 (m, 1H), 7.68 (dd, J=8.5, 2.5 Hz, 1H), 7.73-7.79 (m, 3H), 8.07 (d, J=2.5 Hz, 1H), 8.11 (d, J=2.5 Hz, 1H).

Example 16(39)

1-(3-fluorophenyl)-3-(6-methyl-3-pyridinyl)-1-(1-{[6-(4-{[4-(trifluoromethyl)-1-piperidinyl]sulfonyl}phenoxy)-3-pyridinyl]methyl}-4-piperidinyl)urea TLC: Rf 0.66 (ethyl acetate:methanol=9:1);
$^1$H-NMR (CDCl$_3$): δ 1.35-1.50 (m, 2H), 1.63-1.79 (m, 2H), 1.81-2.06 (m, 5H), 2.10-2.21 (m, 2H), 2.27-2.38 (m, 2H), 2.47 (s, 3H), 2.84-2.93 (m, 2H), 3.45 (s, 2H), 3.86-3.95 (m, 2H), 4.48-4.60 (m, 1H), 5.77 (s, 1H), 6.93 (d, J=8.5 Hz, 1H), 6.96-7.02 (m, 1H), 7.03-7.08 (m, 2H), 7.18-7.28 (m, 3H), 7.45-7.54 (m, 1H), 7.68 (dd, J=8.5, 2.5 Hz, 1H), 7.73-7.79 (m, 3H), 8.06 (d, J=2.5 Hz, 1H), 8.11 (d, J=2.5 Hz, 1H).

Example 16(40)

1-(3-fluorophenyl)-1-{1-[(6-{4-[(4-fluoro-1-piperidinyl)sulfonyl]phenoxy}-3-pyridinyl)methyl]-4-piperidinyl}-3-(6-methyl-3-pyridinyl)urea TLC: Rf 0.69 (chloroform:methanol:aqueous ammonia=90:13:2);
$^1$H-NMR (CDCl$_3$): δ 1.34-1.51 (m, 2H), 1.81-2.04 (m, 6H), 2.10-2.22 (m, 2H), 2.47 (s, 3H), 2.84-3.00 (m, 4H), 3.31-3.41 (m, 2H), 3.45 (s, 2H), 4.48-4.61 (m, 1H), 4.64-4.87 (m, 1H), 5.77 (s, 1H), 6.93 (dd, J=8.5, 0.5 Hz, 1H), 6.96-7.02 (m, 1H), 7.03-7.08 (m, 2H), 7.18-7.28 (m, 3H), 7.50 (td, J=8.0, 6.5 Hz, 1H), 7.68 (dd, J=8.5, 2.5 Hz, 1H), 7.73-7.80 (m, 3H), 8.07 (dd, J=2.5, 0.5 Hz, 1H), 8.11 (dd, J=2.5, 0.5 Hz, 1H).

Example 16(41)

1-{1-[(6-{4-[(4,4-difluoro-1-piperidinyl)sulfonyl]phenoxy}-3-pyridinyl)methyl]-4-piperidinyl}-1-(3-fluorophenyl)-3-(6-methyl-3-pyridinyl)urea TLC: Rf 0.70 (chloroform:methanol:aqueous ammonia=90:13:2);
$^1$H-NMR (CDCl$_3$): δ 1.34-1.50 (m, 2H), 1.80-1.90 (m, 2H), 2.01-2.22 (m, 6H), 2.47 (s, 3H), 2.84-2.93 (m, 2H), 3.19-3.27 (m, 4H), 3.45 (s, 2H), 4.48-4.60 (m, 1H), 5.77 (s, 1H), 6.94 (d, J=8.5 Hz, 1H), 6.96-7.01 (m, 1H), 7.03-7.08 (m, 2H), 7.18-7.29 (m, 3H), 7.50 (td, J=8.0, 6.5 Hz, 1H), 7.68 (dd, J=8.5, 2.5 Hz, 1H), 7.74-7.79 (m, 3H), 8.07 (d, J=2.5 Hz, 1H), 8.11 (d, J=2.5 Hz, 1H).

Example 16(42)

5-[(butyl {1-[(6-{4-[(4-hydroxy-1-piperidinyl)sulfonyl]phenoxy}-3-pyridinyl)methyl]-4-piperidinyl}carbamoyl)amino]-2,4-difluorobenzamide TLC: Rf 0.39 (chloroform:methanol:aqueous ammonia=90:13:2);
$^1$H-NMR (CDCl$_3$): δ 0.98 (t, J=7.5 Hz, 3H), 1.32-1.46 (m, 2H), 1.55-1.83 (m, 9H), 1.88-2.00 (m, 2H), 2.06-2.19 (m, 2H), 2.83-2.99 (m, 4H), 3.14-3.24 (m, 2H), 3.31-3.41 (m, 2H), 3.50 (s, 2H), 3.73-3.83 (m, 1H), 4.09-4.23 (m, 1H), 5.79 (brs, 1H), 6.38 (d, J=3.0 Hz, 1H), 6.52 (brd, J=9.5 Hz, 1H), 6.92 (t, J=10.5 Hz, 1H), 6.97 (dd, J=8.5, 0.5 Hz, 1H), 7.26 (d, J=9.0 Hz, 2H), 7.73-7.80 (m, 3H), 8.13 (d, J=2.0 Hz, 1H), 8.66 (dd, J=9.0, 8.5 Hz, 1H).

Example 16(43)

5-({butyl[1-({2-methyl-6-[4-(methylsulfonyl)phenoxy]-3-pyridinyl}methyl)-4-piperidinyl]carbamoyl}amino)-2,4-difluorobenzamide TLC: Rf 0.49 (dichloromethane:methanol=9:1);
$^1$H-NMR (CDCl$_3$): δ 0.99 (t, J=7.5 Hz, 3H), 1.33-1.46 (m, 2H), 1.56-1.79 (m, 6H), 2.10-2.21 (m, 2H), 2.48 (s, 3H), 2.88-2.97 (m, 2H), 3.07 (s, 3H), 3.15-3.24 (m, 2H), 3.44 (s, 2H), 4.11-4.24 (m, 1H), 5.74 (br. s, 1H), 6.35-6.40 (m, 1H), 6.46-6.57 (m, 1H), 6.77 (d, J=8.2 Hz, 1H), 6.92 (t, J=10.5 Hz, 1H), 7.24-7.30 (m, 2H), 7.66 (d, J=8.2 Hz, 1H), 7.90-7.95 (m, 2H), 8.67 (dd, J=9.1, 8.3 Hz, 1H).

Example 16(44)

5-[(butyl {1-[(2-methyl-6-{4-[(methylamino)sulfonyl]phenoxy}-3-pyridinyl)methyl]-4-piperidinyl}carbamoyl)amino]-2,4-difluorobenzamide TLC: Rf 0.57 (ethyl acetate:methanol=9:1);
$^1$H-NMR (CDCl$_3$): δ 0.99 (t, J=7.2 Hz, 3H), 1.32-1.47 (m, 2H), 1.56-1.81 (m, 6H), 2.07-2.23 (m, 2H), 2.48 (s, 3H), 2.69 (d, J=5.3 Hz, 3H), 2.86-2.99 (m, 2H), 3.13-3.25 (m, 2H), 3.44 (s, 2H), 4.10-4.26 (m, 1H), 4.45 (q, J=5.3 Hz, 1H), 5.82 (s, 1H), 6.35-6.43 (m, 1H), 6.45-6.59 (m, 1H), 6.74 (d, J=8.0 Hz, 1H), 6.92 (t, J=10.5 Hz, 1H), 7.23 (d, J=9.0 Hz, 2H), 7.64 (d, J=8.0 Hz, 1H), 7.85 (d, J=9.0 Hz, 2H), 8.67 (t, J=8.5 Hz, 1H).

Example 16(45)

5-[(butyl {1-[(6-{4-[(dimethylamino)sulfonyl]phenoxy}-2-methyl-3-pyridinyl)methyl]-4-piperidinyl}carbamoyl)amino]-2,4-difluorobenzamide TLC: Rf 0.61 (ethyl acetate:methanol=9:1);
$^1$H-NMR (CDCl$_3$): δ 0.99 (t, J=7.3 Hz, 3H), 1.32-1.48 (m, 2H), 1.52-1.80 (m, 6H), 2.08-2.23 (m, 2H), 2.48 (s, 3H), 2.73 (s, 6H), 2.87-2.98 (m, 2H), 3.13-3.26 (m, 2H), 3.44 (s, 2H), 4.08-4.26 (m, 1H), 5.74 (s, 1H), 6.33-6.43 (m, 1H), 6.45-6.58 (m, 1H), 6.75 (d, J=7.9 Hz, 1H), 6.92 (t, J=10.6 Hz, 1H), 7.25 (d, J=8.6 Hz, 2H), 7.65 (d, J=7.9 Hz, 1H), 7.77 (d, J=8.6 Hz, 2H), 8.68 (t, J=8.8 Hz, 1H).

Example 16(46)

5-[(butyl {1-[(6-{4-[(4-hydroxy-1-piperidinyl)sulfonyl]phenoxy}-2-methyl-3-pyridinyl)methyl]-4-piperidinyl}carbamoyl)amino]-2,4-difluorobenzamide TLC: Rf 0.50 (chloroform:methanol:aqueous ammonia=90:13:2);
$^1$H-NMR (CDCl$_3$): δ 0.99 (t, J=7.0 Hz, 3H), 1.32-1.78 (m, 11H), 1.89-2.00 (m, 2H), 2.10-2.21 (m, 2H), 2.48 (s, 3H), 2.83-2.97 (m, 4H), 3.15-3.24 (m, 2H), 3.30-3.40 (m, 2H), 3.44 (s, 2H), 3.73-3.84 (m, 1H), 4.10-4.24 (m, 1H), 5.77 (brs, 1H), 6.38 (d, J=3.0 Hz, 1H), 6.52 (brd, J=8.5 Hz, 1H), 6.75 (dd, J=8.0, 0.5 Hz, 1H), 6.92 (t, J=10.5 Hz, 1H), 7.23 (d, J=9.0 Hz, 2H), 7.65 (d, J=8.0 Hz, 1H), 7.75 (d, J=9.0 Hz, 2H), 8.63-8.71 (m, 1H).

Example 16(47)

5-[(butyl {1-[(6-{4-[(4-methoxy-1-piperidinyl)sulfonyl]phenoxy}-2-methyl-3-pyridinyl)methyl]-4-piperidinyl}carbamoyl)amino]-2,4-difluorobenzamide TLC: Rf 0.56 (chloroform:methanol:aqueous ammonia=90:13:2);
$^1$H-NMR (CDCl$_3$): δ 0.99 (t, J=7.5 Hz, 3H), 1.33-1.47 (m, 2H), 1.55-1.81 (m, 8H), 1.84-1.96 (m, 2H), 2.10-2.22 (m, 2H), 2.49 (s, 3H), 2.87-3.05 (m, 4H), 3.12-3.25 (m, 4H), 3.25-3.34 (m, 4H), 3.44 (s, 2H), 4.08-4.26 (m, 1H), 5.76 (brs, 1H), 6.38 (d, J=3.0 Hz, 1H), 6.52 (brd, J=9.0 Hz, 1H), 6.75 (d, J=8.0 Hz, 1H), 6.92 (t, J=10.5 Hz, 1H), 7.22 (d, J=9.0 Hz, 2H), 7.65 (d, J=8.0 Hz, 1H), 7.74 (d, J=9.0 Hz, 2H), 8.67 (dd, J=9.0, 8.5 Hz, 1H).

Example 16(48)

2-(5-{[butyl(1-{[2-methyl-6-(4-{[4-(trifluoromethyl)-1-piperidinyl]sulfonyl}phenoxy)-3-pyridinyl]methyl}-4-piperidinyl)carbamoyl]amino}-2,4-difluorophenyl)acetamide TLC: Rf 0.54 (chloroform:methanol:aqueous ammonia=90:13:2);
$^1$H-NMR (CDCl$_3$): δ 0.99 (t, J=7.5 Hz, 3H), 1.33-1.47 (m, 2H), 1.57-1.79 (m, 8H), 1.88-2.06 (m, 3H), 2.10-2.22 (m, 2H), 2.26-2.38 (m, 2H), 2.48 (s, 3H), 2.89-2.98 (m, 2H), 3.14-3.23 (m, 2H), 3.45 (s, 2H), 3.56 (d, J=1.0 Hz, 2H), 3.86-3.96 (m, 2H), 4.08-4.23 (m, 1H), 5.38 (brs, 1H), 5.54 (brs, 1H), 6.44 (d, J=3.5 Hz, 1H), 6.76 (d, J=8.0 Hz, 1H), 6.88 (dd, J=10.5, 9.0 Hz, 1H), 7.24 (d, J=9.0 Hz, 2H), 7.66 (d, J=8.0 Hz, 1H), 7.74 (d, J=9.0 Hz, 2H), 8.09 (t, J=8.5 Hz, 1H).

Example 16(49)

5-{[butyl(1-{[2-methyl-6-(4-{[4-(trifluoromethyl)-1-piperidinyl]sulfonyl}phenoxy)-3-pyridinyl]methyl}-4-piperidinyl)carbamoyl]amino}-2,4-difluorobenzamide TLC: Rf 0.48 (chloroform:methanol:aqueous ammonia=90:13:2);
$^1$H-NMR (CDCl$_3$): δ 0.99 (t, J=7.0 Hz, 3H), 1.33-1.47 (m, 2H), 1.54-1.79 (m, 8H), 1.89-2.06 (m, 3H), 2.09-2.22 (m, 2H), 2.26-2.38 (m, 2H), 2.48 (s, 3H), 2.88-2.97 (m, 2H), 3.15-3.25 (m, 2H), 3.45 (s, 2H), 3.86-3.96 (m, 2H), 4.10-4.25 (m, 1H), 5.74 (brs, 1H), 6.38 (brd, J=3.0 Hz, 1H), 6.51 (brd, J=9.5 Hz, 1H), 6.76 (d, J=8.0 Hz, 1H), 6.88-6.97 (m, 1H), 7.24 (d, J=9.0 Hz, 2H), 7.66 (d, J=8.0 Hz, 1H), 7.75 (d, J=9.0 Hz, 2H), 8.69 (dd, J=9.0, 8.5 Hz, 1H).

Example 16(50)

5-{[{1-[(6-{4-[(4,4-difluoro-1-piperidinyl)sulfonyl]phenoxy}-2-methyl-3-pyridinyl)methyl]-4-piperidinyl}(pentyl)carbamoyl]amino}-2,4-difluorobenzamide TLC: Rf 0.52 (chloroform:methanol:aqueous ammonia=90:13:2);
$^1$H-NMR (CDCl$_3$): δ 0.93 (t, J=6.5 Hz, 3H), 1.27-1.44 (m, 4H), 1.56-1.78 (m, 6H), 2.00-2.22 (m, 6H), 2.48 (s, 3H), 2.88-2.97 (m, 2H), 3.13-3.28 (m, 6H), 3.45 (s, 2H), 4.11-4.26 (m, 1H), 5.78 (s, 1H), 6.38 (d, J=3.5 Hz, 1H), 6.51 (d, J=9.3 Hz, 1H), 6.77 (d, J=8.0 Hz, 1H), 6.92 (t, J=10.5 Hz, 1H), 7.25 (d, J=9.0 Hz, 2H), 7.66 (d, J=8.0 Hz, 1H), 7.75 (d, J=9.0 Hz, 2H), 8.68 (t, J=8.5 Hz, 1H).

Example 16(51)

5-[(butyl {1-[(6-{4-[(4,4-difluoro-1-piperidinyl)sulfonyl]phenoxy}-2-methyl-3-pyridinyl)methyl]-4-piperidinyl}carbamoyl)amino]-2,4-difluorobenzamide TLC: Rf 0.48 (chloroform:methanol:aqueous ammonia=90:13:2);
$^1$H-NMR (CDCl$_3$): δ 0.99 (t, J=7.0 Hz, 3H), 1.32-1.47 (m, 2H), 1.56-1.78 (m, 6H), 2.01-2.22 (m, 6H), 2.48 (s, 3H), 2.87-2.98 (m, 2H), 3.14-3.28 (m, 6H), 3.45 (s, 2H), 4.10-4.26 (m, 1H), 5.76 (brs, 1H), 6.38 (brd, J=3.0 Hz, 1H), 6.52 (brd, J=8.0 Hz, 1H), 6.77 (d, J=8.0 Hz, 1H), 6.92 (t, J=10.5 Hz, 1H), 7.25 (d, J=9.0 Hz, 2H), 7.66 (d, J=8.0 Hz, 1H), 7.75 (d, J=9.0 Hz, 2H), 8.68 (dd, J=9.0, 8.5 Hz, 1H).

Example 16(52)

5-[(butyl {1-[(6-{4-[(4-fluoro-1-piperidinyl)sulfonyl]phenoxy}-2-methyl-3-pyridinyl)methyl]-4-piperidinyl}carbamoyl)amino]-2,4-difluorobenzamide TLC: Rf 0.51 (chloroform:methanol:aqueous ammonia=90:13:2);
$^1$H-NMR (CDCl$_3$): δ 0.99 (t, J=7.5 Hz, 3H), 1.32-1.47 (m, 2H), 1.56-1.78 (m, 6H), 1.82-2.04 (m, 4H), 2.09-2.23 (m, 2H), 2.49 (s, 3H), 2.87-2.99 (m, 4H), 3.14-3.24 (m, 2H), 3.31-3.42 (m, 2H), 3.44 (s, 2H), 4.11-4.26 (m, 1H), 4.65-4.88 (m, 1H), 5.77 (brs, 1H), 6.38 (brd, J=3.0 Hz, 1H), 6.52 (brd, J=9.0 Hz, 1H), 6.76 (d, J=8.0 Hz, 1H), 6.92 (t, J=10.5 Hz, 1H), 7.24 (d, J=9.0 Hz, 2H), 7.65 (d, J=8.0 Hz, 1H), 7.75 (d, J=9.0 Hz, 2H), 8.68 (dd, J=9.0, 8.5 Hz, 1H).

Example 16(53)

5-[(butyl{1-[(6-{4-[(3-hydroxy-1-azetidinyl)sulfonyl]phenoxy}-2-methyl-3-pyridinyl)methyl]-4-piperidinyl}carbamoyl)amino]-2,4-difluorobenzamide TLC: Rf 0.38 (chloroform:methanol:aqueous ammonia=90:13:2);
$^1$H-NMR (CDCl$_3$): δ 0.99 (t, J=7.5 Hz, 3H), 1.33-1.46 (m, 2H), 1.56-1.79 (m, 6H), 2.09-2.22 (m, 2H), 2.48 (s, 3H), 2.88-2.98 (m, 2H), 3.14-3.25 (m, 2H), 3.45 (s, 2H), 3.55-3.63 (m, 2H), 3.99-4.07 (m, 2H), 4.09-4.25 (m, 1H), 4.44-4.55 (m, 1H), 5.79 (brs, 1H), 6.39 (brd, J=3.0 Hz, 1H), 6.53 (brd, J=9.0 Hz, 1H), 6.78 (d, J=8.0 Hz, 1H), 6.92 (t, J=10.5 Hz, 1H), 7.27 (d, J=9.0 Hz, 2H), 7.67 (d, J=8.0 Hz, 1H), 7.83 (d, J=9.0 Hz, 2H), 8.66 (dd, J=9.0, 8.5 Hz, 1H).

Example 16(54)

5-[(butyl {1-[(6-{4-[(cyclopropylamino)sulfonyl]phenoxy}-2-methyl-3-pyridinyl)methyl]-4-piperidinyl}carbamoyl)amino]-2,4-difluorobenzamide TLC: Rf 0.44 (chloroform:methanol:aqueous ammonia=90:13:2);
$^1$H-NMR (d$_6$-DMSO): δ 0.34-0.53 (m, 4H), 0.88 (t, J=7.2 Hz, 3H), 1.19-1.34 (m, 2H), 1.40-1.76 (m, 6H), 1.99-2.16 (m, 3H), 2.36 (s, 3H), 2.79-2.89 (m, 2H), 3.09-3.20 (m, 2H), 3.42 (s, 2H), 3.90 (d, 1H), 6.90 (d, J=8.2 Hz, 1H), 7.24-7.36 (m, 3H), 7.60-7.75 (m, 4H), 7.81 (d, J=8.6 Hz, 2H), 7.87 (brs, 1H), 8.05 (brs, 1H).

Example 16(55)

5-[(butyl {1-[(6-{4-[(cyclobutylamino)sulfonyl]phenoxy}-2-methyl-3-pyridinyl)methyl]-4-piperidinyl}carbamoyl)amino]-2,4-difluorobenzamide TLC: Rf 0.52 (chloroform:methanol:aqueous ammonia=90:13:2);
$^1$H-NMR (d$_6$-DMSO): δ 0.88 (t, J=7.2 Hz, 3H), 1.19-1.35 (m, 2H), 1.39-1.81 (m, 10H), 1.84-1.97 (m, 2H), 1.99-2.12 (m, 2H), 2.34 (s, 3H), 2.78-2.90 (m, 2H), 3.09-3.21 (m, 2H), 3.41 (s, 2H), 3.54-3.68 (m, 1H), 3.90 (d, 1H), 6.88 (d, J=8.2 Hz, 1H), 7.24 (d, J=8.6 Hz, 2H), 7.31 (t, J=10.3 Hz, 1H), 7.60-7.74 (m, 4H), 7.78 (d, J=8.6 Hz, 2H), 7.92 (d, J=8.1 Hz, 1H), 8.04 (brs, 1H).

Example 16(56)

5-[(butyl {1-[(6-{4-[(cyclopentylamino)sulfonyl]phenoxy}-2-methyl-3-pyridinyl)methyl]-4-piperidinyl}carbamoyl)amino]-2,4-difluorobenzamide TLC: Rf 0.54 (chloroform:methanol:aqueous ammonia=90:13:2);
$^1$H-NMR (d$_6$-DMSO): δ 0.88 (t, J=7.3 Hz, 3H), 1.19-1.77 (m, 16H), 1.99-2.13 (m, 2H), 2.35 (s, 3H), 2.78-2.90 (m, 2H), 3.09-3.20 (m, 2H), 3.35-3.46 (m, 3H), 3.83-3.98 (m, 1H), 6.89 (d, J=8.1 Hz, 1H), 7.24 (d, J=9.0 Hz, 2H), 7.31 (t, J=10.4 Hz, 1H), 7.57-7.75 (m, 5H), 7.80 (d, J=9.0 Hz, 2H), 8.04 (brs, 1H).

Example 16(57)

5-{[butyl(1-{[6-(4-{[(4,4-difluorocyclohexyl)amino]sulfonyl}phenoxy)-2-methyl-3-pyridinyl]methyl}-4-piperidinyl)carbamoyl]amino}-2,4-difluorobenzamide TLC: Rf 0.51 (chloroform:methanol:aqueous ammonia=90:13:2);
$^1$H-NMR (d$_6$-DMSO): δ 0.88 (t, J=7.2 Hz, 3H), 1.19-1.35 (m, 2H), 1.35-1.54 (m, 4H), 1.54-1.99 (m, 10H), 1.99-2.12 (m, 2H), 2.35 (s, 3H), 2.78-2.90 (m, 2H), 3.09-3.28 (m, 3H), 3.42 (s, 2H), 3.83-3.98 (m, 1H), 6.89 (d, J=8.1 Hz, 1H), 7.25 (d, J=8.8 Hz, 2H), 7.31 (t, J=10.4 Hz, 1H), 7.59-7.75 (m, 4H), 7.77 (brs, 1H), 7.82 (d, J=8.8 Hz, 2H), 8.04 (brs, 1H).

Example 16(58)

5-{[(1-{[6-(4-acetylphenoxy)-2-methyl-3-pyridinyl]methyl}-4-piperidinyl)(butyl)carbamoyl]amino}-2,4-difluorobenzamide TLC: Rf 0.54 (chloroform:methanol=6:1);
$^1$H-NMR (CD$_3$OD): δ 0.96 (t, J=7.4 Hz, 3H), 1.30-1.45 (m, 2H), 1.50-1.90 (m, 6H), 2.10-2.25 (m, 2H), 2.47 (s, 3H), 2.59 (s, 3H), 2.90-3.05 (m, 2H), 3.20-3.40 (m, 2H), 3.53 (s, 2H), 4.05 (m, 1H), 6.81 (d, J=8.0 Hz, 1H), 7.11-7.16 (m, 3H), 7.75 (d, J=8.0 Hz, 1H), 7.86 (m, 1H), 8.03 (d, J=8.7 Hz, 2H).

Example 16(59)

5-({butyl[1-({2-methyl-6-[4-(methylcarbamoyl)phenoxy]-3-pyridinyl}methyl)-4-piperidinyl]carbamoyl}amino)-2,4-difluorobenzamide TLC: Rf 0.30 (dichloromethane:methanol=9:1);
$^1$H-NMR (CDCl$_3$): δ 0.98 (t, J=7.3 Hz, 3H), 1.33-1.46 (m, 2H), 1.55-1.77 (m, 6H), 2.08-2.20 (m, 2H), 2.47 (s, 3H), 2.87-2.97 (m, 2H), 3.02 (d, J=4.9 Hz, 3H), 3.13-3.24 (m, 2H), 3.42 (s, 2H), 4.09-4.25 (m, 1H), 5.73 (s, 1H), 6.04-6.12 (m, 1H), 6.37 (d, J=4.9 Hz, 1H), 6.47-6.57 (m, 1H), 6.66 (d, J=8.2 Hz, 1H), 6.88-6.95 (m, 1H), 7.12-7.18 (m, 2H), 7.59 (d, J=8.2 Hz, 1H), 7.73-7.79 (m, 2H), 8.64-8.71 (m, 1H).

Example 16(60)

5-{[{1-[(6-{4-[(4-acetyl-1-piperazinyl)carbonyl]phenoxy}-2-methyl-3-pyridinyl)methyl]-4-piperidinyl}(butyl)carbamoyl]amino}-2,4-difluorobenzamide TLC: Rf 0.43 (dichloromethane:methanol=9:1);
$^1$H-NMR (CDCl$_3$): δ 0.98 (t, J=7.2 Hz, 3H), 1.33-1.46 (m, 2H), 1.52-1.77 (m, 6H), 2.07-2.20 (m, 5H), 2.48 (s, 3H), 2.86-2.98 (m, 2H), 3.13-3.24 (m, 2H), 3.43 (s, 2H), 3.46-3.81 (m, 8H), 4.09-4.24 (m, 1H), 5.74 (s, 1H), 6.36-6.41 (m, 1H), 6.47-6.58 (m, 1H), 6.67 (d, J=8.2 Hz, 1H), 6.92 (t, J=10.6 Hz, 1H), 7.14-7.20 (m, 2H), 7.41-7.47 (m, 2H), 7.59 (d, J=8.2 Hz, 1H), 8.63-8.71 (m, 1H).

Example 16(61)

5-({butyl[1-({6-[4-(dimethylcarbamoyl)phenoxy]-2-methyl-3-pyridinyl}methyl)-4-piperidinyl]carbamoyl}amino)-2,4-difluorobenzamide TLC: Rf 0.24 (dichloromethane:methanol=19:1);
$^1$H-NMR (CDCl$_3$): δ 0.98 (t, J=7.3 Hz, 3H), 1.33-1.46 (m, 2H), 1.57-1.77 (m, 6H), 2.08-2.19 (m, 2H), 2.48 (s, 3H), 2.87-2.96 (m, 2H), 3.00-3.24 (m, 8H), 3.42 (s, 2H), 4.10-4.23 (m, 1H), 5.76 (s, 1H), 6.38 (d, J=3.1 Hz, 1H), 6.47-6.57 (m, 1H), 6.63 (d, J=8.2 Hz, 1H), 6.92 (t, J=10.6 Hz, 1H), 7.11-7.16 (m, 2H), 7.42-7.47 (m, 2H), 7.57 (d, J=8.2 Hz, 1H), 8.62-8.70 (m, 1H).

Example 16(62)

5-({butyl[1-({6-[4-(ethylcarbamoyl)phenoxy]-2-methyl-3-pyridinyl}methyl)-4-piperidinyl]carbamoyl}amino)-2,4-difluorobenzamide TLC: Rf 0.48 (ethyl acetate:methanol=19:1);
$^1$H-NMR (CDCl$_3$): δ 0.98 (t, J=7.2 Hz, 3H), 1.26 (t, J=7.3 Hz, 3H), 1.33-1.46 (m, 2H), 1.54-1.77 (m, 6H), 2.08-2.19 (m, 2H), 2.47 (s, 3H), 2.87-2.97 (m, 2H), 3.14-3.24 (m, 2H), 3.42 (s, 2H), 3.46-3.56 (m, 2H), 4.09-4.24 (m, 1H), 5.72 (s, 1H), 5.99-6.08 (m, 1H), 6.37 (d, J=3.1 Hz, 1H), 6.45-6.56 (m, 1H), 6.66 (d, J=8.2 Hz, 1H), 6.92 (t, J=10.5 Hz, 1H), 7.12-7.18 (m, 2H), 7.59 (d, J=8.2 Hz, 1H), 7.74-7.80 (m, 2H), 8.64-8.72 (m, 1H).

Example 16(63)

5-[(butyl{1-[(2-methyl-6-{4-[(4-methyl-1-piperazinyl)carbonyl]phenoxy}-3-pyridinyl)methyl]-4-piperidinyl}carbamoyl)amino]-2,4-difluorobenzamide TLC: Rf 0.44 (dichloromethane:methanol=9:1);
$^1$H-NMR (CDCl$_3$): δ 0.98 (t, J=7.3 Hz, 3H), 1.32-1.46 (m, 2H), 1.56-1.77 (m, 6H), 2.08-2.19 (m, 2H), 2.33 (s, 3H), 2.36-2.51 (m, 7H), 2.87-2.96 (m, 2H), 3.15-3.23 (m, 2H), 3.42 (s, 2H), 3.46-3.89 (m, 4H), 4.10-4.24 (m, 1H), 5.74 (br. s, 1H), 6.38 (d, J=3.1 Hz, 1H), 6.45-6.56 (m, 1H), 6.64 (d, J=8.2 Hz, 1H), 6.92 (t, J=10.6 Hz, 1H), 7.11-7.17 (m, 2H), 7.39-7.45 (m, 2H), 7.58 (d, J=8.2 Hz, 1H), 8.68 (t, J=8.7 Hz, 1H).

Example 16(64)

5-({butyl[1-({6-[4-(1-hydroxy-1-methylethyl)phenoxy]-2-methyl-3-pyridinyl}methyl)-4-piperidinyl]carbamoyl}amino)-2,4-difluorobenzamide TLC: Rf 0.53 (chloroform:methanol=6:1);
$^1$H-NMR (CD$_3$OD): δ 0.96 (t, J=7.2 Hz, 3H), 1.30-1.45 (m, 2H), 1.54 (s, 6H), 1.55-1.90 (m, 6H), 2.05-2.25 (m, 2H), 2.47 (s, 3H), 2.90-3.00 (m, 2H), 3.20-3.40 (m, 2H), 3.48 (s, 2H), 4.00 (m, 1H), 6.59 (d, J=8.2 Hz, 1H), 7.02 (d, J=9.0 Hz, 2H), 7.11 (m, 1H), 7.52 (d, J=9.0 Hz, 2H), 7.65 (d, J=8.2 Hz, 1H), 7.86 (m, 1H).

Example 16(65)

5-[(butyl{1-[(2-methyl-6-{4-[(methylsulfonyl)methyl]phenoxy}-3-pyridinyl)methyl]-4-piperidinyl}carbamoyl)amino]-2,4-difluorobenzamide TLC: Rf 0.50 (chloroform:methanol=9:1);
$^1$H-NMR (CDCl$_3$): δ 0.99 (t, J=7.3 Hz, 3H), 1.29-1.48 (m, 2H), 1.53-1.80 (m, 6H), 2.03-2.21 (m, 2H), 2.48 (s, 3H), 2.80 (s, 3H), 2.85-2.99 (m, 2H), 3.12-3.25 (m, 2H), 3.43 (s, 3H), 4.10-4.23 (m, 1H), 4.25 (s, 2H), 5.71-5.80 (m, 1H), 6.36-6.42 (m, 1H), 6.46-6.57 (m, 1H), 6.66 (d, J=8.2 Hz, 1H), 6.92 (t, J=10.5 Hz, 1H), 7.13-7.20 (m, 2H), 7.36-7.45 (m, 2H), 7.59 (d, J=8.2 Hz, 1H), 8.68 (t, J=9.0 Hz, 1H).

Example 16(66)

5-{[butyl(1-{[2-methyl-6-(4-{[(methylsulfonyl)amino]methyl}phenoxy)-3-pyridinyl]methyl}-4-piperidinyl)carbamoyl]amino}-2,4-difluorobenzamide TLC: Rf 0.43 (chloroform:methanol=9:1);
$^1$H-NMR (CDCl$_3$): δ 0.98 (t, J=7.3 Hz, 3H), 1.24-1.50 (m, 2H), 1.50-1.85 (m, 6H), 2.02-2.22 (m, 2H), 2.46 (s, 3H), 2.86-2.98 (m, 2H), 2.91 (s, 3H), 3.11-3.23 (m, 2H), 3.41 (s, 2H), 4.05-4.23 (m, 1H), 4.33 (d, J=6.1 Hz, 2H), 4.81 (t, J=6.1 Hz, 1H), 5.77-5.93 (m, 1H), 6.30-6.43 (m, 1H), 6.45-6.57 (m, 1H), 6.60 (d, J=8.2 Hz, 1H), 6.92 (t, J=10.5 Hz, 1H), 7.06-7.17 (m, 2H), 7.31-7.41 (m, 2H), 7.56 (d, J=8.2 Hz, 1H), 8.67 (t, J=8.7 Hz, 1H).

Example 16(67)

N-{4-[(5-{[4-((6-methyl-3-pyridinyl){[(6-methyl-3-pyridinyl)amino]carbonyl}amino)-1-piperidinyl]methyl}-2-pyridinyl)oxy]phenyl}methanesulfonamide TLC: Rf 0.28 (dichloromethane:methanol=9:1);
$^1$H-NMR (d$_6$-DMSO): δ 1.04-1.24 (m, 2H), 1.68-1.79 (m, 2H), 1.94-2.06 (m, 2H), 2.34 (s, 3H), 2.52 (s, 3H), 2.70-2.82 (m, 2H), 2.97 (s, 3H), 3.36 (s, 2H), 4.21-4.35 (m, 1H), 6.90 (d, J=8.4 Hz, 1H), 7.03-7.11 (m, 3H), 7.18-7.24 (m, 2H), 7.34 (d, J=8.2 Hz, 1H), 7.53 (dd, J=8.2, 2.6 Hz, 1H), 7.61-7.68 (m, 2H), 7.70 (s, 1H), 7.93 (d, J=2.2 Hz, 1H), 8.27 (d, J=2.4 Hz, 1H), 8.36 (d, J=2.6 Hz, 1H), 9.65 (s, 1H).

Example 16(68)

N-{4-[(5-{[4-((5-methyl-2-pyridinyl){[(6-methyl-3-pyridinyl)amino]carbonyl}amino)-1-piperidinyl]methyl}-2-pyridinyl)oxy]phenyl}methanesulfonamide TLC: Rf 0.50 (chloroform:methanol:aqueous ammonia=90:13:2);
$^1$H-NMR (CDCl$_3$): δ 1.62-1.79 (m, 2H), 1.84-1.94 (m, 2H), 2.06-2.17 (m, 2H), 2.41 (s, 3H), 2.46 (s, 3H), 2.83-2.93 (m, 2H), 3.01 (s, 3H), 3.43 (s, 2H), 4.39 (tt, J=12.0, 4.0 Hz, 1H), 6.74 (brs, 1H), 6.86 (d, J=8.5 Hz, 1H), 7.04 (d, J=8.5 Hz, 1H), 7.11 (d, J=9.0 Hz, 2H), 7.16 (d, J=8.5 Hz, 1H), 7.25 (d, J=9.0 Hz, 2H), 7.32 (s, 1H), 7.61-7.66 (m, 2H), 7.83 (dd, J=8.5, 2.5 Hz, 1H), 8.03 (d, J=2.5 Hz, 1H), 8.15 (d, J=2.5 Hz, 1H), 8.41 (d, J=2.5 Hz, 1H).

Example 16(69)

N-(4-{[5-({4-[{[(5-chloro-2-pyridinyl)amino]carbonyl}(cyclopropyl)amino]-1-piperidinyl}methyl)-2-pyridinyl]oxy}phenyl)methanesulfonamide TLC: Rf 0.33 (ethyl acetate:methanol=9:1);
$^1$H-NMR (CDCl$_3$): δ 0.86-1.13 (m, 4H), 1.68-1.81 (m, 2H), 1.97-2.16 (m, 4H), 2.47-2.56 (m, 1H), 2.86-2.98 (m, 2H), 3.02 (s, 3H), 3.46 (s, 2H), 3.93-4.09 (m, 1H), 6.43-6.55 (m, 1H), 6.90 (dd, J=8.4, 0.6 Hz, 1H), 7.10-7.18 (m, 2H), 7.22-7.30 (m, 2H), 7.60 (dd, J=9.0, 2.6 Hz, 1H), 7.71 (dd, J=8.4, 2.6 Hz, 1H), 8.05-8.12 (m, 3H), 8.15 (dd, J=2.6, 0.6 Hz, 1H).

Example 16(70)

N-[4-({5-[(4-{cyclopropyl[(6-methyl-3-pyridinyl)carbamoyl]amino}-1-piperidinyl)methyl]-2-pyridinyl}oxy)phenyl]methanesulfonamide TLC: Rf 0.22 (dichloromethane:methanol=9:1);
$^1$H-NMR (CDCl$_3$): δ 0.90-1.07 (m, 4H), 1.68-1.82 (m, 2H), 1.95-2.16 (m, 4H), 2.44-2.58 (m, 4H), 2.84-2.98 (m, 2H), 3.02 (s, 3H), 3.46 (s, 2H), 3.96-4.13 (m, 1H), 6.56 (s, 1H), 6.90 (d, J=8.4 Hz, 1H), 7.09 (d, J=8.4 Hz, 1H), 7.14 (d, J=8.8 Hz, 2H), 7.26 (d, J=8.8 Hz, 2H), 7.33 (s, 1H), 7.70 (dd, J=8.4, 2.0 Hz, 1H), 7.96 (dd, J=8.4, 2.7 Hz, 1H), 8.07 (d, J=2.0 Hz, 1H), 8.32 (d, J=2.7 Hz, 1H).

Example 16(71)

2-fluoro-5-{[(5-methyl-2-pyridinyl){1-[(6-{4-[(methylsulfonyl)amino]phenoxy}-3-pyridinyl)methyl]-4-piperidinyl}carbamoyl]amino}benzamide TLC: Rf 0.40 (chloroform:methanol:aqueous ammonia=90:13:2);
$^1$H-NMR (CDCl$_3$): δ 1.57-1.75 (m, 2H), 1.84-1.94 (m, 2H), 2.06-2.17 (m, 2H), 2.42 (s, 3H), 2.83-2.93 (m, 2H), 3.01 (s, 3H), 3.42 (s, 2H), 4.39 (tt, J=12.0, 4.0 Hz, 1H), 5.81 (brs, 1H), 6.60 (brs, 1H), 6.70 (brd, J=11.5 Hz, 1H), 6.86 (d, J=8.0 Hz, 1H), 7.02-7.16 (m, 4H), 7.22 (s, 1H), 7.26 (d, J=9.0 Hz, 2H), 7.45 (dd, J=6.5, 3.0 Hz, 1H), 7.60-7.66 (m, 2H), 8.01-8.09 (m, 2H), 8.42 (d, J=2.5 Hz, 1H).

Example 16(72)

N-[4-({5-[(4-{cyclobutyl[(6-methyl-3-pyridinyl)carbamoyl]amino}-1-piperidinyl)methyl]-2-pyridinyl}oxy)phenyl]methanesulfonamide TLC: Rf 0.31 (dichloromethane:methanol=9:1);
$^1$H-NMR (CDCl$_3$): δ 1.58-1.87 (m, 5H), 2.00-2.13 (m, 2H), 2.14-2.44 (m, 6H), 2.49 (s, 3H), 2.86-2.99 (m, 2H), 3.01 (s, 3H), 3.46 (s, 2H), 3.47-3.60 (m, 1H), 4.08-4.25 (m, 1H), 6.40 (s, 1H), 6.90 (d, J=8.4 Hz, 1H), 7.05-7.17 (m, 3H), 7.27 (d, J=9.0 Hz, 2H), 7.72 (dd, J=8.4, 2.0 Hz, 1H), 7.90 (dd, J=8.4, 2.7 Hz, 1H), 8.04 (d, J=2.0 Hz, 1H), 8.25 (d, J=2.7 Hz, 1H).

Example 16(73)

N-[4-({5-[(4-{2-butyn-1-yl[(6-methyl-3-pyridinyl)carbamoyl]amino}-1-piperidinyl)methyl]-2-pyridinyl}oxy)phenyl]methanesulfonamide TLC: Rf 0.40 (dichloromethane:methanol=9:1);
$^1$H-NMR (CDCl$_3$): δ 1.58-1.80 (m, 4H), 1.87 (t, J=2.3 Hz, 3H), 2.02-2.17 (m, 2H), 2.50 (s, 3H), 2.87-2.98 (m, 2H), 3.02 (s, 3H), 3.46 (s, 2H), 3.88-3.97 (m, 2H), 4.20-4.34 (m, 1H), 6.53 (s, 1H), 6.86-6.94 (m, 2H), 7.06-7.18 (m, 3H), 7.21-7.30 (m, 2H), 7.69 (dd, J=8.4, 2.2 Hz, 1H), 7.85 (dd, J=8.4, 2.2 Hz, 1H), 8.07 (d, J=2.2 Hz, 1H), 8.31 (d, J=2.2 Hz, 1H).

Example 16(74)

N-[4-({5-[(4-{(3-methyl-2-buten-1-yl)[(6-methyl-3-pyridinyl)carbamoyl]amino}-1-piperidinyl)methyl]-2-pyridinyl}oxy)phenyl]methanesulfonamide TLC: Rf 0.59 (chloroform:methanol=10:1);
$^1$H-NMR (CD$_3$OD): δ 1.60-1.90 (m, 4H), 1.73 (s, 3H), 1.73 (s, 3H), 2.05-2.25 (m, 2H), 2.46 (s, 3H), 2.90-3.10 (m, 2H), 2.96 (s, 3H), 3.30-3.40 (m, 2H), 3.53 (s, 2H), 3.95 (d, J=5.1, Hz, 2H), 4.08 (m, 1H), 5.15 (m, 1H), 6.94 (d, J=8.4 Hz, 1H), 7.09 (d, J=9.0 Hz, 2H), 7.21 (d, J=8.5 Hz, 1H), 7.30 (d, J=9.0 Hz, 2H), 7.73 (dd, J=8.4, 2.3 Hz, 1H), 7.81 (dd, J=8.5, 2.5 Hz, 1H), 8.05 (d, J=2.3 Hz, 1H), 8.38 (d, J=2.5 Hz, 1H).

Example 16(75)

N-[4-({5-[(4-{(cyclobutylmethyl)[(6-methyl-3-pyridinyl)carbamoyl]amino}-1-piperidinyl)methyl]-2-pyridinyl}oxy)phenyl]methanesulfonamide TLC: Rf 0.50 (chloroform:methanol=10:1);
$^1$H-NMR (CD$_3$OD): δ 1.60-1.90 (m, 8H), 1.95-2.05 (m, 2H), 2.10-2.20 (m, 2H), 2.46 (s, 3H), 2.60 (m, 1H), 2.90-3.10 (m, 2H), 2.96 (s, 3H), 3.30-3.40 (m, 2H), 3.53 (s, 2H), 3.90 (m, 1H), 6.94 (d, J=8.4 Hz, 1H), 7.09 (d, J=9.2 Hz, 2H), 7.20 (d, J=8.4 Hz, 1H), 7.30 (d, J=9.2 Hz, 2H), 7.73 (dd, J=8.4, 2.3 Hz, 1H), 7.81 (dd, J=8.4, 2.0 Hz, 1H), 8.05 (d, J=2.3 Hz, 1H), 8.39 (d, J=2.0 Hz, 1H).

Example 16(76)

N-[4-({5-[(4-{(3-methylbutyl)[(6-methyl-3-pyridinyl)carbamoyl]amino}-1-piperidinyl)methyl]-2-pyridinyl}oxy)phenyl]methanesulfonamide TLC: Rf 0.54 (chloroform:methanol=10:1);
$^1$H-NMR (CD$_3$OD): δ 0.95 (d, J=6.3 Hz, 6H), 1.45-1.55 (m, 2H), 1.65 (m, 1H), 1.70-1.95 (m, 4H), 2.10-2.20 (m, 2H), 2.46 (s, 3H), 2.90-3.10 (m, 2H), 2.96 (s, 3H), 3.30-3.40 (m, 2H), 3.53 (s, 2H), 4.00 (m, 1H), 6.94 (d, J=8.4 Hz, 1H), 7.09

(d, J=9.2 Hz, 2H), 7.20 (d, J=8.4 Hz, 1H), 7.30 (d, J=9.2 Hz, 2H), 7.73 (dd, J=8.4, 2.2 Hz, 1H), 7.81 (dd, J=8.4, 2.4 Hz, 1H), 8.05 (d, J=2.2 Hz, 1H), 8.39 (d, J=2.4 Hz, 1H).

Example 16(77)

2,4-difluoro-5-{[(3-methylbutyl) {1-[(6-{4-[(methyl-sulfonyl)amino]phenoxy}-3-pyridinyl)methyl]-4-piperidinyl}carbamoyl]amino}benzamide TLC: Rf 0.36 (chloroform:methanol=10:1);
¹H-NMR (CD₃OD): δ 0.95 (d, J=6.3 Hz, 6H), 1.50-1.90 (m, 7H), 2.10-2.20 (m, 2H), 2.90-3.00 (m, 2H), 2.96 (s, 3H), 3.20-3.40 (m, 2H), 3.53 (s, 2H), 4.01 (m, 1H), 6.94 (d, J=8.5 Hz, 1H), 7.08-7.15 (m, 3H), 7.28-7.32 (m, 2H), 7.81 (dd, J=8.5, 2.3 Hz, 1H), 7.87 (m, 1H), 8.05 (d, J=2.3 Hz, 1H).

Example 16(78)

5-{[(cyclobutylmethyl){1-[(6-{4-[(methylsulfonyl)amino]phenoxy}-3-pyridinyl)methyl]-4-piperidinyl}carbamoyl]amino}-2,4-difluorobenzamide TLC: Rf 0.24 (chloroform:methanol=10:1);
¹H-NMR (CD₃OD): δ 1.60-1.90 (m, 8H), 2.00-2.20 (m, 4H), 2.65 (m, 1H), 2.90-3.00 (m, 2H), 2.96 (s, 3H), 3.30-3.35 (m, 2H), 3.52 (s, 2H), 3.88 (m, 1H), 6.94 (d, J=8.5 Hz, 1H), 7.08-7.14 (m, 3H), 7.27-7.32 (m, 2H), 7.81 (dd, J=8.5, 2.2 Hz, 1H), 7.85 (m, 1H), 8.05 (d, J=2.2 Hz, 1H).

Example 16(79)

5-{[(cyclopropylmethyl){1-[(6-{4-[(methylsulfonyl)amino]phenoxy}-3-pyridinyl)methyl]-4-piperidinyl}carbamoyl]amino}-2,4-difluorobenzamide TLC: Rf 0.36 (chloroform:methanol=10:1);
¹H-NMR (CD₃OD): δ 0.34-0.37 (m, 2H), 0.55-0.61 (m, 2H), 1.06 (m, 1H), 1.70-1.90 (m, 4H), 2.10-2.20 (m, 2H), 2.90-3.00 (m, 2H), 2.96 (s, 3H), 3.22 (d, J=6.0 Hz, 1H), 3.53 (s, 2H), 3.97 (m, 1H), 6.94 (d, J=8.6 Hz, 1H), 7.09 (d, J=9.2 Hz, 2H), 7.11 (m, 1H), 7.30 (d, J=9.2 Hz, 2H), 7.81 (dd, J=8.6, 2.4 Hz, 1H), 7.91 (m, 1H), 8.05 (d, J=2.4 Hz, 1H).

Example 16(80)

2,4-difluoro-5-{[(2-hydroxybutyl) {1-[(6-{4-[(methylsulfonyl)amino]phenoxy}-3-pyridinyl)methyl]-4-piperidinyl}carbamoyl]amino}benzamide TLC: Rf 0.27 (chloroform:methanol=10:1);
¹H-NMR (CD₃OD): δ 1.00 (t, J=7.5 Hz, 3H), 1.40-1.60 (m, 2H), 1.70-1.85 (m, 4H), 2.10-2.25 (m, 2H), 2.90-3.00 (m, 2H), 2.96 (s, 3H), 3.20-3.40 (m, 2H), 3.53 (s, 2H), 3.62 (m, 1H), 4.05 (m, 1H), 6.94 (d, J=8.5 Hz, 1H), 7.08-7.12 (m, 3H), 7.30 (d, J=9.0 Hz, 2H), 7.81 (dd, J=8.5, 2.3 Hz, 1H), 8.05 (d, J=2.3 Hz, 1H), 8.14 (m, 1H).

Example 16(81)

5-[(3-butyn-1-yl {1-[(6-{4-[(methylsulfonyl)amino]phenoxy}-3-pyridinyl)methyl]-4-piperidinyl}carbamoyl)amino]-2,4-difluorobenzamide TLC: Rf 0.36 (chloroform:methanol=10:1);
¹H-NMR (CD₃OD): δ 1.70-1.90 (m, 4H), 2.10-2.20 (m, 2H), 2.37 (t, J=2.4 Hz, 1H), 2.40-2.55 (m, 2H), 2.90-3.00 (m, 2H), 2.96 (s, 3H), 3.48 (t, J=7.2 Hz, 2H), 3.53 (s, 2H), 3.94 (m, 1H), 6.94 (d, J=8.4 Hz, 1H), 7.08-7.15 (m, 3H), 7.28-7.32 (m, 2H), 7.80-7.85 (m, 2H), 8.05 (d, J=1.8 Hz, 1H).

Example 16(82)

N-[4-({5-[(4-{butyl[(6-methyl-3-pyridinyl)carbamoyl]amino}-1-piperidinyl)methyl]-2-pyridinyl}oxy)phenyl]methanesulfonamide TLC: Rf 0.36 (chloroform:methanol=10:1);
¹H-NMR (CDCl₃): δ 0.99 (t, J=7.4 Hz, 3H), 1.30-1.50 (m, 2H), 1.55-1.80 (m, 6H), 2.00-2.20 (m, 2H), 2.50 (s, 3H), 2.90-3.00 (m, 2H), 3.02 (s, 3H), 3.10-3.30 (m, 2H), 3.47 (s, 2H), 4.16 (m, 1H), 6.22 (s, 1H), 6.90 (d, J=8.4 Hz, 1H), 7.09 (d, J=8.3 Hz, 1H), 7.12-7.16 (m, 2H), 7.24-7.28 (m, 2H), 7.69 (dd, J=8.4, 2.2 Hz, 1H), 7.87 (dd, J=8.3, 2.6 Hz, 1H), 8.07 (d, J=2.2 Hz, 1H), 8.29 (d, J=2.6 Hz, 1H).

Example 16(83)

N-[4-({5-[(4-{(cyclopropylmethyl)[(6-methyl-3-pyridinyl)carbamoyl]amino}-1-piperidinyl)methyl]-2-pyridinyl}oxy)phenyl]methanesulfonamide TLC: Rf 0.36 (chloroform:methanol=10:1);
¹H-NMR (CDCl₃): δ 0.37-0.39 (m, 2H), 0.76-0.79 (m, 2H), 0.95 (m, 1H), 1.55-1.80 (m, 4H), 2.05-2.20 (m, 2H), 2.50 (s, 3H), 2.90-3.00 (m, 2H), 3.02 (s, 3H), 3.15 (d, J=5.4 Hz, 2H), 3.46 (s, 2H), 4.21 (m, 1H), 6.87 (s, 1H), 6.90 (d, J=8.5 Hz, 1H), 7.09 (d, J=8.5 Hz, 1H), 7.12-7.16 (m, 2H), 7.24-7.28 (m, 2H), 7.69 (dd, J=8.5, 2.2 Hz, 1H), 7.90 (dd, J=8.5, 2.7 Hz, 1H), 8.07 (d, J=2.2 Hz, 1H), 8.31 (d, J=2.7 Hz, 1H).

Example 16(84)

N-[4-({5-[(4-{(2-hydroxybutyl)[(6-methyl-3-pyridinyl)carbamoyl]amino}-1-piperidinyl)methyl]-2-pyridinyl}oxy)phenyl]methanesulfonamide TLC: Rf 0.36 (chloroform:methanol=10:1);
¹H-NMR (CDCl₃): δ 1.02 (t, J=7.4 Hz, 3H), 1.40-1.80 (m, 4H), 2.00-2.20 (m, 2H), 2.45 (s, 3H), 2.85-2.95 (m, 2H), 3.01 (s, 3H), 3.10-3.50 (m, 2H), 3.44 (s, 2H), 3.65 (m, 1H), 4.13 (m, 1H), 6.89 (d, J=8.4 Hz, 1H), 7.04 (d, J=8.4 Hz, 1H), 7.12 (d, J=9.0 Hz, 2H), 7.24-7.27 (m, 3H), 7.66 (dd, J=8.4, 2.4 Hz, 1H), 7.88 (dd, J=8.4, 2.5 Hz, 1H), 8.05 (d, J=2.4 Hz, 1H), 8.13 (d, J=2.5 Hz, 1H), 9.50 (s, 1H).

Example 16(85)

N-[4-({5-[(4-{3-butyn-1-yl[(6-methyl-3-pyridinyl)carbamoyl]amino}-1-piperidinyl)methyl]-2-pyridinyl}oxy)phenyl]methanesulfonamide TLC: Rf 0.38 (chloroform:methanol=10:1);
¹H-NMR (CDCl₃): δ 1.40-1.80 (m, 4H), 2.00-2.20 (m, 2H), 2.21 (t, J=2.6 Hz, 1H), 2.45-2.55 (m, 2H), 2.50 (s, 3H), 2.90-3.05 (m, 2H), 3.01 (s, 3H), 3.40-3.50 (m, 2H), 3.47 (s, 2H), 4.10 (m, 1H), 6.89 (d, J=8.4 Hz, 1H), 6.98 (s, 1H), 7.09 (d, J=8.5 Hz, 1H), 7.12-7.17 (m, 2H), 7.25-7.28 (m, 2H), 7.66 (dd, J=8.4, 2.3 Hz, 1H), 7.88 (dd, J=8.5, 2.6 Hz, 1H), 8.05 (d, J=2.3 Hz, 1H), 8.13 (d, J=2.6 Hz, 1H).

Example 16(86)

5-[(2-butyn-1-yl {1-[(6-{4-[(methylsulfonyl)amino]phenoxy}-3-pyridinyl)methyl]-4-piperidinyl}carbamoyl)amino]-2-fluorobenzamide TLC: Rf 0.45 (dichloromethane:methanol=9:1);
$^1$H-NMR (CDCl$_3$): δ 1.67-1.78 (m, 4H), 1.83-1.89 (m, 3H), 2.03-2.16 (m, 2H), 2.88-2.98 (m, 2H), 3.02 (s, 3H), 3.46 (s, 2H), 3.86-3.96 (m, 2H), 4.14-4.31 (m, 1H), 5.88 (s, 1H), 6.63-6.85 (m, 2H), 6.89 (d, J=8.2 Hz, 1H), 6.98 (s, 1H), 7.04-7.17 (m, 3H), 7.23-7.31 (m, 2H), 7.64-7.76 (m, 2H), 7.90-7.99 (m, 1H), 8.06 (d, J=2.4 Hz, 1H).

Example 16(87)

2,4-difluoro-5-{[(3-methyl-2-buten-1-yl) {1-[(6-{4-[(methylsulfonyl)amino]phenoxy}-3-pyridinyl)methyl]-4-piperidinyl}carbamoyl]amino}benzamide TLC: Rf 0.29 (chloroform:methanol=10:1);
$^1$H-NMR (CD$_3$OD): δ 1.61 (s, 6H), 1.70-1.90 (m, 4H), 2.00-2.20 (m, 2H), 2.90-3.10 (m, 2H), 2.96 (s, 3H), 3.50-3.60 (m, 2H), 3.53 (s, 2H), 3.90-4.00 (m, 2H), 5.15 (m, 1H), 6.94 (d, J=8.4 Hz, 1H), 7.09 (d, J=8.7 Hz, 2H), 7.11 (m, 1H), 7.30 (d, J=8.7 Hz, 2H), 7.82 (dd, J=8.4, 2.4 Hz, 1H), 7.90 (m, 1H), 8.05 (d, J=2.4 Hz, 1H).

Example 16(88)

5-[(butyl {1-[(6-{4-[(methylsulfonyl)amino]phenoxy}-3-pyridinyl)methyl]-4-piperidinyl}carbamoyl)amino]-2-fluorobenzamide TLC: Rf 0.40 (chloroform:methanol=10:1);
$^1$H-NMR (CD$_3$OD): δ 0.95 (t, J=7.4 Hz, 3H), 1.30-1.45 (m, 2H), 1.50-1.70 (m, 2H), 1.75-1.90 (m, 2H), 2.10-2.25 (m, 2H), 2.96 (s, 3H), 3.20-3.40 (m, 4H), 3.53 (s, 2H), 4.00 (m, 1H), 6.93 (d, J=8.4 Hz, 1H), 7.08-7.20 (m, 3H), 7.29 (d, J=8.7 Hz, 2H), 7.54 (m, 1H), 7.74 (dd, J=8.4, 2.7 Hz, 1H), 7.81 (dd, J=8.4, 2.4 Hz, 1H), 8.05 (d, J=2.4 Hz, 1H).

Example 16(89)

N-[4-({5-[(4-{isobutyl[(6-methyl-3-pyridinyl)carbamoyl]amino}-1-piperidinyl)methyl]-2-pyridinyl}oxy)phenyl]methanesulfonamide TLC: Rf 0.48 (chloroform:methanol:aqueous ammonia=90:13:2);
$^1$H-NMR (CDCl$_3$): δ 0.99 (d, J=6.5 Hz, 6H), 1.63-1.89 (m, 4H), 1.89-2.15 (m, 3H), 2.49 (s, 3H), 2.89-2.98 (m, 2H), 3.01 (s, 3H), 3.05 (d, J=7.5 Hz, 2H), 3.46 (s, 2H), 3.94-4.08 (m, 1H), 6.33 (s, 1H), 6.84 (brs, 1H), 6.90 (d, J=8.5 Hz, 1H), 7.08 (d, J=8.5 Hz, 1H), 7.13 (d, J=9.0 Hz, 2H), 7.26 (d, J=9.0 Hz, 2H), 7.69 (dd, J=8.5, 2.5 Hz, 1H), 7.86 (dd, J=8.5, 2.5 Hz, 1H), 8.06 (d, J=2.5 Hz, 1H), 8.27 (d, J=2.5 Hz, 1H).

Example 16(90)

2-fluoro-5-[(isobutyl {1-[(6-{4-[(methylsulfonyl)amino]phenoxy}-3-pyridinyl)methyl]-4-piperidinyl}carbamoyl)amino]benzamide TLC: Rf 0.39 (chloroform:methanol:aqueous ammonia=90:13:2);
$^1$H-NMR (CDCl$_3$): δ 0.98 (d, J=6.5 Hz, 6H), 1.56-1.90 (m, 4H), 1.90-2.15 (m, 3H), 2.89-2.98 (m, 2H), 3.01 (s, 3H), 3.05 (d, J=8.0 Hz, 2H), 3.46 (s, 2H), 3.90-4.03 (m, 1H), 5.91 (s, 1H), 6.53 (s, 1H), 6.69-6.80 (m, 1H), 6.90 (dd, J=8.5, 0.5 Hz, 1H), 7.09 (dd, J=11.5, 9.0 Hz, 1H), 7.13 (d, J=9.0 Hz, 2H), 7.28 (d, J=9.0 Hz, 2H), 7.64-7.72 (m, 2H), 8.00 (ddd, J=9.0, 4.5, 3.0 Hz, 1H), 8.06 (dd, J=2.5, 0.5 Hz, 1H).

Example 16(91)

5-[(2-butyn-1-yl {1-[(6-{4-[(methylsulfonyl)amino]phenoxy}-3-pyridinyl)methyl]-4-piperidinyl}carbamoyl)amino]-2,4-difluorobenzamide TLC: Rf 0.79 (chloroform:methanol=6:1);
$^1$H-NMR (CD$_3$OD): δ 1.66-1.95 (m, 4H), 1.81 (t, J=2.3 Hz, 3H), 2.09-2.21 (m, 2H), 2.93-3.03 (m, 2H), 2.96 (s, 3H), 3.53 (s, 2H), 4.00-4.17 (m, 3H), 6.94 (d, J=8.6 Hz, 1H), 7.04-7.20 (m, 3H), 7.31 (d, J=9.0 Hz, 2H), 7.82 (dd, J=8.6, 2.2 Hz, 1H), 7.96 (dd, J=8.6, 7.9 Hz, 1H), 8.05 (d, J=2.2 Hz, 1H).

Example 16(92)

2,4-difluoro-5-{[{1-[(6-{4-[(methylsulfonyl)amino]phenoxy}-3-pyridinyl)methyl]-4-piperidinyl}(propyl)carbamoyl]amino}benzamide TLC: Rf 0.80 (chloroform:methanol=6:1);
$^1$H-NMR (CD$_3$OD): δ 0.93 (t, J=7.3 Hz, 3H), 1.55-1.95 (m, 6H), 2.04-2.23 (m, 2H), 2.89-3.05 (m, 2H), 2.96 (s, 3H), 3.12-3.27 (m, 2H), 3.52 (s, 2H), 3.94-4.10 (m, 1H), 6.94 (d, J=8.4 Hz, 1H), 7.04-7.17 (m, 3H), 7.30 (d, J=9.0 Hz, 2H), 7.76-7.90 (m, 2H), 8.05 (d, J=2.2 Hz, 1H).

Example 16(93)

5-[(3-buten-1-yl{1-[(6-{4-[(methylsulfonyl)amino]phenoxy}-3-pyridinyl)methyl]-4-piperidinyl}carbamoyl)amino]-2,4-difluorobenzamide TLC: Rf 0.79 (chloroform:methanol=6:1);
$^1$H-NMR (CD$_3$OD): δ 1.66-1.94 (m, 4H), 2.08-2.24 (m, 2H), 2.29-2.45 (m, 2H), 2.92-3.03 (m, 2H), 2.96 (s, 3H), 3.30-3.39 (m, 2H), 3.53 (s, 2H), 3.93-4.07 (m, 1H), 4.98-5.20 (m, 2H), 5.73-5.95 (m, 1H), 6.94 (d, J=8.4 Hz, 1H), 7.04-7.19 (m, 3H), 7.30 (d, J=9.2 Hz, 2H), 7.77-7.91 (m, 2H), 8.05 (d, J=2.4 Hz, 1H).

Example 16(94)

5-{[(cyclopentylmethyl) {1-[(6-{4-[(methylsulfonyl)amino]phenoxy}-3-pyridinyl)methyl]-4-piperidinyl}carbamoyl]amino}-2,4-difluorobenzamide TLC: Rf 0.63 (chloroform:methanol=6:1);
$^1$H-NMR (CD$_3$OD): δ 1.21-1.37 (m, 2H), 1.49-2.00 (m, 8H), 2.07-2.32 (m, 3H), 2.97 (s, 3H), 2.97-3.03 (m, 2H), 3.26-3.33 (m, 4H), 3.52 (s, 2H), 3.77-3.96 (m, 1H), 6.95 (d, J=7.9 Hz, 1H), 7.07-7.18 (m, 1H), 7.07-7.12 (d, J=9.0 Hz, 2H), 7.27-7.35 (d, J=9.0 Hz, 2H), 7.77-7.89 (m, 2H), 8.05 (d, J=1.8 Hz, 1H).

Example 16(95)

2-{5-[(butyl{1-[(2-methyl-6-{4-[(methylsulfonyl)amino]phenoxy}-3-pyridinyl)methyl]-4-piperidinyl}carbamoyl)amino]-2,4-difluorophenyl}acetamide TLC: Rf 0.56 (chloroform:methanol=10:1);
$^1$H-NMR (CD$_3$OD): δ 0.96 (t, J=7.4 Hz, 3H), 1.30-1.45 (m, 2H), 1.50-1.90 (m, 4H), 2.10-2.25 (m, 2H), 2.47 (s, 3H), 2.90-3.00 (m, 2H), 2.98 (s, 3H), 3.20-3.40 (m, 4H), 3.49 (s, 2H), 3.53 (s, 2H), 4.05 (m, 1H), 6.65 (d, J=8.4 Hz, 1H), 6.98 (m, 1H), 7.08 (J=9.0 Hz, 2H), 7.29 (d, J=9.0 Hz, 2H), 7.35 (m, 1H), 7.67 (d, J=8.4 Hz, 1H).

Example 16(96)

5-[(butyl{1-[(2-methyl-6-{4-[(methylsulfonyl)amino]phenoxy}-3-pyridinyl)methyl]-4-piperidinyl}carbamoyl)amino]-2-fluorobenzamide TLC: Rf 0.56 (chloroform:methanol=10:1);
$^1$H-NMR (CD$_3$OD): δ 0.95 (t, J=7.4 Hz, 3H), 1.30-1.45 (m, 2H), 1.50-1.90 (m, 4H), 2.10-2.25 (m, 2H), 2.47 (s, 3H), 2.65-2.80 (m, 2H), 2.96 (s, 3H), 3.20-3.40 (m, 4H), 3.50 (s, 2H), 4.05 (m, 1H), 6.94 (d, J=8.3 Hz, 1H), 7.06-7.16 (m, 3H), 7.29 (d, J=9.0 Hz, 2H), 7.55 (m, 1H), 7.67 (d, J=8.3 Hz, 1H), 7.75 (m, 1H).

Example 16(97)

N-[4-({5-[(4-{butyl[(5-cyano-2,4-difluorophenyl)carbamoyl]amino}-1-piperidinyl)methyl]-6-methyl-2-pyridinyl}oxy)phenyl]methanesulfonamide TLC: Rf 0.26 (dichloromethane:methanol=19:1);
$^1$H-NMR (CDCl$_3$): δ 0.99 (t, J=7.2 Hz, 3H), 1.33-1.46 (m, 2H), 1.54-1.79 (m, 6H), 2.08-2.20 (m, 2H), 2.47 (s, 3H), 2.87-2.97 (m, 2H), 3.02 (s, 3H), 3.14-3.24 (m, 2H), 3.42 (s, 2H), 4.07-4.20 (m, 1H), 6.36 (br. s, 1H), 6.54 (d, J=4.0 Hz, 1H), 6.62 (d, J=8.2 Hz, 1H), 6.99 (dd, J=10.7, 8.4 Hz, 1H), 7.10-7.15 (m, 2H), 7.21-7.27 (m, 2H), 7.56 (d, J=8.2 Hz, 1H), 8.58 (dd, J=8.4, 6.8 Hz, 1H).

Example 16(98)

N-[4-({5-[(4-{butyl[(3-methyl-5-isoxazolyl)carbamoyl]amino}-1-piperidinyl)methyl]-6-methyl-2-pyridinyl}oxy)phenyl]methanesulfonamide TLC: Rf 0.36 (dichloromethane:methanol=19:1);
$^1$H-NMR (CDCl$_3$): δ 0.98 (t, J=7.2 Hz, 3H), 1.31-1.44 (m, 2H), 1.50-1.79 (m, 6H), 2.07-2.19 (m, 2H), 2.24 (s, 3H), 2.46 (s, 3H), 2.88-2.96 (m, 2H), 3.02 (s, 3H), 3.10-3.20 (m, 2H), 3.42 (s, 2H), 3.98-4.16 (m, 1H), 6.03 (s, 1H), 6.40 (s, 1H), 6.62 (d, J=8.2 Hz, 1H), 7.09-7.16 (m, 3H), 7.22-7.27 (m, 2H), 7.55 (d, J=8.2 Hz, 1H).

Example 16(99)

5-[(butyl{1-[(2-methyl-6-{4-[(methylsulfonyl)amino]phenoxy}-3-pyridinyl)methyl]-4-piperidinyl}carbamoyl)amino]-2,4-difluorobenzenesulfonamide TLC: Rf 0.40 (ethyl acetate);
$^1$H-NMR (d$_6$-DMSO): δ 0.88 (t, J=7.3 Hz, 3H), 1.19-1.35 (m, 2H), 1.39-1.77 (m, 6H), 1.96-2.11 (m, 2H), 2.34 (s, 3H), 2.77-2.89 (m, 2H), 2.97 (s, 3H), 3.09-3.22 (m, 2H), 3.39 (s, 2H), 3.82-3.97 (m, 1H), 6.71 (d, J=8.2 Hz, 1H), 7.07 (d, J=9.0 Hz, 2H), 7.22 (d, J=9.0 Hz, 2H), 7.49 (t, J=10.2 Hz, 1H), 7.58-7.76 (m, 2H), 7.63 (d, J=8.2 Hz, 1H), 7.83 (t, J=8.2 Hz, 1H), 8.14 (s, 1H), 9.38-9.95 (m, 1H).

Example 16(100)

N-[4-({5-[(4-{butyl[(6-methyl-3-pyridinyl)carbamoyl]amino}-1-piperidinyl)methyl]-6-methyl-2-pyridinyl}oxy)phenyl]methanesulfonamide TLC: Rf 0.52 (chloroform:methanol:aqueous ammonia=9:1:0.1);
$^1$H-NMR (CD$_3$OD): δ 0.95 (t, J=7.3 Hz, 3H), 1.24-1.44 (m, 2H), 1.50-1.93 (m, 6H), 2.12-2.24 (m, 2H), 2.46 (s, 3H), 2.47 (s, 3H), 2.91-3.02 (m, 2H), 2.96 (s, 3H), 3.19-3.35 (m, 2H), 3.49 (s, 2H), 3.87-4.15 (m, 1H), 6.64 (d, J=8.4 Hz, 1H), 7.00-7.12 (m, 2H), 7.20 (d, J=8.4 Hz, 1H), 7.24-7.34 (m, 2H), 7.67 (d, J=8.4 Hz, 1H), 7.75 (dd, J=8.4, 2.5 Hz, 1H), 8.40 (d, J=2.5 Hz, 1H).

Example 16(101)

5-[(butyl{1-[(6-{4-[(ethylsulfonyl)amino]phenoxy}-2-methyl-3-pyridinyl)methyl]-4-piperidinyl}carbamoyl)amino]-2,4-difluorobenzamide TLC: Rf 0.41 (dichloromethane:ethyl acetate:methanol=5:5:1);
$^1$H-NMR (CDCl$_3$): δ 0.98 (t, J=7.2 Hz, 3H), 1.30-1.50 (m, 5H), 1.51-1.84 (m, 6H), 2.04-2.21 (m, 2H), 2.47 (s, 3H), 2.82-3.00 (m, 2H), 3.05-3.25 (m, 4H), 3.41 (s, 2H), 4.07-4.25 (m, 1H), 5.93 (s, 1H), 6.39 (d, J=3.0 Hz, 1H), 6.46-6.62 (m, 1H), 6.59 (d, J=8.2 Hz, 1H), 6.77-6.94 (m, 1H), 6.92 (t, J=10.6 Hz, 1H), 7.10 (d, J=8.8 Hz, 2H), 7.19-7.31 (m, 2H), 7.55 (d, J=8.2 Hz, 1H), 8.67 (t, J=8.7 Hz, 1H).

Example 16(102)

5-{[(cyclobutylmethyl){1-[(2-methyl-6-{4-[(methylsulfonyl)amino]phenoxy}-3-pyridinyl)methyl]-4-piperidinyl}carbamoyl]amino}-2,4-difluorobenzamide TLC: Rf 0.31 (chloroform:methanol=10:1);
$^1$H-NMR (CD$_3$OD): δ 1.60-1.95 (m, 8H), 2.00-2.25 (m, 4H), 2.46 (s, 3H), 2.60 (m, 1H), 2.90-3.00 (m, 2H), 2.96 (s, 3H), 3.48 (s, 2H), 3.89 (m, 1H), 6.64 (d, J=8.3 Hz, 1H), 7.06-7.15 (m, 3H), 7.29 (d, J=9.0 Hz, 2H), 7.67 (d, J=8.3 Hz, 1H), 7.86 (t, J=8.1 Hz, 1H).

Example 16(103)

5-[(2-butyn-1-yl{1-[(2-methyl-6-{4-[(methylsulfonyl)amino]phenoxy}-3-pyridinyl)methyl]-4-piperidinyl}carbamoyl)amino]-2,4-difluorobenzamide TLC: Rf 0.39 (ethyl acetate:methanol=20:1);
$^1$H-NMR (CDCl$_3$): δ 1.63-1.80 (m, 4H), 1.86 (t, J=2.1 Hz, 3H), 2.05-2.20 (m, 2H), 2.46 (s, 3H), 2.83-2.97 (m, 2H), 3.01 (s, 3H), 3.41 (s, 2H), 3.88-3.96 (m, 2H), 4.21-4.36 (m, 1H), 5.88 (s, 1H), 6.45-6.61 (m, 1H), 6.60 (d, J=8.2 Hz, 1H), 6.69-6.80 (m, 1H), 6.92 (t, J=10.4 Hz, 1H), 7.12 (d, J=9.0 Hz, 2H), 7.18 (d, J=3.3 Hz, 1H), 7.26 (d, J=9.0 Hz, 2H), 7.55 (d, J=8.2 Hz, 1H), 8.59 (t, J=8.6 Hz, 1H).

Example 16(104)

5-{[(cyclopropylmethyl) {1-[(2-methyl-6-{4-[(methylsulfonyl)amino]phenoxy}-3-pyridinyl)methyl]-4-piperidinyl}carbamoyl]amino}-2,4-difluorobenzamide TLC: Rf 0.42 (chloroform:methanol=10:1);
$^1$H-NMR (CD$_3$OD): δ 0.32-0.37 (m, 2H), 0.55-0.61 (m, 2H), 1.04 (m, 1H), 1.70-1.90 (m, 4H), 2.10-2.20 (m, 2H), 2.46 (s, 3H), 2.90-3.00 (m, 2H), 2.96 (s, 3H), 3.22 (d, J=6.0 Hz, 1H), 3.49 (s, 2H), 3.98 (m, 1H), 6.64 (d, J=8.3 Hz, 1H), 7.06-7.15 (m, 3H), 7.29 (d, J=9.2 Hz, 2H), 7.67 (d, J=8.3 Hz, 1H), 7.92 (t, J=8.1 Hz, 1H).

Example 16(105)

N-{4-[(5-{[4-(butyl {[2,4-difluoro-5-(1,3-oxazol-2-yl)phenyl]carbamoyl}amino)-1-piperidinyl]methyl}-6-methyl-2-pyridinyl)oxy]phenyl}methanesulfonamide TLC: Rf 0.70 (chloroform:methanol=10:1);
$^1$H-NMR (CD$_3$OD): δ 0.96 (t, J=7.2 Hz, 3H), 1.29-1.48 (m, 2H), 1.53-1.94 (m, 6H), 2.10-2.26 (m, 2H), 2.47 (s, 3H), 2.80-3.00 (m, 2H), 2.96 (s, 3H), 3.21-3.33 (m, 2H), 3.49 (s, 2H), 3.95-4.12 (m, 1H), 6.64 (d, J=8.3 Hz, 1H), 7.07 (d, J=9.1 Hz, 2H), 7.21 (t, J=10.3 Hz, 1H), 7.29 (d, J=9.1 Hz, 2H), 7.33 (s, 1H), 7.67 (d, J=8.3 Hz, 1H), 8.02 (s, 1H), 8.08 (t, J=8.1 Hz, 1H).

Example 16(106)

N-[4-({5-[(4-{butyl[(6-fluoro-1-oxo-1,2,3,4-tetrahydro-7-isoquinolinyl)carbamoyl]amino}-1-piperidinyl)methyl]-6-methyl-2-pyridinyl}oxy)phenyl]methanesulfonamide TLC: Rf 0.51 (ethyl acetate:methanol=10:1);
$^1$H-NMR (d$_6$-DMSO): δ 0.86 (t, J=7.3 Hz, 3H), 1.22-1.37 (m, J=7.3 Hz, 2H), 1.45-1.61 (m, 2H), 1.61-1.89 (m, 4H), 1.96-2.10 (m, 2H), 2.36 (s, 3H), 2.79-2.92 (m, 4H), 2.92-3.00 (m, 3H), 3.19 (t, J=6.2 Hz, 2H), 3.58 (t, J=6.2 Hz, 2H), 3.64-3.79 (m, 1H), 4.44-4.55 (m, 1H), 4.96 (s, 2H), 6.69 (d, J=7.9 Hz, 1H), 6.96 (d, J=11.7 Hz, 1H), 7.07 (d, J=8.8 Hz, 2H), 7.24 (d, J=8.8 Hz, 2H), 7.42 (d, J=9.3 Hz, 1H), 7.61 (d, J=7.9 Hz, 1H), 9.26-9.38 (m, 1H).

Example 16(107)

2,4-difluoro-5-{[{1-[(2-methyl-6-{4-[(methylsulfonyl)amino]phenoxy}-3-pyridinyl)methyl]-4-piperidinyl}(pentyl)carbamoyl]amino}benzamide TLC: Rf 0.28 (chloroform:methanol=6:1);
$^1$H-NMR (CD$_3$OD): δ 0.92 (t, J=6.4 Hz, 3H), 1.20-1.44 (m, 4H), 1.50-1.97 (m, 6H), 2.04-2.27 (m, 2H), 2.47 (s, 3H), 2.88-3.06 (m, 2H), 2.96 (s, 3H), 3.18-3.30 (m, 2H), 3.48 (s, 2H), 3.91-4.20 (m, 1H), 6.64 (d, J=8.2 Hz, 1H), 7.01-7.18 (m, 3H), 7.29 (d, J=9.0 Hz, 2H), 7.67 (d, J=8.4 Hz, 1H), 7.85 (t, J=8.2 Hz, 1H).

Example 16(108)

2,4-difluoro-5-{[{1-[(2-methyl-6-{4-[(methylsulfonyl)amino]phenoxy}-3-pyridinyl)methyl]-4-piperidinyl}(propyl)carbamoyl]amino}benzamide TLC: Rf 0.66 (chloroform:methanol=6:1);
$^1$H-NMR (CD$_3$OD): δ 0.93 (t, J=7.3 Hz, 3H), 1.55-1.89 (m, 6H), 2.17 (m, 2H), 2.47 (s, 3H), 2.86-3.04 (m, 2H), 2.96 (s, 3H), 3.14-3.27 (m, 2H), 3.48 (s, 2H), 3.98-4.13 (m, 1H), 6.64 (d, J=8.1 Hz, 1H), 7.01-7.19 (m, 3H), 7.29 (d, J=9.0 Hz, 2H), 7.67 (d, J=8.1 Hz, 1H), 7.84 (t, J=8.2 Hz, 1H).

Example 16(109)

2,4-difluoro-5-{[(3-methylbutyl) {1-[(2-methyl-6-{4-[(methylsulfonyl)amino]phenoxy}-3-pyridinyl)methyl]-4-piperidinyl}carbamoyl]amino}benzamide TLC: Rf 0.70 (chloroform:methanol=6:1);
$^1$H-NMR (CD$_3$OD): δ 0.95 (d, J=6.4 Hz, 6H), 1.47-1.58 (m, 2H), 1.58-1.69 (m, 1H), 1.67-1.93 (m, 4H), 2.10-2.27 (m, 2H), 2.47 (s, 3H), 2.89-3.03 (m, 2H), 2.96 (s, 3H), 3.23-3.35 (m, 2H), 3.49 (s, 2H), 3.94-4.08 (m, 1H), 6.65 (d, J=7.9 Hz, 1H), 7.02-7.19 (m, 3H), 7.29 (d, J=9.2 Hz, 2H), 7.68 (d, J=8.2 Hz, 1H), 7.88 (t, J=8.2 Hz, 1H).

Example 16(110)

2,4-difluoro-5-{[(3-methyl-2-buten-1-yl) {1-[(2-methyl-6-{4-[(methylsulfonyl)amino]phenoxy}-3-pyridinyl)methyl]-4-piperidinyl}carbamoyl]amino}benzamide TLC: Rf 0.68 (chloroform:methanol=6:1);
$^1$H-NMR (CD$_3$OD): δ 1.64-1.87 (m, 4H), 1.75 (d, J=2.6 Hz, 6H), 2.16 (s, 2H), 2.46 (s, 3H), 2.86-3.07 (m, 2H), 2.96 (s, 3H), 3.48 (s, 2H), 3.95 (d, J=5.7 Hz, 2H), 4.02-4.22 (m, 1H), 5.10-5.25 (m, 1H), 6.64 (d, J=8.2 Hz, 1H), 7.02-7.19 (m, 3H), 7.29 (d, J=8.8 Hz, 2H), 7.67 (d, J=8.2 Hz, 1H), 8.07 (t, J=8.4 Hz, 1H).

Example 16(111)

5-[(3-buten-1-yl{1-[(2-methyl-6-{4-[(methylsulfonyl)amino]phenoxy}-3-pyridinyl)methyl]-4-piperidinyl}carbamoyl)amino]-2,4-difluorobenzamide TLC: Rf 0.68 (chloroform:methanol=6:1);
$^1$H-NMR (CD$_3$OD): δ 1.67-1.94 (m, 4H), 2.10-2.24 (m, 2H), 2.30-2.43 (m, 2H), 2.46 (s, 3H), 2.89-3.03 (m, 2H), 2.96 (s, 3H), 3.23-3.39 (m, 2H), 3.48 (s, 2H), 3.93-4.08 (m, 1H), 4.96-5.20 (m, 2H), 5.73-5.94 (m, 1H), 6.64 (d, J=8.2 Hz, 1H), 7.02-7.19 (m, 3H), 7.29 (d, J=9.0 Hz, 2H), 7.67 (d, J=8.4 Hz, 1H), 7.85 (t, J=8.3 Hz, 1H).

Example 16(112)

5-[(3-butyn-1-yl {1-[(2-methyl-6-{4-[(methylsulfonyl)amino]phenoxy}-3-pyridinyl)methyl]-4-piperidinyl}carbamoyl)amino]-2,4-difluorobenzamide TLC: Rf 0.66 (chloroform:methanol=6:1);
$^1$H-NMR (CD$_3$OD): δ 1.69-1.95 (m, 4H), 2.10-2.26 (m, 2H), 2.37 (t, J=2.7 Hz, 1H), 2.43-2.57 (m, 2H), 2.47 (s, 3H), 2.88-3.06 (m, 2H), 2.96 (s, 3H), 3.41-3.55 (m, 2H), 3.49 (s, 2H), 3.86-4.05 (m, 1H), 6.64 (d, J=8.4 Hz, 1H), 7.03-7.19 (m, 3H), 7.30 (d, J=8.7 Hz, 2H), 7.68 (d, J=8.4 Hz, 1H), 7.83 (t, J=8.3 Hz, 1H).

Example 16(113)

5-{[(cyclopentylmethyl) {1-[(2-methyl-6-{4-[(methylsulfonyl)amino]phenoxy}-3-pyridinyl)methyl]-4-piperidinyl}carbamoyl]amino}-2,4-difluorobenzamide TLC: Rf 0.60 (chloroform:methanol=6:1);
$^1$H-NMR (CD$_3$OD): δ 1.21-1.36 (m, 2H), 1.60-1.97 (m, 10H), 2.06-2.29 (m, 3H), 2.46 (s, 3H), 2.90-3.01 (m, 2H), 2.94 (s, 3H), 3.24-3.31 (m, 2H), 3.47 (s, 2H), 3.82-4.07 (m, 1H), 6.58-6.66 (m, J=8.3 Hz, 1H), 7.00-7.17 (m, 3H), 7.27 (d, J=9.0 Hz, 2H), 7.66 (d, J=8.3 Hz, 1H), 7.78-7.90 (m, 1H).

Example 16(114)

5-[(butyl{1-[(5-methyl-6-{4-[(methylsulfonyl)amino]phenoxy}-3-pyridinyl)methyl]-4-piperidinyl}carbamoyl)amino]-2,4-difluorobenzamide TLC: Rf 0.45 (dichloromethane:methanol=9:1);
$^1$H-NMR (CDCl$_3$): δ 0.97 (t, J=7.3 Hz, 3H), 1.31-1.45 (m, 2H), 1.54-1.87 (m, 6H), 2.01-2.16 (m, 2H), 2.34 (s, 3H), 2.88-3.03 (m, 5H), 3.14-3.25 (m, 2H), 3.43 (s, 2H), 4.07-4.23 (m, 1H), 6.04 (br. s, 1H), 6.41 (d, J=2.9 Hz, 1H), 6.50-6.60 (m, 1H), 6.91 (t, J=10.5 Hz, 1H), 7.05-7.31 (m, 5H), 7.50-7.57 (m, 1H), 7.86 (d, J=2.2 Hz, 1H), 8.64 (t, J=8.7 Hz, 1H).

Example 16(115)

5-[(butyl{1-[(4-methyl-6-{4-[(methylsulfonyl)amino]phenoxy}-3-pyridinyl)methyl]-4-piperidinyl}carbamoyl)amino]-2,4-difluorobenzamide TLC: Rf 0.40 (chloroform:methanol=10:1);
$^1$H-NMR (CD$_3$OD): δ 0.95 (t, J=7.4 Hz, 3H), 1.30-1.45 (m, 2H), 1.55-1.90 (m, 6H), 2.05-2.25 (m, 2H), 2.42 (s, 3H), 2.90-3.00 (m, 2H), 2.96 (s, 3H), 3.20-3.40 (m, 2H), 3.48 (s, 2H), 4.00 (m, 1H), 6.78 (s, 1H), 7.07 (d, J=9.0 Hz, 2H), 7.14 (m, 1H), 7.29 (d, J=9.0 Hz, 2H), 7.64 (d, J=8.7 Hz, 1H), 7.85 (m, 1H), 7.90 (s, 1H).

Example 16(116)

5-[(butyl{1-[(2-ethyl-6-{4-[(methylsulfonyl)amino]phenoxy}-3-pyridinyl)methyl]-4-piperidinyl}carbamoyl)amino]-2,4-difluorobenzamide TLC: Rf 0.47 (chloroform:methanol:aqueous ammonia=9:1:0.1);
$^1$H-NMR (CDCl$_3$): δ 0.98 (t, J=7.3 Hz, 3H), 1.20 (t, J=7.5 Hz, 3H), 1.31-1.46 (m, 2H), 1.49-1.78 (m, 6H), 2.02-2.17 (m, 2H), 2.77 (q, J=7.51 Hz, 2H), 2.85-2.97 (m, 2H), 3.01 (s, 3H), 3.12-3.24 (m, 2H), 3.43 (s, 2H), 4.08-4.24 (m, 1H), 5.79-5.91 (m, 1H), 6.35-6.41 (m, 1H), 6.45-6.57 (m, 1H), 6.60 (d, J=8.4 Hz, 1H), 6.92 (t, J=10.5 Hz, 1H), 7.09-7.19 (m, 2H), 7.21-7.30 (m, 2H), 7.57 (d, J=8.4 Hz, 1H), 8.68 (t, J=8.7 Hz, 1H).

Example 16(117)

5-[(2-butyn-1-yl {1-[(2-ethyl-6-{4-[(methylsulfonyl)amino]phenoxy}-3-pyridinyl)methyl]-4-piperidinyl}carbamoyl)amino]-2,4-difluorobenzamide TLC: Rf 0.48 (chloroform:methanol=9:1);
$^1$H-NMR (CDCl$_3$): δ 1.20 (t, J=7.5 Hz, 3H), 1.50-1.80 (m, 4H), 1.86 (t, J=2.1 Hz, 3H), 2.02-2.18 (m, 2H), 2.77 (q, J=7.5 Hz, 2H), 2.83-2.97 (m, 2H), 3.02 (s, 3H), 3.43 (s, 2H), 3.84-3.97 (m, 2H), 4.21-4.37 (m, 1H), 5.78-5.94 (m, 1H), 6.44-6.57 (m, 1H), 6.60 (d, J=8.2 Hz, 1H), 6.63-6.74 (m, 1H), 6.93 (t, J=10.2 Hz, 1H), 7.11-7.21 (m, 2H), 7.21-7.33 (m, 2H), 7.57 (d, J=8.2 Hz, 1H), 8.60 (t, J=8.7 Hz, 1H).

Example 16(118)

5-{[(cyclopropylmethyl){1-[(2-ethyl-6-{4-[(methylsulfonyl)amino]phenoxy}-3-pyridinyl)methyl]-4-piperidinyl}carbamoyl]amino}-2,4-difluorobenzamide TLC: Rf 0.39 (chloroform:methanol=9:1);
$^1$H-NMR (CDCl$_3$): δ 0.27-0.42 (m, 2H), 0.67-0.82 (m, 2H), 0.83-1.01 (m, 1H), 1.21 (t, J=7.5 Hz, 3H), 1.59-1.78 (m, 4H), 2.00-2.20 (m, 2H), 2.78 (q, J=7.5 Hz, 2H), 2.86-3.00 (m, 2H), 3.01 (s, 3H), 3.15 (d, J=5.5 Hz, 2H), 3.41-3.45 (m, 2H), 4.12-4.27 (m, 1H), 5.86-6.07 (m, 1H), 6.48-6.56 (m, 1H), 6.59 (d, J=8.2 Hz, 1H), 6.92 (t, J=10.5 Hz, 1H), 6.95-6.97 (m, 1H), 7.07-7.21 (m, 2H), 7.24-7.39 (m, 2H), 7.57 (d, J=8.2 Hz, 1H), 8.71 (t, J=8.8 Hz, 1H).

Example 16(119)

5-{[(cyclobutylmethyl) {1-[(2-ethyl-6-{4-[(methylsulfonyl)amino]phenoxy}-3-pyridinyl)methyl]-4-piperidinyl}carbamoyl]amino}-2,4-difluorobenzamide TLC: Rf 0.43 (chloroform:methanol=9:1);
$^1$H-NMR (CDCl$_3$): δ 1.20 (t, J=7.5 Hz, 3H), 1.56-1.99 (m, 6H), 2.01-2.23 (m, 6H), 2.40-2.59 (m, 1H), 2.77 (q, J=7.5 Hz, 2H), 2.84-2.96 (m, 2H), 3.01 (s, 3H), 3.24 (d, J=6.2 Hz, 2H), 3.43 (s, 2H), 3.99-4.16 (m, 1H), 5.91-6.07 (m, 1H), 6.34-6.42 (m, 1H), 6.49-6.57 (m, 1H), 6.60 (d, J=8.2 Hz, 1H), 6.92 (t, J=10.6 Hz, 1H), 7.10-7.19 (m, 2H), 7.22-7.31 (m, 2H), 7.58 (d, J=8.2 Hz, 1H), 8.69 (t, J=8.7 Hz, 1H).

Example 16(120)

5-[(butyl {1-[(6-{4-[(methylsulfonyl)amino]phenoxy}-2-propyl-3-pyridinyl)methyl]-4-piperidinyl}carbamoyl)amino]-2,4-difluorobenzamide TLC: Rf 0.46 (chloroform:methanol:aqueous ammonia=9:1:0.1);
$^1$H-NMR (CDCl$_3$): δ 0.80-1.07 (m, 6H), 1.19-1.49 (m, 2H), 1.47-1.86 (m, 8H), 1.95-2.24 (m, 2H), 2.63-2.80 (m, 2H), 2.82-2.95 (m, 2H), 3.01 (s, 3H), 3.11-3.31 (m, 2H), 3.43 (s, 2H), 3.95-4.27 (m, 1H), 5.74-5.95 (m, 1H), 6.29-6.44 (m, 1H), 6.47-6.70 (m, 1H), 6.60 (d, J=8.2 Hz, 1H), 6.61-6.83 (m, 1H), 6.92 (t, J=10.5 Hz, 1H), 7.07-7.18 (m, 2H), 7.21-7.37 (m, 2H), 7.58 (d, J=8.2 Hz, 1H), 8.67 (t, J=8.7 Hz, 1H).

Example 16(121)

5-[(butyl {1-[(2-isopropyl-6-{4-[(methylsulfonyl)amino]phenoxy}-3-pyridinyl)methyl]-4-piperidinyl}carbamoyl)amino]-2,4-difluorobenzamide TLC: Rf 0.52 (chloroform:methanol:aqueous ammonia=9:1:0.1);
$^1$H-NMR (CD$_3$OD): δ 0.95 (t, J=7.3 Hz, 3H), 1.13 (d, J=6.8 Hz, 6H), 1.24-1.43 (m, 2H), 1.49-1.91 (m, 6H), 2.08-2.18 (m, 2H), 2.91-2.95 (m, 2H), 2.94 (s, 3H), 3.11-3.45 (m, 3H), 3.48 (s, 2H), 3.88-4.07 (m, 1H), 6.63 (d, J=8.2 Hz, 1H), 7.05-7.18 (m, 3H), 7.20-7.34 (m, 2H), 7.62 (d, J=8.2 Hz, 1H), 7.80-7.89 (m, 1H).

Example 16(122)

5-[(2-butyn-1-yl {1-[(2-isopropyl-6-{4-[(methylsulfonyl)amino]phenoxy}-3-pyridinyl)methyl]-4-piperidinyl}carbamoyl)amino]-2,4-difluorobenzamide TLC: Rf 0.46 (chloroform:methanol=9:1);
¹H-NMR (CDCl₃): δ 1.15 (d, J=6.6 Hz, 6H), 1.46-1.82 (m, 4H), 1.83-1.90 (m, 3H), 1.98-2.23 (m, 2H), 2.74-2.96 (m, 2H), 3.01 (s, 3H), 3.24-3.37 (m, 1H), 3.43 (s, 2H), 3.83-3.97 (m, 2H), 4.14-4.41 (m, 1H), 5.75-5.92 (m, 1H), 6.38-6.62 (m, 1H), 6.57 (d, J=8.2 Hz, 1H), 6.62-6.79 (m, 1H), 6.91 (t, J=10.5 Hz, 1H), 7.02-7.35 (m, 4H), 7.53 (d, J=8.2 Hz, 1H), 8.58 (t, J=8.6 Hz, 1H).

Example 16(123)

5-{[(cyclopropylmethyl) {1-[(2-isopropyl-6-{4-[(methylsulfonyl)amino]phenoxy}-3-pyridinyl)methyl]-4-piperidinyl}carbamoyl]amino}-2,4-difluorobenzamide TLC: Rf 0.42 (chloroform:methanol=9:1);
¹H-NMR (CDCl₃): δ 0.25-0.45 (m, 2H), 0.59-0.80 (m, 2H), 0.81-1.01 (m, 1H), 1.16 (d, J=6.6 Hz, 6H), 1.46-1.88 (m, 4H), 1.90-2.25 (m, 2H), 2.80-2.98 (m, 2H), 3.01 (s, 3H), 3.15 (d, J=5.3 Hz, 2H), 3.21-3.38 (m, 1H), 3.44 (s, 2H), 4.03-4.40 (m, 1H), 5.83-5.98 (m, 1H), 6.37-6.68 (m, 1H), 6.58 (d, J=8.2 Hz, 1H), 6.74-7.07 (m, 2H), 7.09-7.39 (m, 4H), 7.55 (d, J=8.2 Hz, 1H), 8.70 (t, J=8.8 Hz, 1H).

Example 16(124)

5-{[(cyclobutylmethyl) {1-[(2-isopropyl-6-{4-[(methylsulfonyl)amino]phenoxy}-3-pyridinyl)methyl]-4-piperidinyl}carbamoyl]amino}-2,4-difluorobenzamide TLC: Rf 0.44 (chloroform:methanol=9:1);
¹H-NMR (CDCl₃): δ 1.15 (d, J=6.8 Hz, 6H), 1.42-2.33 (m, 12H), 2.35-2.60 (m, 1H), 2.76-2.94 (m, 2H), 3.01 (s, 3H), 3.23 (d, J=6.2 Hz, 2H), 3.23-3.33 (m, 1H), 3.43 (s, 2H), 3.95-4.26 (m, 1H), 5.82-6.01 (m, 1H), 6.28-6.44 (m, 1H), 6.48-6.65 (m, 1H), 6.57 (d, J=8.2 Hz, 1H), 6.91 (t, J=10.5 Hz, 1H), 7.06-7.37 (m, 4H), 7.53 (d, J=8.2 Hz, 1H), 8.66 (t, J=8.0 Hz, 1H).

Example 16(125)

5-[(butyl {1-[(2-chloro-6-{4-[(methylsulfonyl)amino]phenoxy}-3-pyridinyl)methyl]-4-piperidinyl}carbamoyl)amino]-2,4-difluorobenzamide TLC: Rf 0.71 (chloroform:methanol:aqueous ammonia=4:1:0.2);
¹H-NMR (CDCl₃): δ 0.98 (t, J=7.2 Hz, 3H), 1.30-1.91 (m, 8H), 2.14-2.29 (m, 2H), 2.84-2.98 (m, 2H), 3.02 (s, 3H), 3.12-3.26 (m, 2H), 3.54 (s, 2H), 4.05-4.28 (m, 1H), 5.98-6.14 (m, 1H), 6.37-6.46 (m, 1H), 6.48-6.64 (m, 1H), 6.80 (d, J=8.2 Hz, 1H), 6.92 (t, J=10.5 Hz, 1H), 7.13 (d, J=8.8 Hz, 2H), 7.30 (d, J=8.8 Hz, 2H), 7.80 (d, J=8.24 Hz, 1H), 8.66 (t, J=8.7 Hz, 1H).

Example 16(126)

5-[(butyl {1-[(2-methoxy-6-{4-[(methylsulfonyl)amino]phenoxy}-3-pyridinyl)methyl]-4-piperidinyl}carbamoyl)amino]-2,4-difluorobenzamide TLC: Rf 0.77 (chloroform:methanol:aqueous ammonia=4:1:0.2);
¹H-NMR (CDCl₃): δ 0.98 (t, J=7.3 Hz, 3H), 1.29-1.49 (m, 2H), 1.53-2.26 (m, 8H), 2.91-3.06 (m, 2H), 3.01 (s, 3H), 3.11-3.26 (m, 2H), 3.50 (s, 2H), 3.79 (s, 3H), 4.06-4.26 (m, 1H), 5.90-6.03 (m, 1H), 6.35 (d, J=8.1 Hz, 1H), 6.35-6.42 (m, 1H), 6.46-6.59 (m, 1H), 6.92 (t, J=10.5 Hz, 1H), 7.08-7.22 (m, 2H), 7.21-7.34 (m, 2H), 7.60 (d, J=8.1 Hz, 1H), 8.68 (t, J=8.6 Hz, 1H).

Example 16(127)

5-[(2-butyn-1-yl {1-[(2-methoxy-6-{4-[(methylsulfonyl)amino]phenoxy}-3-pyridinyl)methyl]-4-piperidinyl}carbamoyl)amino]-2,4-difluorobenzamide TLC: Rf 0.47 (chloroform:methanol=9:1);
¹H-NMR (CDCl₃): δ 1.45-1.80 (m, 4H), 1.86 (t, J=2.1 Hz, 3H), 1.98-2.27 (m, 2H), 2.79-3.07 (m, 2H), 3.02 (s, 3H), 3.46 (s, 2H), 3.79 (s, 3H), 3.90-3.99 (m, 2H), 4.16-4.37 (m, 1H), 5.79-5.92 (m, 1H), 6.34 (d, J=7.9 Hz, 1H), 6.47-6.63 (m, 1H), 6.92 (t, J=10.5 Hz, 1H), 7.10-7.22 (m, 2H), 7.22-7.32 (m, 2H), 7.59 (d, J=7.9 Hz, 1H), 8.60 (t, J=9.0 Hz, 1H).

Example 16(128)

5-{[(cyclobutylmethyl) {1-[(2-methoxy-6-{4-[(methylsulfonyl)amino]phenoxy}-3-pyridinyl)methyl]-4-piperidinyl}carbamoyl]amino}-2,4-difluorobenzamide TLC: Rf 0.47 (chloroform:methanol=9:1);
¹H-NMR (CDCl₃): δ 1.42-1.99 (m, 8H), 1.96-2.33 (m, 4H), 2.33-2.65 (m, 1H), 2.86-2.99 (m, 2H), 3.01 (s, 3H), 3.24 (d, J=6.2 Hz, 2H), 3.46 (s, 2H), 3.79 (s, 3H), 3.94-4.20 (m, 1H), 5.79-5.90 (m, 1H), 6.33 (d, J=7.9 Hz, 1H), 6.36-6.44 (m, 1H), 6.45-6.69 (m, 1H), 6.90 (t, J=10.6 Hz, 1H), 7.05-7.18 (m, 2H), 7.19-7.36 (m, 2H), 7.58 (d, J=7.9 Hz, 1H), 8.67 (t, J=8.7 Hz, 1H).

Example 16(129)

2,4-difluoro-5-{[{1-[(2-methoxy-6-{4-[(methylsulfonyl)amino]phenoxy}-3-pyridinyl)methyl]-4-piperidinyl}(propyl)carbamoyl]amino}benzamide TLC: Rf 0.45 (chloroform:methanol=9:1);
¹H-NMR (CDCl₃): δ 0.97 (t, J=7.3 Hz, 3H), 1.52-1.94 (m, 6H), 2.00-2.31 (m, 2H), 2.87-3.04 (m, 2H), 3.01 (s, 3H), 3.07-3.22 (m, 2H), 3.47 (s, 2H), 3.79 (s, 3H), 4.04-4.24 (m, 1H), 5.87-5.99 (m, 1H), 6.33 (d, J=7.9 Hz, 1H), 6.36-6.43 (m, 1H), 6.45-6.59 (m, 1H), 6.91 (t, J=10.6 Hz, 1H), 7.06-7.20 (m, 2H), 7.23-7.37 (m, 2H), 7.58 (d, J=7.9 Hz, 1H), 8.66 (t, J=8.7 Hz, 1H).

Example 16(130)

5-[(3-buten-1-yl {1-[(2-methoxy-6-{4-[(methylsulfonyl)amino]phenoxy}-3-pyridinyl)methyl]-4-piperidinyl}carbamoyl)amino]-2,4-difluorobenzamide TLC: Rf 0.57 (chloroform:methanol=9:1);
$^1$H-NMR (CDCl$_3$): δ 1.48-1.89 (m, 4H), 1.98-2.24 (m, 2H), 2.28-2.46 (m, 2H), 2.86-3.05 (m, 2H), 3.01 (s, 3H), 3.23-3.37 (m, 2H), 3.47 (s, 2H), 3.79 (s, 3H), 4.00-4.19 (m, 1H), 5.03-5.30 (m, 2H), 5.66-5.99 (m, 2H), 6.33 (d, J=7.9 Hz, 1H), 6.40-6.64 (m, 2H), 6.91 (t, J=10.5 Hz, 1H), 7.06-7.21 (m, 2H), 7.20-7.32 (m, 2H), 7.58 (d, J=7.9 Hz, 1H), 8.63 (t, J=8.7 Hz, 1H).

Example 16(131)

5-[(butyl {1-[(6-{4-[(methylsulfonyl)amino]phenoxy}-2-phenyl-3-pyridinyl)methyl]-4-piperidinyl}carbamoyl)amino]-2,4-difluorobenzamide TLC: Rf 0.50 (chloroform:methanol:aqueous ammonia=9:1:0.1);
$^1$H-NMR (CDCl$_3$): δ 0.99 (t, J=7.3 Hz, 3H), 1.28-1.48 (m, 2H), 1.49-1.77 (m, 6H), 1.96-2.11 (m, 2H), 2.83-2.92 (m, 2H), 2.99 (s, 3H), 3.10-3.25 (m, 2H), 3.47 (s, 2H), 4.00-4.15 (m, 1H), 5.74-5.85 (m, 1H), 6.32-6.38 (m, 1H), 6.43-6.57 (m, 1H), 6.82 (d, J=8.2 Hz, 1H), 6.91 (t, J=10.7 Hz, 1H), 7.10-7.31 (m, 5H), 7.32-7.45 (m, 2H), 7.50-7.64 (m, 2H), 7.87 (d, J=8.2 Hz, 1H), 8.66 (t, J=8.7 Hz, 1H).

Example 16(132)

5-[(butyl {1-[(2-methyl-6-{2-methyl-4-[(methylsulfonyl)amino]phenoxy}-3-pyridinyl)methyl]-4-piperidinyl}carbamoyl)amino]-2,4-difluorobenzamide TLC: Rf 0.50 (chloroform:methanol=6:1);
$^1$H-NMR (CD$_3$OD): δ 0.96 (t, J=7.2 Hz, 3H), 1.30-1.45 (m, 2H), 1.50-1.90 (m, 6H), 2.10-2.25 (m, 2H), 2.15 (s, 3H), 2.46 (s, 3H), 2.90-3.00 (m, 2H), 2.96 (s, 3H), 3.20-3.40 (m, 2H), 3.47 (s, 2H), 4.05 (m, 1H), 6.51 (d, J=8.7 Hz, 1H), 6.97 (d, J=8.4 Hz, 1H), 7.08-7.19 (m, 3H), 7.64 (d, J=8.7 Hz, 1H), 7.85 (m, 1H).

Example 16(133)

5-({butyl[1-(2-methyl-4-{4-[(methylsulfonyl)amino]phenoxy}benzyl)-4-piperidinyl]carbamoyl}amino)-2,4-difluorobenzamide TLC: Rf 0.47 (chloroform:methanol:aqueous ammonia=90:13:2);
$^1$H-NMR (CDCl$_3$): δ 0.98 (t, J=7.5 Hz, 3H), 1.32-1.45 (m, 2H), 1.56-1.77 (m, 6H), 2.05-2.18 (m, 2H), 2.34 (s, 3H), 2.90-2.99 (m, 2H), 3.00 (s, 3H), 3.14-3.24 (m, 2H), 3.42 (s, 2H), 4.08-4.22 (m, 1H), 5.89 (brs, 1H), 6.39 (d, J=3.0 Hz, 1H), 6.52 (brd, J=8.5 Hz, 1H), 6.69-6.86 (br, 1H), 6.77 (dd, J=8.0, 2.5 Hz, 1H), 6.82 (d, J=2.5 Hz, 1H), 6.92 (t, J=10.5 Hz, 1H), 6.98 (d, J=9.0 Hz, 2H), 7.19-7.25 (m, 3H), 8.69 (dd, J=9.0, 8.5 Hz, 1H).

Example 16(134)

5-[(butyl {1-[4-{4-[(methylsulfonyl)amino]phenoxy}-2-(trifluoromethyl)benzyl]-4-piperidinyl}carbamoyl)amino]-2,4-difluorobenzamide TLC: Rf 0.26 (dichloromethane:methanol=19:1);
$^1$H-NMR (CDCl$_3$): δ 0.99 (t, J=7.3 Hz, 3H), 1.33-1.47 (m, 2H), 1.52-1.86 (m, 6H), 2.12-2.23 (m, 2H), 2.87-2.97 (m, 2H), 3.01 (s, 3H), 3.16-3.26 (m, 2H), 3.61 (s, 2H), 4.07-4.20 (m, 1H), 5.89 (s, 1H), 6.39 (d, J=3.1 Hz, 1H), 6.47-6.59 (m, 1H), 6.74-6.86 (m, 1H), 6.92 (t, J=10.5 Hz, 1H), 6.98-7.04 (m, 2H), 7.12 (dd, J=8.4, 2.6 Hz, 1H), 7.22-7.30 (m, 3H), 7.72 (d, J=8.4 Hz, 1H), 8.65-8.72 (m, 1H).

Example 16(135)

5-[(butyl {2-methyl-1-[(2-methyl-6-{4-[(methylsulfonyl)amino]phenoxy}-3-pyridinyl)methyl]-4-piperidinyl}carbamoyl)amino]-2,4-difluorobenzamide TLC: Rf 0.58 (chloroform:methanol=6:1);
$^1$H-NMR (CD$_3$OD): δ 0.96 (t, J=7.2 Hz, 3H), 1.28 (d, J=6.0 Hz, 3H), 1.30-1.48 (m, 2H), 1.50-1.84 (m, 6H), 2.02-2.14 (m, 1H), 2.33-2.45 (m, 1H), 2.48 (s, 3H), 2.77-2.87 (m, 1H), 2.96 (s, 3H), 3.20-3.30 (m, 2H), 3.99-4.25 (m, 3H), 6.64 (d, J=8.3 Hz, 1H), 7.03-7.18 (m, 3H), 7.28 (d, J=9.0 Hz, 2H), 7.70 (d, J=8.3 Hz, 1H), 7.84 (t, J=8.2 Hz, 1H).

Example 16(136)

5-({butyl[1-({2-methyl-6-[4-(1,3-oxazol-2-yl)phenoxy]-3-pyridinyl}methyl)-4-piperidinyl]carbamoyl}amino)-2,4-difluorobenzamide TLC: Rf 0.54 (ethyl acetate:methanol=9:1);
$^1$H-NMR (CDCl$_3$): δ 0.98 (t, J=7.3 Hz, 3H), 1.31-1.48 (m, 2H), 1.55-1.79 (m, 6H), 2.08-2.21 (m, 2H), 2.49 (s, 3H), 2.87-2.99 (m, 2H), 3.13-3.26 (m, 2H), 3.43 (s, 2H), 4.11-4.26 (m, 1H), 5.78 (s, 1H), 6.39 (d, J=3.3 Hz, 1H), 6.46-6.59 (m, 1H), 6.68 (d, J=8.4 Hz, 1H), 6.92 (t, J=10.6 Hz, 1H), 7.16-7.25 (m, 3H), 7.60 (d, J=8.4 Hz, 1H), 7.70 (d, J=0.7 Hz, 1H), 8.05 (d, J=9.0 Hz, 2H), 8.68 (t, J=8.6 Hz, 1H).

Example 16(137)

5-({butyl[1-({2-methyl-6-[4-(1,3-thiazol-2-yl)phenoxy]-3-pyridinyl}methyl)-4-piperidinyl]carbamoyl}amino)-2,4-difluorobenzamide TLC: Rf 0.54 (ethyl acetate:methanol=9:1);
$^1$H-NMR (CDCl$_3$): δ 0.98 (t, J=7.3 Hz, 3H), 1.31-1.48 (m, 2H), 1.52-1.80 (m, 6H), 2.05-2.22 (m, 2H), 2.49 (s, 3H), 2.86-3.00 (m, 2H), 3.11-3.26 (m, 2H), 3.43 (s, 2H), 4.09-4.28 (m, 1H), 5.75 (s, 1H), 6.38 (d, J=3.1 Hz, 1H), 6.46-6.59 (m, 1H), 6.68 (d, J=8.2 Hz, 1H), 6.92 (t, J=10.6 Hz, 1H), 7.20 (d, J=9.0 Hz, 2H), 7.32 (d, J=3.3 Hz, 1H), 7.59 (d, J=8.2 Hz, 1H), 7.85 (d, J=3.3 Hz, 1H), 7.97 (d, J=9.0 Hz, 2H), 8.68 (t, J=8.7 Hz, 1H).

Example 16(138)

5-{[(1-{[6-(4-nitrophenoxy)-2-methyl-3-pyridinyl]methyl}-4-piperidinyl)(butyl)carbamoyl]amino}-2,4-difluorobenzamide TLC: Rf 0.65 (ethyl acetate:methanol=20:1);
$^1$H-NMR (CDCl$_3$): δ0.99 (t, J=7.3 Hz, 3 H), 1.31-1.48 (m, 2 H), 1.57-1.80 (m, 6 H), 2.09-2.23 (m, 2 H), 2.48 (s, 3 H), 2.86-3.00 (m, 2 H), 3.13-3.26 (m, 2 H), 3.45 (s, 2 H), 4.11-4.29 (m, 1 H), 5.74 (s, 1 H), 6.38 (d, J=2.9 Hz, 1 H), 6.45-6.61 (m, 1 H), 6.80 (d, J=8.2 Hz, 1 H), 6.93 (t, J=10.5 Hz, 1 H), 7.22 (d, J=9.3 Hz, 2 H), 7.68 (d, J=8.2 Hz, 1 H), 8.25 (d, J=9.3 Hz, 2 H), 8.68 (t, J=8.7 Hz, 1 H).

Example 17

5-{[(1-{[6-(4-aminophenoxy)-2-methyl-3-pyridinyl]methyl}-4-piperidinyl)(butyl)carbamoyl]amino}-2,4-difluorobenzamide The procedure similar to that of Example 11 was carried out using the compound prepared in Example 16(138) in place of the compound prepared in Example 8(11) to obtain the following compound of the present invention.

TLC: Rf 0.48 (chloroform:methanol:aqueous ammonia=9:1:0.1);
$^1$H-NMR (CD$_3$OD): δ 0.95 (t, J=7.3 Hz, 3 H), 1.26-1.91 (m, 8 H), 2.08-2.21 (m, 2 H), 2.47 (s, 3 H), 2.89-3.00 (m, 2 H), 3.12-3.36 (m, 2 H), 3.46 (s, 2 H), 3.93-4.09 (m, 1 H), 6.46 (d, J=8.2 Hz, 1 H), 6.72-6.79 (m, 2 H), 6.81-6.89 (m, 2 H), 7.12 (t, J=10.3 Hz, 1 H), 7.60 (d, J=8.2 Hz, 1 H), 7.85 (t, J=8.4 Hz, 1 H).

Example 18

5-{[(1-{[6-(4-acetamidophenoxy)-2-methyl-3-pyridinyl]methyl}-4-piperidinyl)(butyl)carbamoyl]amino}-2,4-difluorobenzamide To a solution of the compound prepared in Example 17 (89 mg) in dimethylacetamide (3 mL) was added pyridine (50 μL) and acetyl chloride (22 μL). The reaction mixture was stirred for 1 hour at room temperature. To reaction mixture was added water, and extracted with ethyl acetate. The organic layer was washed with brine, dried over anhydrous sodium sulfate, and concentrated. The obtained residue was purified by column chromatography on silica gel (ethyl acetate:methanol=50:1→20:1) to give the compound of the present invention (91 mg) having the following physical data.

TLC: Rf 0.45 (chloroform:methanol:aqueous ammonia=9:1:0.1);
$^1$H-NMR (CD$_3$OD): δ 0.96 (t, J=7.2 Hz, 3H), 1.28-1.48 (m, 2H), 1.49-1.92 (m, 6H), 2.12 (s, 3H), 2.12-2.22 (m, 2H), 2.47 (s, 3H), 2.87-3.06 (m, 2H), 3.16-3.33 (m, 2H), 3.48 (s, 2H), 3.87-4.11 (m, 1H), 6.60 (d, J=8.2 Hz, 1H), 7.00-7.07 (m, 2H), 7.12 (t, J=10.4 Hz, 1H), 7.53-7.62 (m, 2H), 7.66 (d, J=8.2 Hz, 1H), 7.85 (t, J=8.4 Hz, 1H).

Examples 19(1)-19(2)

The procedure similar to that of Example 12 was carried out using the compound prepared in Example 17 in place of the compound prepared in Example 11, and N,N-dimethylsulfamoyl chloride or a corresponding sulfamoyl chloride compound to obtain the following compound of the present invention.

Example 19(1)

5-{[butyl(1-{[6-(4-{[(dimethylamino)sulfonyl]amino}phenoxy)-2-methyl-3-pyridinyl]methyl}-4-piperidinyl)carbamoyl]amino}-2,4-difluorobenzamide TLC: Rf 0.53 (ethyl acetate:methanol=20:1);
$^1$H-NMR (CDCl$_3$): δ 0.98 (t, J=7.3 Hz, 3H), 1.30-1.48 (m, 2H), 1.52-1.82 (m, 6H), 2.03-2.20 (m, 2H), 2.46 (s, 3H), 2.78-2.97 (m, 8H), 3.10-3.25 (m, 2H), 3.40 (s, 2H), 4.08-4.25 (m, 1H), 5.87 (s, 1H), 6.38 (d, J=3.1 Hz, 1H), 6.46-6.77 (m, 3H), 6.91 (t, J=10.6 Hz, 1H), 7.07 (d, J=9.0 Hz, 2H), 7.21 (d, J=9.0 Hz, 2H), 7.53 (d, J=8.2 Hz, 1H), 8.66 (t, J=8.6 Hz, 1H).

Example 19(2)

5-{[butyl(1-{[2-methyl-6-(4-{[(methylamino)sulfonyl]amino}phenoxy)-3-pyridinyl]methyl}-4-piperidinyl)carbamoyl]amino}-2,4-difluorobenzamide TLC: Rf 0.30 (ethyl acetate:methanol=20:1);
$^1$H-NMR (CDCl$_3$): δ 0.98 (t, J=7.3 Hz, 3H), 1.30-1.48 (m, 2H), 1.53-1.79 (m, 6H), 2.05-2.19 (m, 2H), 2.47 (s, 3H), 2.77 (d, J=5.4 Hz, 3H), 2.85-2.96 (m, 2H), 3.12-3.25 (m, 2H), 3.41 (s, 2H), 4.08-4.26 (m, 1H), 4.53 (q, J=5.4 Hz, 1H), 5.86 (s, 1H), 6.39 (d, J=3.1 Hz, 1H), 6.47-6.67 (m, 3H), 6.92 (t, J=10.6 Hz, 1H), 7.10 (d, J=9.0 Hz, 2H), 7.23 (d, J=9.0 Hz, 2H), 7.55 (d, J=8.2 Hz, 1H), 8.68 (t, J=8.6 Hz, 1H).

Examples 20(1)-20(32)

The procedure similar to that of Example 8 was carried out using the compound prepared in Example 7 or a corresponding amine compound, and a corresponding aldehyde compound in place of the compound prepared in Example 4 to obtain the following compound of the present invention.

Example 20(1)

N-(1-{[6-(4-{[(2-methoxyethyl)amino]sulfonyl}phenoxy)-3-pyridinyl]methyl}-4-piperidinyl)-N,2-diphenylacetamide TLC: Rf 0.47 (dichloromethane:methanol=9:1);
$^1$H-NMR (CDCl$_3$): δ 1.28-1.43 (m, 2H), 1.72-1.82 (m, 2H), 2.06-2.17 (m, 2H), 2.79-2.88 (m, 2H), 3.11-3.17 (m, 2H), 3.29 (s, 3H), 3.31 (s, 2H), 3.38-3.45 (m, 4H), 4.59-4.71 (m, 1H), 4.81 (t, J=5.9 Hz, 1H), 6.90 (d, J=8.4 Hz, 1H), 6.95-7.03 (m, 4H), 7.16-7.25 (m, 5H), 7.34-7.40 (m, 3H), 7.64 (dd, J=8.4, 2.4 Hz, 1H), 7.82-7.88 (m, 2H), 8.02 (d, J=2.4 Hz, 1H).

Example 20(2)

N-{1-[(6-{4-[(4-hydroxy-1-piperidinyl)sulfonyl]phenoxy}-3-pyridinyl)methyl]-4-piperidinyl}-N,2-diphenylacetamide TLC: Rf 0.30 (dichloromethane:methanol=9:1);
$^1$H-NMR (CDCl$_3$): δ 1.28-1.48 (m, 2H), 1.61-1.82 (m, 4H), 1.89-1.99 (m, 2H), 2.06-2.17 (m, 2H), 2.79-2.93 (m, 4H), 3.30-3.43 (m, 6H), 3.71-3.82 (m, 1H), 4.58-4.71 (m, 1H), 6.90 (d, J=8.4 Hz, 1H), 6.96-7.03 (m, 4H), 7.16-7.27 (m, 5H), 7.34-7.40 (m, 3H), 7.65 (dd, J=8.4, 2.4 Hz, 1H), 7.72-7.78 (m, 2H), 8.04 (d, J=2.4 Hz, 1H).

Example 20(3)

N-{1-[(6-{4-[(methylsulfonyl)amino]phenoxy}-3-pyridinyl)methyl]-4-piperidinyl}-N,2-diphenylacetamide TLC: Rf 0.38 (ethyl acetate:methanol=19:1);
¹H-NMR (CDCl₃): δ 1.27-1.43 (m, 2H), 1.70-1.81 (m, 2H), 2.03-2.15 (m, 2H), 2.78-2.88 (m, 2H), 3.00 (s, 3H), 3.31 (s, 2H), 3.38 (s, 2H), 4.58-4.70 (m, 1H), 6.47 (s, 1H), 6.83 (d, J=8.4 Hz, 1H), 6.95-7.03 (m, 4H), 7.07-7.13 (m, 2H), 7.16-7.28 (m, 5H), 7.34-7.40 (m, 3H), 7.58 (dd, J=8.4, 2.2 Hz, 1H), 7.98 (d, J=2.2 Hz, 1H).

Example 20(4)

2-cyclohexyl-N-{1-[(6-{4-[(methylsulfonyl)amino]phenoxy}-3-pyridinyl)methyl]-4-piperidinyl}-N-phenylacetamide TLC: Rf 0.27 (dichloromethane:methanol=19:1);
¹H-NMR (CDCl₃): δ 0.63-0.80 (m, 2H), 0.99-1.44 (m, 5H), 1.53-1.68 (m, 5H), 1.70-1.88 (m, 5H), 2.04-2.18 (m, 2H), 2.79-2.87 (m, 2H), 3.01 (s, 3H), 3.39 (s, 2H), 4.60-4.72 (m, 1H), 6.46 (s, 1H), 6.84 (d, J=8.3 Hz, 1H), 7.00-7.06 (m, 2H), 7.08-7.14 (m, 2H), 7.22-7.27 (m, 2H), 7.35-7.43 (m, 3H), 7.59 (dd, J=8.3, 2.4 Hz, 1H), 7.99 (d, J=2.4 Hz, 1H).

Example 20(5)

N-{1-[(6-{4-[(methylsulfonyl)amino]phenoxy}-3-pyridinyl)methyl]-4-piperidinyl}-N-phenyl-2-(tetrahydro-2H-pyran-4-yl)acetamide TLC: Rf 0.48 (dichloromethane:methanol=9:1);
¹H-NMR (CDCl₃): δ 1.03-1.18 (m, 2H), 1.29-1.44 (m, 2H), 1.50-1.60 (m, 2H), 1.70-1.79 (m, 2H), 1.83 (d, J=7.0 Hz, 2H), 1.99-2.18 (m, 3H), 2.79-2.89 (m, 2H), 3.01 (s, 3H), 3.31-3.42 (m, 4H), 3.82-3.90 (m, 2H), 4.58-4.71 (m, 1H), 6.42 (s, 1H), 6.84 (d, J=8.4 Hz, 1H), 7.01-7.06 (m, 2H), 7.08-7.14 (m, 2H), 7.22-7.27 (m, 2H), 7.37-7.45 (m, 3H), 7.59 (dd, J=8.4, 2.4 Hz, 1H), 7.99 (d, J=2.4 Hz, 1H).

Example 20(6)

1-acetyl-N-{1-[(6-{4-[(methylsulfonyl)amino]phenoxy}-3-pyridinyl)methyl]-4-piperidinyl}-N-phenyl-4-piperidinecarboxamide TLC: Rf 0.44 (dichloromethane:methanol=9:1);
¹H-NMR (CDCl₃): δ 1.25-1.42 (m, 2H), 1.51-1.84 (m, 6H), 2.01-2.30 (m, 7H), 2.69-2.88 (m, 3H), 3.01 (s, 3H), 3.38 (s, 2H), 3.68-3.78 (m, 1H), 4.44-4.67 (m, 2H), 6.53 (br. s, 1H), 6.84 (d, J=8.4 Hz, 1H), 7.02-7.13 (m, 4H), 7.21-7.28 (m, 2H), 7.38-7.48 (m, 3H), 7.59 (dd, J=8.4, 2.4 Hz, 1H), 7.99 (d, J=2.4 Hz, 1H).

Example 20(7)

N-{1-[(6-{4-[(methylsulfonyl)amino]phenoxy}-3-pyridinyl)methyl]-4-piperidinyl}-N-phenylbicyclo[4.2.0]octa-1,3,5-triene-7-carboxamide TLC: Rf 0.57 (dichloromethane:methanol=9:1);
¹H-NMR (CDCl₃): δ 1.34-1.50 (m, 2H), 1.74-1.86 (m, 2H), 2.04-2.18 (m, 2H), 2.80-2.96 (m, 2H), 3.00 (s, 3H), 3.32-3.41 (m, 3H), 4.01 (dd, J=5.6, 2.8 Hz, 1H), 4.58-4.73 (m, 1H), 6.44 (s, 1H), 6.84 (d, J=8.4 Hz, 1H), 6.96-7.30 (m, 10H), 7.36-7.50 (m, 3H), 7.60 (dd, J=8.4, 2.4 Hz, 1H), 8.00 (d, J=2.4 Hz, 1H).

Example 20(8)

N-{1-[(6-{4-[(methylsulfonyl)amino]phenoxy}-3-pyridinyl)methyl]-4-piperidinyl}-N-phenyl-1-indanecarboxamide TLC: Rf 0.36 (dichloromethane:methanol=19:1);
¹H-NMR (CDCl₃): δ 1.31-1.58 (m, 2H), 1.73-1.92 (m, 2H), 1.99-2.18 (m, 3H), 2.21-2.35 (m, 1H), 2.67-2.79 (m, 1H), 2.80-2.92 (m, 2H), 2.99-3.10 (m, 4H), 3.39 (s, 2H), 3.73 (t, J=8.1 Hz, 1H), 4.66-4.79 (m, 1H), 6.43 (s, 1H), 6.85 (d, J=8.3 Hz, 1H), 7.07-7.29 (m, 10H), 7.35-7.47 (m, 3H), 7.60 (dd, J=8.3, 2.2 Hz, 1H), 8.00 (d, J=2.2 Hz, 1H).

Example 20(9)

N-{1-[(6-{4-[(methylsulfonyl)amino]phenoxy}-3-pyridinyl)methyl]-4-piperidinyl}-N-phenyl-1,2,3,4-tetrahydro-1-naphthalenecarboxamide TLC: Rf 0.31 (dichloromethane:methanol=19:1);
¹H-NMR (CDCl₃): δ 1.35-1.55 (m, 3H), 1.74-2.02 (m, 5H), 2.06-2.18 (m, 2H), 2.57-2.67 (m, 1H), 2.77-2.91 (m, 3H), 3.00 (s, 3H), 3.39 (s, 2H), 3.48-3.55 (m, 1H), 4.66-4.79 (m, 1H), 6.42 (s, 1H), 6.85 (d, J=8.3 Hz, 1H), 6.96-7.16 (m, 7H), 7.20-7.29 (m, 3H), 7.35-7.46 (m, 3H), 7.60 (dd, J=8.3, 2.2 Hz, 1H), 8.00 (d, J=2.2 Hz, 1H).

Example 20(10)

2-(4-methoxyphenyl)-N-{1-[(6-{4-[(methylsulfonyl)amino]phenoxy}-3-pyridinyl)methyl]-4-piperidinyl}-N-phenylacetamide TLC: Rf 0.53 (dichloromethane:methanol=19:1);
¹H-NMR (CDCl₃): δ 1.26-1.42 (m, 2H), 1.70-1.79 (m, 2H), 2.04-2.14 (m, 2H), 2.77-2.87 (m, 2H), 3.01 (s, 3H), 3.23 (s, 2H), 3.37 (s, 2H), 3.76 (s, 3H), 4.55-4.69 (m, 1H), 6.43 (s, 1H), 6.72-6.78 (m, 2H), 6.83 (d, J=8.4 Hz, 1H), 6.89-7.00 (m, 4H), 7.08-7.13 (m, 2H), 7.21-7.27 (m, 2H), 7.34-7.40 (m, 3H), 7.58 (dd, J=8.4, 2.4 Hz, 1H), 7.98 (d, J=2.4 Hz, 1H).

Example 20(11)

2-(4-cyanophenyl)-N-{1-[(6-{4-[(methylsulfonyl)amino]phenoxy}-3-pyridinyl)methyl]-4-piperidinyl}-N-phenylacetamide TLC: Rf 0.61 (dichloromethane:methanol=19:1);
¹H-NMR (CDCl₃): δ 1.28-1.43 (m, 2H), 1.70-1.80 (m, 2H), 2.03-2.15 (m, 2H), 2.78-2.88 (m, 2H), 3.01 (s, 3H), 3.35 (s, 2H), 3.38 (s, 2H), 4.54-4.68 (m, 1H), 6.44 (s, 1H), 6.84 (d, J=8.4 Hz, 1H), 6.96-7.03 (m, 2H), 7.07-7.17 (m, 4H), 7.21-7.28 (m, 2H), 7.37-7.44 (m, 3H), 7.49-7.54 (m, 2H), 7.58 (dd, J=8.4, 2.4 Hz, 1H), 7.98 (d, J=2.4 Hz, 1H).

Example 20(12)

N-{1-[(6-{4-[(methylsulfonyl)amino]phenoxy}-3-pyridinyl)methyl]-4-piperidinyl}-N,1-diphenylcyclopropanecarboxamide TLC: Rf 0.30 (dichloromethane:methanol=19:1);
¹H-NMR (CDCl₃): δ 0.82-0.92 (m, 2H), 1.20-1.36 (m, 2H), 1.40-1.46 (m, 2H), 1.58-1.77 (m, 2H), 2.01-2.17 (m, 2H), 2.74-2.86 (m, 2H), 3.01 (s, 3H), 3.36 (s, 2H), 4.47-4.66

(m, 1H), 6.39-6.70 (m, 5H), 6.82 (d, J=8.4 Hz, 1H), 6.94-7.17 (m, 8H), 7.21-7.27 (m, 2H), 7.57 (dd, J=8.4, 2.4 Hz, 1H), 7.97 (d, J=2.4 Hz, 1H).

Example 20(13)

2-(3-methoxyphenyl)-N-{1-[(6-{4-[(methylsulfonyl)amino]phenoxy}-3-pyridinyl)methyl]-4-piperidinyl}-N-phenylacetamide TLC: Rf 0.42 (dichloromethane:methanol=19:1);
$^1$H-NMR (CDCl$_3$): δ 1.27-1.43 (m, 2H), 1.71-1.81 (m, 2H), 2.04-2.15 (m, 2H), 2.78-2.87 (m, 2H), 3.00 (s, 3H), 3.28 (s, 2H), 3.38 (s, 2H), 3.74 (s, 3H), 4.57-4.70 (m, 1H), 6.49 (s, 1H), 6.55-6.60 (m, 2H), 6.72 (ddd, J=8.2, 2.4, 1.1 Hz, 1H), 6.83 (d, J=8.4 Hz, 1H), 6.95-7.01 (m, 2H), 7.07-7.15 (m, 3H), 7.20-7.27 (m, 2H), 7.33-7.40 (m, 3H), 7.58 (dd, J=8.4, 2.4 Hz, 1H), 7.98 (d, J=2.4 Hz, 1H).

Example 20(14)

2-(2-methoxyphenyl)-N-{1-[(6-{4-[(methylsulfonyl)amino]phenoxy}-3-pyridinyl)methyl]-4-piperidinyl}-N-phenylacetamide TLC: Rf 0.47 (dichloromethane:methanol=9:1);
$^1$H-NMR (CDCl$_3$): δ 1.30-1.44 (m, 2H), 1.74-1.83 (m, 2H), 2.04-2.16 (m, 2H), 2.78-2.89 (m, 2H), 3.00 (s, 3H), 3.27 (s, 2H), 3.38 (s, 2H), 3.67 (s, 3H), 4.59-4.74 (m, 1H), 6.48 (s, 1H), 6.74 (d, J=8.4 Hz, 1H), 6.81-6.88 (m, 2H), 7.02-7.27 (m, 8H), 7.32-7.38 (m, 3H), 7.59 (dd, J=8.4, 2.4 Hz, 1H), 7.99 (d, J=2.4 Hz, 1H).

Example 20(15)

N-(5-methyl-2-pyridinyl)-N-{1-[(6-{4-[(methylsulfonyl)amino]phenoxy}-3-pyridinyl)methyl]-4-piperidinyl}-2-phenylacetamide TLC: Rf 0.45 (dichloromethane:methanol=9:1);
$^1$H-NMR (CDCl$_3$): δ 1.32-1.47 (m, 2H), 1.78-1.88 (m, 2H), 2.03-2.14 (m, 2H), 2.39 (s, 3H), 2.78-2.87 (m, 2H), 3.01 (s, 3H), 3.31 (s, 2H), 3.38 (s, 2H), 4.51-4.65 (m, 1H), 6.48 (s, 1H), 6.83 (d, J=2.4 Hz, 1H), 6.85 (d, J=2.0 Hz, 1H), 7.00-7.26 (m, 9H), 7.47-7.51 (m, 1H), 7.59 (dd, J=8.4, 2.4 Hz, 1H), 8.00 (d, J=2.0 Hz, 1H), 8.40-8.42 (m, 1H).

Example 20(16)

N-{1-[(6-{4-[(methylsulfonyl)amino]phenoxy}-3-pyridinyl)methyl]-4-piperidinyl}-N,2-diphenylpropanamide TLC: Rf 0.50 (dichloromethane:methanol=9:1);
$^1$H-NMR (CDCl$_3$): δ 1.19-1.40 (m, 5H), 1.60-1.81 (m, 2H), 2.01-2.15 (m, 2H), 2.74-2.87 (m, 2H), 3.01 (s, 3H), 3.33-3.43 (m, 3H), 4.57-4.70 (m, 1H), 6.41 (s, 1H), 6.53 (d, J=8.4 Hz, 1H), 6.83 (d, J=8.2 Hz, 1H), 6.93-7.00 (m, 2H), 7.07-7.27 (m, 9H), 7.30-7.47 (m, 2H), 7.58 (dd, J=8.2, 2.4 Hz, 1H), 7.97 (d, J=2.4 Hz, 1H).

Example 20(17)

2-methoxy-N-{1-[(6-{4-[(methylsulfonyl)amino]phenoxy}-3-pyridinyl)methyl]-4-piperidinyl}-N,2-diphenylacetamide TLC: Rf 0.51 (dichloromethane:methanol=9:1);
$^1$H-NMR (CDCl$_3$): δ 1.19-1.43 (m, 2H), 1.57-1.69 (m, 1H), 1.76-1.86 (m, 1H), 2.02-2.18 (m, 2H), 2.73-2.88 (m, 2H), 3.01 (s, 3H), 3.19 (s, 3H), 3.37 (s, 2H), 4.41 (s, 1H), 4.59-4.72 (m, 1H), 6.46 (s, 1H), 6.54 (d, J=8.1 Hz, 1H), 6.82 (d, J=8.4 Hz, 1H), 7.05-7.28 (m, 11H), 7.35-7.48 (m, 2H), 7.57 (dd, J=8.4, 2.4 Hz, 1H), 7.97 (d, J=2.4 Hz, 1H).

Example 20(18)

N-{1-[(6-{4-[(methylsulfonyl)amino]phenoxy}-3-pyridinyl)methyl]-4-piperidinyl}-N-phenyl-2-(2-thienyl)acetamide TLC: Rf 0.51 (dichloromethane:methanol=9:1);
$^1$H-NMR (CDCl$_3$): δ 1.29-1.44 (m, 2H), 1.72-1.83 (m, 2H), 2.03-2.16 (m, 2H), 2.79-2.88 (m, 2H), 3.01 (s, 3H), 3.38 (s, 2H), 3.48 (s, 2H), 4.58-4.71 (m, 1H), 6.46 (s, 1H), 6.63-6.66 (m, 1H), 6.82-6.88 (m, 2H), 7.02-7.16 (m, 5H), 7.21-7.27 (m, 2H), 7.37-7.43 (m, 3H), 7.59 (dd, J=8.3, 2.2 Hz, 1H), 7.99 (d, J=2.2 Hz, 1H).

Example 20(19)

2-(3-methyl-5-isoxazolyl)-N-{1-[(6-{4-[(methylsulfonyl)amino]phenoxy}-3-pyridinyl)methyl]-4-piperidinyl}-N-phenylacetamide TLC: Rf 0.54 (dichloromethane:methanol=9:1);
$^1$H-NMR (CDCl$_3$): δ 1.31-1.47 (m, 2H), 1.74-1.83 (m, 2H), 2.05-2.16 (m, 2H), 2.24 (s, 3H), 2.80-2.89 (m, 2H), 3.01 (s, 3H), 3.39 (s, 2H), 3.40 (s, 2H), 4.55-4.67 (m, 1H), 6.00 (s, 1H), 6.47 (s, 1H), 6.84 (d, J=8.4 Hz, 1H), 7.06-7.14 (m, 4H), 7.21-7.27 (m, 2H), 7.39-7.45 (m, 3H), 7.59 (dd, J=8.4, 2.0 Hz, 1H), 7.99 (d, J=2.0 Hz, 1H).

Example 20(20)

2-(3-cyanophenyl)-N-{1-[(6-{4-[(methylsulfonyl)amino]phenoxy}-3-pyridinyl)methyl]-4-piperidinyl}-N-phenylacetamide TLC: Rf 0.66 (dichloromethane:methanol=9:1);
$^1$H-NMR (CDCl$_3$): δ 1.28-1.44 (m, 2H), 1.71-1.81 (m, 2H), 2.03-2.15 (m, 2H), 2.79-2.88 (m, 2H), 3.01 (s, 3H), 3.32 (s, 2H), 3.38 (s, 2H), 4.54-4.67 (m, 1H), 6.47 (s, 1H), 6.84 (d, J=8.4 Hz, 1H), 6.98-7.03 (m, 2H), 7.07-7.13 (m, 2H), 7.21-7.28 (m, 3H), 7.31-7.35 (m, 2H), 7.39-7.45 (m, 3H), 7.47-7.51 (m, 1H), 7.58 (dd, J=8.4, 2.4 Hz, 1H), 7.98 (d, J=2.4 Hz, 1H).

Example 20(21)

2-(3-acetylphenyl)-N-{1-[(6-{4-[(methylsulfonyl)amino]phenoxy}-3-pyridinyl)methyl]-4-piperidinyl}-N-phenylacetamide TLC: Rf 0.50 (dichloromethane:methanol=9:1);
$^1$H-NMR (CDCl$_3$): δ 1.28-1.44 (m, 2H), 1.70-1.81 (m, 2H), 2.02-2.15 (m, 2H), 2.55 (s, 3H), 2.79-2.88 (m, 2H), 3.01 (s, 3H), 3.36 (s, 2H), 3.38 (s, 2H), 4.55-4.69 (m, 1H), 6.48 (s, 1H), 6.83 (d, J=8.4 Hz, 1H), 6.98-7.04 (m, 2H), 7.07-7.13 (m, 2H), 7.21-7.43 (m, 7H), 7.53-7.55 (m, 1H), 7.58 (dd, J=8.4, 2.4 Hz, 1H), 7.76-7.81 (m, 1H), 7.98 (d, J=2.4 Hz, 1H).

Example 20(22)

2-[3-(1-hydroxyethyl)phenyl]-N-{1-[(6-{4-[(methylsulfonyl)amino]phenoxy}-3-pyridinyl)methyl]-4-piperidinyl}-N-phenylacetamide TLC: Rf 0.48 (dichloromethane:methanol=9:1);
$^1$H-NMR (CDCl$_3$): δ 1.27-1.47 (m, 5H), 1.70-1.82 (m, 2H), 2.03-2.15 (m, 2H), 2.77-2.87 (m, 2H), 3.00 (s, 3H), 3.31 (s, 2H), 3.38 (s, 2H), 4.57-4.70 (m, 1H), 4.81 (q, J=6.2 Hz, 1H), 6.46 (s, 1H), 6.83 (d, J=8.4 Hz, 1H), 6.92-7.02 (m, 4H), 7.07-7.13 (m, 2H), 7.18-7.27 (m, 4H), 7.34-7.41 (m, 3H), 7.58 (dd, J=8.4, 2.4 Hz, 1H), 7.98 (d, J=2.4 Hz, 1H).

Example 20(23)

N-{1-[(6-{4-[(methylsulfonyl)amino]phenoxy}-3-pyridinyl)methyl]-4-piperidinyl}-N-phenyl-2,3-dihydro-1-benzofuran-2-carboxamide TLC: Rf 0.49 (dichloromethane:methanol=9:1);
$^1$H-NMR (CDCl$_3$): δ 1.33-1.49 (m, 2H), 1.74-1.88 (m, 2H), 2.06-2.18 (m, 2H), 2.80-2.90 (m, 2H), 2.96-3.05 (m, 4H), 3.31-3.42 (m, 3H), 4.58-4.71 (m, 1H), 4.83 (dd, J=9.9, 7.9 Hz, 1H), 6.47 (s, 1H), 6.72-6.86 (m, 3H), 7.01-7.14 (m, 5H), 7.21-7.28 (m, 3H), 7.37-7.48 (m, 3H), 7.59 (dd, J=8.4, 2.4 Hz, 1H), 8.00 (d, J=2.4 Hz, 1H).

Example 20(24)

2-fluoro-N-{1-[(6-{4-[(methylsulfonyl)amino]phenoxy}-3-pyridinyl)methyl]-4-piperidinyl}-N,2-diphenylacetamide TLC: Rf 0.44 (dichloromethane:methanol=9:1);
$^1$H-NMR (CDCl$_3$): δ 1.22-1.42 (m, 2H), 1.64-1.73 (m, 1H), 1.76-1.85 (m, 1H), 2.04-2.18 (m, 2H), 2.75-2.88 (m, 2H), 3.00 (s, 3H), 3.38 (s, 2H), 4.59-4.71 (m, 1H), 5.45 (d, J=48.5 Hz, 1H), 6.43 (d, J=7.9 Hz, 1H), 6.53 (s, 1H), 6.83 (d, J=8.4 Hz, 1H), 7.05-7.47 (m, 13H), 7.57 (dd, J=8.4, 2.4 Hz, 1H), 7.98 (d, J=2.4 Hz, 1H).

Example 20(25)

N-{1-[(6-{4-[(methylsulfonyl)amino]phenoxy}-3-pyridinyl)methyl]-4-piperidinyl}-2-phenoxy-N-phenylacetamide TLC: Rf 0.47 (dichloromethane:methanol=9:1);
$^1$H-NMR (CDCl$_3$): δ 1.33-1.49 (m, 2H), 1.75-1.85 (m, 2H), 2.07-2.17 (m, 2H), 2.80-2.90 (m, 2H), 3.00 (s, 3H), 3.39 (s, 2H), 4.23 (s, 2H), 4.58-4.71 (m, 1H), 6.50 (s, 1H), 6.74-6.94 (m, 4H), 7.07-7.27 (m, 8H), 7.40-7.46 (m, 3H), 7.59 (dd, J=8.3, 2.2 Hz, 1H), 7.99 (d, J=2.2 Hz, 1H).

Example 20(26)

(3S)-3-hydroxy-N-{1-[(6-{4-[(methylsulfonyl)amino]phenoxy}-3-pyridinyl)methyl]-4-piperidinyl}-N,3-diphenylpropanamide TLC: Rf 0.35 (dichloromethane:methanol=19:1);
$^1$H-NMR (CDCl$_3$): δ 1.24-1.43 (m, 2H), 1.67-1.80 (m, 2H), 2.05-2.17 (m, 2H), 2.24-2.34 (m, 2H), 2.79-2.89 (m, 2H), 3.01 (s, 3H), 3.39 (s, 2H), 4.56-4.69 (m, 1H), 4.78 (d, J=3.1 Hz, 1H), 4.98-5.06 (m, 1H), 6.37-6.47 (m, 1H), 6.76-6.87 (m, 2H), 6.95-7.01 (m, 1H), 7.08-7.14 (m, 2H), 7.16-7.43 (m, 10H), 7.58 (dd, J=8.4, 2.4 Hz, 1H), 7.99 (d, J=2.4 Hz, 1H).

Example 20(27)

N-{1-[(6-{4-[(methylsulfonyl)amino]phenoxy}-3-pyridinyl)methyl]-4-piperidinyl}-N,1-diphenylmethanesulfonamide TLC: Rf 0.53 (dichloromethane:methanol=9:1);
$^1$H-NMR (CDCl$_3$): δ 1.26-1.40 (m, 2H), 1.51-1.61 (m, 2H), 1.83-1.95 (m, 2H), 2.68-2.77 (m, 2H), 3.01 (s, 3H), 3.31 (s, 2H), 3.61-3.80 (m, 1H), 4.28 (s, 2H), 6.39 (s, 1H), 6.82 (d, J=8.4 Hz, 1H), 7.06-7.14 (m, 4H), 7.21-7.27 (m, 2H), 7.31-7.42 (m, 6H), 7.44-7.50 (m, 2H), 7.54 (dd, J=8.4, 2.4 Hz, 1H), 7.94 (d, J=2.4 Hz, 1H).

Example 20(28)

N-[{1-[(6-{4-[(methylsulfonyl)amino]phenoxy}-3-pyridinyl)methyl]-4-piperidinyl}(phenyl)methyl]benzamide TLC: Rf 0.53 (dichloromethane:methanol=9:1);
$^1$H-NMR (CDCl$_3$): δ 1.32-1.54 (m, 3H), 1.72-2.00 (m, 4H), 2.78-2.94 (m, 2H), 3.01 (s, 3H), 3.42 (s, 2H), 5.04 (t, J=8.4 Hz, 1H), 6.32-6.44 (m, 2H), 6.87 (d, J=8.4 Hz, 1H), 7.09-7.15 (m, 2H), 7.22-7.53 (m, 10H), 7.67 (dd, J=8.4, 2.4 Hz, 1H), 7.73-7.77 (m, 2H), 8.01 (d, J=2.4 Hz, 1H).

Example 20(29)

N-[{1-[(6-{4-[(methylsulfonyl)amino]phenoxy}-3-pyridinyl)methyl]-4-piperidinyl}(phenyl)methyl]cyclohexanecarboxamide TLC: Rf 0.45 (dichloromethane:methanol=9:1);
$^1$H-NMR (CDCl$_3$): δ 1.15-1.96 (m, 17H), 2.01-2.13 (m, 1H), 2.74-2.91 (m, 2H), 3.01 (s, 3H), 3.41 (s, 2H), 4.82 (t, J=8.3 Hz, 1H), 5.69 (d, J=8.3 Hz, 1H), 6.47 (s, 1H), 6.87 (d, J=8.4 Hz, 1H), 7.07-7.36 (m, 9H), 7.67 (dd, J=8.4, 2.5 Hz, 1H), 8.01 (d, J=2.5 Hz, 1H).

Example 20(30)

1-acetyl-N-[{1-[(6-{4-[(methylsulfonyl)amino]phenoxy}-3-pyridinyl)methyl]-4-piperidinyl}(phenyl)methyl]-4-piperidinecarboxamide TLC: Rf 0.39 (dichloromethane:methanol=9:1);
$^1$H-NMR (CDCl$_3$): δ 1.22-1.96 (m, 11H), 2.08 (s, 3H), 2.26-2.39 (m, 1H), 2.57-2.71 (m, 1H), 2.74-2.92 (m, 2H), 2.98-3.13 (m, 4H), 3.41 (s, 2H), 3.78-3.89 (m, 1H), 4.49-4.62 (m, 1H), 4.82 (t, J=8.6 Hz, 1H), 5.76 (d, J=8.6 Hz, 1H), 6.64 (s, 1H), 6.87 (d, J=8.3 Hz, 1H), 7.08-7.36 (m, 9H), 7.67 (dd, J=8.3, 2.3 Hz, 1H), 8.01 (d, J=2.3 Hz, 1H).

Example 20(31)

N-[{1-[(6-{4-[(methylsulfonyl)amino]phenoxy}-3-pyridinyl)methyl]-4-piperidinyl}(phenyl)methyl]tetrahydro-2H-pyran-4-carboxamide TLC: Rf 0.40 (dichloromethane:methanol=9:1);
$^1$H-NMR (CDCl$_3$): δ 1.19-1.46 (m, 3H), 1.52-1.97 (m, 8H), 2.28-2.40 (m, 1H), 2.75-2.92 (m, 2H), 3.01 (s, 3H), 3.33-3.46 (m, 4H), 3.95-4.05 (m, 2H), 4.83 (t, J=8.7 Hz, 1H), 5.73 (d, J=8.7 Hz, 1H), 6.52 (s, 1H), 6.87 (d, J=8.4 Hz, 1H), 7.08-7.36 (m, 9H), 7.67 (dd, J=8.4, 2.2 Hz, 1H), 8.01 (d, J=2.2 Hz, 1H).

Example 20(32)

N-[{1-[(6-{4-[(methylsulfonyl)amino]phenoxy}-3-pyridinyl)methyl]-4-piperidinyl}(phenyl)methyl]benzenesulfonamide TLC: Rf 0.27 (dichloromethane:methanol=19:1);
$^1$H-NMR (CDCl$_3$): δ 1.13-1.37 (m, 3H), 1.50-1.66 (m, 1H), 1.74-1.97 (m, 3H), 2.68-2.77 (m, 1H), 2.82-2.91 (m, 1H), 3.02 (s, 3H), 3.38 (s, 2H), 4.02-4.09 (m, 1H), 4.99 (d, J=8.6 Hz, 1H), 6.52 (s, 1H), 6.84-6.91 (m, 3H), 7.06-7.15 (m, 5H), 7.21-7.29 (m, 4H), 7.34-7.41 (m, 1H), 7.54-7.58 (m, 2H), 7.65 (dd, J=8.3, 2.3 Hz, 1H), 7.99 (d, J=2.3 Hz, 1H).

Examples 21(1)-21(31)

The procedure similar to that of Example 8 was carried out using the compound prepared in Example 7 or a corresponding amine compound, and a corresponding aldehyde compound in place of the compound prepared in Example 4 to obtain the following compound of the present invention.

Example 21(1)

5-[(butyl {1-[(6-{4-[(4-hydroxy-1-piperidinyl)carbonyl]phenoxy}-2-methyl-3-pyridinyl)methyl]-4-piperidinyl}carbamoyl)amino]-2,4-difluorobenzamide TLC: Rf 0.12 (chloroform:methanol=10:1);
$^1$H-NMR (CD$_3$OD): δ 0.96 (t, J=7.4 Hz, 3H), 1.30-1.90 (m, 10H), 2.09-2.27 (m, 2H), 2.47 (s, 3H), 2.91-3.05 (m, 2H), 3.18-3.28 (m, 6H), 3.50 (s, 2H), 3.60-3.82 (m, 1H), 3.84-3.97 (m, 1H), 3.98-4.16 (m, 2H), 6.76 (d, J=8.0 Hz, 1H), 7.07-7.16 (m, 1H), 7.16 (d, J=8.8 Hz, 2H), 7.46 (d, J=8.8 Hz, 2H), 7.73 (d, J=8.0 Hz, 1H), 7.85 (t, J=8.2 Hz, 1H).

Example 21(2)

5-({butyl[1-({2-methyl-6-[4-(4-morpholinylcarbonyl)phenoxy]-3-pyridinyl}methyl)-4-piperidinyl]carbamoyl}amino)-2,4-difluorobenzamide TLC: Rf 0.30 (chloroform:methanol=10:1);
$^1$H-NMR (CD$_3$OD): δ 0.96 (t, J=7.2 Hz, 3H), 1.24-1.49 (m, 4H), 1.52-1.97 (m, 6H), 2.08-2.30 (m, 2H), 2.46 (s, 3H), 3.20-3.29 (m, 2H), 3.52 (s, 2H), 3.54-3.88 (m, 8H), 3.95-4.13 (m, 1H), 6.76 (d, J=8.3 Hz, 1H), 7.06-7.21 (m, 3H), 7.49 (d, J=8.8 Hz, 2H), 7.73 (d, J=8.3 Hz, 1H), 7.85 (t, J=8.3 Hz, 1H).

Example 21(3)

5-{[butyl(1-{[2-methyl-6-(4-{[4-(trifluoromethyl)-1-piperidinyl]carbonyl}phenoxy)-3-pyridinyl]methyl}-4-piperidinyl)carbamoyl]amino}-2,4-difluorobenzamide TLC: Rf 0.27 (chloroform:methanol=10:1);
$^1$H-NMR (CD$_3$OD): δ 0.96 (t, J=7.3 Hz, 3H), 1.28-1.45 (m, 2H), 1.44-1.95 (m, 10H), 2.10-2.27 (m, 2H), 2.46 (s, 3H), 2.48-2.62 (m, 2H), 2.92-3.03 (m, 2H), 3.19-3.29 (m, 4H), 3.50 (s, 2H), 3.95-4.11 (m, 1H), 4.66-4.84 (m, 1H), 6.75 (d, J=8.3 Hz, 1H), 7.06-7.20 (m, 3H), 7.47 (d, J=8.8 Hz, 2H), 7.72 (d, J=8.3 Hz, 1H), 7.85 (t, J=8.3 Hz, 1H).

Example 21(4)

5-{[{1-[(6-{4-[(4-acetyl-1-piperazinyl)carbonyl]phenoxy}-2-methyl-3-pyridinyl)methyl]-4-piperidinyl}(propyl)carbamoyl]amino}-2,4-difluorobenzamide TLC: Rf 0.38 (chloroform:methanol=10:1);
$^1$H-NMR (CD$_3$OD): δ 0.94 (t, J=7.4 Hz, 3H), 1.54-1.94 (m, 6H), 2.13 (s, 3H), 2.15-2.25 (m, 2H), 2.47 (s, 3H), 2.91-3.03 (m, 2H), 3.16-3.26 (m, 2H), 3.50 (s, 2H), 3.53-3.78 (m, 8H), 3.95-4.14 (m, 1H), 6.77 (d, J=8.3 Hz, 1H), 7.08-7.15 (m, 1H), 7.17 (d, J=8.8 Hz, 2H), 7.51 (d, J=8.8 Hz, 2H), 7.73 (d, J=8.3 Hz, 1H), 7.84 (t, J=8.2 Hz, 1H).

Example 21(5)

5-{[{1-[(6-{4-[(4-acetyl-1-piperazinyl)carbonyl]phenoxy}-2-methyl-3-pyridinyl)methyl]-4-piperidinyl}(2-butyn-1-yl)carbamoyl]amino}-2,4-difluorobenzamide TLC: Rf 0.40 (chloroform:methanol=10:1);
$^1$H-NMR (CD$_3$OD): δ 1.67-1.98 (m, 4H), 1.81 (t, J=2.0 Hz, 3H), 2.13 (s, 3H), 2.14-2.26 (m, 2H), 2.47 (s, 3H), 2.90-3.06 (m, 2H), 3.51 (s, 2H), 3.53-3.76 (m, 8H), 4.06 (d, J=2.0 Hz, 2H), 4.09-4.19 (m, 1H), 6.77 (d, J=8.0 Hz, 1H), 7.08-7.21 (m, 3H), 7.51 (d, J=8.8 Hz, 2H), 7.73 (d, J=8.0 Hz, 1H), 7.90-8.02 (m, 1H).

Example 21(6)

2,4-difluoro-5-{[{1-[(2-methyl-6-{4-[(methylsulfonyl)methyl]phenoxy}-3-pyridinyl)methyl]-4-piperidinyl}(propyl)carbamoyl]amino}benzamide TLC: Rf 0.23 (chloroform:methanol=10:1);
$^1$H-NMR (CD$_3$OD): δ 0.94 (t, J=7.4 Hz, 3H), 1.54-1.95 (m, 6H), 2.08-2.24 (m, 2H), 2.47 (s, 3H), 2.89 (s, 3H), 2.92-3.03 (m, 2H), 3.15-3.26 (m, 2H), 3.49 (s, 2H), 3.94-4.12 (m, 1H), 4.42 (s, 2H), 6.70 (d, J=8.5 Hz, 1H), 7.04-7.20 (m, 3H), 7.47 (d, J=8.6 Hz, 2H), 7.69 (d, J=8.5 Hz, 1H), 7.83 (t, J=8.3 Hz, 1H).

Example 21(7)

5-[(2-butyn-1-yl {1-[(2-methyl-6-{4-[(methylsulfonyl)methyl]phenoxy}-3-pyridinyl)methyl]-4-piperidinyl}carbamoyl)amino]-2,4-difluorobenzamide TLC: Rf 0.23 (chloroform:methanol=10:1);
$^1$H-NMR (CD$_3$OD): δ 1.67-1.95 (m, 2H), 1.81 (t, J=2.4 Hz, 3H), 2.10-2.25 (m, 2H), 2.48 (s, 3H), 2.89 (s, 3H), 2.92-3.05 (m, 2H), 3.20-3.29 (m, 2H), 3.50 (s, 2H), 4.06 (d, J=2.4 Hz, 2H), 4.07-4.15 (m, 1H), 4.42 (s, 2H), 6.70 (d, J=8.2 Hz, 1H), 7.03-7.20 (m, 3H), 7.48 (d, J=8.6 Hz, 2H), 7.70 (d, J=8.2 Hz, 1H), 7.96 (t, J=8.3 Hz, 1H).

Example 21(8)

5-[(butyl {1-[(2-isopropyl-6-{4-[(methylsulfonyl)methyl]phenoxy}-3-pyridinyl)methyl]-4-piperidinyl}carbamoyl)amino]-2,4-difluorobenzamide TLC: Rf 0.56 (chloroform:methanol=9:1);
$^1$H-NMR (CDCl$_3$): δ 0.98 (t, J=7.2 Hz, 3H), 1.15 (d, J=6.8 Hz, 6H), 1.34-1.48 (m, 2H), 1.46-1.86 (m, 6H), 1.93-2.23 (m, 2H), 2.77 (s, 3H), 2.82-2.98 (m, 2H), 3.09-3.25 (m, 2H), 3.24-3.38 (m, 1H), 3.44 (s, 2H), 3.94-4.41 (m, 1H), 4.25 (s, 2H), 5.60-5.89 (m, 1H), 6.28-6.43 (m, 1H), 6.41-6.56 (m, 1H), 6.61 (d, J=8.4 Hz, 1H), 6.91 (t, J=10.5 Hz, 1H), 7.09-7.35 (m, 2H), 7.40 (d, J=8.6 Hz, 2H), 7.56 (d, J=8.4 Hz, 1H), 8.67 (t, J=8.7 Hz, 1H).

Example 21(9)

5-[(2-butyn-1-yl{1-[(2-isopropyl-6-{4-[(methylsulfonyl)methyl]phenoxy}-3-pyridinyl)methyl]-4-piperidinyl}carbamoyl)amino]-2,4-difluorobenzamide TLC: Rf 0.56 (chloroform:methanol=9:1);
$^1$H-NMR (CDCl$_3$): δ 1.15 (d, J=6.8 Hz, 6H), 1.45-1.80 (m, 4H), 1.80-1.95 (m, 3H), 1.99-2.26 (m, 2H), 2.78 (s, 3H), 2.84-3.01 (m, 2H), 3.19-3.38 (m, 1H), 3.44 (s, 2H), 3.91 (s, 2H), 4.17-4.44 (m, 1H), 4.26 (s, 2H), 5.64-5.83 (m, 1H), 6.34-6.59 (m, 1H), 6.62 (d, J=8.1 Hz, 1H), 6.92 (t, J=10.6 Hz, 1H), 7.03-7.32 (m, 3H), 7.41 (d, J=8.2 Hz, 2H), 7.56 (d, J=8.1 Hz, 1H), 8.59 (t, J=8.6 Hz, 1H).

Example 21(10)

2,4-difluoro-5-{[{1-[(2-isopropyl-6-{4-[(methylsulfonyl)methyl]phenoxy}-3-pyridinyl)methyl]-4-piperidinyl}(propyl)carbamoyl]amino}benzamide TLC: Rf 0.54 (chloroform:methanol=9:1);
$^1$H-NMR (CDCl$_3$): δ 0.98 (t, J=7.3 Hz, 3H), 1.15 (d, J=6.8 Hz, 6H), 1.55-1.83 (m, 6H), 1.95-2.24 (m, 2H), 2.78 (s, 3H), 2.87-2.97 (m, 2H), 3.07-3.21 (m, 2H), 3.24-3.37 (m, 1H), 3.45 (s, 2H), 4.05-4.23 (m, 1H), 4.26 (s, 2H), 5.73-5.95 (m, 1H), 6.33-6.43 (m, 1H), 6.46-6.58 (m, 1H), 6.63 (d, J=8.4 Hz, 1H), 6.92 (t, J=10.6 Hz, 1H), 7.22 (d, J=8.4 Hz, 2H), 7.42 (d, J=8.4 Hz, 2H), 7.58 (d, J=8.4 Hz, 1H), 8.66 (t, J=8.7 Hz, 1H).

Example 21(11)

2,4-difluoro-5-{[(1-{[2-methyl-6-(4-{[(methylsulfonyl)amino]methyl}phenoxy)-3-pyridinyl]methyl}-4-piperidinyl)(propyl)carbamoyl]amino}benzamide TLC: Rf 0.13 (chloroform:methanol=10:1);
$^1$H-NMR (CD$_3$OD): δ 0.94 (t, J=7.4 Hz, 3H), 1.73 (m, 6H), 2.10-2.25 (m, 2H), 2.46 (s, 3H), 2.87 (s, 3H), 2.92-3.02 (m, 2H), 3.13-3.27 (m, 2H), 3.48 (s, 2H), 3.89-4.15 (m, 1H), 4.25 (s, 2H), 6.62 (d, J=8.3 Hz, 1H), 6.99-7.21 (m, 3H), 7.41 (d, J=8.6 Hz, 2H), 7.66 (d, J=8.3 Hz, 1H), 7.83 (t, J=8.3 Hz, 1H).

Example 21(12)

5-{[2-butyn-1-yl(1-{[2-methyl-6-(4-{[(methylsulfonyl)amino]methyl}phenoxy)-3-pyridinyl]methyl}-4-piperidinyl)carbamoyl]amino}-2,4-difluorobenzamide TLC: Rf 0.17 (chloroform:methanol=10:1);
$^1$H-NMR (CD$_3$OD): δ 1.67-1.98 (m, 4H), 1.81 (t, J=2.2 Hz, 3H), 2.10-2.24 (m, 2H), 2.47 (s, 3H), 2.87 (s, 3H), 2.92-3.03 (m, 2H), 3.49 (s, 2H), 4.06 (d, J=2.2 Hz, 2H), 4.07-4.18 (m, 1H), 4.25 (s, 2H), 6.62 (d, J=8.1 Hz, 1H), 7.01-7.21 (m, 3H), 7.41 (d, J=8.8 Hz, 2H), 7.67 (d, J=8.1 Hz, 1H), 7.96 (dd, J=8.8, 7.9 Hz, 1H).

Example 21(13)

5-{[butyl(1-{[2-isopropyl-6-(4-{[(methylsulfonyl)amino]methyl}phenoxy)-3-pyridinyl]methyl}-4-piperidinyl)carbamoyl]amino}-2,4-difluorobenzamide TLC: Rf 0.26 (chloroform:methanol=10:1);
$^1$H-NMR (CD$_3$OD): δ 0.96 (t, J=7.3 Hz, 3H), 1.12 (d, J=6.8 Hz, 6H), 1.28-1.43 (m, 2H), 1.49-1.90 (m, 6H), 2.08-2.20 (m, 2H), 2.84 (s, 3H), 2.89-3.02 (m, 2H), 3.17-3.28 (m, 2H), 3.32-3.43 (m, 1H), 3.49 (s, 2H), 3.91-4.12 (m, 1H), 4.25 (s, 2H), 6.63 (d, J=8.3 Hz, 1H), 7.03-7.19 (m, 3H), 7.40 (d, J=8.6 Hz, 2H), 7.62 (d, J=8.3 Hz, 1H), 7.84 (t, J=8.3 Hz, 1H).

Example 21(14)

2,4-difluoro-5-{[(1-{[2-isopropyl-6-(4-{[(methylsulfonyl)amino]methyl}phenoxy)-3-pyridinyl]methyl}-4-piperidinyl)(propyl)carbamoyl]amino}benzamide TLC: Rf 0.23 (chloroform:methanol=10:1);
$^1$H-NMR (CD$_3$OD): δ 0.93 (t, J=7.3 Hz, 3H), 1.12 (d, J=6.6 Hz, 6H), 1.54-1.93 (m, 6H), 2.05-2.21 (m, 2H), 2.84 (s, 3H), 2.90-3.01 (m, 2H), 3.15-3.25 (m, 2H), 3.31-3.44 (m, 1H), 3.49 (s, 2H), 3.94-4.10 (m, 1H), 4.25 (s, 2H), 6.63 (d, J=8.2 Hz, 1H), 7.04-7.18 (m, 3H), 7.40 (d, J=8.6 Hz, 2H), 7.63 (d, J=8.2 Hz, 1H), 7.83 (t, J=8.3 Hz, 1H).

Example 21(15)

5-{[2-butyn-1-yl(1-{[2-isopropyl-6-(4-{[(methylsulfonyl)amino]methyl}phenoxy)-3-pyridinyl]methyl}-4-piperidinyl)carbamoyl]amino}-2,4-difluorobenzamide TLC: Rf 0.27 (chloroform:methanol=10:1);
$^1$H-NMR (CD$_3$OD): δ 1.13 (d, J=6.8 Hz, 6H), 1.68-1.91 (m, 4H), 1.81 (t, J=2.3 Hz, 3H), 2.13 (m, 2H), 2.84 (s, 3H), 2.90-3.00 (m, 2H), 3.32-3.45 (m, 1H), 3.46-3.52 (m, 2H), 4.05 (d, J=2.3 Hz, 2H), 4.06-4.17 (m, 1H), 4.25 (s, 2H), 6.63 (d, J=8.3 Hz, 1H), 7.04-7.22 (m, 3H), 7.40 (d, J=8.8 Hz, 2H), 7.63 (d, J=8.3 Hz, 1H), 7.95 (t, J=8.4 Hz, 1H).

Example 21(16)

5-({butyl[1-({2-isopropyl-6-[4-(methylsulfonyl)phenoxy]-3-pyridinyl}methyl)-4-piperidinyl]carbamoyl}amino)-2,4-difluorobenzamide TLC: Rf 0.53 (chloroform:methanol=10:1);
$^1$H-NMR (CD$_3$OD): δ 0.96 (t, J=7.3 Hz, 3H), 1.13 (d, J=6.8 Hz, 6H), 1.29-1.46 (m, 2H), 1.61 (m, 2H), 1.66-1.92 (m, 4H), 2.08-2.26 (m, 2H), 2.89-2.99 (m, 2H), 3.14 (s, 3H), 3.19-3.28 (m, 2H), 3.35-3.46 (m, 1H), 3.52 (s, 2H), 3.89-4.11 (m, 1H), 6.82 (d, J=8.1 Hz, 1H), 7.12 (t, J=10.3 Hz, 1H), 7.34 (d, J=9.0 Hz, 2H), 7.73 (d, J=8.1 Hz, 1H), 7.80-7.91 (m, 1H), 7.96 (d, J=9.0 Hz, 2H).

Example 21(17)

2,4-difluoro-5-({[1-({2-isopropyl-6-[4-(methylsulfonyl)phenoxy]-3-pyridinyl}methyl)-4-piperidinyl](propyl)carbamoyl}amino)benzamide TLC: Rf 0.50 (chloroform:methanol=10:1);
$^1$H-NMR (CD$_3$OD): δ 0.96 (t, J=7.3 Hz, 3H), 1.13 (d, J=6.8 Hz, 6H), 1.29-1.46 (m, 2H), 1.61 (m, 2H), 1.66-1.92 (m, 4H), 2.08-2.26 (m, 2H), 2.89-2.99 (m, 2H), 3.14 (s, 3H), 3.19-3.28 (m, 2H), 3.35-3.46 (m, 1H), 3.52 (s, 2H), 3.89-4.11 (m, 1H), 6.82 (d, J=8.1 Hz, 1H), 7.12 (t, J=10.3 Hz, 1H), 7.34 (d, J=9.0 Hz, 2H), 7.73 (d, J=8.1 Hz, 1H), 7.80-7.91 (m, 1H), 7.96 (d, J=9.0 Hz, 2H).

Example 21(18)

5-({2-butyn-1-yl[1-({2-isopropyl-6-[4-(methylsulfonyl)phenoxy]-3-pyridinyl}methyl)-4-piperidinyl]carbamoyl}amino)-2,4-difluorobenzamide TLC: Rf 0.58 (chloroform:methanol=10:1);
$^1$H-NMR (CD$_3$OD): δ 1.14 (d, J=6.8 Hz, 6H), 1.68-1.92 (m, 4H), 1.81 (t, J=2.0 Hz, 3H), 2.08-2.22 (m, 2H), 2.87-3.06

(m, 2H), 3.14 (s, 3H), 3.34-3.51 (m, 1H), 3.53 (s, 2H), 4.05 (d, J=2.0 Hz, 2H), 4.08-4.13 (m, 1H), 6.82 (d, J=8.2 Hz, 1H), 7.14 (t, J=10.4 Hz, 1H), 7.35 (d, J=8.8 Hz, 2H), 7.74 (d, J=8.2 Hz, 1H), 7.90-8.01 (m, 3H).

Example 21(19)

2,4-difluoro-5-({[1-({2-methyl-6-[4-(methylsulfonyl]phenoxy]-3-pyridinyl}methyl)-4-piperidinyl](propyl)carbamoyl}amino)benzamide TLC: Rf 0.20 (ethyl acetate:methanol=20:1);
$^1$H-NMR (CDCl$_3$): δ 0.99 (t, J=7.4 Hz, 3H), 1.63-1.81 (m, 6H), 2.07-2.23 (m, 2H), 2.48 (s, 3H), 2.86-2.99 (m, 2H), 3.07 (s, 3H), 3.11-3.23 (m, 2H), 3.44 (s, 2H), 4.06-4.27 (m, 1H), 5.68-5.82 (m, 1H), 6.32-6.40 (m, 1H), 6.46-6.59 (m, 1H), 6.76 (d, J=8.2 Hz, 1H), 6.92 (dd, J=10.5, 10.5 Hz, 1H), 7.21-7.31 (m, 2H), 7.65 (d, J=8.2 Hz, 1H), 7.87-7.96 (m, 2H), 8.60-8.70 (m, 1H).

Example 21(20)

5-({2-butyn-1-yl[1-({2-methyl-6-[4-(methylsulfonyl)phenoxy]-3-pyridinyl}methyl)-4-piperidinyl]carbamoyl}amino)-2,4-difluorobenzamide TLC: Rf 0.30 (ethyl acetate:methanol=20:1);
$^1$H-NMR (CDCl$_3$): δ 1.63-1.82 (m, 4H), 1.83-1.90 (m, 3H), 2.07-2.23 (m, 2H), 2.47 (s, 3H), 2.85-2.98 (m, 2H), 3.07 (s, 3H), 3.43 (s, 2H), 3.88-3.97 (m, 2H), 4.21-4.39 (m, 1H), 5.67-5.80 (m, 1H), 6.46-6.60 (m, 1H), 6.75 (d, J=8.2 Hz, 1H), 6.91 (dd, J=10.5, 10.5 Hz, 1H), 7.14-7.20 (m, 1H), 7.22-7.30 (m, 2H), 7.64 (d, J=8.2 Hz, 1H), 7.88-7.96 (m, 2H), 8.58 (dd, J=8.6, 8.6 Hz, 1H).

Example 21(21)

5-[(2-butyn-1-yl {1-[(6-{4-[(3-hydroxy-1-azetidinyl)sulfonyl]phenoxy}-2-methyl-3-pyridinyl)methyl]-4-piperidinyl}carbamoyl)amino]-2,4-difluorobenzamide TLC: Rf 0.34 (ethyl acetate:methanol=9:1);
$^1$H-NMR (CDCl$_3$): δ 1.66-1.81 (m, 4H), 1.87 (t, J=2.2 Hz, 3H), 2.10-2.22 (m, 2H), 2.38-2.44 (m, J=7.3 Hz, 1H), 2.48 (s, 3H), 2.86-2.98 (m, 2H), 3.44 (s, 2H), 3.55-3.64 (m, 2H), 3.89-3.97 (m, 2H), 3.99-4.08 (m, 2H), 4.22-4.38 (m, 1H), 4.42-4.57 (m, 1H), 5.76 (s, 1H), 6.47-6.63 (m, 1H), 6.78 (d, J=8.2 Hz, 1H), 6.93 (t, J=10.7 Hz, 1H), 7.19 (d, J=3.3 Hz, 1H), 7.27 (d, J=8.8 Hz, 2H), 7.67 (d, J=8.2 Hz, 1H), 7.84 (d, J=8.8 Hz, 2H), 8.59 (dd, J=8.6 Hz, 1H).

Example 21(22)

2,4-difluoro-5-{[{1-[(6-{4-[(3-hydroxy-1-azetidinyl)sulfonyl]phenoxy}-2-methyl-3-pyridinyl)methyl]-4-piperidinyl}(propyl)carbamoyl]amino}benzamide TLC: Rf 0.30 (ethyl acetate:methanol=9:1);
$^1$H-NMR (CDCl$_3$): δ 0.99 (t, J=7.3 Hz, 3H), 1.62-1.81 (m, 6H), 2.09-2.23 (m, 2H), 2.47 (d, J=7.1 Hz, 1H), 2.48 (s, 3H), 2.87-2.99 (m, 2H), 3.09-3.23 (m, 2H), 3.45 (s, 2H), 3.54-3.64 (m, 2H), 3.98-4.09 (m, 2H), 4.09-4.27 (m, 1H), 4.42-4.57 (m, 1H), 5.76 (s, 1H), 6.38 (d, J=2.2 Hz, 1H), 6.47-6.62 (m, 1H), 6.79 (d, J=8.1 Hz, 1H), 6.93 (t, J=10.5 Hz, 1H), 7.27 (d, J=8.8 Hz, 2H), 7.67 (d, J=8.1 Hz, 1H), 7.84 (d, J=8.8 Hz, 2H), 8.65 (t, J=8.8 Hz, 1H).

Example 21(23)

2,4-difluoro-5-{[{1-[(6-{4-[(3-hydroxy-1-azetidinyl)sulfonyl]phenoxy}-2-isopropyl-3-pyridinyl)methyl]-4-piperidinyl}(propyl)carbamoyl]amino}benzamide TLC: Rf 0.24 (ethyl acetate:methanol=20:1);
$^1$H-NMR (CDCl$_3$): δ 0.98 (t, J=7.4 Hz, 3H), 1.14 (d, J=6.7 Hz, 6H), 1.61-1.80 (m, 6H), 2.05-2.20 (m, 3H), 2.85-2.98 (m, 2H), 3.09-3.21 (m, 2H), 3.24-3.37 (m, 1H), 3.46 (s, 2H), 3.56-3.64 (m, 2H), 3.99-4.08 (m, 2H), 4.08-4.24 (m, 1H), 4.43-4.56 (m, 1H), 5.65-5.79 (m, 1H), 6.32-6.39 (m, 1H), 6.46-6.58 (m, 1H), 6.73 (d, J=8.2 Hz, 1H), 6.91 (dd, J=10.5, 10.5 Hz, 1H), 7.31-7.38 (m, 2H), 7.63 (d, J=8.2 Hz, 1H), 7.80-7.88 (m, 2H), 8.60-8.69 (m, 1H).

Example 21(24)

5-[(butyl {1-[(6-{4-[(3-hydroxy-1-azetidinyl)sulfonyl]phenoxy}-2-isopropyl-3-pyridinyl)methyl]-4-piperidinyl}carbamoyl)amino]-2,4-difluorobenzamide TLC: Rf 0.29 (ethyl acetate:methanol=20:1);
$^1$H-NMR (CDCl$_3$): δ 0.98 (t, J=7.3 Hz, 3H), 1.14 (d, J=6.7 Hz, 6H), 1.30-1.47 (m, 2H), 1.61-1.80 (m, 6H), 2.05-2.24 (m, 3H), 2.84-2.98 (m, 2H), 3.11-3.24 (m, 2H), 3.25-3.37 (m, 1H), 3.46 (s, 2H), 3.55-3.64 (m, 2H), 3.98-4.08 (m, 2H), 4.09-4.25 (m, 1H), 4.41-4.57 (m, 1H), 5.64-5.82 (m, 1H), 6.32-6.41 (m, 1H), 6.45-6.59 (m, 1H), 6.72 (d, J=8.2 Hz, 1H), 6.91 (dd, J=10.5, 10.5 Hz, 1H), 7.29-7.38 (m, 2H), 7.63 (d, J=8.2 Hz, 1H), 7.79-7.87 (m, 2H) 8.61-8.70 (m, 1H).

Example 21(25)

5-[(2-butyn-1-yl {1-[(6-{4-[(3-hydroxy-1-azetidinyl)sulfonyl]phenoxy}-2-isopropyl-3-pyridinyl)methyl]-4-piperidinyl}carbamoyl)amino]-2,4-difluorobenzamide TLC: Rf 0.32 (ethyl acetate:methanol=20:1);
$^1$H-NMR (CDCl$_3$): δ 1.14 (d, J=6.5 Hz, 6H), 1.63-1.82 (m, 4H), 1.82-1.91 (m, 3H), 2.06-2.19 (m, 2H), 2.19-2.31 (m, 1H), 2.84-2.97 (m, 2H), 3.23-3.38 (m, 1H), 3.46 (s, 2H), 3.54-3.66 (m, 2H), 3.85-3.97 (m, 2H), 3.98-4.07 (m, 2H), 4.19-4.37 (m, 1H), 4.41-4.56 (m, 1H), 5.66-5.85 (m, 1H), 6.46-6.61 (m, 1H), 6.72 (d, J=8.2 Hz, 1H), 6.91 (dd, J=10.4, 10.4 Hz, 1H), 7.13-7.21 (m, 1H), 7.30-7.39 (m, 2H), 7.62 (d, J=8.0 Hz, 1H), 7.79-7.88 (m, 2H) 8.56 (dd, J=8.6, 8.6 Hz, 1H).

Example 21(26)

5-[(butyl {1-[(6-{2-chloro-4-[(methylsulfonyl)amino]phenoxy}-2-methyl-3-pyridinyl)methyl]-4-piperidinyl}carbamoyl)amino]-2,4-difluorobenzamide TLC: Rf 0.44 (ethyl acetate:methanol=9:1);
$^1$H-NMR (CDCl$_3$): δ 0.98 (t, J=7.3 Hz, 3H), 1.30-1.48 (m, 2H), 1.52-1.81 (m, 6H), 2.00-2.20 (m, 2H), 2.42 (s, 3H), 2.83-2.97 (m, 2H), 3.06 (s, 3H), 3.12-3.26 (m, 2H), 3.40 (s, 2H), 4.06-4.26 (m, 1H), 5.96 (s, 1H), 6.40 (d, J=3.1 Hz, 1H), 6.49-6.59 (m, 1H), 6.62 (d, J=8.4 Hz, 1H), 6.93 (t, J=10.5 Hz, 1H), 7.13-7.22 (m, 2H), 7.41 (t, J=1.5 Hz, 1H), 7.57 (d, J=8.4 Hz, 1H), 8.69 (t, J=8.7 Hz, 1H).

Example 21(27)

N-(4-{[5-({4-[butyl(cyclohexylcarbamoyl)amino]-1-piperidinyl}methyl)-6-methyl-2-pyridinyl]oxy}phenyl)methanesulfonamide TLC: Rf 0.42 (chloroform:methanol=10:1);
$^1$H-NMR (CD$_3$OD): δ 0.93 (t, J=7.2 Hz, 3H), 1.08-1.42 (m, 8H), 1.42-1.55 (m, 2H), 1.56-1.94 (m, 8H), 2.05-2.24 (m, 2H), 2.46 (s, 3H), 2.84-2.94 (m, 2H), 2.96 (s, 3H), 3.03-3.17 (m, 2H), 3.47 (s, 2H), 3.50-3.66 (m, 1H), 3.88-4.04 (m, 1H), 5.63 (d, J=7.7 Hz, 1H), 6.63 (d, J=8.2 Hz, 1H), 7.07 (d, J=9.1 Hz, 2H), 7.28 (d, J=9.1 Hz, 2H), 7.66 (d, J=8.2 Hz, 1H).

Example 21(28)

N-[4-({5-[(4-{butyl[(cis-4-hydroxycyclohexyl)carbamoyl]amino}-1-piperidinyl)methyl]-6-methyl-2-pyridinyl}oxy)phenyl]methanesulfonamide TLC: Rf 0.23 (chloroform:methanol=10:1);
$^1$H-NMR (CD$_3$OD): δ 0.94 (t, J=7.3 Hz, 3H), 1.22-1.80 (m, 16H), 2.08-2.23 (m, 2H), 2.46 (s, 3H), 2.86-3.00 (m, 2H), 2.96 (s, 3H), 3.06-3.18 (m, 2H), 3.48 (s, 2H), 3.59-3.79 (m, 1H), 3.80-3.92 (m, 1H), 3.93-4.07 (m, 1H), 5.59 (d, J=9.0 Hz, 1H), 6.64 (d, J=8.3 Hz, 1H), 7.07 (d, J=9.2 Hz, 2H), 7.29 (d, J=9.2 Hz, 2H), 7.67 (d, J=8.3 Hz, 1H).

Example 21(29)

N-[4-({5-[(4-{butyl[(4,4-difluorocyclohexyl)carbamoyl]amino}-1-piperidinyl)methyl]-6-methyl-2-pyridinyl}oxy)phenyl]methanesulfonamide TLC: Rf 0.33 (chloroform:methanol=10:1);
$^1$H-NMR (CD$_3$OD): δ 0.93 (t, J=7.2 Hz, 3H), 1.20-2.24 (m, 18H), 2.46 (s, 3H), 2.86-3.03 (m, 2H), 2.96 (s, 3H), 3.04-3.16 (m, 2H), 3.48 (s, 2H), 3.63-3.79 (m, 1H), 3.87-4.04 (m, 1H), 5.86 (d, J=7.3 Hz, 1H), 6.63 (d, J=8.2 Hz, 1H), 7.07 (d, J=9.0 Hz, 2H), 7.28 (d, J=9.0 Hz, 2H), 7.66 (d, J=8.2 Hz, 1H).

Example 21(30)

N-(4-{[5-({4-[butyl(tetrahydro-2H-pyran-4-ylcarbamoyl)amino]-1-piperidinyl}methyl)-6-methyl-2-pyridinyl]oxy}phenyl)methanesulfonamide TLC: Rf 0.26 (chloroform:methanol=10:1);
$^1$H-NMR (CD$_3$OD): δ 0.93 (t, J=7.2 Hz, 3H), 1.27-1.36 (m, 2H), 1.38-1.86 (m, 10H), 2.08-2.26 (m, 2H), 2.46 (s, 3H), 2.85-2.95 (m, 2H), 2.96 (s, 3H), 3.04-3.17 (m, 2H), 3.36-3.46 (m, 2H), 3.47 (s, 2H), 3.72-3.86 (m, 1H), 3.86-4.01 (m, 3H), 5.87 (d, J=8.1 Hz, 1H), 6.64 (d, J=8.2 Hz, 1H), 7.07 (d, J=8.8 Hz, 2H), 7.29 (d, J=8.8 Hz, 2H), 7.67 (d, J=8.2 Hz, 1H).

Example 21(31)

N-[4-({5-[(4-{[(1-acetyl-4-piperidinyl)carbamoyl](butyl)amino}-1-piperidinyl)methyl]-6-methyl-2-pyridinyl}oxy)phenyl]methanesulfonamide TLC: Rf 0.17 (chloroform:methanol=10:1);
$^1$H-NMR (CD$_3$OD): δ 0.93 (t, J=7.2 Hz, 3H), 1.15-1.99 (m, 12H), 2.06-2.22 (m, 2H), 2.09 (s, 3H), 2.46 (s, 3H), 2.59-2.78 (m, 2H), 2.87-3.02 (m, 2H), 2.96 (s, 3H), 3.02-3.25 (m, 2H), 3.47 (s, 2H), 3.73-4.07 (m, 3H), 4.42-4.57 (m, 1H), 5.88 (d, J=6.8 Hz, 1H), 6.63 (d, J=8.2 Hz, 1H), 7.07 (d, J=9.2 Hz, 2H), 7.07 (d, J=9.2 Hz, 2H), 7.66 (d, J=8.2 Hz, 1H).

Examples 22(1)-22(2)

The procedure similar to that of Example 12 was carried out using the compound prepared in Example 17 in place of the compound prepared in Example 11, and a corresponding sulfamoyl chloride compound in place of N,N-dimethylsulfamoyl chloride to obtain the following compound of the present invention.

Example 22(1)

5-[(butyl{1-[(2-methyl-6-{4-[(1-ptrrolidinylsulfonyl)amino]phenoxy}-3-pyridinyl)methyl]-4-piperidinyl}carbamoyl)amino]-2,4-difluorobenzamide TLC: Rf 0.52 (ethyl acetate:methanol=9:1);
$^1$H-NMR (CDCl$_3$): δ 0.98 (t, J=7.2 Hz, 3H), 1.31-1.47 (m, 2H), 1.47-1.79 (m, 8H), 1.80-1.91 (m, 4H), 2.46 (s, 3H), 2.85-2.97 (m, 2H), 3.12-3.25 (m, 2H), 3.28-3.38 (m, 4H), 3.41 (s, 2H), 4.07-4.27 (m, 1H), 5.81 (s, 1H), 6.38 (d, J=3.1 Hz, 1H), 6.46-6.64 (m, 2H), 6.92 (t, J=10.6 Hz, 1H), 7.08 (d, J=9.0 Hz, 2H), 7.21 (d, J=9.0 Hz, 2H), 7.54 (d, J=8.2 Hz, 1H), 8.68 (t, J=8.7 Hz, 1H).

Example 22(2)

5-[(butyl{1-[(2-methyl-6-{4-[(1-piperidinylsulfonyl)amino]phenoxy}-3-pyridinyl)methyl]-4-piperidinyl}carbamoyl)amino]-2,4-difluorobenzamide TLC: Rf 0.35 (ethyl acetate:methanol=20:1);
$^1$H-NMR (CDCl$_3$): δ 0.98 (t, J=7.3 Hz, 3H), 1.28-1.81 (m, 14H), 2.03-2.20 (m, 2H), 2.46 (s, 3H), 2.84-2.97 (m, 2H), 3.11-3.30 (m, 6H), 3.40 (s, 2H), 4.06-4.26 (m, 1H), 5.73-5.87 (m, 1H), 6.33-6.41 (m, 1H), 6.43-6.61 (m, 3H), 6.91 (dd, J=10.5, 10.5 Hz, 1H), 7.03-7.11 (m, 2H), 7.15-7.23 (m, 2H), 7.53 (d, J=8.2 Hz, 1H), 8.62-8.72 (m, 1H).

Biological Example

It was proved by the following procedure that the compound represented by formula (I) of the present invention strongly binds a chemokine receptor (especially CCR5). This procedure was conducted by MDS Corporation in Taiwan.

Biological Example 1

CCR5 Binding Test

A membrane fraction of the human CCR5 stably overexpressing CHO-K1 cell was suspended in assay buffer (50 mM HEPES/0.5% BSA/1 mM calcium chloride/5 mM magnesium chloride, pH 7.4) and dispensed in a 48 well polypropylene plate with U-shaped bottom in the amount corresponding to 1 μg of protein/well. Then, an unlabelled ligand was added so as to obtain a concentration of 0.1 μM in a non-specific binding group, while a compound was added so as to obtain a final concentration of 0.003 to 0.3 μM in a compound group. Subsequently, [$^{125}$I]MIP-1β was added so as to obtain a final concentration of 0.1 nM and a mixture thereof was incubated at 25° C. for 120 minutes. The membrane fraction was trapped with a filter, washed, and then radioactivity of [$^{125}$I]MIP-1β was measured by a γ counter.

Inhibition ratio (%) of the test compound was calculated by the following calculation formula.

Inhibition ratio=[(Ec−Ea)/Ec]×100

Ec: Radioactivity of when DMSO control solution is added−radioactivity of non-specific binding group
Ea: Radioactivity of when test compound is added−radioactivity of non-specific binding group As a result, it was found that the compound of the present invention shows $IC_{50}$ value of 10 μM or less. For example, both $IC_{50}$ value of the compound prepared in Example 15(1) and that of the compounds prepared in Example 16(61) and Example 16(62) were 0.1 μM or less.

Biological Example 2

Evaluation Experiment of an Inhibitory Activity Against Drug-Metabolizing Enzymes of the Compound of the Present Invention (i) Inhibitory Activity Against Human CYP2C9

Inhibitory activity against human CYP2C9 of the compound of the present invention can be evaluated by a method of Sato et al. (Yakubutsudotai (Xenobio. Metabol. and Dispos.), 16(2), 115-126 (2001)), which is improved in assaying accuracy and/or assaying sensitivity.

(ii) Inhibitory Activity Against Human CYP3A4

Inhibitory activity against human CYP3A4 of the compound of the present invention can be evaluated by an improved method described in Drug Metabolism and Disposition, Vol. 28(12), 1440-1448 (2000).

For example, a reaction solution consisted of potassium phosphate buffer (pH 7.4) (final concentration: 200 mM), magnesium chloride hexahydrate (final concentration: 5 mM), substrate (7-benzyloxyquinoline (7-BQ), final concentration: 40 μM), and expression system microsome (Daiichikagakuyakuhin, final concentration: 0.25 mg/mL) was prepared. 100 μL of the reaction solution is dispensed in 96 well plate, and added by 50 μL of an aqueous solution containing test a compound and 0.8% acetonitrile, to carry out 10 minutes of preincubation at 37° C. 50 μL of a reduced nicotinamide adenine dinucleotide phosphate (NADPH, 4 mM) is added to initiate a reaction. The fluorescence intensity of each well was measured at the time when NADPH was added and after incubated for 30 minutes. Excitation wavelength at 409 nm and emission wavelength at 530 nm of quinolinol, which is metabolite of substrate, was measured. Inhibition ratio (%) of the test compound was calculated by the following calculation formula to obtain $IC_{50}$ value.

Inhibition ratio(%)=[1−{(measured value when a test compound is added)−(blank value)/(control value−blank value)}]×100

As a result, it was found that the compounds of the present invention scarcely exert the CYP3A4 inhibitory effect. For example, $IC_{50}$ values of the compounds prepared in Example 16(60), Example 16(61) and Example 16(63) were 30 μM or more.

Formulation Example

Formulation Example 1

N-(3-fluorophenyl)-N-{1-[(6-{4-[(4-methyl-1-piperazinyl)sulfonyl]phenoxy}-3-pyridinyl)methyl]-4-piperidinyl}-N'-(6-methyl-3-pyridinyl)urea (10 g), calcium carboxymethyl cellulose (disintegrant, 2.0 g), magnesium stearate (lubricant, 1.0 g), microcrystalline cellulose (87 g) were admixed in a conventional manner, punched them out to give 1,000 tablets each containing 10 mg of active ingredient.

Formulation Example 2

N-(3-fluorophenyl)-N-{1-[(6-{4-[(4-methyl-1-piperazinyl)sulfonyl]phenoxy}-3-pyridinyl)methyl]-4-piperidinyl}-N'-(6-methyl-3-pyridinyl)urea (10 g), mannitol (200 g) and distilled water (5 L) were admixed in a conventional manner. Then the solution was filtered through a dustproofing filter, and then 5 ml aliquots were charged into ampoules, which were autoclaved to give 1,000 ampoules each containing 10 mg of active ingredient.

INDUSTRIAL APPLICABILITY

The compounds of the present invention represented by formula (I) specifically bind chemokine receptor, especially CCR5, and have an antagonistic activity against it, so they are useful for preventing and/or treating CCR5-related diseases, for example, various inflammatory diseases (asthma, nephritis, nephropathy, hepatitis, arthritis, rheumatoid arthritis, rhinitis, conjunctivitis, inflammatory bowel disease such as ulcerative colitis, etc.); immunological diseases (autoimmune diseases, rejection in organ transplantation (rejection of graft of solid organ, rejection of graft of pancreatic islet cells in therapy for diabetes, graft-versus-host disease), etc.); immunosuppression, psoriasis, multiple sclerosis, etc.; infectious diseases (infection with human immunodeficiency virus, acquired immunodeficiency syndrome, infection with RSV, etc.); allergic diseases (atopic dermatitis, urticaria, allergic bronchopulmonary aspergillosis, allergic eosinophilic gastroenteritis, etc.); cardiovascular diseases (arteriosclerosis, ischemic reperfusion injury, etc.); acute respiratory distress syndrome, shock accompanying bacterial infection, diabetes, cancer metastasis and so on.

The invention claimed is:
1. A compound selected from the group consisting of
(1) N-(3-fluorophenyl)-N-{1-[(6-{4-[(4-methyl-1-piperazinyl)sulfonyl]phenoxy}-3-pyridinyl)methyl]-4-piperidinyl}-N'-(6-methyl-3-pyridinyl)urea,
(2) 4-[(5-{[4-((3-fluorophenyl){[(6-methyl-3-pyridinyl)amino]carbonyl}amino)-1-piperidinyl]methyl}-2-pyridinyl)oxy]-N-(2-methoxyethyl)benzenesulfonamide,
(3) N-(3-fluorophenyl)-N'-(6-methyl-3-pyridinyl)-N-[1-({6-[4-(4-morpholinylsulfonyl)phenoxy]-3-pyridinyl}methyl)-4-piperidinyl]urea,
(4) N-(1-{[6-(4-cyanophenoxy)-3-pyridinyl]methyl}-4-piperidinyl)-N-(3-fluorophenyl)-N'-(6-methyl-3-pyridinyl)urea,
(5) N-(3-fluorophenyl)-N'-(6-methyl-3-pyridinyl)-N-[1-({6-[4-(1H-tetrazol-5-yl)phenoxy]-3-pyridinyl}methyl)-4-piperidinyl]urea,
(6) 4-[(5-{[4-((3-fluorophenyl){[(6-methyl-3-pyridinyl)amino]carbonyl}amino)-1-piperidinyl]methyl}-2-pyridinyl)oxy]-N-1H-tetrazol-5-ylbenzamide,
(7) N-[1-({6-[(2,2-dioxido-1H-2,1,3-benzothiadiazin-6-yl)oxy]-3-pyridinyl}methyl)-4-piperidinyl]-N-(3-fluorophenyl)-N'-(6-methyl-3-pyridinyl)urea,
(8) N,N'-bis(4-chlorophenyl)-N-[1-({6-[4-(methylsulfonyl)phenoxy]-3-pyridinyl}methyl)-4-piperidinyl]urea,
(9) N-{4-[(5-{[4-((4-chlorophenyl){[(4-chlorophenyl)amino]carbonyl}amino)-1-piperidinyl]methyl}-2-pyridinyl)oxy]phenyl}methanesulfonamide,

(10) N-{1-[(6-{4-[(4-acetyl-1-piperazinyl)sulfonyl]phenoxy}-3-pyridinyl)methyl]-4-piperidinyl}-N-(3-fluorophenyl)-N'-(6-methyl-3-pyridinyl)urea,

(11) N-(4-{[5-({4-[(anilinocarbonyl)(phenyl)amino]piperidin-1-yl}methyl)pyridin-2-yl]oxy}phenyl)methanesulfonamide,

(12) N-(3-fluorophenyl)-N'-(6-methyl-3-pyridinyl)-N-(1-{[6-(4-nitrophenoxy)-3-pyridinyl]methyl}-4-piperidinyl)urea,

(13) N-(3-fluorophenyl)-N'-(6-methyl-3-pyridinyl)-N-{1-[(6-{4-[(4-oxo-1-piperidinyl)sulfonyl]phenoxy}-3-pyridinyl)methyl]-4-piperidinyl}urea,

(14) phenyl (3-fluorophenyl){1-[(6-{4-[(methylsulfonyl)amino]phenoxy}-3-pyridinyl)methyl]-4-piperidinyl}carbamate,

(15) phenyl{1-[(6-{4-[(methylsulfonyl)amino]phenoxy}-3-pyridinyl)methyl]-4-piperidinyl}phenylcarbamate,

(16) 2-(3-fluorophenyl)-N-(6-methyl-3-pyridinyl)-2-{1-[(6-{4-[(methylsulfonyl)amino]phenoxy}-3-pyridinyl)methyl]-4-piperidinyl}acetamide,

(17) 2-(3-fluorophenyl)-N-(6-methyl-3-pyridinyl)-2-[1-({6-[4-(methylsulfonyl)phenoxy]-3-pyridinyl}methyl)-4-piperidinyl]acetamide,

(18) 2-(3-fluorophenyl)-2-{1-[(6-{4-[(methylsulfonyl)amino]phenoxy}-3-pyridinyl)methyl]-4-piperidinyl}-N-phenylacetamide,

(19) N-(4-{[5-({4-[(anilinocarbonyl)(phenyl)amino]-1-oxido-1-piperidinyl}methyl)-2-pyridinyl]oxy}phenyl)methanesulfonamide,

(20) N-(3-fluorophenyl)-N'-{1-[(6-{4-[(4-hydroxy-1-piperidinyl)sulfonyl]phenoxy}-3-pyridinyl)methyl]-4-piperidinyl}-N'-(6-methyl-3-pyridinyl)urea,

(21) 1-(1-{[6-(4-aminophenoxy)pyridin-3-yl]methyl}piperidin-4-yl)-1-(3-fluorophenyl)-3-(6-methylpyridin-3-yl)urea,

(22) N-(1-{[6-(4-{[(dimethylamino)sulfonyl]amino}phenoxy)-3-pyridinyl]methyl}-4-piperidinyl)-N-(3-fluorophenyl)-N'-(6-methyl-3-pyridinyl)urea,

(23) N-(3-fluorophenyl)-N-(1-{[6-(4-{[(methylamino)sulfonyl]amino}phenoxy)-3-pyridinyl]methyl}-4-piperidinyl)-N'-(6-methyl-3-pyridinyl)urea,

(24) N-{1-[(6-{4-[(aminosulfonyl)amino]phenoxy}-3-pyridinyl)methyl]-4-piperidinyl}-N-(3-fluorophenyl)-N'-(6-methyl-3-pyridinyl)urea,

(25) N-{4-[(5-{[4-((3-fluorophenyl){[(6-methyl-3-pyridinyl)amino]carbonyl}amino)-1-piperidinyl]methyl}-2-pyridinyl)oxy]phenyl}-2-(4-morpholinyl)ethanesulfonamide,

(26) N-(3-fluorophenyl)-N-(1-{[6-(4-{[(methylamino)carbonothioyl]amino}phenoxy)-3-pyridinyl]methyl}-4-piperidinyl)-N'-(6-methyl-3-pyridinyl)urea,

(27) N-(3-fluorophenyl)-N'-(6-methyl-3-pyridinyl)-N-{1-[(6-{4-[({[2-(4-morpholinyl)ethyl]amino}carbonothioyl)amino]phenoxy}-3-pyridinyl)methyl]-4-piperidinyl}urea,

(28) benzyl[({4-[(5-{[4-((3-fluorophenyl){[(6-methyl-3-pyridinyl)amino]carbonyl}amino)-1-piperidinyl]methyl}-2-pyridinyl)oxy]phenyl}amino)sulfonyl]carbamate,

(29) N-[1-({6-[4-(4,4-dioxido-2-oxo-1,4,3,5-oxathiadiazepan-5-yl)phenoxy]-3-pyridinyl}methyl)-4-piperidinyl]-N-(3-fluorophenyl)-N'-(6-methyl-3-pyridinyl)urea,

(30) 4-[(5-{[4-((3-fluorophenyl){[(6-methyl-3-pyridinyl)amino]carbonyl}amino)-1-piperidinyl]methyl}-2-pyridinyl)oxy]-N-(2-hydroxyethyl)benzenesulfonamide,

(31) N-[1-({6-[4-(1,1-dioxido-1,2,6-thiadiazinan-2-yl)phenoxy]-3-pyridinyl}methyl)-4-piperidinyl]-N-(3-fluorophenyl)-N'-(6-methyl-3-pyridinyl)urea,

(32) N-(3-fluorophenyl)-N-[1-({6-[4-(6-methyl-1,1-dioxido-1,2,6-thiadiazinan-2-yl)phenoxy]-3-pyridinyl}methyl)-4-piperidinyl]-N'-(6-methyl-3-pyridinyl)urea,

(33) N-(3-fluorophenyl)-N-{1-[(6-{4-[6-(2-methoxyethyl)-1,1-dioxido-1,2,6-thiadiazinan-2-yl]phenoxy}-3-pyridinyl)methyl]-4-piperidinyl}-N'-(6-methyl-3-pyridinyl)urea,

(34) 2-hydroxy-N-{1-[(6-{4-[(methylsulfonyl)amino]phenoxy}-3-pyridinyl)methyl]-4-piperidinyl}-N,2-diphenylacetamide,

(35) 4-[(5-{[4-((3-fluorophenyl){[(6-methyl-3-pyridinyl)amino]carbonyl}amino)-1-piperidinyl]methyl}-2-pyridinyl)oxy]-N-(2-hydroxy-2-methylpropyl)benzenesulfonamide,

(36) N-(3-fluorophenyl)-2-hydroxy-N-{1-[(6-{4-[(methylsulfonyl)amino]phenoxy}-3-pyridinyl)methyl]-4-piperidinyl}-2-phenylacetamide,

(37) 4-[(5-{[4-((3-fluorophenyl){[(6-methyl-3-pyridinyl)amino]carbonyl}amino)-1-piperidinyl]methyl}-2-pyridinyl)oxy]-N-(3-methoxypropyl)benzenesulfonamide,

(38) N-(3-fluorophenyl)-N-{1-[(6-{4-[(2-hydroxyethyl)sulfonyl]phenoxy}-3-pyridinyl)methyl]-4-piperidinyl}-N'-(6-methyl-3-pyridinyl)urea,

(39) N-{4-[(5-{[4-((3-fluorophenyl){[(6-methyl-3-pyridinyl)amino]carbonyl}amino)-1-piperidinyl]methyl}-2-pyridinyl)oxy]phenyl}cyclopropanesulfonamide,

(40) 4-[(5-{[4-((3-fluorophenyl){[(6-methyl-3-pyridinyl)amino]carbonyl}amino)-1-piperidinyl]methyl}-2-pyridinyl)oxy]-N-(3-hydroxy-3-methylbutyl)benzenesulfonamide,

(41) N-(3-fluorophenyl)-N-{1-[(6-{4-[(3-hydroxypropyl)sulfonyl]phenoxy}-3-pyridinyl)methyl]-4-piperidinyl}-N'-(6-methyl-3-pyridinyl)urea,

(42) N-(2-methoxyethyl)-4-[(5-{[4-46-methyl-3-pyridinyl){[(6-methyl-3-pyridinyl)amino]carbonyl}amino)-1-piperidinyl]methyl}-2-pyridinyl)oxy]benzenesulfonamide,

(43) N-{1-[(6-{4-[(4-hydroxy-1-piperidinyl)sulfonyl]phenoxy}-3-pyridinyl)methyl]-4-piperidinyl}-N,N'-bis(6-methyl-3-pyridinyl)urea,

(44) 4-[(5-{[4-((4-chlorophenyl){[(6-methyl-3-pyridinyl)amino]carbonyl}amino)-1-piperidinyl]methyl}-2-pyridinyl)oxy]-N-(2-methoxyethyl)benzenesulfonamide,

(45) N-{1-[(6-{4-[(4-methyl-1-piperazinyl)sulfonyl]phenoxy}-3-pyridinyl)methyl]-4-piperidinyl}-N,N'-bis(6-methyl-3-pyridinyl)urea,

(46) 4-{[5-({4-[{[(5-chloro-2-pyridinyl)amino]carbonyl}(6-methyl-3-pyridinyl)amino]-1-piperidinyl}methyl)-2-pyridinyl]oxy}-N-(2-methoxyethyl)benzenesulfonamide,

(47) 5-({[(4-chlorophenyl)(1-{[6-(4-{[(2-methoxyethyl)amino]sulfonyl}phenoxy)-3-pyridinyl]methyl}-4-piperidinyl)amino]carbonyl}amino)-2-fluorobenzamide,

(48) 5-{[((4-chlorophenyl){1-[(6-{4-[(4-hydroxy-1-piperidinyl)sulfonyl]phenoxy}-3-pyridinyl)methyl]-4-piperidinyl}amino)carbonyl]amino}-2-fluorobenzamide,

(49) N'-(5-chloro-2-pyridinyl)-N-{1-[(6-{4-[(4-hydroxy-1-piperidinyl)sulfonyl]phenoxy}-3-pyridinyl)methyl]-4-piperidinyl}-N-(6-methyl-3-pyridinyl)urea,

(50) 2-fluoro-5-({[(1-{[6-(4-{[(2-methoxyethyl)amino]sulfonyl}phenoxy)-3-pyridinyl]methyl}-4-piperidinyl)(6-methyl-3-pyridinyl)amino]carbonyl}amino)benzamide,

(51) 2-fluoro-5-({[{1-[(6-{4-[(4-hydroxy-1-piperidinyl)sulfonyl]phenoxy}-3-pyridinyl)methyl]-4-piperidinyl}(6-methyl-3-pyridinyl)amino]carbonyl}amino)benzamide,

(52) N-(4-chlorophenyl)-N'-(5-chloro-2-pyridinyl)-N-{1-[(6-{4-[(4-hydroxy-1-piperidinyl)sulfonyl]phenoxy}-3-pyridinyl)methyl]-4-piperidinyl}urea,

(53) 4-[(5-{[4-((4-chlorophenyl){[(5-chloro-2-pyridinyl)amino]carbonyl}amino)-1-piperidinyl]methyl}-2-pyridinyl)oxy]-N-(2-methoxyethyl)benzenesulfonamide,

(54) N-(2-methoxyethyl)-4-[(5-{[4-45-methyl-2-pyridinyl){[(6-methyl-3-pyridinyl)amino]carbonyl}amino)-1-piperidinyl]methyl}-2-pyridinyl)oxy]benzenesulfonamide,

(55) N-{1-[(6-{4-[(4-hydroxy-1-piperidinyl)sulfonyl]phenoxy}-3-pyridinyl)methyl]-4-piperidinyl}-N-(5-methyl-2-pyridinyl)-N'-(6-methyl-3-pyridinyl)urea,

(56) N'-(5-chloro-2-pyridinyl)-N-cyclopropyl-N-{1-[(6-{4-[(4-hydroxy-1-piperidinyl)sulfonyl]phenoxy}-3-pyridinyl)methyl]-4-piperidinyl}urea,

(57) 4-{[5-({4-[{[(5-chloro-2-pyridinyl)amino]carbonyl}(cyclopropyl)amino]-1-piperidinyl}methyl)-2-pyridinyl]oxy}-N-(2-methoxyethyl)benzenesulfonamide,

(58) 1-cyclopropyl-1-{1-[(6-{4-[(4-hydroxy-1-piperidinyl)sulfonyl]phenoxy}-3-pyridinyl)methyl]-4-piperidinyl}-3-(6-methyl-3-pyridinyl)urea,

(59) 4-({5-[(4-{cyclopropyl[(6-methyl-3-pyridinyl)carbamoyl]amino}-1-piperidinyl)methyl]-2-pyridinyl}oxy)-N-(2-methoxyethyl)benzenesulfonamide,

(60) 2-fluoro-5-{[(1-{[6-(4-{[(2-methoxyethyl)amino]sulfonyl}phenoxy)-3-pyridinyl]methyl}-4-piperidinyl)(5-methyl-2-pyridinyl)carbamoyl]amino}benzamide,

(61) 2-fluoro-5-{[{1-[(6-{4-[(4-hydroxy-1-piperidinyl)sulfonyl]phenoxy}-3-pyridinyl)methyl]-4-piperidinyl}(5-methyl-2-pyridinyl)carbamoyl]amino}benzamide,

(62) 5-[(cyclopropyl{1-[(6-{4-[(4-hydroxy-1-piperidinyl)sulfonyl]phenoxy}-3-pyridinyl)methyl]-4-piperidinyl}carbamoyl)amino]-2-fluorobenzamide,

(63) 5-{[cyclopropyl(1-{[6-(4-{[(2-methoxyethyl)amino]sulfonyl}phenoxy)-3-pyridinyl]methyl}-4-piperidinyl)carbamoyl]amino}-2-fluorobenzamide,

(64) 4-({5-[(4-{cyclobutyl[(6-methyl-3-pyridinyl)carbamoyl]amino}-1-piperidinyl)methyl]-2-pyridinyl}oxy)-N-(2-methoxyethyl)benzenesulfonamide,

(65) 1-cyclobutyl-1-{1-[(6-{4-[(4-hydroxy-1-piperidinyl)sulfonyl]phenoxy}-3-pyridinyl)methyl]-4-piperidinyl}-3-(6-methyl-3-pyridinyl)urea,

(66) 4-({5-[(4-{2-butyn-1-yl[(6-methyl-3-pyridinyl)carbamoyl]amino}-1-piperidinyl)methyl]-2-pyridinyl}oxy)-N-(2-methoxyethyl)benzenesulfonamide,

(67) 1-(2-butyn-1-yl)-1-{1-[(6-{4-[(4-hydroxy-1-piperidinyl)sulfonyl]phenoxy}-3-pyridinyl)methyl]-4-piperidinyl}-3-(6-methyl-3-pyridinyl)urea,

(68) 2,4-difluoro-5-{[(1-{[6-(4-{[(2-methoxyethyl)amino]sulfonyl}phenoxy)-3-pyridinyl]methyl}-4-piperidinyl)(3-methylbutyl)carbamoyl]amino}benzamide,

(69) 2,4-difluoro-5-{[{1-[(6-{4-[(4-hydroxy-1-piperidinyl)sulfonyl]phenoxy}-3-pyridinyl)methyl]-4-piperidinyl}(3-methylbutyl)carbamoyl]amino}benzamide,

(70) 5-{[(cyclobutylmethyl)(1-{[6-(4-{[(2-methoxyethyl)amino]sulfonyl}phenoxy)-3-pyridinyl]methyl}-4-piperidinyl)carbamoyl]amino}-2,4-difluorobenzamide,

(71) 5-{[(cyclopropylmethyl)(1-{[6-(4-{[(2-methoxyethyl)amino]sulfonyl}phenoxy)-3-pyridinyl]methyl}-4-piperidinyl)carbamoyl]amino}-2,4-difluorobenzamide,

(72) 2,4-difluoro-5-{[(2-hydroxybutyl)(1-{[6-(4-{[(2-methoxyethyl)amino]sulfonyl}phenoxy)-3-pyridinyl]methyl}-4-piperidinyl)carbamoyl]amino}benzamide,

(73) 5-{[3-butyn-1-yl(1-{[6-(4-{[(2-methoxyethyl)amino]sulfonyl}phenoxy)-3-pyridinyl]methyl}-4-piperidinyl)carbamoyl]amino}-2,4-difluorobenzamide,

(74) 1-{1-[(6-{4-[(4-hydroxy-1-piperidinyl)sulfonyl]phenoxy}-3-pyridinyl)methyl]-4-piperidinyl}-1-isobutyl-3-(6-methyl-3-pyridinyl)urea,

(75) 5-{[2-butyn-1-yl(1-{[6-(4-{[(2-methoxyethyl)amino]sulfonyl}phenoxy)-3-pyridinyl]methyl}-4-piperidinyl)carbamoyl]amino}-2-fluorobenzamide,

(76) 5-[(2-butyn-1-yl{1-[(6-{4-[(4-hydroxy-1-piperidinyl)sulfonyl]phenoxy}-3-pyridinyl)methyl]-4-piperidinyl}carbamoyl)amino]-2-fluorobenzamide,

(77) 2-fluoro-5-{[{1-[(6-{4-[(4-hydroxy-1-piperidinyl)sulfonyl]phenoxy}-3-pyridinyl)methyl]-4-piperidinyl}(isobutyl)carbamoyl]amino}benzamide,

(78) 1-(3-fluorophenyl)-1-{1-[(6-{4-[(4-methoxy-1-piperidinyl)sulfonyl]phenoxy}-3-pyridinyl)methyl]-4-piperidinyl}-3-(6-methyl-3-pyridinyl)urea,

(79) 1-(3-fluorophenyl)-3-(6-methyl-3-pyridinyl)-1-(1-{[6-(4-{[4-(trifluoromethyl)-1-piperidinyl]sulfonyl}phenoxy)-3-pyridinyl]methyl}-4-piperidinyl)urea,

(80) 1-(3-fluorophenyl)-1-{1-[(6-{4-[(4-fluoro-1-piperidinyl)sulfonyl]phenoxy}-3-pyridinyl)methyl]-4-piperidinyl}-3-(6-methyl-3-pyridinyl)urea,

(81) 1-{1-[(6-{4-[(4,4-difluoro-1-piperidinyl)sulfonyl]phenoxy}-3-pyridinyl)methyl]-4-piperidinyl}-1-(3-fluorophenyl)-3-(6-methyl-3-pyridinyl)urea,

(82) 5-[(butyl{1-[(6-{4-[(4-hydroxy-1-piperidinyl)sulfonyl]phenoxy}-3-pyridinyl)methyl]-4-piperidinyl}carbamoyl)amino]-2,4-difluorobenzamide,

(83) 5-({butyl[1-({2-methyl-6-[4-(methylsulfonyl)phenoxy]-3-pyridinyl}methyl)-4-piperidinyl]carbamoyl}amino)-2,4-difluorobenzamide,

(84) 5-[(butyl{1-[(2-methyl-6-{4-[(methylamino)sulfonyl]phenoxy}-3-pyridinyl)methyl]-4-piperidinyl}carbamoyl)amino]-2,4-difluorobenzamide,

(85) 5-[(butyl{1-[(6-{4-[(dimethylamino)sulfonyl]phenoxy}-2-methyl-3-pyridinyl)methyl]-4-piperidinyl}carbamoyl)amino]-2,4-difluorobenzamide,

(86) 5-[(butyl{1-[(6-{4-[(4-hydroxy-1-piperidinyl)sulfonyl]phenoxy}-2-methyl-3-pyridinyl)methyl]-4-piperidinyl}carbamoyl)amino]-2,4-difluorobenzamide,

(87) 5-[(butyl{1-[(6-{4-[(4-methoxy-1-piperidinyl)sulfonyl]phenoxy}-2-methyl-3-pyridinyl)methyl]-4-piperidinyl}carbamoyl)amino]-2,4-difluorobenzamide,

(88) 2-(5-{[butyl(1-{[2-methyl-6-(4-{[4-(trifluoromethyl)-1-piperidinyl]sulfonyl}phenoxy)-3-pyridinyl]methyl}-4-piperidinyl)carbamoyl]amino}-2,4-difluorophenyl)acetamide,

(89) 5-{[butyl(1-{[2-methyl-6-(4-{[4-(trifluoromethyl)-1-piperidinyl]sulfonyl}phenoxy)-3-pyridinyl]methyl}-4-piperidinyl)carbamoyl]amino}-2,4-difluorobenzamide,

(90) 5-{[{1-[(6-{4-[(4,4-difluoro-1-piperidinyl)sulfonyl]phenoxy}-2-methyl-3-pyridinyl)methyl]-4-piperidinyl}(pentyl)carbamoyl]amino}-2,4-difluorobenzamide,

(91) 5-[(butyl{1-[(6-{4-[(4,4-difluoro-1-piperidinyl)sulfonyl]phenoxy}-2-methyl-3-pyridinyl)methyl]-4-piperidinyl}carbamoyl)amino]-2,4-difluorobenzamide,
(92) 5-[(butyl{1-[(6-{4-[(4-fluoro-1-piperidinyl)sulfonyl]phenoxy}-2-methyl-3-pyridinyl)methyl]-4-piperidinyl}carbamoyl)amino]-2,4-difluorobenzamide,
(93) 5-[(butyl{1-[(6-{4-[(3-hydroxy-1-azetidinyl)sulfonyl]phenoxy}-2-methyl-3-pyridinyl)methyl]-4-piperidinyl}carbamoyl)amino]-2,4-difluorobenzamide,
(94) 5-[(butyl{1-[(6-{4-[(cyclopropylamino)sulfonyl]phenoxy}-2-methyl-3-pyridinyl)methyl]-4-piperidinyl}carbamoyl)amino]-2,4-difluorobenzamide,
(95) 5-[(butyl{1-[(6-{4-[(cyclobutylamino)sulfonyl]phenoxy}-2-methyl-3-pyridinyl)methyl]-4-piperidinyl}carbamoyl)amino]-2,4-difluorobenzamide,
(96) 5-[(butyl{1-[(6-{4-[(cyclopentylamino)sulfonyl]phenoxy}-2-methyl-3-pyridinyl)methyl]-4-piperidinyl}carbamoyl)amino]-2,4-difluorobenzamide,
(97) 5-{[butyl(1-{[6-(4-{[(4,4-difluorocyclohexyl)amino]sulfonyl}phenoxy)-2-methyl-3-pyridinyl]methyl}-4-piperidinyl)carbamoyl]amino}-2,4-difluorobenzamide,
(98) 5-{[(1-{[6-(4-acetylphenoxy)-2-methyl-3-pyridinyl]methyl}-4-piperidinyl)(butyl)carbamoyl]amino}-2,4-difluorobenzamide,
(99) 5-({butyl[1-({2-methyl-6-[4-(methylcarbamoyl)phenoxy]-3-pyridinyl}methyl)-4-piperidinyl]carbamoyl}amino)-2,4-difluorobenzamide,
(100) 5-{[{1-[(6-{4-[(4-acetyl-1-piperazinyl)carbonyl]phenoxy}-2-methyl-3-pyridinyl)methyl]-4-piperidinyl}(butyl)carbamoyl]amino}-2,4-difluorobenzamide,
(101) 5-({butyl[1-({6-[4-(dimethylcarbamoyl)phenoxy]-2-methyl-3-pyridinyl}methyl)-4-piperidinyl]carbamoyl}amino)-2,4-difluorobenzamide,
(102) 5-({butyl[1-({6-[4-(ethylcarbamoyl)phenoxy]-2-methyl-3-pyridinyl}methyl)-4-piperidinyl]carbamoyl}amino)-2,4-difluorobenzamide,
(103) 5-[(butyl{1-[(2-methyl-6-{4-[(4-methyl-1-piperazinyl)carbonyl]phenoxy}-3-pyridinyl)methyl]-4-piperidinyl}carbamoyl)amino]-2,4-difluorobenzamide,
(104) 5-({butyl[1-({6-[4-(1-hydroxy-1-methylethyl)phenoxy]-2-methyl-3-pyridinyl}methyl)-4-piperidinyl]carbamoyl}amino)-2,4-difluorobenzamide,
(105) 5-[(butyl{1-[(2-methyl-6-{4-[(methylsulfonyl)methyl]phenoxy}-3-pyridinyl)methyl]-4-piperidinyl}carbamoyl)amino]-2,4-difluorobenzamide,
(106) 5-{[butyl(1-{[2-methyl-6-(4-{[(methylsulfonyl)amino]methyl}phenoxy)-3-pyridinyl]methyl}-4-piperidinyl)carbamoyl]amino}-2,4-difluorobenzamide,
(107) N-{4-[(5-{[4-((6-methyl-3-pyridinyl){[(6-methyl-3-pyridinyl)amino]carbonyl}amino)-1-piperidinyl]methyl}-2-pyridinyl)oxy]phenyl}methanesulfonamide,
(108) N-{4-[(5-{[4-((5-methyl-2-pyridinyl){[(6-methyl-3-pyridinyl)amino]carbonyl}amino)-1-piperidinyl]methyl}-2-pyridinyl)oxy]phenyl}methanesulfonamide,
(109) N-(4-{[5-({4-[{[(5-chloro-2-pyridinyl)amino]carbonyl}(cyclopropyl)amino]-1-piperidinyl}methyl)-2-pyridinyl]oxy}phenyl)methanesulfonamide,
(110) N-[4-({5-[(4-{cyclopropyl[(6-methyl-3-pyridinyl)carbamoyl]amino}-1-piperidinyl)methyl]-2-pyridinyl}oxy)phenyl]methanesulfonamide,
(111) 2-fluoro-5-{[(5-methyl-2-pyridinyl){1-[(6-{4-[(methylsulfonyl)amino]phenoxy}-3-pyridinyl)methyl]-4-piperidinyl}carbamoyl]amino}benzamide,
(112) N-[4-({5-[(4-{cyclobutyl[(6-methyl-3-pyridinyl)carbamoyl]amino}-1-piperidinyl)methyl]-2-pyridinyl}oxy)phenyl]methanesulfonamide,
(113) N-[4-({5-[(4-{2-butyn-1-yl[(6-methyl-3-pyridinyl)carbamoyl]amino}-1-piperidinyl)methyl]-2-pyridinyl}oxy)phenyl]methanesulfonamide,
(114) N-[4-({5-[(4-{(3-methyl-2-buten-1-yl)[(6-methyl-3-pyridinyl)carbamoyl]amino}-1-piperidinyl)methyl]-2-pyridinyl}oxy)phenyl]methanesulfonamide,
(115) N-[4-({5-[(4-{(cyclobutylmethyl)[(6-methyl-3-pyridinyl)carbamoyl]amino}-1-piperidinyl)methyl]-2-pyridinyl}oxy)phenyl]methanesulfonamide,
(116) N-[4-({5-[(4-{(3-methylbutyl)[(6-methyl-3-pyridinyl)carbamoyl]amino}-1-piperidinyl)methyl]-2-pyridinyl}oxy)phenyl]methanesulfonamide,
(117) 2,4-difluoro-5-{[(3-methylbutyl){1-[(6-{4-[(methylsulfonyl)amino]phenoxy}-3-pyridinyl)methyl]-4-piperidinyl}carbamoyl]amino}benzamide,
(118) 5-{[(cyclobutylmethyl){1-[(6-{4-[(methylsulfonyl)amino]phenoxy}-3-pyridinyl)methyl]-4-piperidinyl}carbamoyl]amino}-2,4-difluorobenzamide,
(119) 5-{[(cyclopropylmethyl){1-[(6-{4-[(methylsulfonyl)amino]phenoxy}-3-pyridinyl)methyl]-4-piperidinyl}carbamoyl]amino}-2,4-difluorobenzamide,
(120) 2,4-difluoro-5-{[(2-hydroxybutyl){1-[(6-{4-[(methylsulfonyl)amino]phenoxy}-3-pyridinyl)methyl]-4-piperidinyl}carbamoyl]amino}benzamide,
(121) 5-[(3-butyn-1-yl{1-[(6-{4-[(methylsulfonyl)amino]phenoxy}-3-pyridinyl)methyl]-4-piperidinyl}carbamoyl)amino]-2,4-difluorobenzamide,
(122) N-[4-({5-[(4-{butyl[(6-methyl-3-pyridinyl)carbamoyl]amino}-1-piperidinyl)methyl]-2-pyridinyl}oxy)phenyl]methanesulfonamide,
(123) N-[4-({5-[(4-{(cyclopropylmethyl)[(6-methyl-3-pyridinyl)carbamoyl]amino}-1-piperidinyl)methyl]-2-pyridinyl}oxy)phenyl]methanesulfonamide,
(124) N-[4-({5-[(4-{(2-hydroxybutyl)[(6-methyl-3-pyridinyl)carbamoyl]amino}-1-piperidinyl)methyl]-2-pyridinyl}oxy)phenyl]methanesulfonamide,
(125) N-[4-({5-[(4-{3-butyn-1-yl[(6-methyl-3-pyridinyl)carbamoyl]amino}-1-piperidinyl)methyl]-2-pyridinyl}oxy)phenyl]methanesulfonamide,
(126) 5-[(2-butyn-1-yl{1-[(6-{4-[(methylsulfonyl)amino]phenoxy}-3-pyridinyl)methyl]-4-piperidinyl}carbamoyl)amino]-2-fluorobenzamide,
(127) 2,4-difluoro-5-{[(3-methyl-2-buten-1-yl){1-[(6-{4-[(methylsulfonyl)amino]phenoxy}-3-pyridinyl)methyl]-4-piperidinyl}carbamoyl]amino}benzamide,
(128) 5-[(butyl{1-[(6-{4-[(methylsulfonyl)amino]phenoxy}-3-pyridinyl)methyl]-4-piperidinyl}carbamoyl)amino]-2-fluorobenzamide,
(129) N-[4-({5-[(4-{isobutyl[(6-methyl-3-pyridinyl)carbamoyl]amino}-1-piperidinyl)methyl]-2-pyridinyl}oxy)phenyl]methanesulfonamide,
(130) 2-fluoro-5-[(isobutyl{1-[(6-{4-[(methylsulfonyl)amino]phenoxy}-3-pyridinyl)methyl]-4-piperidinyl}carbamoyl)amino]benzamide,
(131) 5-[(2-butyn-1-yl{1-[(6-{4-[(methylsulfonyl)amino]phenoxy}-3-pyridinyl)methyl]-4-piperidinyl}carbamoyl)amino]-2,4-difluorobenzamide,
(132) 2,4-difluoro-5-{[{1-[(6-{4-[(methylsulfonyl)amino]phenoxy}-3-pyridinyl)methyl]-4-piperidinyl}(propyl)carbamoyl]amino}benzamide,
(133) 5-[(3-buten-1-yl{1-[(6-{4-[(methylsulfonyl)amino]phenoxy}-3-pyridinyl)methyl]-4-piperidinyl}carbamoyl)amino]-2,4-difluorobenzamide, (134) 5-{[(cyclopentylmethyl){1-[(6-{4-[(methylsulfonyl)amino]phenoxy}-3-pyridinyl)methyl]-4-piperidinyl}carbamoyl]amino}-2,4-difluorobenzamide, (135) 2-{5-[(butyl{1-[(2-methyl-6-{4-[(methylsulfonyl)amino]phenoxy}-3-pyridinyl)methyl]-4-piperidinyl}carbamoyl)amino]-2,4-difluorophenyl}acetamide, (136) 5-[(butyl{1-[(2-methyl-6-{4-[(methylsulfonyl)amino]phenoxy}-3-pyridinyl)methyl]-4-piperidinyl}carbamoyl)amino]-2-fluorobenzamide, (137) N-[4-({5-[(4-{butyl[(5-cyano-2,4-difluorophenyl)carbamoyl]amino}-1-piperidinyl)methyl]-6-methyl-2-pyridinyl}oxy)phenyl]methanesulfonamide, (138) N-[4-({5-[(4-{butyl[(3-methyl-5-isoxazolyl)carbamoyl]amino}-1-piperidinyl)methyl]-6-methyl-2-pyridinyl}oxy)phenyl]methanesulfonamide, (139) 5-[(butyl{1-[(2-methyl-6-{4-[(methylsulfonyl)amino]phenoxy}-3-pyridinyl)methyl]-4-piperidinyl}carbamoyl)amino]-2,4-difluorobenzenesulfonamide, (140) N-[4-({5-[(4-{butyl[(6-methyl-3-pyridinyl)carbamoyl]amino}-1-piperidinyl)methyl]-6-methyl-2-pyridinyl}oxy)phenyl]methanesulfonamide, (141) 5-[(butyl{1-[(6-{4-[(ethylsulfonyl)amino]phenoxy}-2-methyl-3-pyridinyl)methyl]-4-piperidinyl}carbamoyl)amino]-2,4-difluorobenzamide, (142) 5-{[(cyclobutylmethyl){1-[(2-methyl-6-{4-[(methylsulfonyl)amino]phenoxy}-3-pyridinyl)methyl]-4-piperidinyl}carbamoyl]amino}-2,4-difluorobenzamide, (143) 5-[(2-butyn-1-yl{1-[(2-methyl-6-{4-[(methylsulfonyl)amino]phenoxy}-3-pyridinyl)methyl]-4-piperidinyl}carbamoyl)amino]-2,4-difluorobenzamide, (144) 5-{[(cyclopropylmethyl){1-[(2-methyl-6-{4-[(methylsulfonyl)amino]phenoxy}-3-pyridinyl)methyl]-4-piperidinyl}carbamoyl]amino}-2,4-difluorobenzamide, (145) N-{4-[(5-{[4-(butyl{[2,4-difluoro-5-(1,3-oxazol-2-yl)phenyl]carbamoyl}amino)-1-piperidinyl]methyl}-6-methyl-2-pyridinyl)oxy]phenyl}methanesulfonamide, (146) N-[4-({5-[(4-{butyl[(6-fluoro-1-oxo-1,2,3,4-tetrahydro-7-isoquinolinyl)carbamoyl]amino}-1-piperidinyl)methyl]-6-methyl-2-pyridinyl}oxy)phenyl]methanesulfonamide, (147) 2,4-difluoro-5-{[{1-[(2-methyl-6-{4-[(methylsulfonyl)amino]phenoxy}-3-pyridinyl)methyl]-4-piperidinyl}(pentyl)carbamoyl]amino}benzamide, (148) 2,4-difluoro-5-{[{1-[(2-methyl-6-{4-[(methylsulfonyl)amino]phenoxy}-3-pyridinyl)methyl]-4-piperidinyl}(propyl)carbamoyl]amino}benzamide, (149) 2,4-difluoro-5-{[(3-methylbutyl){1-[(2-methyl-6-{4-[(methylsulfonyl)amino]phenoxy}-3-pyridinyl)methyl]-4-piperidinyl}carbamoyl]amino}benzamide, (150) 2,4-difluoro-5-{[(3-methyl-2-buten-1-yl){1-[(2-methyl-6-{4-[(methylsulfonyl)amino]phenoxy}-3-pyridinyl)methyl]-4-piperidinyl}carbamoyl]amino}benzamide, (151) 5-[(3-buten-1-yl{1-[(2-methyl-6-{4-[(methylsulfonyl)amino]phenoxy}-3-pyridinyl)methyl]-4-piperidinyl}carbamoyl)amino]-2,4-difluorobenzamide, (152) 5-[(3-butyn-1-yl{1-[(2-methyl-6-{4-[(methylsulfonyl)amino]phenoxy}-3-pyridinyl)methyl]-4-piperidinyl}carbamoyl)amino]-2,4-difluorobenzamide, (153) 5-{[(cyclopentylmethyl){1-[(2-methyl-6-{4-[(methylsulfonyl)amino]phenoxy}-3-pyridinyl)methyl]-4-piperidinyl}carbamoyl]amino}-2,4-difluorobenzamide, (154) 5-[(butyl{1-[(5-methyl-6-{4-[(methylsulfonyl)amino]phenoxy}-3-pyridinyl)methyl]-4-piperidinyl}carbamoyl)amino]-2,4-difluorobenzamide, (155) 5-[(butyl{1-[(4-methyl-6-{4-[(methylsulfonyl)amino]phenoxy}-3-pyridinyl)methyl]-4-piperidinyl}carbamoyl)amino]-2,4-difluorobenzamide, (156) 5-[(butyl{1-[(2-ethyl-6-{4-[(methylsulfonyl)amino]phenoxy}-3-pyridinyl)methyl]-4-piperidinyl}carbamoyl)amino]-2,4-difluorobenzamide, (157) 5-[(2-butyn-1-yl{1-[(2-ethyl-6-{4-[(methylsulfonyl)amino]phenoxy}-3-pyridinyl)methyl]-4-piperidinyl}carbamoyl)amino]-2,4-difluorobenzamide, (158) 5-{[(cyclopropylmethyl){1-[(2-ethyl-6-{4-[(methylsulfonyl)amino]phenoxy}-3-pyridinyl)methyl]-4-piperidinyl}carbamoyl]amino}-2,4-difluorobenzamide, (159) 5-{[(cyclobutylmethyl){1-[(2-ethyl-6-{4-[(methylsulfonyl)amino]phenoxy}-3-pyridinyl)methyl]-4-piperidinyl}carbamoyl]amino}-2,4-difluorobenzamide, (160) 5-[(butyl{1-[(6-{4-[(methylsulfonyl)amino]phenoxy}-2-propyl-3-pyridinyl)methyl]-4-piperidinyl}carbamoyl)amino]-2,4-difluorobenzamide, (161) 5-[(butyl{1-[(2-isopropyl-6-{4-[(methylsulfonyl)amino]phenoxy}-3-pyridinyl)methyl]-4-piperidinyl}carbamoyl)amino]-2,4-difluorobenzamide, (162) 5-[(2-butyn-1-yl{1-[(2-isopropyl-6-{4-[(methylsulfonyl)amino]phenoxy}-3-pyridinyl)methyl]-4-piperidinyl}carbamoyl)amino]-2,4-difluorobenzamide, (163) 5-{[(cyclopropylmethyl){1-[(2-isopropyl-6-{4-[(methylsulfonyl)amino]phenoxy}-3-pyridinyl)methyl]-4-piperidinyl}carbamoyl]amino}-2,4-difluorobenzamide, (164) 5-{[(cyclobutylmethyl){1[(2-isopropyl-6-{4-[(methylsulfonyl)amino]phenoxy}-3-pyridinyl)methyl]-4-piperidinyl}carbamoyl]amino}-2,4-difluorobenzamide, (165) 5-[(butyl{1-[(2-chloro-6-{4-[(methylsulfonyl)amino]phenoxy}-3-pyridinyl)methyl]-4-piperidinyl}carbamoyl)amino]-2,4-difluorobenzamide, (166) 5-[(butyl{1-[(2-methoxy-6-{4-[(methylsulfonyl)amino]phenoxy}-3-pyridinyl)methyl]-4-piperidinyl}carbamoyl)amino]-2,4-difluorobenzamide, (167) 5-[(2-butyn-1-yl{1-[(2-methoxy-6-{4-[(methylsulfonyl)amino]phenoxy}-3-pyridinyl)methyl]-4-piperidinyl}carbamoyl)amino]-2,4-difluorobenzamide, (168) 5-{[(cyclobutylmethyl){1-[(2-methoxy-6-{4-[(methylsulfonyl)amino]phenoxy}-3-pyridinyl)methyl]-4-piperidinyl}carbamoyl]amino}-2,4-difluorobenzamide, (169) 2,4-difluoro-5-{[{1-[(2-methoxy-6-{4-[(methylsulfonyl)amino]phenoxy}-3-pyridinyl)methyl]-4-piperidinyl}(propyl)carbamoyl]amino}benzamide, (170) 5-[(3-buten-1-yl{1-[(2-methoxy-6-{4-[(methylsulfonyl)amino]phenoxy}-3-pyridinyl)methyl]-4-piperidinyl}carbamoyl)amino]-2,4-difluorobenzamide, (171) 5-[(butyl{1-[(6-{4-[(methylsulfonyl)amino]phenoxy}-2-phenyl-3-pyridinyl)methyl]-4-piperidinyl}carbamoyl)amino]-2,4-difluorobenzamide, (172) 5-[(butyl{1-[(2-methyl-6-{2-methyl-4-[(methylsulfonyl)amino]phenoxy}-3-pyridinyl)methyl]-4-piperidinyl}carbamoyl)amino]-2,4-difluorobenzamide, (173) 5-({butyl[1-(2-methyl-4-{4-[(methylsulfonyl)amino]phenoxy}benzyl)-4-piperidinyl]carbamoyl}amino)-2,4-difluorobenzamide, (174) 5-[(butyl{1-[4-{4-[(methylsulfonyl)amino]phenoxy}-2-(trifluoromethyl)benzyl]-4-piperidinyl}carbamoyl)amino]-2,4-difluorobenzamide, (175) 5-[(butyl{2-methyl-1-[(2-methyl-6-{4-[(methylsulfonyl)amino]phenoxy}-3-pyridinyl)methyl]-4-piperidinyl}carbamoyl)amino]-2,4-difluorobenzamide, (176) 5-({butyl[1-({2-methyl-6-[4-(1,3-ox azol-2-yl)phenoxy]-3-pyridinyl}methyl)-4-piperidinyl]carbamoyl}amino)-2,4-difluorobenzamide, (177) 5-({butyl[1-({2-methyl-6-[4-(1,3-thiazol-2-yl)phenoxy]-3-pyridinyl}methyl)-4-piperidinyl]carbamoyl}amino)-2,4-difluorobenzamide, (178) 5-{[(1-{[6-(4-nitrophenoxy)-2-methyl-3-pyridinyl]methyl}-4-piperidinyl)(butyl)carbamoyl]amino}-2,4-difluorobenzamide, (179) 5-{[(1-{[6-(4-aminophenoxy)-2-methyl-3-pyridinyl]methyl}-4-piperidinyl)(butyl)carbamoyl]amino}-2,4-difluorobenzamide, (180) 5-{[(1-{[6-(4-acetamidophenoxy)-2-methyl-3-pyridinyl]methyl}-4-piperidinyl)(butyl)carbamoyl]amino}-2,4-difluorobenzamide, (181) 5-{[butyl(1-{[6-(4-{[(dimethylamino)sulfonyl]amino}phenoxy)-2-methyl-3-pyridinyl]methyl}-4-piperidinyl)carbamoyl]amino}-2,4-difluorobenzamide, (182) 5-{[butyl(1-{[2-methyl-6-(4-{[(methylamino)sulfonyl]amino}phenoxy)-3-pyridinyl]methyl}-4-piperidinyl)carbamoyl]amino}-2,4-difluorobenzamide, (183) N-(1-{[6-(4-{[(2-methoxyethyl)amino]sulfonyl}phenoxy)-3-pyridinyl]methyl}-4-piperidinyl)-N,2-diphenylacetamide, (184) N-{1-[(6-{4-[(4-hydroxy-1-piperidinyl)sulfonyl]phenoxy}-3-pyridinyl)methyl]-4-piperidinyl}-N,2-diphenylacetamide, (185) N-{1-[(6-{4-[(methylsulfonyl)amino]phenoxy}-3-pyridinyl)methyl]-4-piperidinyl}-N,2-diphenylacetamide, (186) 2-cyclohexyl-N-{1-[(6-{4-[(methylsulfonyl)amino]phenoxy}-3-pyridinyl)methyl]-4-piperidinyl}-N-phenylacetamide, (187) N-{1-[(6-{4-[(methylsulfonyl)amino]phenoxy}-3-pyridinyl)methyl]-4-piperidinyl}-N-phenyl-2-(tetrahydro-2H-pyran-4-yl)acetamide, (188) 1-acetyl-N-{1-[(6-{4-[(methylsulfonyl)amino]phenoxy}-3-pyridinyl)methyl]-4-piperidinyl}-N-phenyl-4-piperidinecarboxamide, (189) N-{1-[(6-{4-[(methylsulfonyl)amino]phenoxy}-3-pyridinyl)methyl]-4-piperidinyl}-N-phenylbicyclo[4.2.0]octa-1,3,5-triene-7-carboxamide, (190) N-{1-[(6-{4-[(methylsulfonyl)amino]phenoxy}-3-pyridinyl)methyl]-4-piperidinyl}-N-phenyl-1-indanecarbox amide, (191) N-{1-[(6-{4-[(methylsulfonyl)amino]phenoxy}-3-pyridinyl)methyl]-4-piperidinyl}-N-phenyl-1,2,3,4-tetrahydro-1-naphthalenecarboxamide, (192) 2-(4-methoxyphenyl)-N-{1-[(6-{4-[(methylsulfonyl)amino]phenoxy}-3-pyridinyl)methyl]-4-piperidinyl}-N-phenylacetamide, (193) 2-(4-cyanophenyl)-N-{1-[(6-{4-[(methylsulfonyl)amino]phenoxy}-3-pyridinyl)methyl]-4-piperidinyl}-N-phenylacetamide, (194) N-{1-[(6-{4-[(methylsulfonyl)amino]phenoxy}-3-pyridinyl)methyl]-4-piperidinyl}-N,1-diphenylcyclopropanecarboxamide, (195) 2-(3-methoxyphenyl)-N-{1-[(6-{4-[(methylsulfonyl)amino]phenoxy}-3-pyridinyl)methyl]-4-piperidinyl}-N-phenylacetamide, (196) 2-(2-methoxyphenyl)-N-{1-[(6-{4-[(methylsulfonyl)amino]phenoxy}-3-pyridinyl)methyl]-4-piperidinyl}-N-phenylacetamide, (197) N-(5-methyl-2-pyridinyl)-N-{1-[(6-{4-[(methylsulfonyl)amino]phenoxy}-3-pyridinyl)methyl]-4-piperidinyl}-2-phenylacetamide, (198) N-{1-[(6-{4-[(methylsulfonyl)amino]phenoxy}-3-pyridinyl)methyl]-4-piperidinyl}-N,2-diphenylpropanamide, (199) 2-methoxy-N-{1-[(6-{4-[(methylsulfonyl)amino]phenoxy}-3-pyridinyl)methyl]-4-piperidinyl}-N,2-diphenylacetamide, (200) N-{1-[(6-{4-[(methylsulfonyl)amino]phenoxy}-3-pyridinyl)methyl]-4-piperidinyl}-N-phenyl-2-(2-thienyl)acetamide, (201) 2-(3-methyl-5-isoxazolyl)-N-{1-[(6-{4-[(methylsulfonyl)amino]phenoxy}-3-pyridinyl)methyl]-4-piperidinyl}-N-phenylacetamide, (202) 2-(3-cyanophenyl)-N-{1-[(6-{4-[(methylsulfonyl)amino]phenoxy}-3-pyridinyl)methyl]-4-piperidinyl}-N-phenylacetamide, (203) 2-(3-acetylphenyl)-N-{1-[(6-{4-[(methylsulfonyl)amino]phenoxy}-3-pyridinyl)methyl]-4-piperidinyl}-N-phenylacetamide, (204) 2-[3-(1-hydroxyethyl)phenyl]-N-{1-[(6-{4-[(methylsulfonyl)amino]phenoxy}-3-pyridinyl)methyl]-4-piperidinyl}-N-phenylacetamide, (205) N-{1-[(6-{4-[(methylsulfonyl)amino]phenoxy}-3-pyridinyl)methyl]-4-piperidinyl}-N-phenyl-2,3-dihydro-1-benzofuran-2-carboxamide, (206) 2-fluoro-N-{1-[(6-{4-[(methylsulfonyl)amino]phenoxy}-3-pyridinyl)methyl]-4-piperidinyl}-N,2-diphenylacetamide, (207) N-{1-[(6-{4-[(methylsulfonyl)amino]phenoxy}-3-pyridinyl)methyl]-4-piperidinyl}-2-phenoxy-N-phenylac etamide, (208) (3S)-3-hydroxy-N-{1-[(6-{4-[(methylsulfonyl)amino]phenoxy}-3-pyridinyl)methyl]-4-piperidinyl}-N,3-diphenylpropanamide, (209) N-{1-[(6-{4-[(methylsulfonyl)amino]phenoxy}-3-pyridinyl)methyl]-4-piperidinyl}-N,1-diphenylmethanesulfonamide, (210) N-[{1-[(6-{4-[(methylsulfonyl)amino]phenoxy}-3-pyridinyl)methyl]-4-piperidinyl}(phenyl)methyl]benzamide, (211) N-[{1-[(6-{4-[(methylsulfonyl)amino]phenoxy}-3-pyridinyl)methyl]-4-piperidinyl}(phenyl)methyl]cyclohexanecarboxamide, (212) 1-acetyl-N-[{1-[(6-{4-[(methylsulfonyl)amino]phenoxy}-3-pyridinyl)methyl]-4-piperidinyl}(phenyl)methyl]-4-piperidinecarboxamide, (213) N-[{1-[(6-{4-[(methylsulfonyl)amino]phenoxy}-3-pyridinyl)methyl]-4-piperidinyl}(phenyl)methyl]tetrahydro-2H-pyran-4-carboxamide, (214) N-[{1-[(6-{4-[(methylsulfonyl)amino]phenoxy}-3-pyridinyl)methyl]-4-piperidinyl}(phenyl)methyl]benzenesulfonamide, (215) 5-[(butyl{1-[(6-{4-[(4-hydroxy-1-piperidinyl)carbonyl]phenoxy}-2-methyl-3-pyridinyl)methyl]-4-piperidinyl}carbamoyl)amino]-2,4-difluorobenzamide, (216) 5-({butyl[1-({2-methyl-6-[4-(4-morpholinylcarbonyl)phenoxy]-3-pyridinyl}methyl)-4-piperidinyl]carbamoyl}amino)-2,4-difluorobenzamide, (217) 5-{[butyl(1-{[2-methyl-6-(4-{[4-(trifluoromethyl)-1-piperidinyl]carbonyl}phenoxy)-3-pyridinyl]methyl}-4-piperidinyl)carbamoyl]amino}-2,4-difluorobenzamide,
(218) 5-{[{1-[(6-{4-[(4-acetyl-1-piperazinyl)carbonyl]phenoxy}-2-methyl-3-pyridinyl)methyl]-4-piperidinyl}(propyl)carbamoyl]amino}-2,4-difluorobenzamide,
(219) 5-{[{1-[(6-{4-[(4-acetyl-1-piperazinyl)carbonyl]phenoxy}-2-methyl-3-pyridinyl)methyl]-4-piperidinyl}(2-butyn-1-yl)carbamoyl]amino}-2,4-difluorobenzamide,
(220) 2,4-difluoro-5-{[{1-[(2-methyl-6-{4-[(methylsulfonyl)methyl]phenoxy}-3-pyridinyl)methyl]-4-piperidinyl}(propyl)carbamoyl]amino}benzamide,
(221) 5-[(2-butyn-1-yl{1-[(2-methyl-6-{4-[(methylsulfonyl)methyl]phenoxy}-3-pyridinyl)methyl]-4-piperidinyl}carbamoyl)amino]-2,4-difluorobenzamide,
(222) 5-[(butyl{1-[(2-isopropyl-6-{4-[(methylsulfonyl)methyl]phenoxy}-3-pyridinyl)methyl]-4-piperidinyl}carbamoyl)amino]-2,4-difluorobenzamide,
(223) 5-[(2-butyn-1-yl{1-[(2-isopropyl-6-{4-[(methylsulfonyl)methyl]phenoxy}-3-pyridinyl)methyl]-4-piperidinyl}carbamoyl)amino]-2,4-difluorobenzamide,
(224) 2,4-difluoro-5-{[{1[(2-isopropyl-6-{4-[(methylsulfonyl)methyl]phenoxy}-3-pyridinyl)methyl]-4-piperidinyl}(propyl)carbamoyl]amino}benzamide,
(225) 2,4-difluoro-5-{[(1-{[2-methyl-6-(4-{[(methylsulfonyl)amino]methyl}phenoxy)-3-pyridinyl]methyl}-4-piperidinyl)(propyl)carbamoyl]amino}benzamide,
(226) 5-{[2-butyn-1-yl(1-{[2-methyl-6-(4-{[(methylsulfonyl)amino]methyl}phenoxy)-3-pyridinyl]methyl}-4-piperidinyl)carbamoyl]amino}-2,4-difluorobenzamide,
(227) 5-{[butyl(1-{[2-isopropyl-6-(4-{[(methylsulfonyl)amino]methyl}phenoxy)-3-pyridinyl]methyl}-4-piperidinyl)carbamoyl]amino}-2,4-difluorobenzamide,
(228) 2,4-difluoro-5-{[(1-{[2-isopropyl-6-(4-{[(methylsulfonyl)amino]methyl}phenoxy)-3-pyridinyl]methyl}-4-piperidinyl)(propyl)carbamoyl]amino}benzamide,
(229) 5-{[2-butyn-1-yl(1-{[2-isopropyl-6-(4-{[(methylsulfonyl)amino]methyl}phenoxy)-3-pyridinyl]methyl}-4-piperidinyl)carbamoyl]amino}-2,4-difluorobenzamide,
(230) 5-({butyl[1-({2-isopropyl-6-[4-(methylsulfonyl)phenoxy]-3-pyridinyl}methyl)-4-piperidinyl]carbamoyl}amino)-2,4-difluorobenzamide,
(231) 2,4-difluoro-5-({[1-({2-isopropyl-6-[4-(methylsulfonyl)phenoxy]-3-pyridinyl}methyl)-4-piperidinyl](propyl)carbamoyl}amino)benzamide,
(232) 5-({2-butyn-1-yl[1-({2-isopropyl-6-[4-(methylsulfonyl)phenoxy]-3-pyridinyl}methyl)-4-piperidinyl]carbamoyl}amino)-2,4-difluorobenzamide,
(233) 2,4-difluoro-5-({[1-({2-methyl-6-[4-(methylsulfonyl)phenoxy]-3-pyridinyl}methyl)-4-piperidinyl](propyl)carbamoyl}amino)benzamide,
(234) 5-({2-butyn-1-yl[1-({2-methyl-6-[4-(methylsulfonyl)phenoxy]-3-pyridinyl}methyl)-4-piperidinyl]carbamoyl}amino)-2,4-difluorobenzamide,
(235) 5-[(2-butyn-1-yl{1-[(6-{4-[(3-hydroxy-1-azetidinyl)sulfonyl]phenoxy}-2-methyl-3-pyridinyl)methyl]-4-piperidinyl}carbamoyl)amino]-2,4-difluorobenzamide,
(236) 2,4-difluoro-5-{[{1-[(6-{4-[(3-hydroxy-1-azetidinyl)sulfonyl]phenoxy}-2-methyl-3-pyridinyl)methyl]-4-piperidinyl}(propyl)carbamoyl]amino}benzamide,
(237) 2,4-difluoro-5-{[{1-[(6-{4-[(3-hydroxy-1-azetidinyl)sulfonyl]phenoxy}-2-isopropyl-3-pyridinyl)methyl]-4-piperidinyl}(propyl)carbamoyl]amino}benzamide,
(238) 5-[(butyl{1-[(6-{4-[(3-hydroxy-1-azetidinyl)sulfonyl]phenoxy}-2-isopropyl-3-pyridinyl)methyl]-4-piperidinyl}carbamoyl)amino]-2,4-difluorobenzamide,
(239) 5-[(2-butyn-1-yl{1-[(6-{4-[(3-hydroxy-1-azetidinyl)sulfonyl]phenoxy}-2-isopropyl-3-pyridinyl)methyl]-4-piperidinyl}carbamoyl)amino]-2,4-difluorobenzamide,
(240) 5-[(butyl{1-[(6-{2-chloro-4-[(methylsulfonyl)amino]phenoxy}-2-methyl-3-pyridinyl)methyl]-4-piperidinyl}carbamoyl)amino]-2,4-difluorobenzamide,
(241) N-(4-{[5-({4-[butyl(cyclohexylcarbamoyl)amino]-1-piperidinyl}methyl)-6-methyl-2-pyridinyl]oxy}phenyl)methanesulfonamide,
(242) N-[4-({5-[(4-{butyl[(cis-4-hydroxycyclohexyl)carbamoyl]amino}-1-piperidinyl)methyl]-6-methyl-2-pyridinyl}oxy)phenyl]methanesulfonamide,
(243) N-[4-({5-[(4-{butyl[(4,4-difluorocyclohexyl)carbamoyl]amino}-1-piperidinyl)methyl]-6-methyl-2-pyridinyl}oxy)phenyl]methanesulfonamide,
(244) N-(4-{[5-({4-[butyl(tetrahydro-2H-pyran-4-ylcarbamoyl)amino]-1-piperidinyl}methyl)-6-methyl-2-pyridinyl]oxy}phenyl)methanesulfonamide,
(245) N-[4-({5-[(4-{[(1-acetyl-4-piperidinyl)carbamoyl](butyl)amino}-1-piperidinyl)methyl]-6-methyl-2-pyridinyl}oxy)phenyl]methanesulfonamide,
(246) 5-[(butyl{1-[(2-methyl-6-{4-[(1-pyrrolidinylsulfonyl)amino]phenoxy}-3-pyridinyl)methyl]-4-piperidinyl}carbamoyl)amino]-2,4-difluorobenzamide, and
(247) 5-[(butyl{1-[(2-methyl-6-{4-[(1-piperidinylsulfonyl)amino]phenoxy}-3-pyridinyl)methyl]-4-piperidinyl}carbamoyl)amino]-2,4-difluorobenzamide, or a salt thereof.

2. A compound selected from the group consisting of
(83) 5-({butyl[1-({2-methyl-6[4-(methylsulfonyl)phenoxy]-3-pyridinyl}methyl)-4-piperidinyl]carbamoyl}amino)-2,4-difluorobenzamide,
(89) 5-{[butyl(1-{[2-methyl-6-(4-{[4-(trifluoromethyl)-1-piperidinyl]sulfonyl}phenoxy)-3-pyridinyl]methyl}-4-piperidinyl)carbamoyl]amino}-2,4-difluorobenzamide,
(100) 5-{[{1-[(6-{4-[(4-acetyl-1-piperazinyl)carbonyl]phenoxy}-2-methyl-3-pyridinyl)methyl]-4-piperidinyl}(butyl)carbamoyl]amino}-2,4-difluorobenzamide,
(102) 5-({butyl[1-({6-[4-(ethylcarbamoyl)phenoxy]-2-methyl-3-pyridinyl}methyl)-4-piperidinyl]carbamoyl}amino)-2,4-difluorobenzamide,
(105) 5-[(butyl{1-[(2-methyl-6-{4-[(methylsulfonyl)methyl]phenoxy}-3-pyridinyl)methyl]-4-piperidinyl}carbamoyl)amino]-2,4-difluorobenzamide,
(132) 2,4-difluoro-5-{[{1-[(6-{4-[(methylsulfonyl)amino]phenoxy}-3-pyridinyl)methyl]-4-piperidinyl}(propyl)carbamoyl]amino}benzamide,
(143) 5-[(2-butyn-1-yl{1-[(2-methyl-6-{4-[(methylsulfonyl)amino]phenoxy}-3-pyridinyl)methyl]-4-piperidinyl}carbamoyl)amino]-2,4-difluorobenzamide,
(156) 5-[(butyl{1-[(2-ethyl-6-{4-[(methylsulfonyl)amino]phenoxy}-3-pyridinyl)methyl]-4-piperidinyl}carbamoyl)amino]-2,4-difluorobenzamide, (161) 5-[(butyl{1-[(2-isopropyl-6-{4-[(methylsulfonyl)amino]phenoxy}-3-pyridinyl)methyl]-4-piperidinyl}carbamoyl)amino]-2,4-difluorobenzamide, (215) 5-[(butyl{1-[(6-{4-[(4-hydroxy-1-piperidinyl)carbonyl]phenoxy}-2-methyl-3-pyridinyl)methyl]-4-piperidinyl}carbamoyl)amino]-2,4-difluorobenzamide, and (230) 5-({butyl[1-({2-isopropyl-6-[4-(methylsulfonyl)phenoxy]-3-pyridinyl}methyl)-4-piperidinyl]carbamoyl}amino)-2,4-difluorobenzamide, or a salt thereof.

3. A pharmaceutical composition comprising the compound according to claim 1 or 2, or a salt thereof.

* * * * *